(12) United States Patent
Biedermann et al.

(10) Patent No.: US 6,593,344 B1
(45) Date of Patent: Jul. 15, 2003

(54) PIPERADINYL-SUBSTITUTED PYRIDYLALKANE, ALKENE AND ALKINE CARBOXAMIDES

(75) Inventors: Elfi Biedermann, Vaterstetten (DE); Max Hasmann, Neuried (DE); Roland Löser, Feldafing (DE); Benno Rattel, Munich (DE); Friedemann Reiter, Putzbrunn (DE); Barbara Schein, Neufahrn (DE); Klaus Seibel, Gräfelfing (DE); Klaus Vogt, Munich (DE); Katja Wosikowski, Poing (DE); Isabel Schemainda, Munich (DE)

(73) Assignee: Klinge Pharma GmbH, Munich (DE)

( * ) Notice: Subject to any disclaimer, the term of this patent is extended or adjusted under 35 U.S.C. 154(b) by 0 days.

(21) Appl. No.: 09/595,547

(22) Filed: Jun. 16, 2000

Related U.S. Application Data

(63) Continuation of application No. PCT/EP98/08269, filed on Dec. 16, 1998.

(30) Foreign Application Priority Data

Dec. 17, 1997 (DE) .......................... 197 56 235

(51) Int. Cl.[7] ...................... A01N 43/60; C07D 211/06; C07D 405/00

(52) U.S. Cl. ..................... 514/318; 514/231.5; 544/124; 546/193

(58) Field of Search .............................. 514/318, 231.5; 544/124; 546/193

(56) References Cited

U.S. PATENT DOCUMENTS

| | | | |
|---|---|---|---|
| 4,283,541 A | 8/1981 | Shroff et al. ................ | 546/336 |
| 5,169,856 A | 12/1992 | Goto et al. .................. | 514/331 |
| 5,260,323 A | 11/1993 | Baader et al. .............. | 514/356 |
| 5,317,020 A * | 5/1994 | Emonds-Alt et al. .. | 514/252.12 |
| 5,326,772 A | 7/1994 | Klemm et al. .............. | 514/318 |
| 5,710,169 A * | 1/1998 | Russell ....................... | 514/327 |

FOREIGN PATENT DOCUMENTS

| | | |
|---|---|---|
| CA | 2085954 | 6/1993 |
| DE | 4020570 | 1/1992 |
| EP | 048045 | 3/1982 |
| EP | 210782 | 2/1987 |
| EP | 271023 | 6/1988 |
| EP | 330026 | 8/1989 |
| EP | 343307 | 11/1989 |
| EP | 416581 | 3/1991 |
| EP | 471236 | 2/1992 |
| EP | 479601 | 4/1992 |
| EP | 522606 | 1/1993 |
| EP | 530444 | 3/1993 |
| EP | 548883 | 6/1993 |
| EP | 512902 | 4/1994 |
| EP | 428434 | 5/1994 |
| GB | 2304714 | 11/1998 |
| JP | 57136518 | 8/1982 |
| JP | 63179869 | 7/1988 |

(List continued on next page.)

OTHER PUBLICATIONS

Nishikawa et al., "Acrylamide Derivatives as Antiallergic Agents. 2. Synthesis and Structure–Activity Relationships of N–[4–[4–(Diphenylmethyl)–1–piperazinyl]butyl ]–3–(3–pyridyl)acrylamides" Chem. Pharm. Bull. 37(1) 100–105 (1989).

Nishikawa et al., "Acrylamide Derivatives as Antiallergic Agents. 2. Synthesis and Structure–Activity Relationships of N–[4–[4–(Diphenylmethyl)–1–piperazinyl]butyl] –3–(3–pyridyl)acrylamides" J. Med. Chem. 1989, 32, 583–593.

Ishihara et al., "Central Cholinergic Agents. II. Synthesis and Acetylcholinesterase Inhibitory Activities of N–[W– [N–Alkyl–N–(phenylmethyl)amino]alkyl]–3–arylpropenamides" Chem. Pharm. Bull. 39 (12) 3236–3234 (1991).

Ross, "The Preparation of Some 4–Substituted Nicotinic Acids and Nicotinamides" J. Chem. Soc. (C), 1966, 1816–1820.

Rote Liste, 1997.

*Primary Examiner*—Richard L Raymond
*Assistant Examiner*—Tamthom N. Truong
(74) *Attorney, Agent, or Firm*—Fitch, Even, Tabin & Flannery

(57) ABSTRACT

The invention relates to new piperidinyl-substituted pyridyl carboxamides of the general formula (I), wherein the structure element E has meanings (E1) or (E2) and whereby the heterocyclic ring can optionally have a double bond. These substances have especially high cytostatic activities and pronounced immunosuppressive properties which make them suitable for therapeutic treatment in broad tumor spectrum.

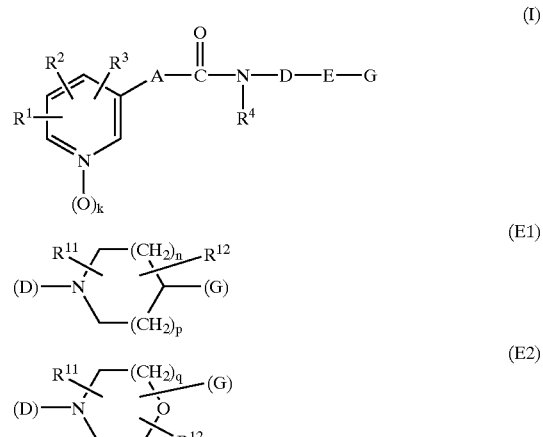

29 Claims, No Drawings

FOREIGN PATENT DOCUMENTS

| WO | WO89/07443 | 8/1989 |
| --- | --- | --- |
| WO | WO91/15484 | 10/1991 |
| WO | WO91/15485 | 10/1991 |
| WO | WO93/14113 | 7/1993 |
| WO | WO95/10514 | 4/1995 |
| WO | WO95/10515 | 4/1995 |
| WO | WO95/10516 | 4/1995 |
| WO | WO95/24894 | 9/1995 |
| WO | WO93/14070 | 9/1996 |
| WO | WO96/31478 | 10/1996 |
| WO | WO94/01402 | 3/1997 |
| WO | WO93/13083 | 4/1997 |
| WO | WO97/48397 | 12/1997 |
| WO | WO96/31477 | 1/1998 |
| WO | WO97/48695 | 1/1998 |

* cited by examiner

PIPERADINYL-SUBSTITUTED PYRIDYLALKANE, ALKENE AND ALKINE CARBOXAMIDES

This is a continuation of prior application number PCT/EP98/08269, filed Dec. 16, 1998 and designating the U.S., which is hereby incorporated herein by reference in its entirety.

The invention relates to new piperidinyl-substituted pyridyl-alkane, alkene and alkine carboxamides with a saturated or one or several-fold unsaturated hydrocarbon residue in the carboxylic acid portion, methods for the synthesis of these compounds, medicaments containing these and their production as well as their therapeutic use especially as cytostatic agents and immunosuppresive agents, for example, in the treatment or prevention of various types of tumors and control of immune reactions, for example of autoimmune diseases.

A pressing need exists for new pharmaceuticals and/or medicaments for cytostatic and immunosuppressive therapy which not only possess a strong activity, but also exert diminished side effects in comparison to many classical cancerostatic agents. At the same time treatment of a broad as possible spectrum of tumors should be made accessible. Furthermore, effective cytostatic agents for an efficient therapy should be made available. Active ingredients of this type should also be exceptionally suitable in the mentioned indications for a combination therapy, be it in connection with other cytostatic agents or with radiation (for example X-rays, radioactive elements, such as cobalt, or linear accelerator, etc.), with operative procedures, heat treatment, etc.

Additionally, from another point of view, there exists a strong need in the field of tumor therapy for new compounds, for example for overcoming or avoiding resistances, which enrich the pallet of cancerostatics based on new modes of action in the ideal case.

This object was successfully solved by the creation of the piperidinyl-substituted pyridylalkane, alkene and alkine carboxamide derivatives as defined in detail in the claims and medicaments containing these as well as the use of these compounds, optionally in combination with other suitable active ingredients and adjuvants, for cytostatic and immunosuppressive therapy or prevention.

It is known that various pyridine compounds or substituted in a specific manner have pharmacologically useful properties; however, in contrast to the actions of the compounds according to the invention, these lie in completely different fields of indication.

Thus, ω-pyridyl-alkane and/or alkene amides with antiallergic activity are described in EP 0 210 782 which are referred to as having a 5-lipoxygenase-inhibiting and antihistamine action, wherein the amide components of these compounds contain a piperizine or homopiperizine ring and the pyridine ring can be linked together in the 2-, 3- or 4-position. JP 63,179,869 describes further pyridyl amides, ω-pyridylalkane and alkene amides as anti-allergic effective substances containing a substituted piperidine ring in the amine component. However, corresponding overlapping compound groups are excluded from the present claimed scope of protection according to the invention. Similarly compounds with the same properties are mentioned in Chem. Pharm. Bull 37, 100–105 (1989) and in J. Med. Chem. 1989, 583–593 whereby corresponding known substitutions are also excluded from the present scope of protection.

Pyridyl ureas, pyridyl thioureas and pyridyl carbonamides, wherein the amide portion is bound over an aryl-substituted alkyl chain with a piperidine ring or piperidine ring or piperazine ring, are described for example in EP-A-0 428 434 or in EP-A-0 512 902 as antagonists of the neurokinin receptor and substance P. Furthermore, pyridyl (alkyl)carbonamides, pyridyl(alkyl)sulfonamides and analogous ureas, wherein the pyridine ring is bound directly or over a methylene bridge with the amide group are disclosed in EP-A-0 479 601 as active ingredients with antiarrhythmic properties.

Other structurally closely related compounds are represented by the piperidine compounds described in EP-A-0 330 026. These known compounds are distinguished by an anti-cholinesterase activity, an anti-amnesia activity as well as activities directed against hyperkinesia, senile dementia, mania and Alzheimer's disease.

In WO 91/15 485, the production of pyridine-3,5-dicarboxylic acid esters and amides as well as their use for the treatment of tumor conditions is described. These compounds differ from the compounds according to the invention described below in very important structural features, for example by the dicarboxyl grouping on the pyridine ring or the absence of the hydrocarbon chain between the pyridine ring and the amide grouping. The compounds disclosed in WO 89/07 443 in the form of optically pure R(–)-niguldipin and further analogous dihydropyridines with cytotoxic activity have larger structural differences. However, as compared to these known compounds, the compounds according to the invention possess a higher activity and a wider spectrum of action despite the large structural differences.

In the international PCT patent applications WO 96/31477 or for example WO 96/31478 tricyclic anellated compounds are described which possess an antiproliferative activity. All of these compounds described therein are distinguished in that they must imperatively possess a tricyclic anellated ring system with at least one nitrogen atom, for example 6, 11-dihydro-5H-benzo[5,6] cyclohepta[1,2-b]pyridinyl ring system as a pharmaphoric group. The molecule portion at the other end of this tricyclic anellated system is uncommonly variable such that the pyridyl substitution given therein among numerous substitution possibilities merely represents one of many variation possibilities. A further meaningful difference in the substitution of these molecules in comparison to the compounds according to the invention is to be seen in the lack of the present structural element D (i.e. the inserted, optionally unsaturated hydrocarbon chain between the two essential terminal and/or opposite heterocycles); expressed in other words, the known compounds have a direct bond between the carboxy group and the piperidine ring.

A further essential difference of the compounds according to the invention in comparison to these known tricyclic anellated compounds is to be recognized in the presence of the terminal 3-pyridyl-substitution which must be present. The presence of this heterocyclic ring required according to the invention as well as this particular bond site in the substituted compounds according to the invention in comparison to the above mentioned anti-proliferative compounds of the state of the art with a tricyclic ring system is to be understood as a meaningful indication that, in a completely surprising manner, the pyridyl group is responsible for the anti-tumor action according to the invention.

In fact, the compounds according to the invention cover a different tumor spectrum from those named in the PCT/WO publications with this necessarily present tricyclic anellated ring system. In the mentioned PCT/WO publications of the state of the art, a treatment possibility in tumors is merely mentioned which is made in connection with a potential inhibition of the farnesyl protein transferase, whereby this mechanism relates to the expression of the activated rasoncogene. In contrast to this, the presently claimed new compounds with the 3-pyridyl-substitution required according to the invention are not limited to the therapy of tumor cells of this type with abnormal production of the ras-oncogene; rather, the therapy possibilities with the new compounds according to the invention extend to the combat of numerous other types of tumors with different causal mechanisms as well as immunosuppressive treatment possibilities such as autoimmune diseases.

In view of this art, the finding demonstrated in the pharmacological experimental section below according to which the compounds according to the general formula (I) with the particular substitutions defined below have superior pharmacological activities which make them particularly suitable in an excellent manner for the therapy of tumor illnesses over a broad anti-proliferative spectrum, was completely unexpected. The pharmacological finding that, aside from the cytostatic effectiveness, and the ability to inhibit abnormal cell growth especially with different tumor spectra, the compounds according to the invention also possess immunosuppressive properties and additionally favorable abortive properties without harmful mutagenic effects is to be considered as equally surprising.

Pyridyl compounds wherein, a non-aromatic heterocyclic ring with merely one ring nitrogen atom and optionally an additional ring oxygen atom, preferably a piperidinyl residue, is also incorporated—however, in opposite orientation—as well as their use especially as cytostatic agents are subject matter of the older patent application P 196 24 704.7-44 which has not yet been published.

Therewith, the most important differentiating feature of the new compounds according to the invention with respect to these older, non-prepublished compounds is the orientation of the structural feature E which in the present application is always integrated in the opposite direction in the general formula (I). This novel construction of these structurally complicated compounds not only has an unexpected positive effect for the amenability of the synthesis, but also for the multiple variation possibilities of the structural element G found at the outer end of the molecule. As a result of this particular molecular structure now found, a novel class of compounds with, among others, pronounced cancerostatic effect is offered.

These new piperidinyl-substituted pyridyl carboxamides correspond to the following general formula:

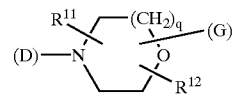

(I)

wherein the structural element E has the following meaning:

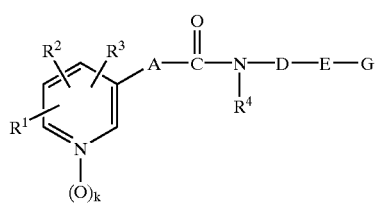

(E1)

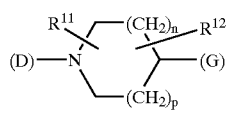

(E2)

and whereby the heterocyclic ring can optionally have a double bond and n and p can be, independent from each other, 0, 1, 2 or 3 with the proviso that n+p≦4, and whereby q is 1; 2 or 3.

The substituent E can especially be present in the form of azetidine, pyrrolidine, piperidine, hexahydroazepine, octahydroazocine, morpholine, hexahydro-1,4-oxazepine and octahydro-1,4-oxacocine.

The meaning of the remaining substituents and the preferred embodiments of the compound groups according to the invention falling under the general formula as well as particularly preferred end products are defined in claims 1 to 7 in detail. In this connection, reference is also made to the substituent meanings which are illustrated as follows and are partially emphasized as preferred.

The compounds of Formula (I), which represent the end products can optionally exist as cis- and trans-isomers, E- and Z-isomers, for example when A is a cyclopropane ring or D contains one or more double bonds. Subject matter of the invention is the pure isomers as well as their mixtures.

Furthermore, the compounds of Formula (I) can contain one or more asymmetric carbon atoms and, as a result, exist in the form of different optical isomers (enantiomers, diastereomers). The invention includes all optical isomers and their racemic or non-racemic mixtures. Finally, compounds of Formula (I) can exist as endo/exo-isomers in case the ring system E is bicyclic. The pure endo- and exo-isomers as well as their mixtures are also comprised by the invention.

Compounds of Formula (I), in which G is a heterocyclic aromatic ring or contains such in an anellated ring system can optionally be present as tautomers when this heterocyclic ring is substituted by free hydroxy-, mercapto- or amino groups. In this case, the invention includes all tautomeric forms.

Subject matter of the invention are further pharmacologically acceptable acid addition salts of the compounds of Formula (I) with inorganic or organic acids. Preferable examples for addition salts with suitable inorganic acids are hydrochlorides, hydrobromides, hydroiodides, sulfates and phosphates. Addition salts of organic acids are preferably acetates, benzoates, citrates, fumarates, gluconates, malates, maleates, methanesulfonates, lactates, oxalates, succinates, tartrates and tosylates.

Compounds of Formula (I) as well as their acid addition salts can also be optionally present as hydrates or other solvates. The invention includes such hydrates and solvates.

In the compounds of Formula (I), the definitions for the atoms or atomic groups preferably have the following meanings:

Halogen means fluorine, chlorine, bromine or iodine;

Alkyl can be straight chained or branched and preferably signifies a $C_1$–$C_6$-alkyl residue, especially a methyl-, ethyl-, propyl-, isopropyl-, butyl-, isobutyl-, sec-butyl-, tert-butyl-, cyclopropylmethyl-, pentyl-, isopentyl-, tert-pentyl-, neopentyl-, cyclopropylethyl-, cyclobutylmethyl- or hexyl group.

Alkylene signifies for example methylene, ethylene, propylene, tetramethylene, pentamethylene, hexamethylene, heptamethylene, octamethylene, nonamethylene or decamethylene.

Alkenyl preferably signifies $C_3$–$C_6$-alkenyl and can be straight chained or branched and preferably signifies an allyl-, 2-butenyl-, 3-butenyl-, 2-methyl-2-propenyl-, 2-pentenyl-, 4-pentenyl-, 2-methyl-2-butenyl-, 3-methyl-2-butenyl-, 2-hexenyl-, 5-hexenyl-, 4-methyl-3-pentenyl- or 2,2-dimethyl-3-butenyl-group.

Alkenylene signifies for example ethenylene, propenylene, butenylene, pentenylene, hexenylene, hexadienylene, heptenylene, octenylene, nonenylene or decenylene.

Alkinyl preferably signifies $C_2$–$C_6$-alkinyl which can be straight chained or branched and can preferably signify an ethinyl-, propargyl-, 2-butinyl-, 3-butinyl-, 4-pentinyl-, 5-hexinyl- or 4-methyl-2-pentinyl group.

Alkinylene signifies for example propinylene, butinylene, pentinylene, hexinylene, hexeninylene, heptinylene, octinylene, noninylene or decinylene.

Cycloalkyl is preferably a $C_3$–$C_8$-cycloalkyl residue, especially a cyclopropyl-, cyclobutyl-, cyclopentyl-, cyclohexyl-, cycloheptyl- or cyclooctyl group.

Hydroxyalkyl contains a hydroxyl group in one of the above mentioned alkyl residues, especially in a $C_1$–$C_6$-alkyl residue, whereby among the $C_1$–$C_6$-hydroxyalkyl residues, the hydroxymethyl- and the hydroxyethyl residue are preferred.

Aside from the oxygen atom, alkoxy, preferably $C_1$–$C_6$ alkoxy, alkenyloxy, and alkinyloxy especially $C_1$–$C_6$ contain one of the above mentioned preferred $C_1$–$C_6$-alkyl-, $C_3$–$C_6$-alkenyl- and/or $C_3$–$C_6$-Alkinyl groups. Particularly preferred groups for this are the methoxy-, ethoxy-, isopropoxy-, tert-butoxy-, allyloxy- and propargyloxy groups.

Alkoxy, especially $C_1$–$C_6$-alkoxy, entirely or partially replaced by fluorine is for example difluoromethoxy, trifluoromethoxy or 2,2,2-trifluoroethoxy.

Aside from the sulphur atom, alkylthio, alkenylthio, alkinyl-thio contain one of the above mentioned preferred $C_1$–$C_6$-alkyl-, $C_3$–$C_6$-alkenyl- or $C_3$–$C_6$-alkinyl groups. Preferred groups among these are the methylthio-, ethylthio-, isopropylthio- and tert-butylthio groups.

Cyclopentyloxy- and cyclopentylthio- and/or cyclohexyloxy- and cyclohexylthio residues represent preferred $C_3$–$C_8$-cycloalkyloxy and $C_3$–$C_8$-cycloalkylthio.

Aside from the oxygen atom, alkanoyloxy groups preferably contain an aliphatic acyl group with 1 to 7 carbon atoms. Among preferred alkanoyloxy groups are the acetoxy-, propionyloxy- and pivaloyloxy groups.

Alkoxycarbonyl groups, preferably $C_2$–$C_7$-alkoxycarbonyl groups contain, aside from the carbonyl group, one of the above mentioned alkoxy groups, especially $C_1$–$C_6$-alkoxy groups. Preferred alkoxycarbonyl groups are the methoxycarbonyl-, ethoxycarbonyl-, isopropoxycarbonyl-, isobutoxycarbonyl- and tert-butoxycarbonyl groups.

Aside from the oxygen atom, alkoxycarbonyloxy groups preferably contain one of the above mentioned $C_2$–$C_7$-alkoxy-carbonyl residues. Among preferred alkoxycarbonyl groups are the methoxycarbonyloxy-, ethoxycarbonyloxy-, isopropoxycarbonyloxy-, isobutoxycarbonyloxy- and tert-butoxycarbonyl groups as well as allyloxycarbonyloxy groups.

Aside from the carbonyl group, alkylaminocarbonyl, especially $C_2$–$C_7$-alkylaminocarbonyl and dialkylaminocarbonyl groups, preferably $C_3$–$C_{13}$-dialkylaminocarbonyl groups, contain an alkylamino- and/or dialkylamino residue whose alkyl groups correspond especially to the $C_1$–$C_6$-alkyl groups of the above description. Preferred groups are the dimethylaminocarbonyl-, diethylaminocarbonyl- and diisopropylamino-carbonyl groups.

Aside from the unsubstituted amino group, the amino groups of the Formula $NR^5R^6$ are one of the below mentioned alkylamino groups, especially $C_1$–$C_6$-alkylamino groups and/or dialkyl-amino groups, especially di-($C_1$–$C_6$-alkyl)amino groups.

Alkylamino especially contains one of the above mentioned $C_1$–$C_6$-alkyl groups. Preferred groups are the methylamino-, ethylamino-, propylamino-, isopropylamino-, butylamino-, and the tert-butylamino groups.

The preferred di-($C_1$–$C_6$-alkyl)amino residue carries two of the same or different of the above mentioned $C_1$–$C_6$-alkyl groups on the nitrogen atom. Preferred groups are the dimethylamino-, diethylamino-, dipropylamino-, diisopropylamino-, isopropyl-, methylamino-, dibutylamino- or tert-butylmethylamino groups.

Acyl, especially $C_1$–$C_6$-acyl, signifies the residue of an aliphatic saturated or unsaturated, straight chained, branched or cyclic carboxylic acid. Preferred acyl residues are formyl-, acetyl-, propionyl-, acryloyl-, butyryl-, isobutyryl-, methacryloyl-, cyclopropylcarbonyl-, pentanoyl-, pivaloyl-, cyclobutylcarbonyl-, hexanoyl- and dimethylacryloyl groups.

Alkanesulfonyl, especially $C_1$–$C_6$-alkanesulfonyl is preferably the methanesulfonyl-, ethanesulfonyl-, propanesulfonyl-, butanesulfonyl-, pentanesulfonyl- or hexanesulfonyl groups.

Saturated or unsaturated, preferably four- to eight-membered heterocycles with one or two hetero-atoms, are for example azetidine, tetrahydrofuran, tetrahydrothiophene, pyrrolidine, tetrahydropyran, tetrahydropyridine, piperidine, tetrahydroazepine, hexahydroazepine, octahydroazocine, pyrazolidine, piperazine, morpholine, thiomorpholine, thiomorpholin-1,1-dioxide, hexahydrodiazepine or hexahydrooxazepine.

Preferred monocyclic aromatic five- or six-membered heterocycles with one to three hetero-atoms are for example furyl, thienyl, pyrrolyl, oxazolyl, isoxazolyl, thiazolyl, isothiazolyl, imidazolyl, pyrazolyl, oxadiazolyl, thiadiazolyl, triazolyl, pyridyl, pyrazinyl, pyridazinyl, pyrimidinyl or triazinyl.

Anellated bi- and tricyclic aromatic or partially hydrated carbocyclic ring systems with 8 to 16 ring atoms and at least one aromatic ring are preferably benzocyclobutyl, indanyl, indenyl, naphthyl, dihydronaphthyl, tetrahydronaphthyl, biphenylenyl, fluoroenyl, anthryl, dihydroanthryl, phenanthryl, dihydrophenanthryl, dihydrodibenzocycloheptenyl, tetrahydrobenzocycloheptenyl, dibenzocycloheptenyl, dihydrodibenzocycloheptenyl, dihydrodibenzocyclooctenyl or tetrahydrodibenzocyclooctenyl. Their mono- or dioxo-derivates, i.e. for example the following rings: indanone, tetralone, anthrone, anthraquinone, fluoroenone, phenanthrone, dibenzocycloheptenone, dihydrodibenzocycloheptenone or tetrahydrodibenzocyclooctenone are also to be understood as partially hydrated carbocyclic ring systems.

Anellated bi- and tricyclic aromatic or partially hydrated heterocyclic ring systems with 8 to 16 ring atoms and at least one aromatic ring are, for example, imidazothiazolyl, benzofuryl, dihydrobenzofuryl, benzothienyl, dihydrobenzothienyl, indolyl, indolinyl, isoindolinyl, bennzimidazolyl, indazolyl, benzoxazolyl, benzoisoxazolyl, benzothiazolyl, benzoisothiazolyl, benzofurazanyl, benzothiadiazolyl, benzotriazolyl, oxazolopyridyl, thiazolopyridyl, isothiazolopyridyl, imidazopyridyl, pyrazolopyridyl, thienopyrimidinyl, chromanyl, benzopyranyl, quinolyl, isoquinolyl, dihydroquinolyl, tetrahydroquinolyl, benzodioxanyl, quinoxalinyl, quinazolinyl, naphthyridinyl, carbazolyl, tetrahydrocarbazolyl, pyridoindolyl, acridinyl, phenanthridinyl, dihydrophenanthridinyl, dibenzoisoquinolinyl, dihydrodibenzoisoquinolinyl, phenothiazinyl, dihydrodibenzooxepinyl, benzocycloheptathienyl, dihydrothienobenzothiepinyl, dihydrodibenzothiepinyl, octahydrodibenzothiepinyl, dibenzoazepinyl, dihydrodibenzoazepnyl, octahydrodibenzoazepinyl, benzocycloheptapyridyl, dihydrobenzocycloheptapyridyl, pyridobenzoazepinyl, dihydropyridobenzoazepinyl, dihydropyridobenzodiazepinyl, dihydrodibenzoxazepinyl, dihydropyridobenzoxepinyl, dihydropyridobenzooxazepinyl, dihydrodibenzothiazepinyl or dihydropyridobenzothiazepinyl.

Furthermore, their mono- or dioxo-derivates and/or optionally their possible tautomers are also to be understood as partially hydrated heterocyclic ring systems, i.e. for example the residues of indolinone, isatin of benzoxazolone and/or its tautomer hydroxybenzoxazole, of benzisoxazolone, benzothiazolone, benzoisothiazolone and benzimidazolone and/or their corresponding tautomers hydroxybenzisoxazole, hydroxybenzothiazole, hydroxybenzoisothiazole and hydroxybenzimidazole, as well as indazolinone, of oxazolopyridinones, thiazolopyridinones, pyrazolopyridinones and imidazopyridinones and/or their corresponding tautomers hydroxyoxazolopyridine, hydroxythiazolopyridine, hydroxypyrazolopyridine and hydroxyimidazopyridine, the residues for the series chromanone, chromone, quinolinone, dihydroquinolinone, tetrahydrocarbazolone, acridone, phenannthridone, benzoisoquinolone, dihydrodibenzooxepinones, benzocycloheptathiophenones, dihydrothienobenzothiepinones, dihydrodibenzothiepinones, dihydrodibenzoazepinones, benzocycloheptapyridinones, dihydropyridobenzoazepinones, dihydropyridobenzodiazepinones/dihydropyridobenzoxazeninones, dihydrodibenzothiazepinones and of dihydropyridobenzothiazepinones.

Saturated and unsaturated monocyclic, four- to eight-membered heterocycles (as the group $-NR^{13}R^{15}$) which, aside from the essential nitrogen atom, can optionally contain one or two further hetero-atoms selected from N and/or S and/or O, are for example azetidine, pyrrolidine, piperidine, (1H)-tetrahydropyridine, hexahydroazepine, (1H)-tetrahydroazepine,. octahydroazocine. pyrazolidine, piperazine, hexahydrodiazepine, morpholine, hexahydroxazepine, thiomorpholine or thiomorpholin-1,1-dioxide.

Saturated or unsaturated bi- or tricyclic, anellated or bridged heterocycles with 8 to 16 ring atoms, (in the form of the group $-NR^{13}R^{15}$) which, aside from the essential nitrogen atom, can optionally contain one or two further hetero-atoms, selected from N and/or S and/or O, are for example 5-aza-bicyclo[2.1.1]hexane, 2-aza-bicyclo[2.2.1] heptane, 7-aza-bicyclo[2.2.1]heptane, 2,5-diaza-bicyclo [2.2.1]heptane, 2-aza-bicyclo[2.2.2]octane, 8-aza-bicyclo [3.2.1]octane, 2,5-diaza-bicyclo[2.2.2]octane, 9-aza-bicyclo [3.3.1]nonane, indoline, isoindoline, (1H)-dihydroquinoline, (1H)-tetrahydroquinoline, (2H)-tetrahydroisoquinoline, (1H)-tetrahydroquinoxaline, (4H)-dihydrobenzoxazine, (4H)-dihydrobenothiazine, (1H)-tetrahydrobenzo[b] azepine, (1H)-tetrahydrobenzo[c]azepine, (1H)-tetrahydrobenzo[d]azepine, (5H)-tetrahydrobenzo[b]oxazepine, (5H)-tetrahydrobenzo[b]thiazepine, 1,2,3,4-tetrahydro-9H-pyrido[3,4-b]indole, (10H)-dihydroacridine, (10H)-dihydrophenanthridine, 1,2,3,4-tetrahydroacridanone, (10H)-phenoxazine, (10H)-phenothiazine, (5H)-dibenzazepine, (5H)-dihydrodibenzazepine, (5H)-octahydrodibenzazepine, dihydrobenzo[d,e]isoquinoline, (5H)-dihydrodibenzodiazepine, (5H)-benzo[b]pyrido[f]azepine, (5H)-dihydrobenzo[b]pyrido-[f]azepine, (11H)-dihydrodibenzo[b,e]oxazepine, (11H)-dihydrodibenzo[b,e]thiazepine, (10H)-dihydrodibenzo[b,f]oxazepine, (10H)-dihydrodibenzo[b,f]thiazepine, (5H)-tetrahydrodibenzazocine, (11H)-dihydrobenzo[e]pyrido[b]-1,4-diazepin-6-one, (11H)-dihydrobenzo[b]pyrido[e]-1,4-diazepin-5-one.

Spirocyclic ring system (in the form of the group $ER^{13}$, $R^{15}$), comprising the residue E and a $C_3$–$C_8$-cycloalkane ring, are for example 2-azaspiro[3,4]octane, or the residue 2-azaspirononanes, azaspirodecanes and azaspiroundecanes.

Spirocyclic ring systems (in the form of the group $ER^{13}$, $R^{15}$), comprising the residue E and a saturated four to seven-membered heterocycle with one or two hetero-atoms respectively are for example 5,8-dioxa-2-aza-spiro[3,4] octane or a residue from the series of dioxaazaspirononanes, dithiaazaspirononanes, oxadiazaspirononanes, triazaspirononanes, diazaspirodecanes, dioxaazaspirodecanes, dithiaazaspirodecanes, oxadiazaspirodecanes, triazaspirodecanes, dioxaazaspiroundecanes, dithiaazaspiroundecanes, oxadiazaspiroundecanes or triazaspiroundecanes as well as their mono- and dioxo derivates.

Spirocyclic ring systems (in the form of the group $ER^{13}R^{15}$), comprising the residue E and an anellated, bi- or tricyclic, partially hydrated carbocyclic or heterocyclic ring system are preferably spiro[indan-piperidines], spiro [piperidin-tetrahydronaphthalines], spiro[benzodioxol-pyrrolidines], spiro[benzodioxol-piperidines], spiro [benzodioxol-hexahydroazepines], spiro[benzo-1,3-dioxin-piperidines], spiro[dihydrobenzo-1,3-oxazin-piperidines], spiro[oxodihydrobenz-1,3-oxazin-piperidines] and spiro [piperidin-oxo-1,2,3,4-tetrahydrochinazolines].

Very particularly preferred embodiments of the invention are represented by the following end products:

N-[4-(4-phenyl-piperidin-1-yl)-butyl]-3-pyridin-3-yl-acrylamide;

N-{4-[4-(1H-indol-3-yl)-piperidin-1-yl]-butyl}-3-pyridin-3-yl-acrylamide;

N-{4-[4-(2-oxo-2,3-dihydro-benzoimidazol-1-yl)-piperidin-1-yl]-butyl}-3-pyridin-3-yl-acrylamide;

N-[4-(4-benzotriazol-1-yl-piperidin-1-yl)-butyl]-3-pyridin-3-yl-acrylamide;

N-{4-[4-(hydroxy-diphenylmethyl)-piperidin-1-yl]-butyl}-2-(pyridin-3-yloxy)-acetamide;

N-[4-(4,4-diphenyl-piperidin-1-yl)-butyl]-3-pyridin-3-yl-acrylamide;

N-{4-[4-(6,11-dihydro-dibenzo[b,e]thiepin-11-yliden)-piperidin-1-yl]-butyl}-3-pyridin-3-yl-propionamide dihydrochloride/semi-isopropanol;

N-{4-[4-(6,11-dihydro-dibenzo[b,e]thiepin-11-yliden)-piperidin-1-yl]-butyl}-5-pyridin-3-yl-pentanamide;

N-{4-[4-(4,9-dihydro-thieno[2,3-b]-benzo[e]thiepin-4-yliden)-piperidin-1-yl]-butyl}-3-pyridin-3-yl-propionamide;

N-{4-[4-(4,9-dihydro-thieno[2,3-b]-benzo[e]thiepin-4-yliden)-piperidin-1-yl]-butyl}-3-pyridin-3-yl-acrylamide;

N-[4-(4-diphenylphosphinoyloxy-piperidin-1-yl)-butyl]-3-pyridin-3-yl-acrylamide;

N-[4-(1,4-dioxa-8-azaspiro[4.5]dec-8-yl)-butyl]-3-pyridin-3-yl-acrylamide.

Concretely, the invention relates to new compounds of the general Formula (I)

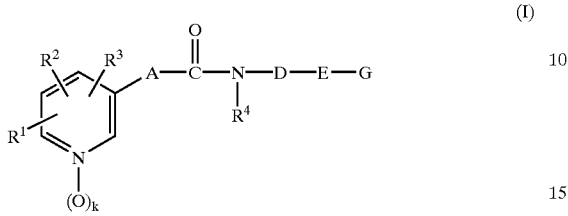

(I)

wherein $R^1$ is selected from hydrogen, hydroxy, halogen, cyano, carboxy; saturated, single or several-fold unsaturated, branched or straight chained or cyclic hydrocarbon residues such as alkyl, alkenyl, alkinyl or cycloalkyl; trifluoromethyl or hydroxyalkyl;

aryl such as phenyl or heteroaryl such as pyridyl;

alkoxy, cycloalkyloxy, alkenyloxy, alkinyloxy or aralkyloxy such as the benzyloxy group, alkoxycarbonyl; aminocarbonyl, alkylaminocarbonyl, dialkylaminocarbonyl, alkanoyloxy, alkoxycarbonyloxy; alkylthio, cycloalkylthio, alkenylthio, alkinylthio; aryloxy such as phenoxy, heteroaryloxy such as pyridyloxy, heteroarylthio such as pyridylthio, and $NR^5R^6$, whereby $R^5$ and $R^6$ are selected independent of each other from hydrogen, saturated or unsaturated hydrocarbon residues such as alkyl, alkenyl, alkinyl, or aryl such as phenyl and aralkyl such as benzyl;

$R^2$ is selected from hydrogen, halogen, cyano, saturated hydrocarbon residues such as alkyl, or halogenated hydrocarbon residues such as trifluoromethyl, hydroxy, alkoxy, aralkyloxy residues such as benzyloxy, as well as alkanoyloxy, whereby $R^1$ and $R^2$, in the case that they are immediately adjacent to each other, optionally form a bridge which is selected from —(CH$_2$)$_4$— and —(CH=CH)$_2$— and —CH$_2$O—CR$^7$R$^8$—C—, wherein $R^7$ and $R^8$ are selected independently of each other from hydrogen and alkyl residues;

$R^3$ is selected from hydrogen, halogen, saturated hydrocarbon residues such as alkyl, or halogenated hydrocarbon residues such as trifluoromethyl, or hydroxyalkyl;

$R^4$ is selected from hydrogen, hydroxy, saturated, single or several-fold unsaturated, branched or straight chained or cyclic hydrocarbon residues such as alkyl, alkenyl, alkinyl or cycloalkyl, alkoxy and aralkyloxy such as benzyloxy;

k is 0 or 1;

A is selected from alkylene with at least 2 carbon atoms which is optionally substituted one to three-fold by straight chained or branched chained hydrocarbon residues such as alkyl, hydroxy, alkoxy, halogen such as fluorine, or aryl such as phenyl, alkylene with at least 2 carbon atoms, wherein a methylene unit is isosterically replaced by O, S, $NR^9$, CO, SO or SO$_2$ whereby, with the exception of CO, the isosteric substitution cannot be adjacent to the amide group and, in $NR^9$, the residue $R^9$ is selected from hydrogen, alkyl, alkenyl, alkinyl, acyl or alkanesulfonyl;

cycloalkylene such as 1,2-cyclopropylene;

alkenylene with at least 2 carbon atoms which is optionally substituted one to three-fold by alkyl, hydroxy, alkoxy, fluorine, cyano or aryl such as phenyl;

kadienylene with at least 4 carbon atoms, which is optionally substituted once or twice by alkyl, fluorine, cyano or aryl such as phenyl;

1,3,5-hexatrienylene, which is optionally substituted by alkyl, fluorine, cyano or aryl such as phenyl; as well as ethinylene;

D is selected from alkylene with at least 2 carbon atoms, which is optionally substituted once or twice by alkyl, hydroxy, or alkoxy; alkenylene with at least 4 carbon atoms, which is optionally substituted once or twice by alkyl, hydroxy, or alkoxy;

alkinylene with at least 4 carbon atoms, which is optionally substituted once or twice by alkyl, hydroxy, or alkoxy; as well as alkylene, alkenylene or alkinylene with at least 2 or 4 carbon atoms respectively, wherein one to three methylene units is each isosterically replaced by O, S, $NR^{10}$, CO, SO or SO$_2$, wherein $R^{10}$ has the same meaning as $R^9$ but is selected independently thereof;

E is selected from

(E1)

and

(E2)

whereby the heterocyclic ring can optionally have a double bond and n and p can be, independent of each other, 0, 1, 2 or 3 with the proviso that n+p≦4.

q is 1, 2 or 3;

$R^{11}$ is selected from hydrogen, alkyl, hydroxy, hydroxymethyl, carboxy, or alkoxycarbonyl with at least 2 carbon atoms and $R^{12}$ is selected from hydrogen, alkyl or an oxo group adjacent to a nitrogen atom or $R^{11}$ and $R^{12}$, optionally together, form a C$_1$–C$_3$-alkylene bridge under formation of a bicyclic ring system;

G is selected from G1, G2, G3, G4 or G5, wherein

G1 is the residue

(G1)

and r is a number from 0 to 3, and s is 0 or 1;

$R^{13}$ is selected from hydrogen, alkyl, or alkenyl, alkinyl, cycloalkyl with at least 3 carbon atoms in the saturated or cyclic residues;

saturated or unsaturated, four to seven-membered heterocycles which can contain one or two hetero-atoms selected from N and/or S and/or O;

benzyl, phenyl;

monocyclic aromatic five- or six-membered heterocycles which can contain 1 to 3 hetero-atoms selected from N and/or S and/or O and are either directly bound or bound over a methelyene group;

anellated bi- and tricyclic aromatic or partially hydrated carbocyclic ring systems with 8 to 18, preferably up to 16 ring atoms, and at least one aromatic ring, whereby the bond can occur either over an aromatic or a hydrated ring and either directly or over a methylene group;

anellated bi- and tricyclic aromatic or.partially hydrated heterocyclic ring systems with 8 to 18, preferably up to 16 ring atoms, and at least one aromatic ring, whereby one to three ring atoms can be selected from N and/or S and/or O and the bond can occur either over an aromatic or a hydrated ring and either directly or over a methylene group;

$R^{14}$ has the same meaning as $R^{13}$ but is selected independently thereof;

$R^{15}$ is selected from hydrogen, hydroxy, methyl, benzyl, phenyl; monocyclic aromatic five or six-membered heterocycles, which can contain one to three heteroatoms selected from the group N and/or S and/or O and are either bound directly or over a methylene group;

anellated bi- and tricyclic aromatic or partially hydrated carbocyclic ring systems with 8 to 18, preferably up to 16 ring atoms, and at least one aromatic ring, wherein the linkage can occur either over an aromatic or a hydrated ring and either directly or over a methylene group;

anellated bi- and tricyclic aromatic or partially hydrated heterocyclic ring systems with 8 to 18, preferably up to 16 ring atoms, and at least one.aromatic ring, wherein one to three ring atoms can be selected from N and/or S and/or O and the linkage can occur either over an aromatic ring or a hydrated ring and either directly or over a methylene group;

$G^2$ has the meaning

 (G2), whereby $R^{13}$ and $R^{15}$ have the above meaning and u represents the number 0 or 1, or signifies the residue

which is sound by means of a double bond to E in the case that u=1, or can signify a ring system bound over the carbon atom selected from cycloalkyl with at least 3 carbon atoms; saturated, four to seven-membered heterocycles which can contain one or two heteroatoms selected from N and/or S and/or O;

anellated bi- and tricyclic partially hydrated carboxocyclic ring system with 8 to 18, preferably up to 16 ring atoms, and at least one aromatic ring;

anellated bi- and tricyclic partially hydrated heterocyclic ring systems with 8 to 18, preferably up to 16 ring atoms, and at least one aromatic ring, wherein one to three ring atoms can be selected from N and/or S and/or O;

or, in the case that u=0, the two germinal substituents $R^{13}$ and $R^{15}$ can form a spirocycle together with the bonding atom of the ring E selected from cycloalkyl, saturated, four to seven-membered heterocycles which can contain one or two hetero-atoms selected from N and/or S and/or O;

anellated bi- and tricyclic partially hydrated carbocyclic ring systems with 8 to 18, preferably 16 ring atoms, and at least one aromatic ring;

anellated bi- and tricyclic partially hydrated heterocyclic ring systems with 8 to 18, preferably up to 16 ring atoms, and at least one aromatic ring, whereby 1 to 3 ring atoms can be selected from N and/or S and/or O;

$G^3$ is selected from

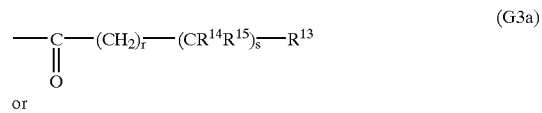 (G3a)

or

 (G3b)

whereby r and s as well as the substituents $R^{13}$, $R^{14}$ and $R^{15}$ can have the above meanings, or the grouping

can also be a nitrogen heterocycle bound over the nitrogen atom selected from saturated or unsaturated monocyclic, four to eight-heterocycles which, aside from the essential nitrogen atom, can optionally further contain one or two further hetero-atoms selected from N and/or S and/or O, or saturated or unsaturated bi- or tricyclic, anellated or bridged heterocycles with 8 to 18, preferably up to 16 ring atoms, which, aside from the essential nitrogen atom, can optionally contain one or two further hetero-atoms selected from N and/or S and/or O;

$G^4$ is selected from

 (G4a)

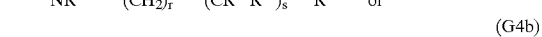 (G4b)

 (G4c)

 (G4d)

 (G4e)

 (G4f)

whereby r and s as well as the substituents $R^{13}$, $R^{14}$ and $R^{15}$ can have the above meanings and $R^{16}$ has the same meanings as $R^5$ but is selected independently thereof, $R^{17}$ is selected from trifluoromethyl, alkoxy, alkenyloxy with at least 3 carbon atoms; or benzyloxy; and Ar$^1$ and Ar$^2$ are selected independently from each other from phenyl, pyridyl or naphthyl;

G$^5$ has the meaning

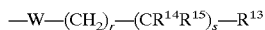

—W—(CH$_2$)$_r$—(CR$^{14}$R$^{15}$)$_s$—R$^{13}$ (G5a)

or

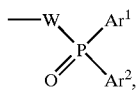

(G5b)

whereby r and s as well as the substitutents R$^{13}$, R$^{14}$, R$^{15}$, Ar$^1$ and Ar$^2$ can have the above meanings and W is O or S, whereby the ring systems =CR$^{13}$R$^{15}$, —NR$^{13}$R$^{15}$ and optionally ER$^{13}$, R$^{15}$ as well as aromatic ring systems in the substituents R$^1$, R$^2$, R$^4$, R$^5$, R$^6$, R$^{13}$, R$^{14}$, R$^{15}$, R$^{16}$, R$^{17}$, Ar$^1$ and Ar$^2$ can be substituted independently from each other by one to three of the same or different groups selected from halogen, cyano, alkyl, trifluoromethyl, cycloalkyl with at least 3 carbon atoms, phenyl, benzyl, hydroxy, hydroxyalkyl, alkoxy, alkoxy entirely or partially substituted by fluorine, benzyloxy, phenoxy, mercapto, alkylthio, carboxy, carboxyalkyl, carboxyalkenyl with at least 2 carbon atoms or alkoxycarbonyl with at least 2 carbon atoms, benzyl-oxycarbonyl, nitro, amino, monoalkylamino, dialkylamino and, for two adjacent residues on the aromatic ring, methylenedioxy, and whereby alkyl-, alkenyl- and cycloalkyl residues in the groups G$^1$ to G$^5$ can be substituted by one or two of the same or different groups selected from hydroxy, carboxy, alkoxycarbonyl with at least 2 carbon atoms, benzyloxycarbonyl, amino, monoalkylamino and dialkylamino, whereby G cannot signify the residue —CHR$^{14}$—R$^{13}$ or —C(OH)R$^{14}$—R$^{13}$ or =CR$^{13}$R$^{15}$ or —O—CHR$^{14}$—R$^{13}$ in the case when simultaneously R$^{13}$ is hydrogen, alkyl or phenyl optionally substituted by halogen, alkyl, hydroxy, alkoxy or trifluoromethyl R$^{14}$ and/or R$^{15}$ is pyridyl or phenyl optionally substituted with halogen, alkyl, hydroxy, alkoxy or trifluoromethyl, A is alkylene, optionally substituted ethenylene or butadienylene, D is alkylene and E is piperidine substituted in the 4-position;

the cis- and trans-isomers, E- and Z-isomers of the above defined compounds, especially in case that A is a cyclopropane ring or D contains one or more double bonds, including the enantiomers, diastereomers and other isomers of the above defined compounds as well as their racemic or non-racemic mixtures as well as the pure endo- and/or exo-isomers of the above defined compounds as well as their mixtures;

the respective tautomeric compounds;

and the acid addition salts of the above defined compounds including their hydrates and solvates.

According to a further embodiment of the invention, the new, pyridylalkane, pyridylalkene and pyridylalkine acid amide compounds correspond with respect to their substitutions formula (I)

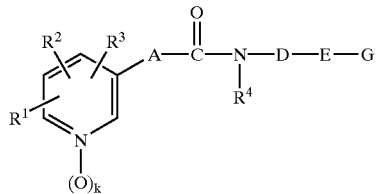

(I)

wherein

R$^1$ is selected from hydrogen, halogen, cyano, C$_1$–C$_6$-alkyl, C$_3$–C$_6$-alkenyl, C$_3$–C$_6$-alkinyl, trifluoromethyl, C$_3$–C$_8$-cycloalkyl, C$_1$–C$_6$-hydroxyalkyl, hydroxy, C$_1$–C$_6$-alkoxy, C$_3$–C$_6$-alkenyloxy, C$_3$–C$_6$-alkinyloxy, benzyloxy, C$_1$–C$_7$-alkanoyloxy, C$_2$–C$_7$-alkoxycarbonyloxy, C$_1$–C$_6$-alkylthio, C$_3$–C$_6$-alkenylthio, C$_3$–C$_6$-alkinylthio, C$_3$–C$_8$-cycloalkyloxy, C$_3$–C$_8$-cycloalkylthio, C$_2$–C$_7$-alkoxycarbonyl, aminocarbonyl, C$_2$–C$_7$-alkylaminocarbonyl, C$_3$–C$_{13}$-dialkylaminocarbonyl, carboxy, phenyl, phenoxy, phenylthio, pyridyloxy, pyridylthio, and NR$^5$R$^6$, wherein R$^5$ and R$^6$ are selected independently of each other from hydrogen, C$_1$–C$_6$-alkyl, C$_3$–C$_6$-alkenyl, C$_3$–C$_6$-alkinyl, benzyl and phenyl;

R$^2$ is selected from hydrogen, halogen, cyano, C$_1$–C$_6$-alkyl, trifluoromethyl, hydroxy, C$_1$–C$_6$-alkoxy, benzyloxy and C$_1$–C$_7$-alkanoyloxy; R$^1$ and R$^2$, if adjacent, optionally form a bridge selected from —(CH$_2$)$_4$— and —(CH=CH)$_2$— or —CH$_2$O—CR$^7$R$^8$—O—, wherein R$^7$ and R$^8$ are selected independently from each other from hydrogen and C$_1$–C$_6$-alkyl;

R$^3$ is selected from hydrogen, halogen, C$_1$–C$_6$-alkyl, trifluoromethyl and C$_1$–C$_6$-hydroxyalkyl;

R$^4$ is selected from hydrogen, C$_1$–C$_6$-alkyl, C$_3$–C$_6$-alkenyl, C$_3$–C$_6$-alkinyl, C$_3$–C$_6$-cycloalkyl, hydroxy, C$_1$–C$_6$-alkoxy and benzyloxy;

k is 0 or 1,

A is selected from
C$_1$–C$_6$-alkylene, optionally substituted one to threefold by C$_1$–C$_3$-alkyl, hydroxy, C$_1$–C$_3$-alkoxy, fluorine, or phenyl, C$_2$–C$_6$-alkylene, in which a methylene unit is isosterically replaced by O, S, NR$^9$, CO, SO or SO$_2$, whereby, with the exception of CO, the isosteric substitution cannot be adjacent to the amide group and R$^9$ is selected from hydrogen, C$_1$–C$_6$-alkyl, C$_3$–C$_6$-alkenyl, C$_3$–C$_6$-alkinyl, C$_1$–C$_6$-acyl or C$_1$–C$_6$-alkanesulfonyl, 1,2-cyclopropylene, C$_2$–C$_6$-Alkenylene, optionally substituted once to three-fold by C$_1$–C$_3$-alkyl, hydroxy, C$_1$–C$_3$-alkoxy, fluorine, cyano or phenyl, C$_4$–C$_6$-alkadienylene, optionally substituted once or twice by C$_1$–C$_3$-alkyl, fluorine, cyano or phenyl;

1,3,5-hexatrienylene, optionally substituted by C$_1$–C$_3$-alkyl, fluorine, cyano or phenyl, and ethinylene D is selected from C$_2$–C$_{10}$-alkylene, optionally substituted once or twice by C$_1$–C$_6$-alkyl, hydroxy, or C$_1$–C$_6$-alkoxy;

C$_4$–C$_{10}$-alkenylene, optionally substituted once or twice by C$_1$–C$_6$-alkyl, hydroxy, or C$_1$–C$_6$-alkoxy;

C$_4$–C$_{10}$-alkinylene, optionally substituted once or twice by C$_1$–C$_6$-alkyl, hydroxy, or C$_1$–C$_6$-alkoxy; and $C_2$–$C_{10}$-alkylene, $C_4$–$C_{10}$-alkenylene or $C_4$–$C_{10}$-alkinylene, in which one to three methylene units are isosterically replaced by O, S, $NR^{10}$, CO, SO or $SO_2$, whereby $R^{10}$ has the same meaning as $R^9$, but is selected independently thereof;

E is selected from

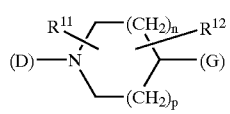 (E1)

and

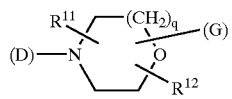 (E2)

whereby the heterocyclic ring can optionally have a double bond and n and p can be, independent of each other, 0, 1, 2 or 3 with the proviso that n+p≦4, wherein q is 1,2 or 3;

$R^{11}$ is selected from hydrogen, $C_1$–$C_6$-alkyl, hydroxy, hydroxymethyl, carboxy, or $C_2$ $C_7$-alkoxycarbonyl and $R^{12}$ is selected from hydrogen, $C_1$–$C_6$-alkyl or an oxo group adjacent to a nitrogen atom, $R^{11}$ and $R^{12}$ optionally together, form a $C_1$–$C_3$-alkylene bridge under formation of a bicyclic ring system;

G is selected from G1, G2, G3, G4 or G5, whereby $G^1$ is —$(CH_2)_r$—$(CR^{14}R^{15})_s$—$R^{13}$ (G1)

r is a number from 0 to 3, s is 0 or 1 and $R^{13}$ is selected from hydrogen, $C_1$–$C_6$-alkyl, $C_3$–$C_6$-alkenyl, $C_3$–$C_6$-alkinyl, $C_3$–$C_8$-cycloalkyl;

saturated or unsaturated, four to seven-membered heterocycles, which can contain one or two heteroatoms selected from N and/or S and/or O;

benzyl, phenyl;

monocyclic aromatic five or six-membered heterocycles, which can contain one to three heteroatoms selected from N and/or S and/or O and are either bound directly or over a methylene group, anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group, anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic ring or a hydrated ring and either directly or over a methylene group, $R^{14}$ has the same meaning as $R^{13}$, but is selected independently thereof;

$R^{15}$ is selected from hydrogen, hydroxy, methyl, benzyl, phenyl; monocyclic aromatic five or six-membered heterocycles, which can contain one to three heteroatoms selected from N and/or S and/or O and are either bound directly or over a methylene group, anellated bi- and tricyclic aromatic or partially hydrated carbocyclic ring systems with 8 to 16 ring atoms and at least one aromatic ring wherein the linkage can occur either over an aromatic or a hydrated ring and either directly or over a methylene group, anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic ring or a hydrated ring and either directly or over a methylene group, $G^2$ is

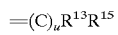 (G2), whereby $R^{13}$ and $R^{15}$ have the above meaning and u represents the number 0 to 1, or signifies the residue

which is bound by means of a double bond to E in the case that u=1, or can signify a ring system bound over the carbon atom.selected from $C_3$–$C_8$-cycloalkyl;

saturated, four to seven-membered heterocycles which can contain one or two hetero-atoms selected from N and/or S and/or O;

anellated bi- and tricyclic partially hydrated carboxocyclic ring system with 8 to 16 ring atoms and at least one aromatic ring;

anellated bi- and tricyclic partially hydrated heterocyclic ring systems with 8 to 16 ring atoms and at least one aromatic ring, wherein one to three ring atoms can be selected from N and/or S and/or O;

or, in the case that u=0, the two germinal substituents $R^{13}$ and $R^{15}$ can form a spirocycle together with the bonding atom of the ring E selected from cycloalkyl, saturated, four to seven-membered heterocycles which can contain one or two hetero-atoms selected from N and/or S and/or O;

anellated bi- and tricyclic partially hydrated carbocyclic ring systems with 8 to 16 ring atoms and at least one aromatic ring;

anellated bi- and tricyclic partially hydrated heterocyclic ring systems with 8 to 16 ring atoms and at least one aromatic ring, whereby 1 to 3 ring atoms can be selected from N and/or S and/or O;

$G^3$ is selected from

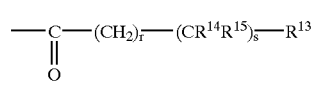 (G3a)

or

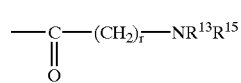 (G3b)

whereby r and s as well as the substituents $R^{13}$, $R^{14}$ and $R^{15}$ can have the above meanings, or the grouping

can also be a nitrogen heterocycle bound over the nitrogen atom selected from saturated or unsaturated monocyclic, four to eight-membered heterocycles which, aside from the essential nitrogen atom, can optionally further contain one or two further heteroatoms selected from N and/or S and/or O, or saturated or unsaturated bi- or tricyclic, anellated or bridged heterocycles with 8 to 16 ring atoms, which, aside from the essential nitrogen atom, can optionally contain one or two further hetero-atoms selected from N and/or S and/or O;

$G^4$ is selected from

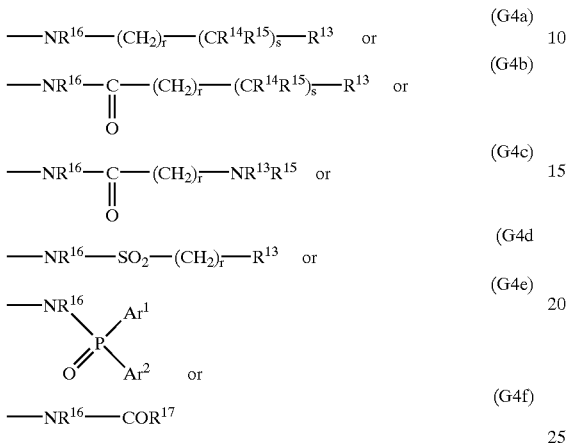

whereby r and s as well as the substituents $R^{13}$, $R^{14}$ and $R^{15}$ can have the above meanings and $R^{16}$ has the same meanings as $R^5$, but is selected independently thereof, $R^{17}$ is selected from trifluoromethyl, $C_1$–$C_6$-alkoxy, $C_3$–$C_6$-alkenyloxy and benzyoxy; and $Ar^1$ and $Ar^2$, are selected independently from each other from phenyl, pyridyl or naphthyl;

$G^5$ has the meaning

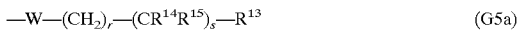

or

whereby r and s as well as the substitutents $R^{13}$, $R^{14}$, $R^{15}$, $Ar^1$ and $Ar^2$ can have the above meanings and W is O or S, whereby the ring systems $=CR^{13}R^{15}$, $-NR^{13}R^{15}$ and optionally $ER^{13}$, $R^{15}$ as well as aromatic ring systems in the substituents $R^1$, $R^2$, $R^4$, $R^5$, $R^6$, $R^{13}$, $R^{14}$, $R^{15}$, $R^{16}$, $R^{17}$, $Ar^1$ and $Ar^2$ can be substituted independently from each other by one to three of the same or different groups selected from halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, mono-$C_1$–$C_6$-alkylamino, di-($C_1$–$C_6$-alkyl)amino and, for two adjacent residues on the aromatic ring, methylenedioxy, and whereby alkyl-, alkenyl- and cycloalkyl residues in the groups $G^1$ to $G^5$ can be substituted by one or two of the same or different groups selected from hydroxy, carboxy, $C_2$–$C_7$-alkoxycarbonyl, benzyloxycarbonyl, amino, mono-$C_1$–$C_6$-alkylamino and di-($C_1$–$C_6$-alkyl)amino, whereby G cannot signify the residue $-CHR^{14}-R^{13}$ or $-C(OH)R^{14}-R^{13}$ or $=CR^{13}R^{15}$ or $-O-CHR^{14}-R^{13}$ in the case when simultaneously $R^{13}$ is hydrogen, alkyl or phenyl (optionally substituted by halogen, alkyl, hydroxy, alkoxy or trifluoromethyl)

$R^{14}$ and/or $R^{15}$ is pyridyl or phenyl optionally substituted with halogen, alkyl, hydroxy, alkoxy or trifluoromethyl, A is alkylene, optionally substituted ethenylene or butadienylene, D is alkylene and E is piperidine substituted in the 4-position;

the cis- and trans-isomers, E- and Z-isomers of the respective above defined compounds, especially in case that A is a cyclopropane ring or D contains one or more double bonds, including the enantiomers, diastereomers and other isomers of the respective above defined compounds as well as their racemic or non-racemic mixtures, the pure endo- and exo-isomers of these compounds as well as their mixtures;

their respective tautomers compounds as well as the corresponding acid addition salts including their hydrates and solvates.

According to a preferred embodiment, the invention relates to compounds of the general Formula (I),

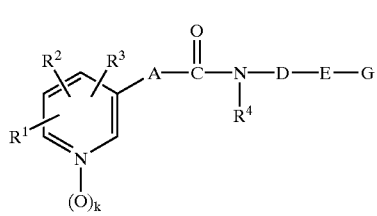

wherein $R^1$ is selected from hydrogen, halogen, cyano, $C_1$–$C_6$-alkyl, trifluoromethyl, $C_3$–$C_8$-cycloalkyl, $C_1$–$C$-hydroxyalkyl, hydroxy, $C_1$–$C_4$-alkoxy, benzyloxy, $C_1$–$C_4$-alkylthio, $C_1$–$C_5$-alkanoyloxy, $C_1$–$C_4$-alkylthio, $C_2$–$C_5$-alkoxycarbonyl, aminocarbonyl, $C_2$–$C_5$-alkylaminocarbonyl, $C_3$–$C_9$-dialkylaminocarbonyl, carboxy, phenyl, phenoxy, phenylthio, pyridyloxy, and $NR^5R^6$, whereby $R^5$ and $R^6$ are selected independently from each other from hydrogen and $C_1$–$C_6$-alkyl;

$R^2$ is selected from hydrogen, halogen, cyano, $C_1$–$C_6$-alkyl, trifluoromethyl, hydroxy, $C_1$–$C_4$-alkoxy;

$R^3$ is selected from hydrogen, halogen and $C_1$–$C_6$-alkyl;

$R^4$ is selected from hydrogen, $C_1$–$C_6$-alkyl, $C_3$–$C_6$-alkenyl, $C_3$–$C_6$-cycloalkyl, hydroxy, $C_1$–$C_6$-alkoxy and benzyloxy;

k is 0 or 1,

A is selected from $C_2$–$C_6$-alkylene, optionally substituted one to three-fold by $C_1$–$C_3$-alkyl, hydroxy, fluorine, or phenyl, $C_2$–$C_6$-alkylene, in which a methylene unit is isosterically replaced by O, S, $NR^9$, CO or $SO_2$, whereby, with the exception of CO, the isosteric substitution cannot be adjacent to the amide group and $R^9$ is selected from hydrogen, $C_1$–$C_6$-alkyl, $C_1$–$C_6$-acyl or methanesulfonyl;

1,2-cyclopropylene, $C_2$–$C_6$-Alkenylene, optionally substituted once to three-fold by $C_1$–$C_3$-alkyl, hydroxy, fluorine, cyano or phenyl, $C_4$–$C_6$-alkadienylene, optionally substituted once to twice by $C_1$–$C_3$-alkyl, fluorine, cyano or phenyl;

1,3,5-hexatrienylene, optionally substituted by $C_1$–$C_3$-alkyl, fluorine, cyano, and ethinylene D is selected from $C_2$–$C_{10}$-alkylene, optionally substituted once or twice by $C_1$–$C_3$-alkyl or hydroxy;

$C_4$–$C_{10}$-alkenylene, optionally substituted once or twice by $C_1$–$C_3$-alkyl or hydroxy;

$C_4$–$C_{10}$-alkinylene, optionally substituted once or twice by $C_1$–$C_3$-alkyl or hydroxy; as well as $C_2$–$C_{10}$-alkylene, $C_4$–$C_{10}$-alkenylene or $C_4$–$C_{10}$-alkinylene, in which one to three methylene units are isosterically replaced by O, S, $NR^{10}$, CO, SO or $SO_2$, whereby $R^{10}$ has the same meaning as $R^9$, but is selected independently thereof;

E is selected from

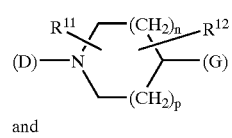

(E1)

and

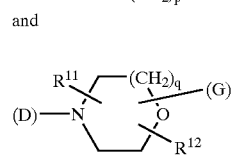

(E2)

whereby the heterocyclic ring can optionally have a double bond and n and p can be, independent of each other, 0, 1, 2 or 3 with the proviso that n+p≦4, and q is one or 2;

$R^{11}$ is selected from hydrogen, $C_1$–$C_3$-alkyl, hydroxy, hydroxymethyl, carboxy, or $C_2$–$C_7$-alkoxycarbonyl and $R^{12}$ is selected from hydrogen or an oxo group adjacent to a nitrogen atom or $R^{11}$ and $R^{12}$, optionally together, form a $C_1$–$C_3$-alkylene bridge under formation of a bicyclic ring system;

G is selected from G1, G2, G3, G4 or G5, whereby $G^1$ is

—(CH$_2$)$_r$—(CR$^{14}$R$^{15}$)$_s$—R$^{13}$  (G1)

whereby r signifies the number 0 to 2, s signifies the number 0 or 1 and $R^{13}$ is selected from hydrogen, $C_1$–$C_6$-alkyl, $C_3$–$C_6$-alkenyl, $C_3$–$C_6$-alkinyl, $C_3$–$C_8$-cycloalkyl;

benzyl, phenyl;

monocyclic aromatic five or six-membered heterocycles, which can contain one to three heteroatoms selected from N and/or S and/or O and are either bound directly or over a methylene group, anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group, anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic ring or a hydrated ring and either directly or over a methylene group, $R^{14}$ has the same meaning as $R^{13}$, but is selected independently thereof;

$R^{15}$ is selected from hydrogen, hydroxy, methyl, benzyl, phenyl; monocyclic aromatic five or six-membered heterocycles, which can contain one to three heteroatoms selected from N and/or S and/or C and are either bound directly or over a methylene group, anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group, anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic ring or a hydrated ring and either directly or over a methylene group;

$G^2$ is

=(C)$_u$R$^{13}$R$^{15}$  (G2), whereby $R^{13}$ and $R^{15}$ have the above meanings and u is the number 0 or 1, or the grouping

=CR$^{13}$R$^{15}$ which is bound by means of a double bond to E in the case that u=1 can also be a ring system bound over the carbon atom selected from anellated bi- and tricyclic partially hydrated carboxocyclic ring system with 8 to 16 ring atoms, and at least one aromatic ring;

anellated bi- and tricyclic partially hydrated heterocyclic ring systems with 8 to 16 ring atoms, and at least one aromatic ring, wherein one to three ring atoms can be selected from N and/or S and/or O;

or, in the case that u=0, the two germinal substituents $R^{13}$ and $R^{15}$ can form a spirocycle together with the bonding atom of the ring E selected from saturated, four to seven-membered heterocycles which can contain one or two hetero-atoms selected from N and/or S and/or O;

anellated bi- and tricyclic partially hydrated carbocyclic ring systems with 8 to 16 ring atoms, and at least one aromatic ring;

anellated bi- and tricyclic partially hydrated heterocyclic ring systems with 8 to 16 ring atoms, and at least one aromatic ring, whereby 1 to 3 ring atoms can be selected from N and/or S and/or O;

$G^3$ is selected from

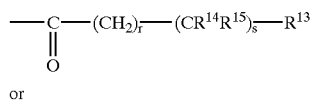 (G3a)

or

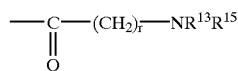 (G3b)

whereby r and s as well as the substituents $R^{13}$, $R^{14}$ and $R^{15}$ can have the above meanings, or the grouping

can also be nitrogen heterocycle bound over the nitrogen atom selected from saturated or unsaturated monocyclic, four to eight-heterocycles which, aside from the essential nitrogen atom, can optionally further contain one or two further hetero-atoms selected from N and/or S and/or O, or saturated or unsaturated bi- or tricyclic, anellated or bridged heterocycles with 8 to 16 ring atoms, which, aside from the essential nitrogen atom, can optionally contain one or two further heteroatoms selected from N and/or S and/or O;

$G^4$ is selected from

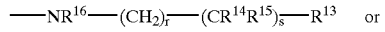 (G4a)

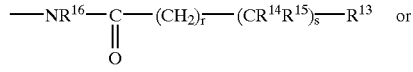 (G4b)

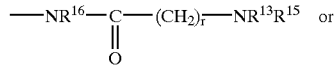 (G4c)

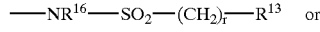 (G4d)

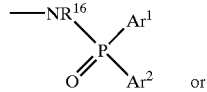 (G4e)

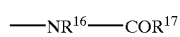 (G4f)

whereby r and s as well as the substituents $R^{13}$, $R^{14}$ and $R^{15}$ and optionally the group —$NR^{13}R^{15}$ can have the above meanings and $R^{16}$ is selected from hydrogen, $C_1-C_6$-alkyl, $C_3-C_6$-alkenyl, $C_3-C_6$-alkinyl, benzyl and phenyl;

$R^{17}$ is selected from trifluoromethyl, $C_1-C_6$-alkoxy, $C_3-C_6$-alkenyloxy and benzyloxy; and whereby $Ar^1$ and $Ar^2{}_1$ are selected independently from each other from phenyl, pyridyl or naphthyl;

$G^5$ has the meaning

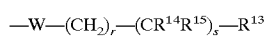 (G5a)

or

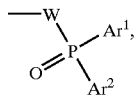 (G5b)

whereby r and s as well as the substitutents $R^{13}$, $R^{14}$, $R^{15}$, $Ar^1$ and $Ar^2$ can have the above meanings and W is O or S, whereby the ring systems =$CR^{13}R^{15}$, —$NR^{13}R^{15}$ and optionally $ER^{13}$, $R^{15}$ as well as aromatic ring systems in the substituents $R^1$, $R^4$, $R^5$, $R^{13}$, $R^{14}$, $R^{15}$, $R^{16}$, $R^{17}$, $Ar^1$ and $Ar^2$ can be substituted independently from each other by one to three of the same or different groups selected from halogen, cyano, $C_1-C_6$-alkyl, trifluoromethyl, $C_3-C_8$-cycloalkyl, phenyl, benzyl, hydroxy, $C_1-C_6$-hydroxyalkyl, $C_1-C_6$-alkoxy, $C_1-C_6$-alkoxy entirely or partially substituted by fluorine, benzyloxy, phenoxy, mercapto, $C_1-C_6$-alkylthio, carboxy, $C_2-C_7$-carboxyalkyl, $C_2-C_7$-carboxyalkenyl, $C_2-C_7$-alkoxycarbonyl, benzyloxycarbonyl, nitro, amino, mono-$C_1-C_6$-alkylamino, di-($C_1-C_6$-alkyl) amino and, for two adjacent residues on the aromatic ring, methylendioxy, and whereby alkyl-, alkenyl- and cycloalkyl residues in the groups $G^1$ to $G^5$ can be substituted by one or two of the same or different groups selected from hydroxy, carboxy, $C_2-C_7$-alkoxycarbonyl benzyloxycarbonyl, amino, mono-$C_1-C_6$-alkylamino and di-($C_1-C_6$-alkyl)amino;

the salts, isomers and tautomers of the above defined compounds as well as their mixtures.

According to a particularly preferred embodiment, the invention relates to compounds of the general Formula (1)

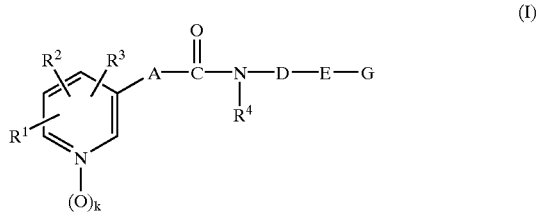 (I)

wherein the substituents have the following meanings:

$R^1$ is selected from hydrogen, halogen, cyano, methyl, ethyl, trifluoromethyl, hydroxy, $C_1-C_4$-alkoxy, benzyloxy, $C_1-C_5$-alkanoyloxy, methylthio, ethylthio, methoxycarbonyl, tert-butoxycarbonyl aminocarbonyl, carboxy, phenoxy, and phenylthio;

$R^2$ is selected from hydrogen, halogen, trifluoromethyl, hydroxy;

$R^3$ is selected from hydrogen, halogen;

$R^4$ is selected from hydrogen, $C_1-C_3$-alkyl, allyl, hydroxy and $C_1-C_3$-alkoxy;

k is 0 or 1,

A is selected from $C_2-C_6$-alkylene, optionally substituted once or twice by $C_1-C_3$-alkyl, hydroxy or fluorine;
$C_2-C_6$-alkylene, in which a methylene unit is isosterically replaced by O, S. CO, or $SO_2$, whereby, with the exception of CO, the isosteric substitution cannot be adjacent to the amide group,
$C_2-C_6$-alkenylene, optionally substituted once or twice by $C_1-C_3$ alkyl, hydroxy and/or fluorine;

C$_4$–C$_6$-alkadienylene, optionally substituted by C$_1$–C$_3$-alkyl or one or two fluorine atoms;

1,3,5-hexatrienylene, optionally substituted by fluorine;

D is selected from C$_2$–C$_8$-alkylene, optionally substituted once or twice by methyl or hydroxy;
C$_4$–C$_8$-alkenylene, optionally substituted once or twice by methyl or hydroxy;
C$_4$–C$_8$-alkinylene, optionally substituted once or twice by methyl or hydroxy; and
C$_2$–C$_8$-alkylene, C$_4$–C$_8$-alkenylene or C$_4$–C$_8$-alkinylene, in which one to three methylene units are isosterically replaced by O, S, NH, N(CH$_3$) N(COCH$_3$), N(SO$_2$CH$_3$), CO, SO or SO$_2$;

E is selected from

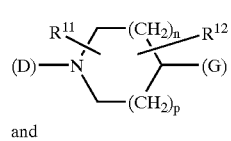
(E1)

and

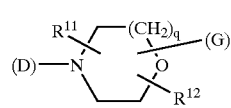
(E2)

whereby the heterocyclic ring can optionally have a double bond and n and p can be, independent of each other, the number 0, 1, 2 or 3 with the proviso that n+p≦3 and q is 1 or 2;

R$^{11}$ is selected from hydrogen, C$_1$–C$_3$-alkyl, hydroxymethyl, or carboxy, and R$^{12}$ is selected from hydrogen or an oxo group adjacent to a nitrogen atom G is selected from G1, G2, G3, G4 or G5, whereby G$^1$ is

(G1)

r is 0 to 2 as well as s is 0 or 1,

R$^{13}$ is selected from hydrogen, C$_1$–C$_6$-alkyl, C$_3$–C$_8$-cycloalkyl; benzyl, phenyl; benzocyclobutyl, indanyl, indenyl, oxoindanyl, naphthyl, dihydronaphthyl, tetrahydronaphthyl, biphenylenyl, fluorenyl, oxofluorenyl, anthryl, dihydroanthryl, oxodihydroanthryl, dioxodihydroanthryl, phenanthryl, dibenzocycloheptenyl, dihydrodibenzocycloheptenyl, oxodihydrodibenzocycloheptenyl, dihydrodibenzocyclooctenyl, or tetrahydrodibenzocyclooctenyl bound directly or over a methylene group;

furyl, thienyl, pyrrolyl, oxazolyl, isoxazolyl, thiazolyl, isothiazolyl, pyrazolyl, imidazolyl, oxadiazolyl, thiadiazolyl, triazolyl, pyridyl, pyrazinyl, pyridazinyl, pyrimidinyl, triazinyl, benzofuryl, dihydrobenzofurl, benzothienyl, dihydrobenzothienyl, indolyl, indolinyl, isoindolinyl, oxoindolinyl, dioxoindolinyl, benzooxazolyl, oxobenzooxazolinyl, benzoisoxazolyl, oxobenzoisoxazolinyl, benzothiazolyl, oxobenzthiazolinyl, benzoisothiazolyl, oxobenzoisothiazolinyl, benzoimidazolyl, oxobenzoimidazolinyl, indazolyl, oxoindazolinyl, benzofurazanyl, benzothiadiazolyl, benzotriazolyl, oxazolopyridyl, oxodihydrooxazolopyridyl, thiazolopyridyl, oxodihydrothiazolopyridyl, isothiazolopyridyl, imidazopyridyl, oxodihydroimidazopyridyl, pyrazolopyridyl, oxodihydropyrazolopyridyl, thienopyrimidinyl, chromanyl, chromanonyl, benzopyranyl, chromonyl, quinolyl, isoquinolinoyl, dihydroquinolinyl, oxodihydroquinolinyl, tetrahydroquinolinyl, oxotetrahydroquinolinyl, bernzodioxanyl, quinoxalinyl, quinazolinyl, naphthyridinyl, carbazolyl, tetrahydrocarbazolyl, pyridoindolyl, acridinyl, oxodihydroacridinyl, phenanthridinyl, oxodihydrophenanthridinyl, dibenzoisoquinolinyl, oxodihydrodibenzoisoquinolinyl, phenothiazinyl, dihydrodibenzooxepinyl, oxodihydrodibenzooxepinyl, benzocycloheptathienyl, oxobenzocycloheptathienyl, dihydrothienobenzothiepinyl, oxodihydrothienobenzothiepinyl, dihydrodibenzothiepinyl, oxodihydrodibenzothiepinyl, octahydrodibenzothiepinyl, dibenzoazepinyl, dihydrodibenzoazepinyl, oxodihydrodibenzoazepinyl, octahydrodibenzoazepinyl, benzocycloheptapyridyl, oxobenzocycloheptapyridyl, pyridobenzoazepinyl, dihydropyridobenzoazepinyl, oxodihydropyridobenzoazepinyl, dihydropyridobenzodiazepinyl, oxodihydropyridobenzodiazepinyl, dihydrodibenzooxazepinyl, dihydropyridobenzooxepinyl, dihydropyridobenzooxazepinyl, oxodihydropyridobenzooxazepinyl, dihydrodibenzothiazepinyl, oxodihydrodibenzothiazepinyl, dihydropyridobenzothiazepinyl or oxodihydropyridobenzothiazepinyl bound directly or over a methylene group;

R$^{14}$ is synonymous with R$^{13}$ but is selected independent thereof;

R$^{15}$ is selected from hydrogen, hydroxy, methyl, benzyl, phenyl; indanyl, indenyl, naphthyl, tetrahydronaphthyl, furyl, thienyl, pyrrolyl, oxazolyl, isoxazolyl, thiazolyl, isothiazolyl, pyrazolyl, imidazolyl, oxadiazolyl, thiadiazolyl, triazolyl, pyridyl, pyrazinyl, pyridazinyl, pyrimidinyl, triazinyl, benzofuryl, benzothienyl, indolyl, indolinyl, benzooxazolyl, benzothiazolyl, benzoimidazolyl, chromanyl, quinolinyl or tetrahydroquinolinyl bound directly or over a methylene group;

G$^2$ is

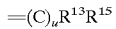
(G2)

whereby R$^{13}$ and R$^{15}$ have the above meaning and u is 0 or 1, or the grouping

bound to E by means of a double bond in the case that V=1 can also be a ring system bound over the carbon atom selected from indanyl, tetrahydronaphthyl, fluoroenyl, dihydroanthryl, tetrahydrobenzocycloheptenyl, dibenzocycloheptenyl, dihydrodibenzocycloheptenyl; tetrahydroquinolinyl, dihydroacridinyl, dihydrodibenzooxepinyl, dihydrothienobenzothiepinyl, dihydrodibenzothiepinyl, dibenzoazepinyl, dihydrodibenzoazepinyl, benzocycloheptapyridinyl, dihydrobenzocycloheptapyridinyl, pyridobenzoazepinyl, dihydropyridobenzoazepinyl; or the two germinal substituents $R^{13}$ and $R^{15}$ can, in the case that u=0, form a spirocycle $ER^{13}R^{15}$ together with the ring E selected from dioxaazaspirononane, dithioazaspirononane, oxadiazaspirononane, oxadiazasprionanandione, triazaspirononane, triazaspirononanandione, diazaspriodecanone, diazaspirodecandione, dioxaazaspirodecane, dithiaazaspirodecane, oxadiazaspirodecane, triazaspriodecane, triazaspirodecanone, triazaspirodecandione, dioxaazaspiroundecane, dithiaazaspriundecane, oxadiazaspiroundecanone, triazaspiroundecanone, spiro[benzodioxol-pyrrolidine], spiro[benzodioxol-piperidine], spiro[benzodioxin-piperidine] or spiro[dihydrobenzooxazin-piperdine];

G3 is selected from

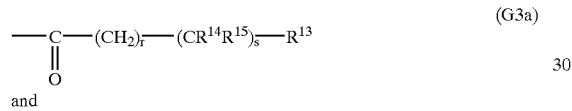

(G3a)

and

(G3b)

whereby r and s as well as the sustituents $R^{13}$, $R^{14}$ and $R^{15}$ can have the above meanings or the grouping

represents the ring bound over the nitrogen atom of the following ring systems;

pyrrolidine, piperidine, hexahydroazepine, octahydroazocine, piperazine, hexahydrodiazepine, morpholine, hexahydrooxazepine, thiomorpholine, thiomorpholin-1,1-dioxide, 2-azabicyclo[2.2.1] heptane, 7-azabicyclo[2.2.1]heptane, 2,5-diazabicyclo[2.2.1]heptane, 2-azabicyclo[2.2.2] octane, 8-azabicyclo[3.2.1]octane, 2,5-diazabicyclo [2.2.2]octane, indoline, isoindoline, (1H)-dihydroquinoline, (1H)-tetrahydroquinoline, (2H)-tetrahydroisoquinoline, (4H)-dihydrobenzooxazine, (4H)-dihydrobenzothiazine, (1H)-tetrahydrobenzo[b]azepine, (1H)-tetrahydrobenzo[c]azepine, (1H)-tetrahydrobenzo[d]azepine, (5H)-tetrahydrobenzo[b]oxazepine, (5H)-tetrahydrobenzo[b]thiazepine, 1,2,3,4-tetrahydro-9H-pyrido[3,4-b]indole, carbazole, (10H)-dihydroacridine, (10H)-dihydrophenanthridine, 1,2,3,4-tetrahydroacridanone, (10H)-phenoxazine, (10H)-phenothiazine, (5H)-dibenzoazepine, (5H)-dihydrodibenzoazepine, (5H)-octahydrodibenzoazepine, dihydrobenzo[d,e]isoquinoline, (5H)-dihydrodibenzodiazepine, (5H)-benzo[b]pyrido[f]azepine, (5H)-dihydrobenzo[b]pyrido[f]azepine, (11H)-dihydrodibenzo[b,e]oxazepine, (11H)-dihydrodibenzo[b,e]thiazepine, (10H)-dihydrodibenzo[b,f]oxazepine, (10)-dihydrodibenzo-[b,f]thiazepine, (5)-tetrahydrodibenzoazocine, (11H)-dihydrobenzo[e]pyrido[b]-1,4-diazepin-6-one or (11H)-dihydrobenzo[b]pyrido[e]-1,4-diazepin-5-one;

$G^4$ is selected from

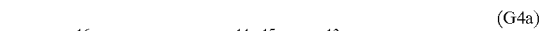

(G4a)

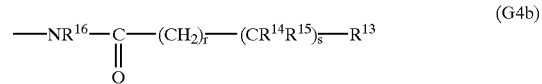

(G4b)

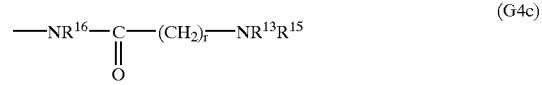

(G4c)

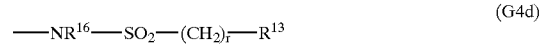

(G4d)

(G4e)

(G4f)

whereby r and s as well as the substituents $R^{13}$, $R^{14}$, $R^{15}$ and optionally the grouping —$NR^{13}R^{15}$ can have the above meanings;

$R^{16}$ is selected from hydrogen, $C_1$–$C_6$-alkyl, benzyl and phenyl;

$R^{17}$ is selected from Trifluoromethyl, $C_1$–$C_6$-alkoxy, and benzyloxy, and $Ar^1$ and $Ar^2$ are selected independent from each other from phenyl, pyridyl or naphthyl;

$G^5$ is

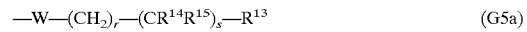

(G5a)

or

(G5b)

whereby r and s as well as the substituents $R^{13}$, $R^{14}$, $R^{15}$, $Ar^1$ and $Ar^2$ can have the above meanings, and W is O, and the rings systems =$CR^{13}R^{15}$, —$NR^{13}R^{15}$ and optionally $ER^{13}$, $R^{15}$ as well as aromatic ring systems in the substituents $R^1$, $R^{13}$, $R^{14}$, $R^{15}$, $R^{16}$, $R^{17}$, $Ar^1$ and $Ar^2$ can be substituted independently from each other by one to three of the same or different groups selected from halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, mono-$C_1$–$C_6$-alkylamino, di-($C_1$–$C_6$-alkyl)amino and, for two adjacent residues on the aromatic ring, methylenedioxy, and whereby alkyl-, alkenyl- and cycloalkyl residues in the groups $G^1$ to $G^5$ can be substituted by one or two of the same or different groups selected from hydroxy, carboxy, $C_2$–$C_7$-alkoxycarbonyl, benzyloxycarbonyl, amino, mono-$C_1$–$C_6$-alkylamino and di-($C_1$–$C_6$-alkyl)-amino; the salts, isomers and tautomers of the above defined compounds as well as optionally their mixtures.

The invention especially relates to compounds of the general formula (I),

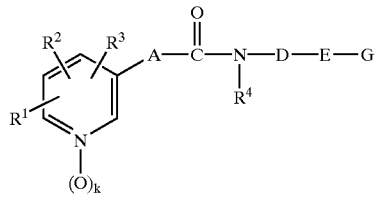

according to claim 1, 2, 3 or 4, wherein the substituents have the following meanings:

$R^1$ is selected from hydrogen, fluorine, chlorine, bromine, methyl, ethyl, trifluoromethyl, hydroxy, $C_1$–$C_4$-alkoxy, methylthio, ethylthio, carboxy and phenoxy;

$R^2$ is selected from hydrogen, chlorine and methyl;

$R^3$ is hydrogen;

$R^4$ is selected from hydrogen, $C_1$–$C_3$-alkyl and hydroxy, k is 0

A is selected from $C_2$–$C_6$-alkylene, which is optionally substituted once or twice by hydroxy or fluorine;
  $C_2$–$C_6$-alkylene, wherein a methylene unit is isosterically replaced by O, S or CO, whereby, with the exception of CO, the isosteric substitution cannot be adjacent to the amide group;
  $C_2$–$C_6$-alkenylene which is optionally substituted by $C_1$–$C_3$-alkyl and/or fluorine;
  $C_4$–$C_6$-alkadienylene;

D is selected from $C_4$–$C_8$-alkylene which is optionally substituted by methyl or hydroxy;
  $C_4$–$C_8$-alkenylene, which is optionally substituted by hydroxy;
  $C_4$–$C_8$-alkinylene, which is optionally substituted by hydroxy;
  $C_4$–$C_8$-alkylene, $C_4$–$C_8$-alkenylene, $C_4$–$C_8$-alkinylene wherein a methylene unit is respectively isosterically replaced by O, NH, N(CH$_3$), CO or SO$_2$ or an ethylene group is isosterically replaced by a group NH—CO and/or CO—NH or a propylene group is isosterically replaced by a group NH—CO—O and/or O—CO—NH;

E is selected from pyrrolidine, piperidine, hexahydroazepine or morpholine, wherein the ring can be optionally substituted by a methyene group and/or by an oxo group adjacent to a nitrogen atom;

G is selected from methoxycarbonylamino, ethoxycarbonylamino tert-butoxycarbonylamino, benzyloxycarbonylamino, trifluoroacetylamino, diphenylphosphinoylamino, diphenylphosphinoyloxy, diphenylmethyloxy, or a group

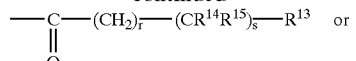

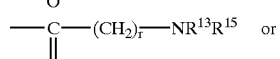

-continued

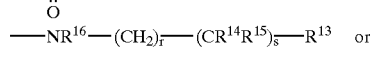

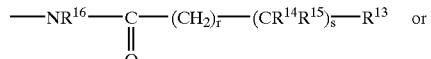

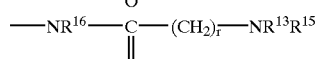

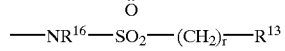

whereby
r is 0 or 1, and
s is 0 or 1, as well as
u is 0 or 1, $R^{13}$ is selected from hydrogen, methyl, benzyl, phenyl;
  indanyl, indenyl, oxoindanyl, naphthyl, tetrahydronaphthyl, fluorenyl, anthryl, phenanthryl, dibenzocycloheptenyl, dihydrodibenzocycloheptenyl or oxodihydrodibenzocycloheptenyl;
  thienyl, thiazolyl, imidazolyl, oxadiazolyl, thiadiazolyl, triazolyl, pyridyl, pyrazinyl, pyridazinyl, pyrimidinyl, benzofuryl, benzothienyl, indolyl, indolinyl, isoindolinyl, oxoindolinyl, dioxoindolinyl, benzooxazolyl, oxobenzooxazolinyl, benzoisoxazolyl, oxobenzoisoxazolinyl, benzothiazolyl, oxobenzothiazolinyl, benzoisothiazolyl, oxobenzoisothiazolinyl, benzoimidazolyl, oxobenzoimidazolinyl, benzotriazolyl, oxazolopyridyl, oxodihydrooxazolopyridyl, thiazolopyridyl, oxodihydrothiazolopyridyl, imidazopyridyl, oxodihydroimidazopyridyl, quinolyl, isochinolinyl, dihydroquinolinyl, oxodihydroquinolinyl, tetrahydroquinolinyl, oxotetrahydroquirclinyl, carbazolyl, tetrahydrocarbazolyl, pyridoindolyl, acridinyl, oxodihydroacridinyl, phenanthridinyl, dihydrophenanthridinyl, oxodihydrophenanthridinyl, dihydrobenzoisoquinolinyl, oxodihydrobenzoisoquinolinyl, phenothiazinyl, dihydrodibenzooxepinyl, benzocycloheptathienyl, dihydrothienobenzothiepinyl, dihydrodibenzothiepinyl, dibenzoazepinyl, dihydrodibenzoazepinyl, oxodihydrodibenzoazepinyl, benzocycloheptapyridyl, oxodihydrobenzocycloheptapyridyl, pyridobenzoazepinyl, dihydropyridobenzoazepinyl, oxodihydropyridobenzoazepinyl, dihydropyridobenzodiazepinyl, oxodihydropyridobenzodiazepinyl, dihydrodibenzooxazepinyl, dihydropyridobenzooxazepinyl, dihydrodibenzothiazepinyl or dihydropyridobenzothiazepinyl;

$R^{14}$ is selected from hydrogen, methyl, benzyl, phenyl;

$R^{15}$ is selected from hydrogen, hydroxy, methyl, benzyl, phenyl, indanyl, inaenyl, naphthyl, tetrahydronaphthyl, furyl, thienyl, pyridyl, pyrazinyl, pyridazinyl, pyrimidinyl, benzofuryl, benzothienyl, indolyl, indolinyl, benzoxazolyl, benzothiazolyl, benzimidazolyl, quinolinyl or tetrahydroquinolinyl;

R[16] is selected from hydrogen, $C_1$–$C_4$-alkyl, benzyl and phenyl;

Ar[1] and Ar[2] are selected independent from each other from phenyl, pyridyl or naphthyl; and the grouping =(C)$_u$R[13]R[15] is selected from indanyl, tetrahydronaphthyl, fluorenyl, tetrahydrobenzocycloheptenyl, dibenzocycloheptenyl, dihydrodibenzocycloheptenyl;

tetrahydroquinolinyl, dihydrodibenzooxepinyl, dihydrothienobenzothiepinyl, dihydrodibenzothiepinyl, dibenzoazepinyl, dihydrodibenzoazepinyl, benzocycloheptapyridinyl, dihydrobenzocycloheptapyridinyl pyridobenzoazepinyl, dihydropyridobenzoazepinyl;

and the grouping ER[13], R[15] represents a spirocycle selected from dioxaazaspirodecane, dithiaazaspirodecane, diazaspirodecanone, diazaspirodecandione, triazaspirodecanone, triazaspiro-decandione, dioxaazaspiroundecane, dithiaazaspiroundecane, oxadiazaspiroundecanone, triazaspiroundecanone, spiro[benzo-dioxol-pyrrolidin], spiro[benzodioxol-piperidine], spiro-[benzodioxin-piperidine], spiro [dihydrobenzoxazin-piperi-dine];

and whereby the grouping —NR[13]R[15] represents a ring of heterocycle bound over the nitrogen atom selected from the following: piperidine, hexahydroazepine, piperazine hexahydrodiazepine, morpholine, thiomorpholine, indoline, isoindoline, (1H)-dihydroquinoline, (1H)-tetrahydroquinoline, (2H)-tetrahydroisoquinoline, (4H)-dihydrobenzooxazine, (4H)-dihydrobenzothiazine, (1H)-tetrahydrobenzo[b]azepine, (1H)-tetrahydrobenzo[c]azepine, (1H)-tetrahydrobenzo[d]azepine, (5H)-tetrahydro-benzo[b]oxazepine, (5H)-tetrahydrobenzo[b]thiazepine, carbazole, (10H)-dihydroacridine, (10H)-dihydrophenanthridine, (5H)-dibenzoazepine, (5H)-dihydrodibenzoazepine, (5H)-dihydrodibenzodiazepine, (5H)-benzo[b]pyrido[f]azepine, (5H)-dihydrobenzo[b]pyrido[f]azepine, (11H)-dihydrodibenzo[b,e]oxazepine, (11H)-dihydrodibenzo[b,e]thiazepine, (10H)-dihydrodibenzo[b,f]oxazepine, (10H)-dihydrodibenzo[b,f]thiazepine, (11H)-dihydrobenzo[e]pyrido[b]-1,4-diazepin-6-one or (11H)-dihydrobenzo[b]pyrido[e]-1,4-diazepin-5-one, whereby the ring systems =CR[13]R[15], —NR[13]R[15] and optionally ER[13], R[15] as well as aromatic ring systems in the substituents R[1], R[13], R[14], R[15], R[16], Ar[1] and Ar[2] can be substituted independently of each other by one to three of the same or different groups selected from halogen, cyano, $C_1$–$C_6$-Alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, $C_1$–$C_6$-alkoxy entirely or partially substituted by benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, mono-$C_1$–$C_6$-alkylamino, Di-($C_1$–$C_6$-alkyl)-amino and, for two adjacent residues on the aromatic ring, methylenedioxy, and whereby alkyl-, alkenyl- and cycloalkyl residues in the groups G can be substituted by one or two of the same or different groups selected from hydroxy, carboxy, $C_2$–$C_7$-alkoxycarbonyl, benzyloxycarbonyl, amino, mono-$C_1$–$C_6$-alkylamino and di-($C_1$–$C_6$-alkyl)-amino.

According to a further particular embodiment, the invention relates to new compounds of the general formula (I)

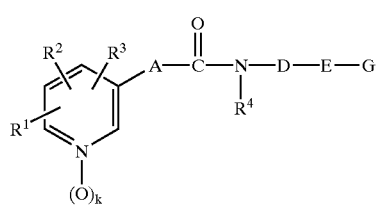

(I)

R[1] is selected from hydrogen, fluorine, methyl, trifluoromethyl ethylthio;

R[2], R[3] and R[4] are each hydrogen;

k has the meaning 0,

A is selected from
ethylene, propylene or butylene optionally substituted by hydroxy or one or two fluorine atoms; or $OCH_2$ or $SCH_2$;
ethenylene, or 1,3-butadienylene;

D is selected from $C_4$–$C_6$-alkylene which is optionally substituted by hydroxy;
$C_4$–$C_6$ alkenylene;
$C_4$–$C_6$ alkinylene; or
$C_4$–$C_6$ alkylene, $C_4$–$C_6$ alkenylene or $C_4$–$C_6$ alkinylene, wherein one or two methylene units is isosterically replaced by O, NH, CO or $SO_2$;

E is piperidine

G is selected from diphenylmethyl, diphenylhydroxymethyl, diphenylmethylene, naphthyl, tetrahydronaphthyl, tetrahydronaphthylidene, flqoroenyl, fluorenylidene, tetrahydrobenzocycloheptenyl or tetrahydrobenzocycloheptenylidene, dihydrodibenzoycloheptenyl or dihydrodibenzocycloheptenylidene;

mixed diphenyl;

phenyl-thienylmethyl, phenyl-thienylmethylene, phenyl-pyridylmethyl, phenyl-pyridylmethylene, tetrahydroquinolinyl, tetrahydroisoguinolinyl, benzocycloheptapyridinyl, benzocycloheptapyridinylidene, dihydrobenzocycloheptapyridinyl, dihydrobenzocycloheptapyridinylidene, dihydrodibenzooxepinyl, dihydrodibenzooxepinylidene, dihydrodibenzothiepinyl, Dihydrodibenzothiepinylidene, Dihydrobenzothienothiepinyl or dihydrobenzothienothiepinylidene;

indolyl, oxobenzoimidazolyl, oxobenzothiazolyl, benzoisothiazolyl or benzotriazolyl;

dibenzylaminocarbonyl, diphenylaminocarbonyl, indolinyl-N-carbonyl, isoindolinyl-N-carbonyl, tetrahydroquinolinyl-N-carbonyl, tetrahydrobenzoazepinyl-N-carbonyl, carbazolyl-N-carbonyl, dihydrodibenzoazepinyl-N-carbonyl or oxodihydrobenzopyridodiazepinyl-N-carbonyl;

diphenylmethylamino, diphenylmethyl-methylamino, dibenzylamino, benzylphenylamino or triphenylmethylamino; acetylamino, pivaloylamino, phenylacetylamino, diphenylacetylamino, diphenylpropionylamino, naphthylacetylamin, benzoylamino, benzoylmethylamino, naphthoylamino or oxofluorenylcarbonylamino;

furoylamino, pyridylacetylamino or pyridyicarbonylamino; benzylaminocarbonylamino, naphthylmethylaminocarbonylamino, indanylaminocarbonylamino, tetrahydronaphthylaminocarbonyl, dibenzylaminocarbonylamino, phenylylaminocarbonylamino, naphthylaminocarbonylamino, benzylphenylaminocarbonylamino or diphenylaminocarbonylamino; indolinyl-N-carbonylamino, isoindolinyl-N-carbonylamino, tetrahydraquinolinyl-N-carbonylamino, tetrahydrobenzoazepinyl-N-carbonylamino, carbazolyl-N-carbonylamino, dihydrophenanthridinyl-N-carbonylamino, dihydrodibenzoazepin-N-carbonylamino, dihydrobenzopyridoazepinyl-N-carbonylamino or oxodihydrobenzopyridodiazepinyl-N-carbonylamino; methanesulfonylamino, tolylsulfonylamino, naphthylsulfonylamino or diphenylphosphinoylamino;
diphenylmethyloxy or diphenylphosphinoyloxy, whereby aromatic ring systems can be substituted independently of each other by one to three of the same or different groups selected from halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, $C_1$–$C_6$-alkoxy entirely or partially substituted by fluorine, benzyl-oxy, phenoxy, mercapto, $C_1$–$C_6$-alkylthio, carboxy, $C_2$–$C_7$-carb-oxyalkyl, $C_2$–$C_7$-carboxyalkenyl, $C_2$–$C_7$-alkoxycarbonyl, benzyl-oxycarbonyl, nitro, amino, mono-$C_1$–$C_6$-alkylamino, di-($C_1$–$C_6$-al-kyl)-amino and, for two adjacent residues on the aromatic ring, methylenedioxy, and whereby alkyl-, alkenyl- and cycloalkyl residues in the group G can be substituted by one or two of the same or different groups selected from hydroxy, carboxy, $C_2$–$C_7$-alkoxycarbonyl, benzyloxycarbonyl, amino, mono-$C_1$–$C_6$-alkylamino and di-($C_1$–$C_6$-alkyl)amino;

In the following, a series of compounds with the respective specific substituent definitions are listed in Table 1 without any limitation for further illustration of the compounds according to the invention.

TABLE 1

Exemplifying compounds of formula (I) according to the invention

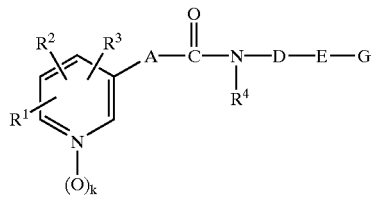

| Nr | $R^1$—$R^3$ | k | A | $R^4$ | D—E—G |
|---|---|---|---|---|---|
| 1 | H | 0 | CH=CH | H | CH₂CH₂CH₂CH₂—N⟨azetidine⟩—CH(phenyl)(phenyl) |
| 2 | H | 0 | CH=CH | H | CH₂CH₂CH₂CH₂—N⟨azetidine⟩—C(phenyl)(phenyl)OH |
| 3 | H | 0 | CH₂CH₂ | H | (CH₂)₆—N⟨azetidine⟩—C(phenyl)(phenyl)OH |

TABLE 1-continued
Exemplifying compounds of formula (I) according to the invention
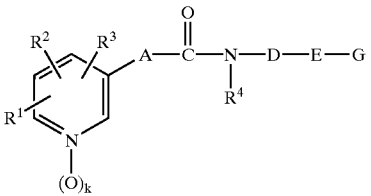
| Nr | R¹—R³ | k | A | R⁴ | D—E—G |
|---|---|---|---|---|---|
| 4 | H | 0 | CH₂CH₂ | H | 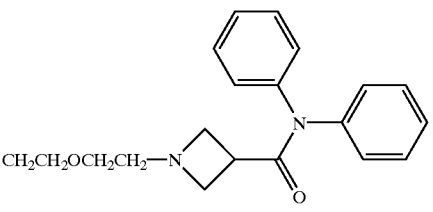 |
| 5 | H | 0 | CH=CH | H | 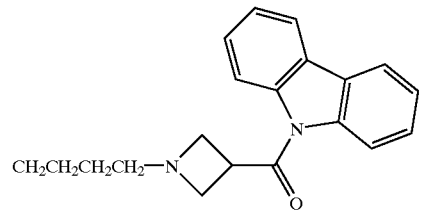 |
| 6 | H | 0 | CH=CH | H | 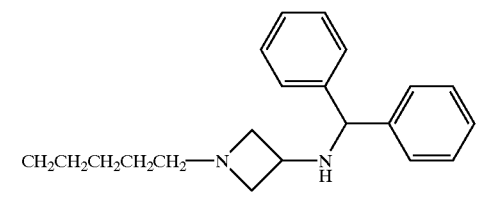 |
| 7 | H | 0 | CH=CH | H | 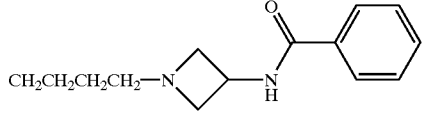 |
| 8 | H | 0 | CH₂CH₂ | H | 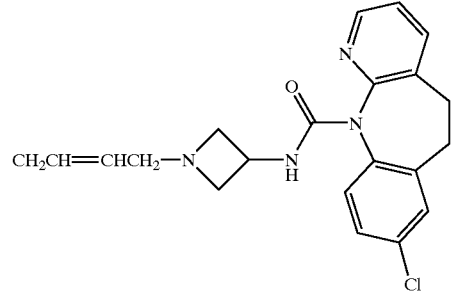 |
| 9 | H | 0 | CH₂CH₂ | H | 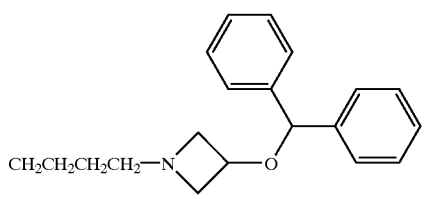 |

TABLE 1-continued

Exemplifying compounds of formula (I) according to the invention

| Nr | R¹—R³ | k | A | R⁴ | D—E—G |
|---|---|---|---|---|---|
| 10 | H | 0 | CH=CH | H | " |
| 11 | H | 0 | CH=CH | H | (CH₂)₆—N⟨azetidine⟩—O—CH(phenyl)(phenyl) |
| 12 | H | 0 | CH=CH | H | CH₂CH₂CH₂CH₂—N⟨pyrrolidine⟩—CH(phenyl)(phenyl) |
| 13 | H | 0 | CH=CH | H | CH₂CH₂OCH₂CH₂—N⟨pyrrolidine⟩—C(OH)(phenyl)(phenyl) |
| 14 | H | 0 | OCH₂ | H | " |
| 15 | H | 0 | CH₂CH₂ | H | CH₂CH₂CH₂CH₂—N⟨pyrrolidine⟩=C(phenyl)(phenyl) |
| 16 | H | 0 | CH=CH | H | " |
| 17 | H | 0 | CH₂CH₂CH₂CH₂ | H | CH₂CH₂—N⟨pyrrolidine⟩—C(=O)—N⟨isoindoline⟩ |

TABLE 1-continued
Exemplifying compounds of formula (I) according to the invention
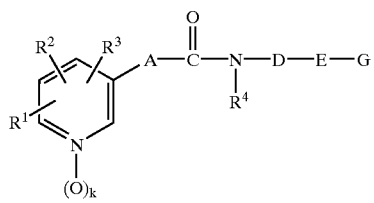
| Nr | R¹—R³ | k | A | R⁴ | D—E—G |
|---|---|---|---|---|---|
| 18 | H | 0 | CH=CH | H | |
| 19 | H | 0 | CH=CH—CH=CH | H | |
| 20 | H | 0 | CH=CH | H | |
| 21 | H | 0 | CH$_2$CH$_2$ | H | |
| 22 | H | 0 | CH$_2$CH$_2$ | H | |
| 23 | H | 0 | CH=CH | H | " |
| 24 | H | 0 | OCH$_2$ | H | |
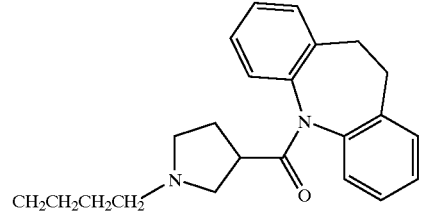
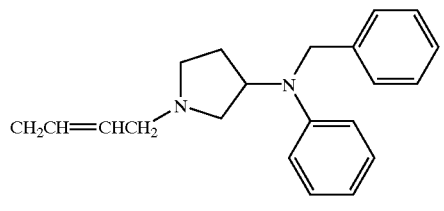
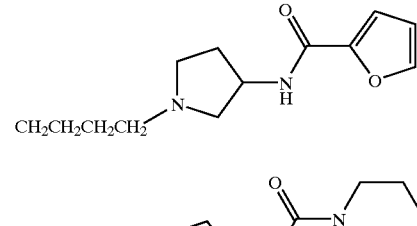
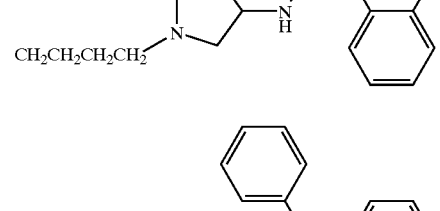
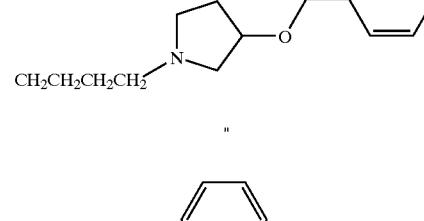
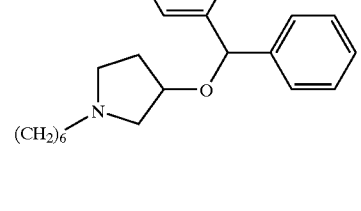

TABLE 1-continued
Exemplifying compounds of formula (I) according to the invention
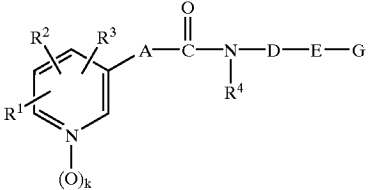
| Nr | R¹—R³ | k | A | R⁴ | D—E—G |
|---|---|---|---|---|---|
| 25 | H | 0 | CH₂CH₂ | H | 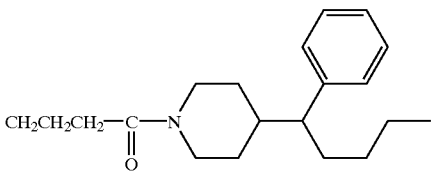 |
| 26 | H | 0 | SCH₂ | H | 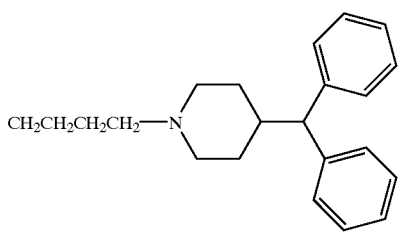 |
| 27 | H | 0 | CHCF₂ \| OH | H | " |
| 28 | H | 0 | △ | H | " |
| 29 | H | 0 | CH=CH | H |  |
| 30 | H | 0 | CH₂CH₂ | H | 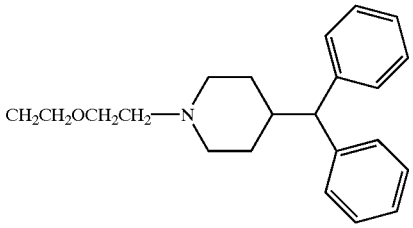 |
| 31 | H | 0 | CH=CH | H | " |
| 32 | H | 0 | CH=CH | H | 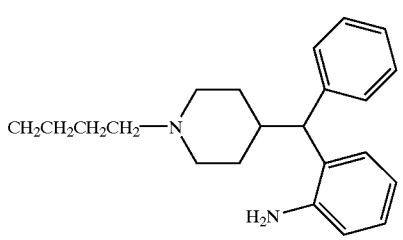 |

TABLE 1-continued
Exemplifying compounds of formula (I) according to the invention
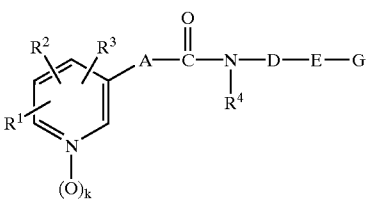
| Nr | R¹—R³ | k | A | R⁴ | D—E—G |
|----|-------|---|------|----|-------|
| 33 | H | 0 | CH=CH | H | 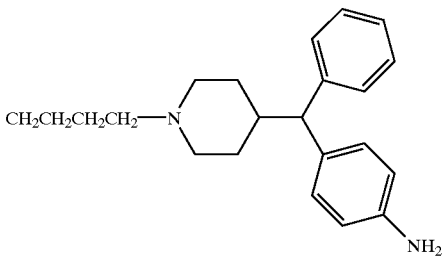 |
| 34 | H | 0 | CH=CH | H | 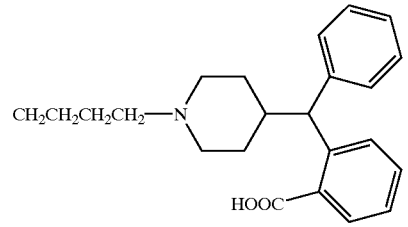 |
| 35 | H | 0 | CH=CH | H | 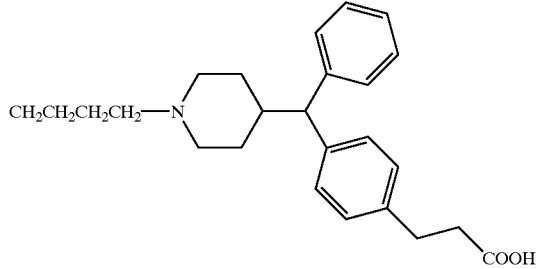 |
| 36 | H | 0 | OCH₂ | H | 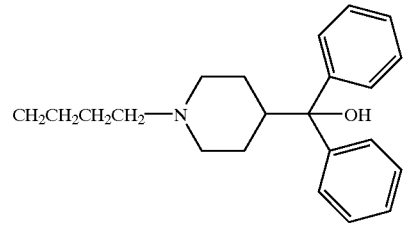 |
| 37 | H | 0 | C≡C | H | " |
| 38 | H | 0 | CH=CH | H | 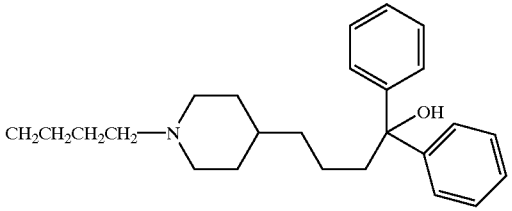 |

TABLE 1-continued
Exemplifying compounds of formula (I) according to the invention
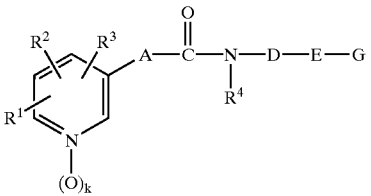
| Nr | R¹—R³ | k | A | R⁴ | D—E—G |
|---|---|---|---|---|---|
| 39 | H | 0 | CH=CH—CH=CH | H | 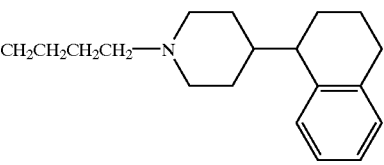 |
| 40 | H | 0 | CH$_2$CH$_2$ | H | 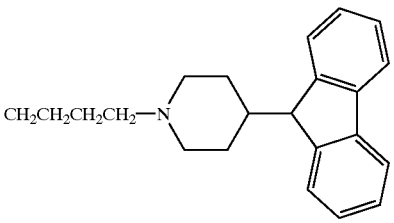 |
| 41 | H | 0 | CHCH$_2$<br>\|<br>OH | H | " |
| 42 | H | 0 | CH=CH—CH=CH | H | " |
| 43 | H | 0 | CH=CH | H |  |
| 44 | H | 0 | CH$_2$CH$_2$ | H | 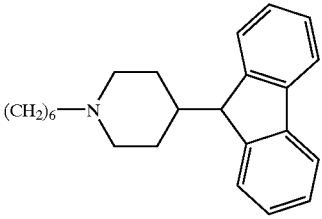 |
| 45 | H | 0 | CH=CH | H | 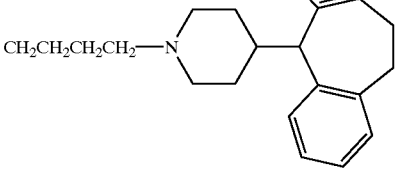 |

TABLE 1-continued
Exemplifying compounds of formula (I) according to the invention
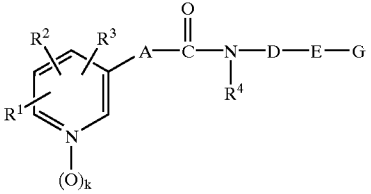
| Nr | R¹—R³ | k | A | R⁴ | D—E—G |
|----|-------|---|------|----|-------|
| 46 | H | 0 | OCH₂ | H | 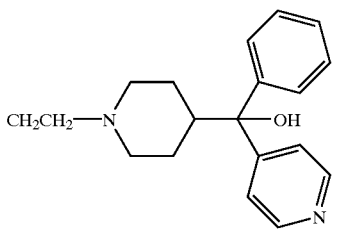 |
| 47 | H | 0 | CH₂CH₂ | H | 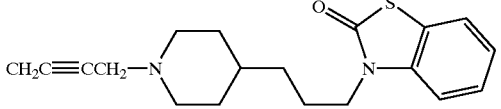 |
| 48 | H | 0 | OCH₂ | H | 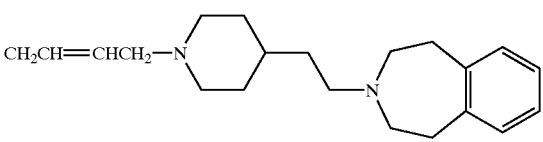 |
| 49 | H | 0 | CH=CH | H | 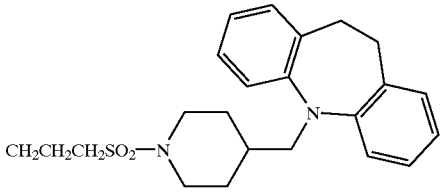 |
| 50 | H | 0 | CH₂CH₂ | H | 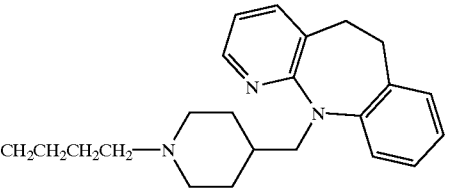 |
| 51 | H | 0 | CH=CH | H | " |
| 52 | H | 0 | CH=CH | H | 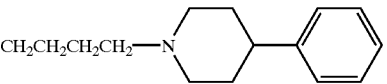 |
| 53 | H | 0 | CHFCH₂ | H | 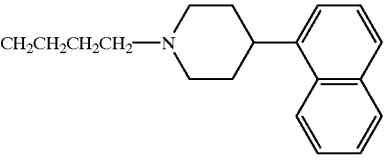 |

TABLE 1-continued
Exemplifying compounds of formula (I) according to the invention
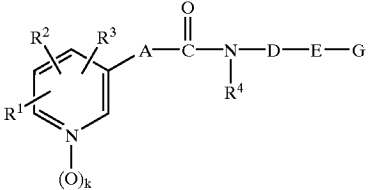
| Nr | R¹–R³ | k | A | R⁴ | D—E—G |
|---|---|---|---|---|---|
| 54 | H | 0 | CH=CH | H | 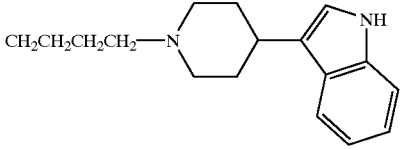 |
| 55 | H | 0 | CH=CH | H | 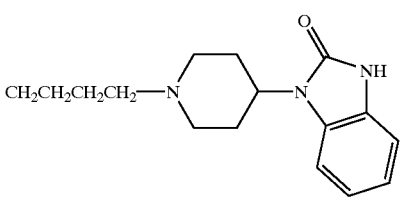 |
| 56 | H | 0 | OCH$_2$ | H | " |
| 57 | 6-C$_2$H$_5$S | 0 | CH=CH | H | 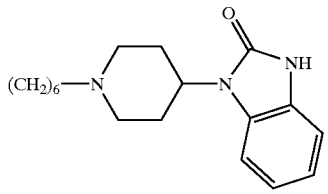 |
| 58 | H | 0 | CH=CH | H | 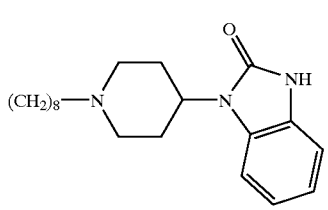 |
| 59 | H | 0 | CH=CH | H | 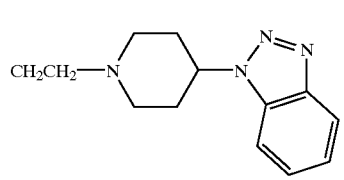 |
| 60 | H | 0 | CH=CH | H | 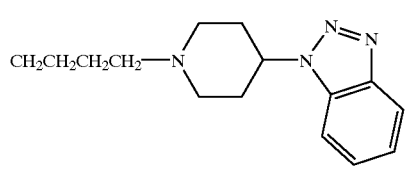 |
| 61 | H | 1 | CH=CH | H | " |
| 62 | 2-Cl | 0 | CH=CH | H | " |
| 63 | 6-CH$_3$ | 0 | CH=CH | H | " |
| 64 | H | 0 | CHCH$_2$<br>\|<br>OH | H | " |

TABLE 1-continued
Exemplifying compounds of formula (I) according to the invention
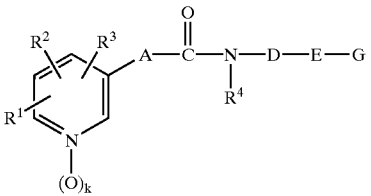
| Nr | R¹—R³ | k | A | R⁴ | D—E—G |
|----|-------|---|---|----|----|
| 65 | H | 0 | SCH₂ | H | " |
| 66 | H | 0 | CH₂NCH₂CH₂<br>     |<br>    CH₃ | H | " |
| 67 | H | 0 | CH₂CH₂ | H | 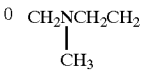 |
| 68 | H | 0 | CH=CH | H | 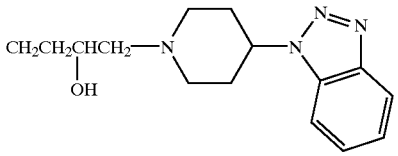 |
| 69 | H | 0 | CH₂CH₂ | H | 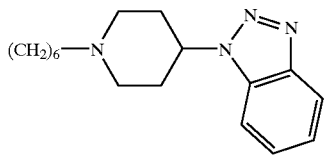 |
| 70 | H | 0 | CH=CH | H | 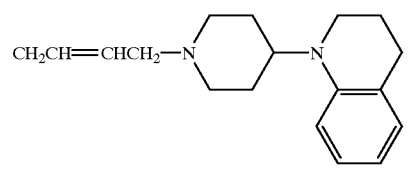 |
| 71 | H | 0 | CH₂CH₂ | H | 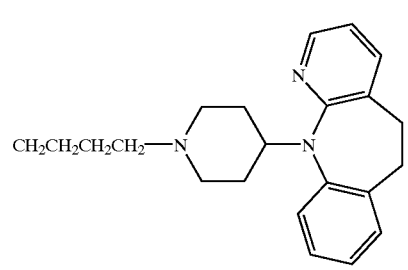 |
| 72 | H | 0 | CH=CH | H | " |
| 73 | 6-C₆H₅S | 0 | CH=CH | H | " |

TABLE 1-continued

Exemplifying compounds of formula (I) according to the invention

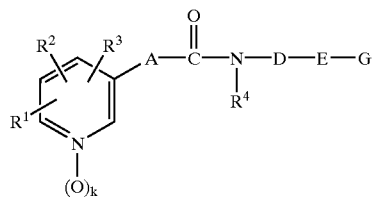

| Nr | R¹—R³ | k | A | R⁴ | D—E—G |
|---|---|---|---|---|---|
| 74 | H | 0 | CH₂C(=O) | H | " |
| 75 | H | 0 | CH₂CH(OH) | H | " |
| 76 | H | 0 | △ | H | " |
| 77 | H | 0 | CH=CH | CH₃ | (structure: CH₂CH₂N(CH₃)—C(=O)—piperidine-dibenzazepine-pyridine with Cl) |
| 78 | H | 0 | CH=CH | H | (structure: CH₂CH₂CH₂CH₂—piperidine-dibenzazepine-pyridine) |
| 79 | H | 0 | CH=CH | H | (structure: CH₂CH₂CH₂—N-piperidine-4-phenyl-4-OH) |
| 80 | H | 0 | CH=C(C₆H₅) | H | (structure: CH₂CH₂—N-piperidine-4,4-diphenyl) |

TABLE 1-continued
Exemplifying compounds of formula (I) according to the invention
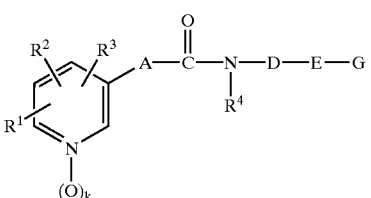
| Nr | R¹—R³ | k | A | R⁴ | D—E—G |
|---|---|---|---|---|---|
| 81 | H | 0 | CH₂CH\|OH | H | 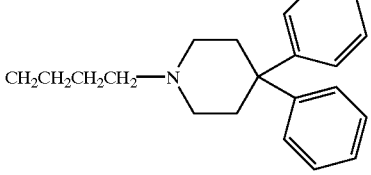 |
| 82 | H | 0 | CH=CH | H | " |
| 83 | H | 1 | CH=CH | H | " |
| 84 | 2,6-(CH₃)₂ | 0 | CH=CH | H | " |
| 85 | H | 0 | C≡C | H | " |
| 86 | H | 0 | CH=CH | H | 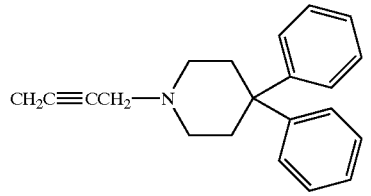 |
| 87 | 6-CH₃ | 0 | CH=CH | H | " |
| 88 | H | 0 | OCH₂ | H | " |
| 89 | H | 0 | CH=CH | H | 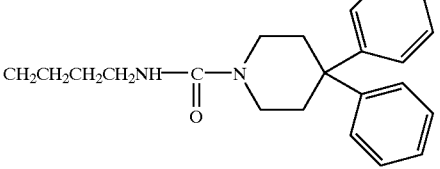 |
| 90 | H | 0 | CH=CH | H | 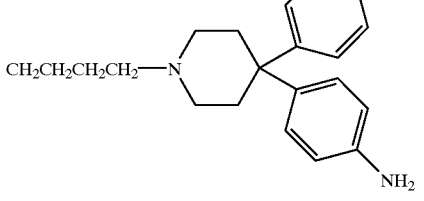 |
| 91 | H | 0 | CH=CH | H | 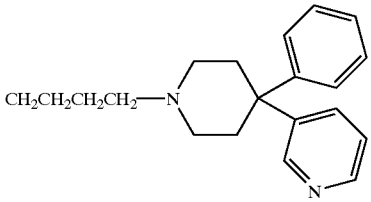 |

TABLE 1-continued

Exemplifying compounds of formula (I) according to the invention

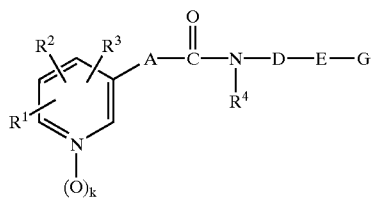

| Nr | R¹—R³ | k | A | R⁴ | D—E—G |
|---|---|---|---|---|---|
| 92 | H | 0 | CH=CH | H | CH₂CH₂CH₂CH₂—N(piperidine-spiro-1,3-dioxolane) |
| 93 | H | 0 | CH=CH | H | CH₂CH₂CH₂CH₂—N(piperidine-spiro-imidazolidinone) |
| 94 | H | 0 | CH₂CH₂ | H | CH₂CH₂—N(piperidine-spiro-N-phenyl-imidazolidinone) |
| 95 | H | 0 | CH₂CF₂ | H | CH₂CH₂CH₂CH₂—N(piperidine-spiro-benzodioxole) |
| 96 | H | 0 | OCH₂ | H | " |
| 97 | H | 0 | CH=CH | H | CH₂CH₂CH₂CH₂—N(piperidine-spiro-benzoxazine) |
| 98 | H | 0 | CH=CH | H | CH₂CH₂OCH₂CH₂—N(4-(1-phenylbutylidene)piperidine) |
| 99 | H | 0 | OCH₂ | H | CH₂CH₂CH₂CH₂—N(4-(diphenylmethylene)piperidine) |
| 100 | H | 0 | SCH₂ | H | " |
| 101 | H | 0 | C≡C | H | " |

TABLE 1-continued

Exemplifying compounds of formula (I) according to the invention

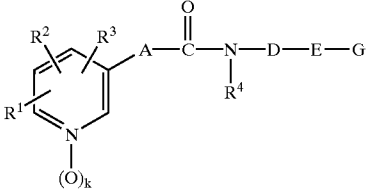

| Nr | R¹—R³ | k | A | R⁴ | D—E—G |
|---|---|---|---|---|---|
| 102 | H | 0 | CH=CH | H | CH₂CH₂CH=CHCH₂CH₂—N⟨piperidinyl⟩=C(C₆H₅)₂ |
| 103 | H | 0 | CH₂CH₂ | H | CH₂CH₂CH₂CH₂—N⟨piperidinyl⟩=C(C₆H₅)(2-H₂N-C₆H₄) |
| 104 | H | 0 | CH=CH | H | " |
| 105 | H | 0 | CH=CH | H | CH₂CH₂CH₂CH₂—N⟨piperidinyl⟩=C(C₆H₅)(4-H₂N-C₆H₄) |
| 106 | H | 0 | CH=CH | H | CH₂CH₂CH₂CH₂—N⟨piperidinyl⟩=C(C₆H₅)(2-HOOC-C₆H₄) |
| 107 | 5-F | 0 | CH=CH | H | CH₂CH₂CH₂CH₂CH₂—N⟨piperidinyl⟩=fluorenyl |
| 108 | H | 0 | CH=CH | C₂H₅ | " |

TABLE 1-continued
Exemplifying compounds of formula (I) according to the invention
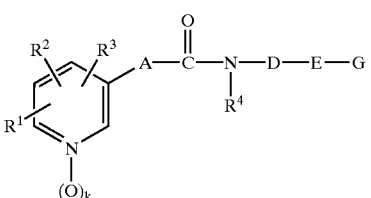
| Nr | R¹—R³ | k | A | R⁴ | D—E—G |
|---|---|---|---|---|---|
| 109 | H | 0 | CH=CH | H | 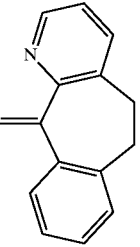 |
| 110 | H | 0 | CH₂CH₂ | H | 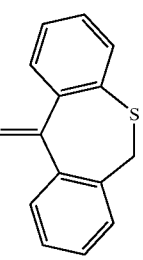 |
| 111 | H | 0 | CHCF₂<br>\|<br>OH | H | " |
| 112 | H | 0 | CH₂CH₂CH₂CH₂ | H | " |
| 113 | H | 0 | CH=CH | H |  |
| 114 | H | 1 | CH=CH | H | " |
| 115 | H | 0 | SCH₂ | H | " |
| 116 | H | 0 | CH=CH | H | 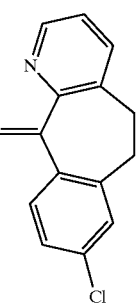 |

TABLE 1-continued
Exemplifying compounds of formula (I) according to the invention
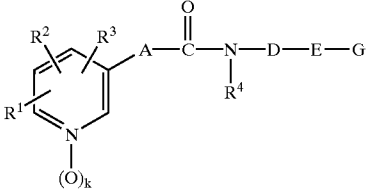
| Nr | R¹—R³ | k | A | R⁴ | D—E—G |
|---|---|---|---|---|---|
| 117 | H | 0 | CH₂CH₂ | H | 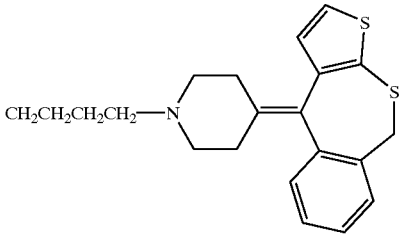 |
| 118 | H | 0 | CH=CH | H | " |
| 119 | H | 0 | CHCH₂<br>\|<br>OH | H | " |
| 120 | H | 0 | CH=CH | H | 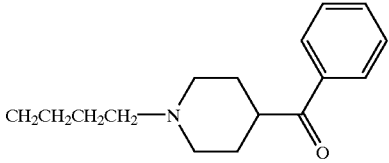 |
| 121 | H | 0 | CH₂CH₂ | H | 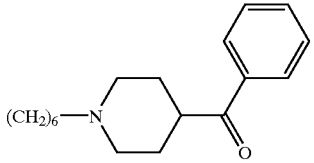 |
| 122 | H | 0 | CH₂CH₂ | H | 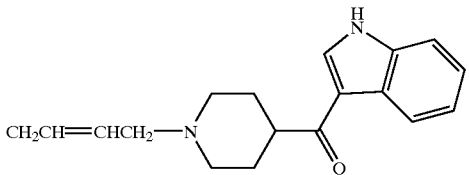 |
| 123 | H | 0 | CH=CH | H | 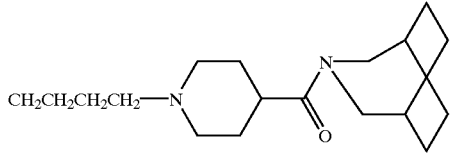 |
| 124 | H | 0 | CH=CH | H | 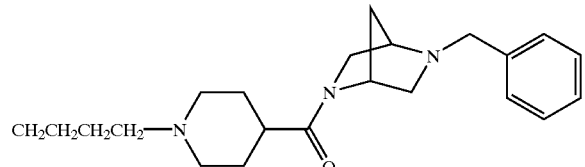 |

TABLE 1-continued

Exemplifying compounds of formula (I) according to the invention

| Nr | R¹—R³ | k | A | R⁴ | D—E—G |
|---|---|---|---|---|---|
| 125 | H | 0 | CH₂CH₂ | H | (quinuclidine-N-CH₃ connected via N to C(=O)-piperidine-N-CH₂CH₂CH₂CH₂—) |
| 126 | H | 0 | CH=CH | H | (2,3-dihydroindole-N-C(=O)-piperidine-N-CH₂CH₂CH₂CH₂—) |
| 127 | H | 0 | CH=CH—CH=CH | H | (2,3,4,5-tetrahydro-1-benzazepine-N-C(=O)-piperidine-N-CH₂CH₂CH₂CH₂—) |
| 128 | H | 0 | CH=CH | H | (10,11-dihydrodibenzazepine-N-C(=O)-piperidine-N-CH₂CH₂CH₂CH₂—) |
| 129 | 6-C₆H₅O | 0 | CH=CH | H | " |
| 130 | H | 0 | CH=CH | H | (dibenzazepine-N-C(=O)-piperidine-N-CH₂CH₂CH₂CH₂—) |
| 131 | H | 0 | CH=CH | H | (pyrido-benzodiazepinone-N-C(=O)-piperidine-N-CH₂CH₂CH₂CH₂—) |

TABLE 1-continued
Exemplifying compounds of formula (I) according to the invention
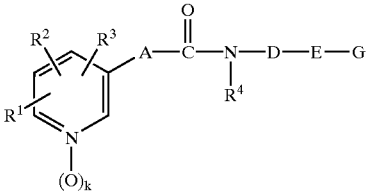
| Nr | R¹—R³ | k | A | R⁴ | D—E—G |
|----|-------|---|---|----|----|
| 132 | H | 0 | OCH₂ | H | 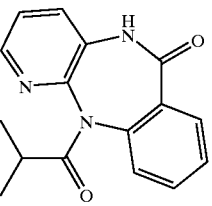 |
| 133 | H | 0 | CH=CH | H | CH₂CH₂CH₂CH₂—N(piperidine)—NH₂ |
| 134 | H | 0 | CH=CH | H | (CH₂)₆—N(piperidine)—NH₂ |
| 135 | H | 0 | CH=CH | H | 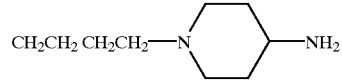 |
| 136 | H | 0 | CH₂CH₂ | H | 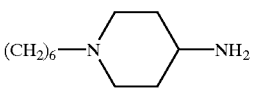 |
| 137 | H | 0 | CH=CH—CH=CH | H | " |
| 138 | H | 0 | CH=CH | H | 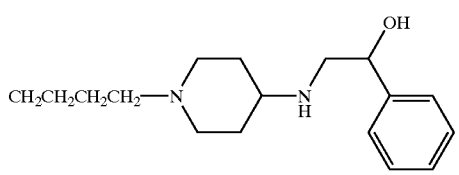 |
| 139 | H | 0 | CH=CH | H | 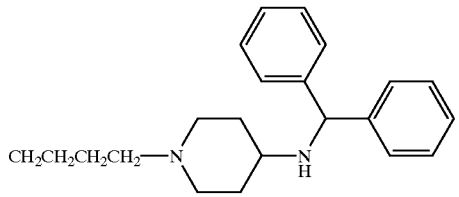 |

TABLE 1-continued
Exemplifying compounds of formula (I) according to the invention
| Nr | R¹—R³ | k | A | R⁴ | D—E—G |
|---|---|---|---|---|---|
| 140 | H | 0 | CH=CH | H | 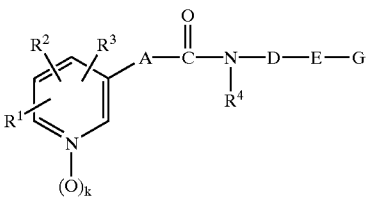 |
| 141 | H | 0 | OCH$_2$ | H | 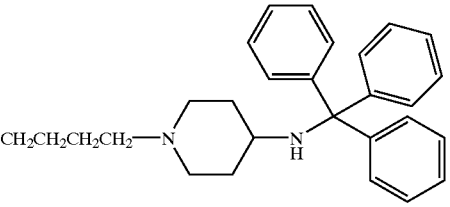 |
| 142 | H | 0 | CH=CH | H | 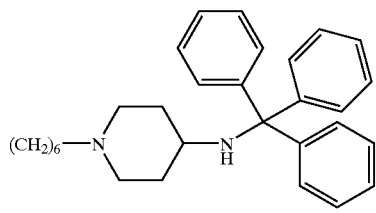 |
| 143 | H | 0 | CH=C(C$_6$H$_5$) | H | 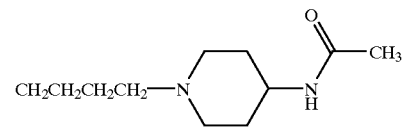 |
| 144 | H | 0 | CH$_2$CH$_2$ | H | 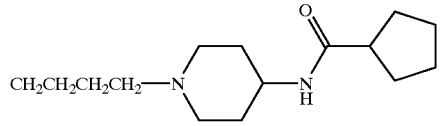 |
| 145 | H | 0 | CH=CH | H | " |
| 146 | H | 0 | CH$_2$CH$_2$ | H | 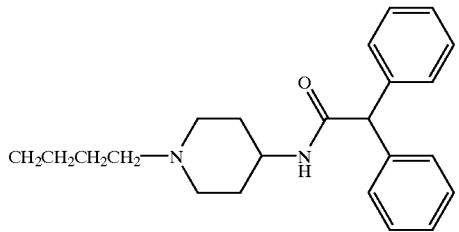 |
| 147 | H | 0 | CH=CH | H | " |

TABLE 1-continued
Exemplifying compounds of formula (I) according to the invention
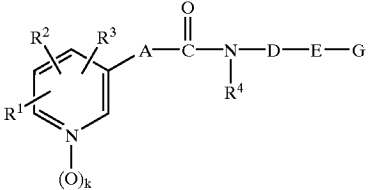
| Nr | R¹–R³ | k | A | R⁴ | D—E—G |
|---|---|---|---|---|---|
| 148 | H | 0 | CH=CH | H | 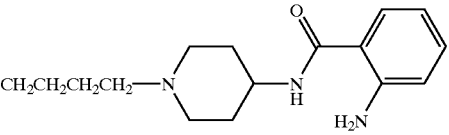 |
| 149 | H | 0 | CH=CH | H | 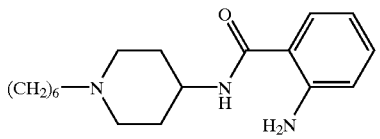 |
| 150 | H | 0 | CH=CH | H | 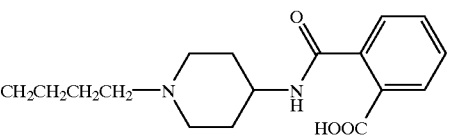 |
| 151 | H | 0 | CH=CH | CH₃ | 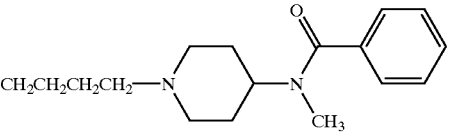 |
| 152 | H | 0 | CH₂CH₂ | H | 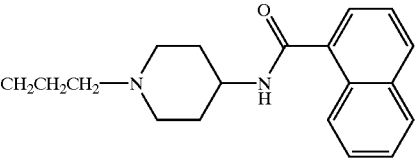 |
| 153 | H | 0 | CH=CH | H | 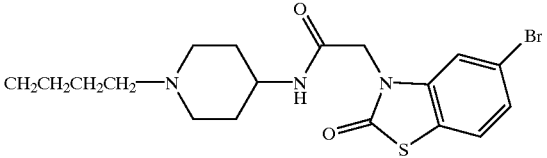 |
| 154 | H | 0 | CH=CH | H | 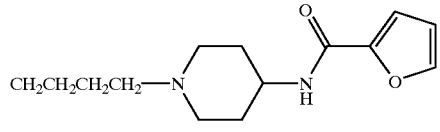 |
| 155 | H | 0 | CH=C(CH₃) | H | 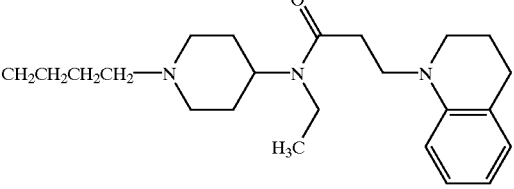 |

TABLE 1-continued

Exemplifying compounds of formula (I) according to the invention

| Nr | R¹–R³ | k | A | R⁴ | D—E—G |
|----|-------|---|---|----|-------|
| 156 | H | 0 | CH=CH | H | (4-butylpiperidin-1-yl)-N-(naphthalen-1-ylmethyl)urea derivative |
| 157 | H | 0 | CHCF₂ / OH | H | (1-allylpiperidin-4-yl)-N-cyclopentylurea derivative |
| 158 | H | 0 | CH=CH—CH=CH | H | (1-butylpiperidin-4-yl)-N-(indan-1-yl)urea derivative |
| 159 | H | 0 | CH₂CH₂ | H | [1-(2-hydroxypropyl)piperidin-4-yl]-N-(1H-indol-5-yl)urea derivative |
| 160 | H | 0 | CH=CH | H | (1-allylpiperidin-4-yl)-N,N-diphenylurea derivative |
| 161 | H | 0 | CH₂CH₂ | H | [1-hexylpiperidin-4-yl]-isoindoline-2-carboxamide derivative |

TABLE 1-continued
Exemplifying compounds of formula (I) according to the invention
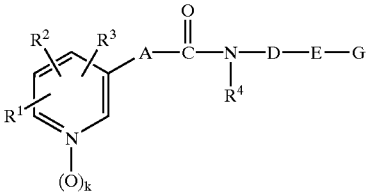
| Nr | R¹—R³ | k | A | R⁴ | D—E—G |
|---|---|---|---|---|---|
| 162 | H | 0 | C≡C | H | 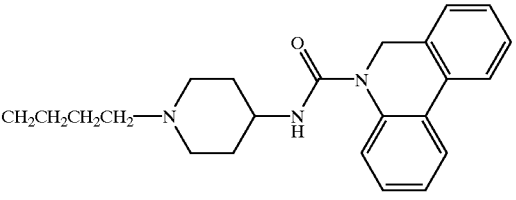 |
| 163 | H | 0 | CH=CH | H | 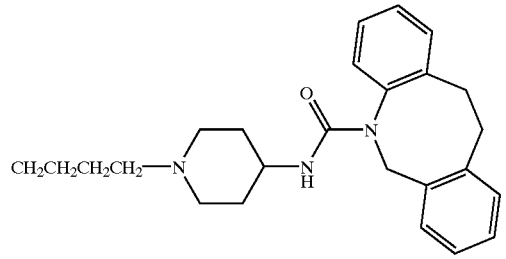 |
| 164 | H | 0 | △ | H | " |
| 165 | H | 0 | CH=CH | H | 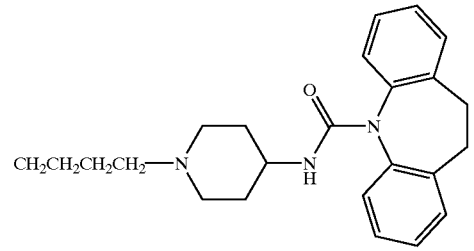 |
| 166 | H | 0 | OCH₂ | H | " |
| 167 | H | 0 | CH₂CH₂ | H | 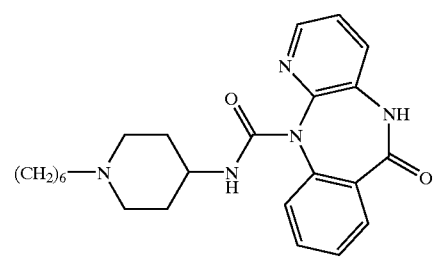 |
| 168 | H | 0 | CH=CH | H | " |
| 169 | H | 0 | CH=CH | H | 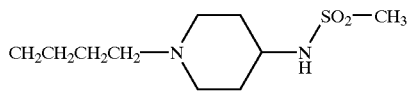 |

TABLE 1-continued
Exemplifying compounds of formula (I) according to the invention
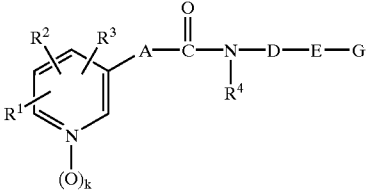
| Nr | R¹—R³ | k | A | R⁴ | D—E—G |
|---|---|---|---|---|---|
| 170 | H | 0 | CH=CH | H | 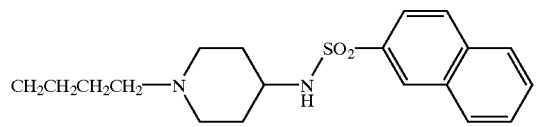 |
| 171 | H | 0 | CH=CH | H | 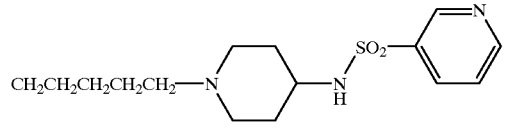 |
| 172 | H | 0 | CH₂CH₂ | H | 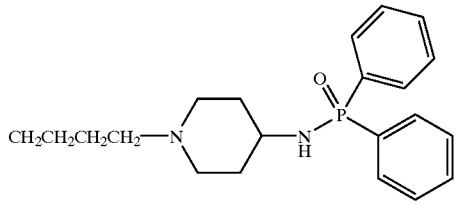 |
| 173 | H | 0 | CH=CH | H | " |
| 174 | H | 0 | SCH₂ | H | " |
| 175 | H | 0 | CH=CH | H | 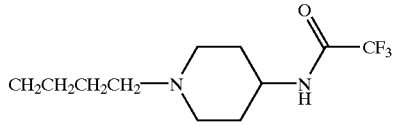 |
| 176 | H | 0 | CH=CH | H | 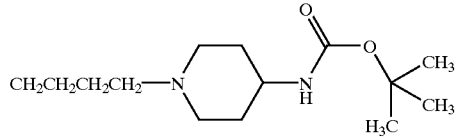 |
| 177 | H | 0 | CH=CH—CH=CH | H | " |
| 178 | H | 0 | CH=CH | H | 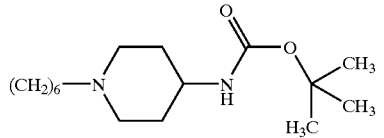 |
| 179 | H | 0 | CH₂CH₂ | H | 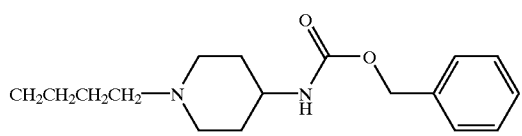 |

TABLE 1-continued

Exemplifying compounds of formula (I) according to the invention

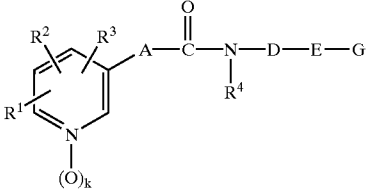

| Nr | R¹–R³ | k | A | R⁴ | D–E–G |
|---|---|---|---|---|---|
| 180 | H | 0 | C=CH<br>\|<br>CH₃ | H | CH₂CH₂CH₂CH₂CH₂–N⟨piperidine⟩–O–CH₂–CH(OH)–phenyl |
| 181 | H | 0 | OCH₂ | H | CH₂CH₂CH₂CH₂–N⟨piperidine⟩–O–CH(phenyl)₂ |
| 182 | H | 0 | △ | H | " |
| 183 | H | 0 | CH=CH | H | CH₂CH=CHCH₂–N⟨piperidine⟩–O–CH(phenyl)₂ |
| 184 | H | 0 | CH=CH | H | CH₂C≡CCH₂–N⟨piperidine⟩–O–CH(phenyl)₂ |
| 185 | H | 0 | CH₂CH₂ | H | CH₂CH₂CH₂CH₂–N⟨piperidine⟩–S–CH(phenyl)₂ |
| 186 | H | 0 | CH=CH | H | CH₂CH₂CH₂CH₂–N⟨piperidine⟩–S–benzothiazole |

TABLE 1-continued
Exemplifying compounds of formula (I) according to the invention
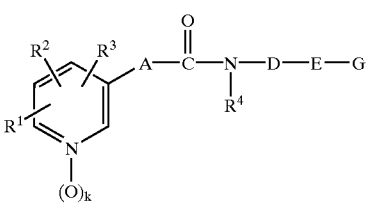
| Nr | R¹—R³ | k | A | R⁴ | D—E—G |
|---|---|---|---|---|---|
| 187 | H | 0 | CH₂CH₂ | H | 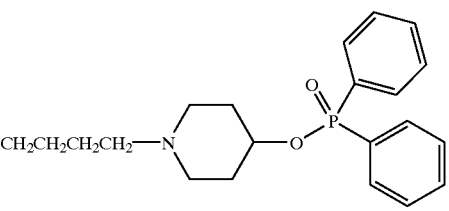 |
| 188 | H | 0 | CH=CH | H | " |
| 189 | H | 0 | CH=CH | H | 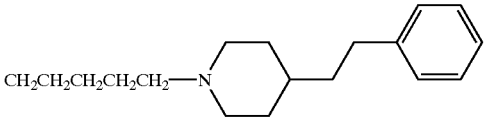 |
| 190 | H | 0 | CH=CH | H | 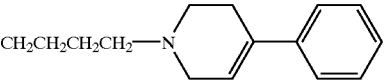 |
| 191 | H | 0 | CH=CH | H | 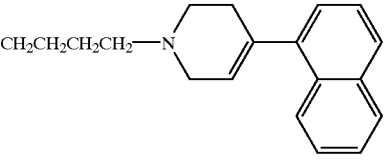 |
| 192 | H | 0 | CH=CH | H | 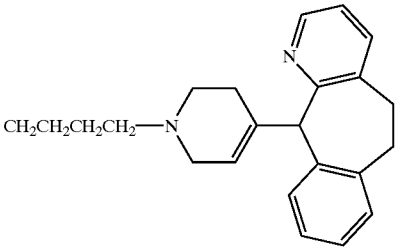 |
| 193 | H | 0 | CH=CH | H | 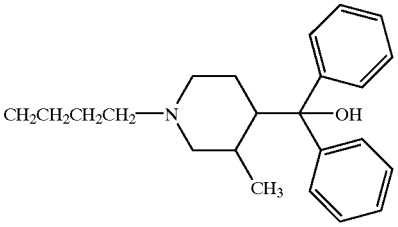 |

TABLE 1-continued
Exemplifying compounds of formula (I) according to the invention
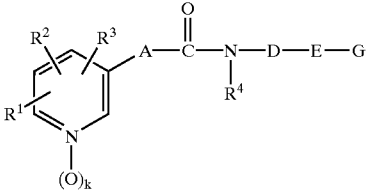
| Nr | R¹—R³ | k | A | R⁴ | D—E—G |
|---|---|---|---|---|---|
| 194 | H | 0 | CH₂CH₂ | H | 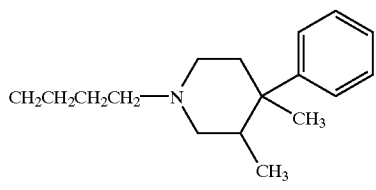 |
| 195 | H | 0 | OCH₂ | H | 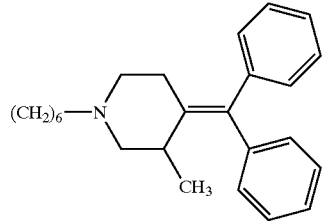 |
| 196 | H | 0 | CH₂CH₂ | H | 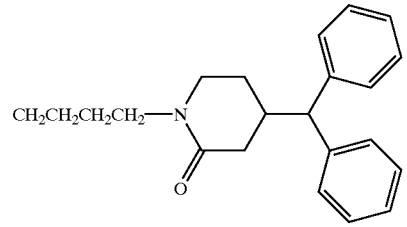 |
| 197 | H | 0 | CH=CH | H | 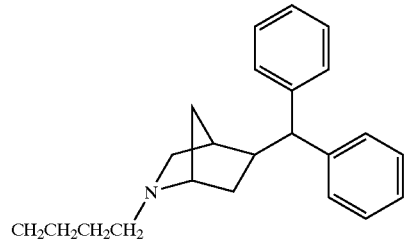 |
| 198 | H | 0 | CH=CH | H | 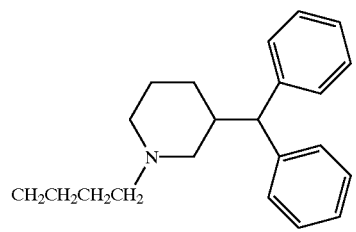 |

TABLE 1-continued

Exemplifying compounds of formula (I) according to the invention

| Nr | R¹—R³ | k | A | R⁴ | D—E—G |
|---|---|---|---|---|---|
| 199 | H | 0 | CH=CH | H | (piperidine with N-CH₂CH₂CH₂CH₂, 3-position bearing C(OH)(phenyl)(phenyl)) |
| 200 | H | 0 | OCH₂ | H | " |
| 201 | H | 0 | CH=CH | H | (piperidine with N-CH₂CH₂CH₂CH₂, 3,3-diphenyl) |
| 202 | H | 0 | CHFCH₂ | H | (piperidine with N-CH₂CH₂CH₂SO₂, 3,3-diphenyl) |
| 203 | H | 0 | CH₂CH₂CH₂CH₂ | H | (piperidine with N-CH₂CH₂CH₂CH₂, 3-position =C(phenyl)(phenyl)) |
| 204 | H | 0 | CH=CH | H | (azatricyclic system with (CH₂)₆) |

TABLE 1-continued

Exemplifying compounds of formula (I) according to the invention

| Nr | R¹—R³ | k | A | R⁴ | D—E—G |
|----|-------|---|---|----|-------|
| 205 | H | 0 | CH=CH | H | 1-(CH₂CH₂OCH₂CH₂)-piperidin-3-yl-C(O)-N(2,3,4,5-tetrahydro-1H-3-benzazepin-3-yl) |
| 206 | H | 0 | CH=CH | H | 1-(CH₂CH₂CH₂CH₂)-piperidin-3-yl-NH-CH(phenyl)₂ |
| 207 | H | 0 | CH₂CH₂ | H | 1-(CH₂CH₂)-piperidin-3-yl-NH-C(O)-CH(phenyl)₂ |
| 208 | H | 0 | CH=CH | H | 1-(CH₂CH₂CH₂CH₂)-piperidin-3-yl-NH-C(O)-(furan-2-yl) |
| 209 | H | 0 | CH=CH—CH=CH | H | 1-(CH₂CH₂CH₂CH₂)-piperidin-3-yl-NH-C(O)-N(phenanthridin-5(6H)-yl) |

TABLE 1-continued

Exemplifying compounds of formula (I) according to the invention

| Nr | R¹—R³ | k | A | R⁴ | D—E—G |
|---|---|---|---|---|---|
| 210 | H | 0 | CH=CH | H | (1-butylpiperidin-3-yl)NH-P(=O)(phenyl)₂ |
| 211 | H | 0 | CH=CH | H | 1-butyl-3-(diphenylmethoxy)piperidine |
| 212 | H | 0 | CH₂CH₂CH₂CH₂ | H | " |
| 213 | H | 0 | CH₂CH₂ | H | 4-butyl-2-(diphenylmethyl)morpholine |
| 214 | H | 0 | CH=CH | H | " |
| 215 | H | 0 | CH=CH | H | 4-hexyl-2-(diphenylmethyl)morpholine |
| 216 | H | 0 | CH=CH | H | 4-butyl-2-(hydroxydiphenylmethyl)morpholine |

TABLE 1-continued
Exemplifying compounds of formula (I) according to the invention
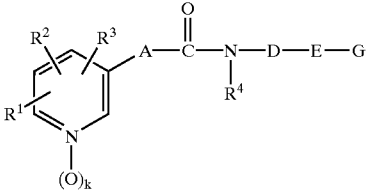
| Nr | R¹—R³ | k | A | R⁴ | D—E—G |
|---|---|---|---|---|---|
| 217 | H | 0 | $CH_2CF_2$ | H | 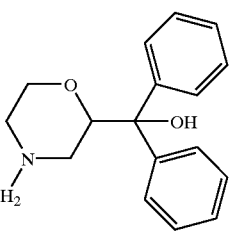 |
| 218 | H | 0 | CH=CH | H | 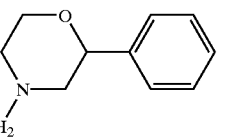 |
| 219 | H | 0 | $CH_2CH_2$ | H | 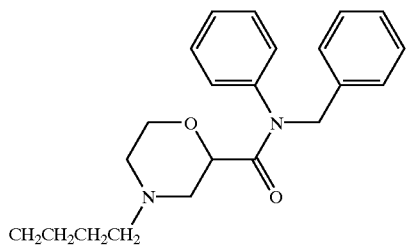 |
| 220 | H | 0 | CH=CH | H | 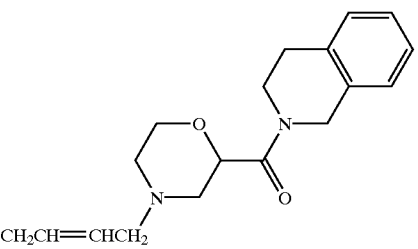 |
| 221 | H | 0 | CH=CH | H | 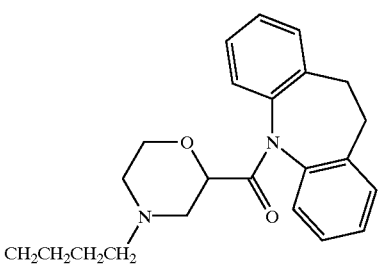 |

TABLE 1-continued
Exemplifying compounds of formula (I) according to the invention
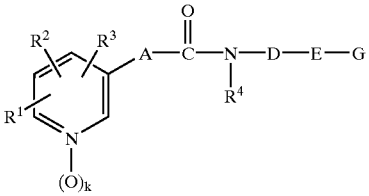
| Nr | R¹—R³ | k | A | R⁴ | D—E—G |
|---|---|---|---|---|---|
| 222 | H | 0 | CH=CH | H | 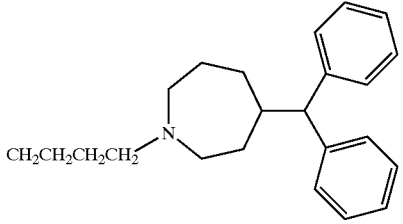 |
| 223 | H | 0 | CH₂CH₂CH₂CH₂ | H | 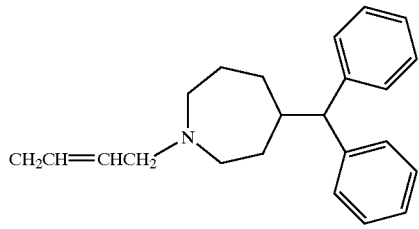 |
| 224 | H | 0 | CH=CH | H | 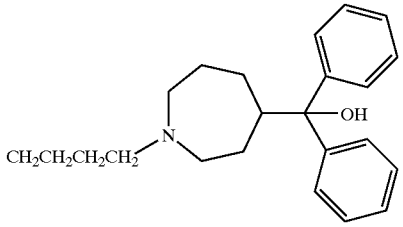 |
| 225 | H | 0 | OCH₂ | H | 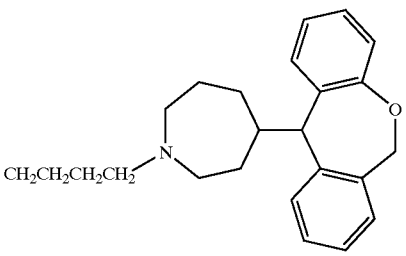 |
| 226 | H | 0 | CH=CH | H | 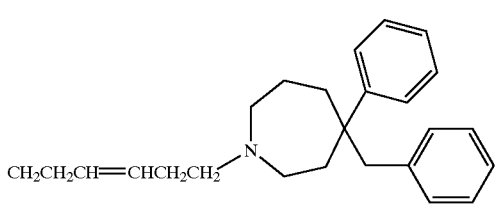 |

TABLE 1-continued

Exemplifying compounds of formula (I) according to the invention

| Nr | R¹—R³ | k | A | R⁴ | D—E—G |
|---|---|---|---|---|---|
| 227 | H | 0 | SCH$_2$ | H | [structure: 1-butyl-azepan-4-ylidene(diphenyl)methane] |
| 228 | H | 0 | CH$_2$CH$_2$ | H | [structure: 1-butyl-azepan-4-ylidene dibenzosuberane] |
| 229 | H | 0 | CH=CH | H | " |
| 230 | H | 0 | CH=CH | H | [structure: N-(benzhydryl)-1-butyl-azepan-4-amine] |
| 231 | H | 0 | CH=CH | H | [structure: N-(1-butyl-azepan-4-yl)-2,2-diphenylacetamide] |
| 232 | H | 0 | CH$_2$CH$_2$ | H | [structure: N-(1-butyl-azepan-4-yl)benzamide] |

TABLE 1-continued
Exemplifying compounds of formula (I) according to the invention
| Nr | R¹–R³ | k | A | R⁴ | D—E—G |
|---|---|---|---|---|---|
| 233 | H | 0 | CH=CH | H | 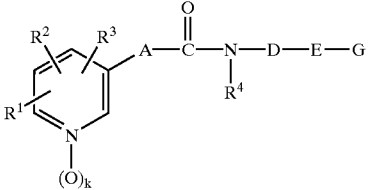 |
| 234 | H | 0 | CH=CH | H | 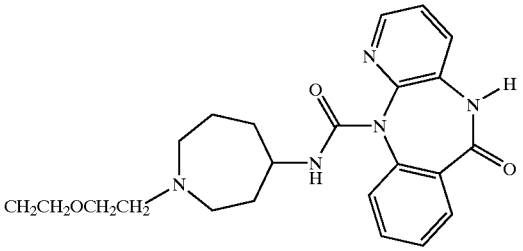 |
| 235 | H | 0 | CH₂CH₂ | H | 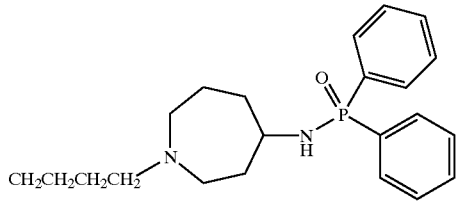 |
| 236 | H | 0 | CH=CH | H | " |
| 237 | H | 0 | CH=CH | H | 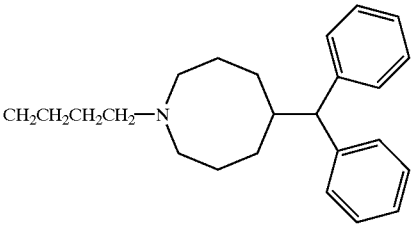 |
| 238 | H | 0 | CH₂CH₂ | H | 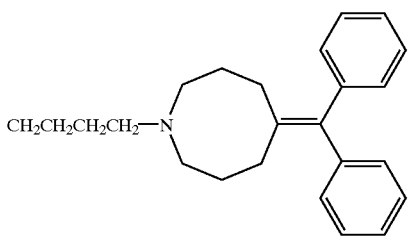 |

TABLE 1-continued
Exemplifying compounds of formula (I) according to the invention
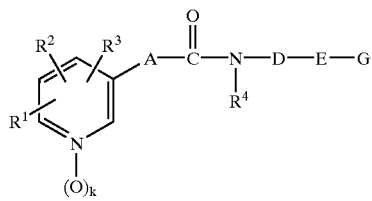
| Nr | R¹–R³ | k | A | R⁴ | D—E—G |
|----|-------|---|-----|-----|-------|
| 239 | H | 0 | CH=CH | H | |
| 240 | H | 0 | CH=CH | H | |
| 241 | H | 0 | CH=CH | H | |
| 242 | H | 0 | CH=CH | H | |
| 243 | H | 0 | CH₂CH₂ | H | |

Further subject-matter of the claims are analogous methods for the production of the compounds of formula (I) according to the invention.

According to method variant (A), compounds of formula (I) are obtained in the manner by reacting carboxylic acids of formula (II)

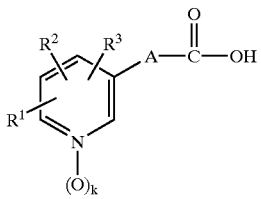
(II)

in which $R^1$, $R^2$, $R^3$, A and k have the meaning given above or their reactive derivatives with compounds of formula (III)

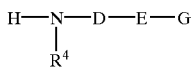
(III)

wherein D, E, G and $R^4$ are defined as above.

Reactive derivatives of compound (II) can be, for example, activated esters, anhydrides, acid halides (especially acid chlorides) or simple low alkyl esters. Suitable activated esters are, for example, p-nitrophenyl ester, 2,4,6-trichlorphenyl ester, pentachlorophenyl ester, cyanomethyl ester, esters of N-hydroxysuccinimide, N-hydroxyphthalimides, 1-hydroxybenzotriazole, N-hydroxypiperidine, 2-hydroxypyridine or 2-mercaptopyridine, etc.

Anhydrides can be symmetric anhydrides or mixed, as they are obtained, for example, with pivaloyl chloride or with chloroformates. Aromatic (for example chloroformic phenyl ester), araliphatic (for example chloroformic benzyl ester) or aliphatic chloroformates (for example chloroformic methyl ester, ethyl ester or isobutyl ester) can be used for this.

Reaction of the compounds of formula (II) with the compounds of formula (III) can also be carried out in the presence of condensation agents such as dicyclohexylcarbodiimide, 1-ethyl-3-(3-dimethylaminpropyl)carbodiimide.hydrochloride, N,N'-carbonyldiimidazole, 1-ethoxycarbonyl-2-ethoxy-1,2-dihydroquinoline, etc. If carbodiimides are used as the condensation agent, reagents such as N-hydroxysuccinimide, N-hydroxyphthalimide, 1-hydroxybenzotriazole, N-hydroxypiperidine, etc. can be advantageously added.

Compounds of formula (III) can be used for reaction as free bases as well as in the form of their acid addition salts. For this, the salts of inorganic acids are to be preferred, i.e. hydrochlorides, hydrobromides or sulfates for example.

Reaction of compounds (II) or their reactive derivatives with compounds (III) are normally carried out in a suitable, preferably inert solvent. As examples, aromatic hydrocarbons such as benzene, toluene, xylene, halogenated hydrocarbons (for example dichloromethane, chloroform, 1,2-dichloroethane, trichloroethylene), or ethers such as for example diethyl ether, tetrahydrofuran, dioxane, glycol dimethyl ether, ethyl acetate, acetonitrile or polar aprotic solvents such as, for example, dimethylsulfoxide, dimethylformamide or N-methylpyrrolidone are to be named. Pure solvents, as well as mixtures of two or more, can be used.

The reaction is optionally carried out in the presence of an auxiliary base. Suitable examples for this are alkali metal carbonates such as sodium carbonate or potassium carbonate, alkali metal hydrogen carbonates such as sodium hydrogen carbonate or potassium hydrogen carbonate or organic bases such as, for example, triethylamine, ethyl diisopropylamine, tributylamine, N-metbylmorpholine or pyridine. A suitable excess of the compound of formula (III) can also be used as a base. If compounds of formula (III) are used in form of their acid addition salts, then it is appropriate to consider the amount of auxiliary base used as equivalent.

The reaction temperatures can—depending on reactivity of the starting materials—vary in a wide range. Generally, the reaction is carried out at temperatures between −40° C. and 180° C., preferably between −10° C. and 130° C., especially at the boiling point of the solvent used.

The starting compounds (II) and (III) are known and/or can be produced according to known methods in an analogous manner. Moreover, the production of representative examples is described below.

Additionally, compounds of formula (I) wherein G corresponds to the definitions G4a to G4e can also be produced according to the variant pursuant to Method B by reacting compounds of formula (I) wherein G=NHR$^{16}$, and which themselves represent active ingredients according to the invention with suitable alkylation or arylation agents and/or carboxylic acid, carboxaminic acid, sulfonic acid or phosphinic acid derivatives of the formula (IVa) to (IVe)

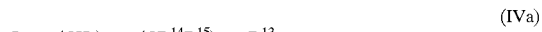
(IVa)

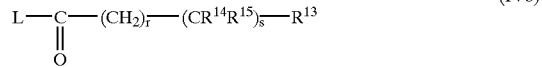
(IVb)

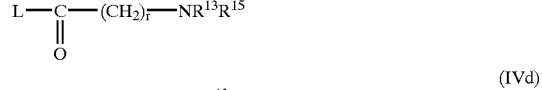
(IVc)

L—SO$_2$——(CH$_2$)$_r$—R$^{13}$
(IVd)

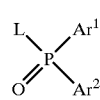
(IVe)

wherein L signifies respectively a suitable nucleofuge. The type of nucleofuge L and the conditions of the reaction are dependent of the nature of the residue to be transferred.

By means of method variant (B1), compounds of formula (I), in which G, with the exception of NHR$^{16}$, has the meaning of G4a according to the above definition can also be synthesized by reacting compounds of formula (I), in which G is NHR$^{16}$, with a suitable alkylation agent and/or arylation agent of formula (IIVa), wherein r, s, R$^{13}$, R$^{14}$, and R$^{15}$, are defined above and the leaving group L can be a reactive derivative of an alcohol, for example, a halogen atom such as chlorine, bromine or iodine or a sulfonic acid ester, i.e. for example a methanesulfonyloxy group, trifluoromethanesulfonyloxy-, ethanesulfonyloxy-, benzenesulfonyloxy-, p-toluenesulfonyloxy-, p-bromobenzenesulfonyloxy-, m-nitrobenzenesulfonyloxy group.

The reaction of compounds of formula (I), in which G is the residue NHP$^{16}$ with the compounds of formula (IVa) is usually conducted in a suitably inert solvent. Such solvents can be for example the following: aromatic hydrocarbons such as benzene, toluene, xylene; ethers such as for example tetrahydrofuran, dioxane, glycol dimethyl ether, ethyl acetate or acetonitrile, ketones such as acetone or ethyl methyl ketones, polar protic solvents such as alcohols for example ethanol, isopropanol or butanol or also glycol monomethyl ether; or polar aprotic solvents such as, for example, dimethylsulfoxide, dimethylformamide or N-methylpyrrolidone. Pure solvents as well as mixtures of two or more can also be used.

Preferably, the reactions are carried out in the presence of bases, whereby the same bases as named in method variant (A) above can be used. If chlorides or bromides are used as the compound of formula (IVa), the reaction can be accelerated in this manner by the addition of alkali metal iodides such as sodium iodide or potassium iodide. The reaction temperatures can vary between 0° C. and 180° C. depending on the reactivity of the educts, but preferably lie between 20° C. and 130° C.

According to the method variant (B2), compounds of formula (I), in which G has the meaning of G4b to G4e according to the above definition, can also be produced by reacting compounds of formula (I), wherein G is the residue $NHR^{16}$, with a carboxylic acid, carbamic acid, sulfonic acid and/or phosphinic acid of formula (Vb) to (Ve) wherein r, s, $R^{13}$, $R^{14}$, $R^{15}$, $Ar^1$, $Ar^2$ and optionally the group $NR^{13}R^{15}$ have the present meanings,

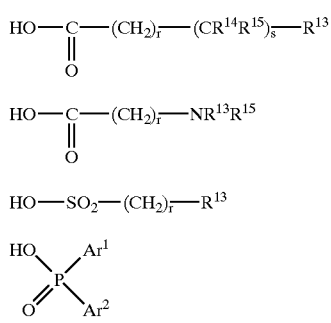

or their derivatives capable of reaction. Preferred derivatives of carboxylic acids according to formulas (Vb) and (Vc) and/or sulfonic acids of formula (Vd) which are capable of reaction are representatives of symmetric or unsymmetric carboxylic acid anhydrides and/or sulfonic acid anhydrides or carboxylic halides and/or sulfonyl halides, especially carboxylic and/or sulfonyl chlorides. Preferred derivatives of carbamates according to formula (Vc), wherein r=0, and/or phosphinic acids of formula (Ve) which are capable of reaction are the carbamoyl halides and/or phosphinyl halides, especially carbamyl- and/or phosphinyl chlorides. The reaction of the acids according to formula (V) and/or their reactive derivatives with compounds of formula (I), in which G is the residue $NHR^{16}$, preferably occurs in the presence of auxiliary bases in solvents and under conditions as they are described in method variant (A).

Compounds of formula (I), wherein G represents a carbamoyl residue according to the definition (G4c) with r=0, i.e. a group

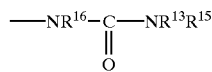

can also be produced aside according to variants (A) and (B2), pursuant to the variant method (B3) by reacting compounds of formula (I), in which G represents the residue $NHR^{16}$, with a carbonyl group transmitter to an intermediate product and subsequently reacting this directly with a primary or secondary amine with the formula (VI)

$$H-NR^{13}R^{15} \qquad (VI)$$

wherein the residues $R^{13}$ and $R^{15}$ have the meanings according to the above definitions without purifying or isolating the intermediate product.

Bis-trichloromethyl carbonate (triphosgene) and carbonyldiimidazole have been proven as particularly reactive carbonyl group transmitters. The reaction of compounds of formula (I), wherein G is residue $NHR^{16}$, with triphosgene and/or carbonyldiimidazole are typically conducted in an absolute, inert solvent in the presence of a tertiary organic amine as an auxiliary base in such a manner that the solution of compounds (I) and the auxiliary base are slowly poured into a solution of an equivalent amount of carbonyl group transmitter. Thereby, the reaction requires molar ratios of 1:1 for the reaction of compound (I) and carbonyldiimidazole, and, in contrast, a ratio of 1:0.35 for the use of triphosgene. After complete reaction of the components to the intermediate product, compound (VI) is added in stochiometric amounts or in excess as a solution or a solid and the reaction is typically completed at elevated temperature. Suitable inert solvents are, for example hydrocarbons such as hexane, heptane, benzene, toluene, xylene, chlorinated hydrocarbons such as for example dichloromethane, chloroform, 1,2-dichloroethane or trichloroethylene, ethers such as for example diethyl ether, tetrahydrofuran or dioxane, esters such as ethyl acetate, butyl acetate, acetonitrile; or polar aprodic solvents such as formamide or dimethylformamide. Pure solvents as well as mixtures of various solvents can be used. Amines such as for example triethylamine, ethyl diisopropylamine, tributylamine, N-methylmorpholine or pyridine are suitable as auxiliary bases.

If the compounds or formula (I) or formula (VI) are used as salts, the amount of the auxiliary base is increased accordingly. The reaction temperatures can lie between −40° C. and 50° C. for the first partial reaction, preferably 0° C. to 30° C., and between 0° C. and 150° C. for the second partial reaction, preferably 20° C. to 120° C.

According to method variant pursuant (B4), compounds of formula (I), wherein G represents a carbamoyl residue according to the definition (G4c) with r=0 and $R^{15}$ hydrogen, i.e. the group

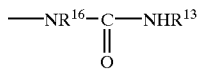

can also be produced, aside according to variants (A), (B2) and (B3), by reacting the compounds of formula (I) in which G is the residue $NHR^{16}$, with an isocyanate of formula (VII)

$$O=C=N-R^{13} \qquad (VII).$$

in which $R^{13}$ has the above defined meaning

Reaction of the compounds of formula (I), in which G is the residue $NHR^{16}$, with the isocyanates of formula (VII) are conducted thereby in absolute, inert solvents as they are named above in method (B3). Mixtures of various solvents can also be used. Thereby, the reaction temperatures can vary in the region from −20° C. to 150° C., but preferably lie at 20° C. to 100° C.

As already mentioned, the compounds of formula (I), wherein G represents the residue $NHR^{16}$, are themselves active ingredients according to the invention with tumor growth inhibiting activity. However, independent of their therapeutic applicability, they also represent useful intermediate compounds for the production of a multitude of other compounds according to the invention corresponding to the method variants (B1) to (B4).

In principle, they themselves, can be produced according to method A by reacting a carboxylic acid of formula (II) with amines of formula (III) in which G is the residue NHR$^{16}$ as. described above. However, since the compounds of formula (III) with NHR$^{16}$ as G represent α, ω-diamines, the formation of product mixtures is always to be expected in their reaction with carboxylic acids (II). In this case, this makes a subsequent separation necessary.

In contrast, compounds of formula (I), in which G is the residue NHR$^{16}$, are essentially more advantageously produced from other compounds of formula (I), in which G, within the meaning of G4, is a selectively cleavable group under mild conditions which corresponds to a nitrogen protective group.

In this connection, among the compounds according to formula (I) with the named pharmacological properties, compounds in which the nitrogen atom of G4 carries, aside from the residue R$^{16}$, G a benzyl group, a 4-methoxybenzyl group, a diphenylmethyl group, a triphenylmethyl group, a benzyloxy-carbonyl group, a methoxy- and/or ethoxycarbonyl group, a tert-butoxycarbonyl group, an allyloxycarbonyl group or a trifluoroacetyl group are particularly suitable. Thus, compounds of formula (I) with NR$^{16}$-benzyl, NR$^{16}$-diphenylmethyl, NR$^{16}$-triphenylmethyl or NR$^{16}$-benzyloxycarbonyl groups as G can already be catalytically transformed into compounds of formula (I) with NHR$^{16}$ as G at room temperature under mild conditions with elementary hydrogen or by transfer hydration. Compounds of formula (I) with a NR$^{16}$-(4-methoxybenzyl) group are converted to compounds of formula (I) with NHR$^{16}$ as G by selective oxidation with ammonium-cer(IV)-nitrate. The cleavage of simple NR$^{16}$-alkoxycarbonyl groups such as the methoxy - or ethoxycarbonyl group as well as the NR$^{16}$-trifluoroacetyl group as G in compounds of formula (I) succeed by alkali hydrolysis under mild conditions without cleaving the A and D linked amide function. This is suitably valid for the cleavage of the NR$^{16}$-triphenylmethyl group and the NR$^{16}$-tert-butoxycarbonyl group as G in compounds of formula (I) which occurs in acidic medium under mild conditions. Finally, compounds of formula (I) with an NR$^{16}$-allyloxycarbonyl group as G can be converted into such with NHR$^{16}$ G in neutral medium with palladium catalyst.

All these methods are fully familiar to the person skilled in the art, and are furthermore also documented in various monographs, see for example Greene, Wuts: Protective Groups in Organic Synthesis, New York, 1991.

The compounds of formula (I) produced according to the methods (A) to (B) can be isolated and purified in a known manner, for example by subjecting the residue after distillation of the solvent to partition, extraction, re-precipitation or re-crystallization or another purification method. For this, column chromatography on a suitable support or preparative middle or high pressure liquid chromatography (HPLC) are preferred for this.

The compounds (I) are first normally obtained in form of their free bases or their hydrates or solvates, depending on the type of isolation and purification. Their addition salts with pharmaceutically suitable acids are obtained in a typical manner by converting the base with the desired acid in a suitable solvent. Depending on the number of basic centers of compounds (I), one or more equivalent acids per mole of base can be bound.

Suitable solvents are, for example, chlorinated hydrocarbons such as dichloromethane or chloroform; ethers such as diethyl ether, dioxane or tetrahydrofuran; acetonitrile; ketones such as acetone or ethyl methyl ketone; esters such as methyl acetate or ethyl acetate or low molecular alcohols such as methanol, ethanol or isopropanol; as well as water. Pure solvents as well as mixtures of two or three solvents can also be used. The salts can be isolated by crystallization, precipitation or the evaporation of the solvent. Thereby, they optionally accumulate as hydrates or solvates.

The bases can be recovered from the salts by alkalization, for example with aqueous ammonia solution, alkali carbonate or diluted sodium hydroxide solution.

In the following, a series of compounds, according to the invention as well as the following synthetic examples are given for illustration of the above methods:

SYNTHETIC EXAMPLES

For the End Products of the Invention According to Formula (I)

In the production examples for the end products, the abbreviations stand for the following terms:

MP=melting point,

RT=room temperature,

MPLC=intermediate pressure liquid chromatography

THF=tetrahydrofuran,

DMF=dimethylformamide, abs.=absolute,

CDI=carbonyldiimidazole,

EDC=N-(3-dimethylaminopropyl)-N'-ethyl-carbodiimide hydrochloride,

HOBT=1-hydroxybenzotriazole,

TEA=triethylamine.

$^1$H-NMR-Spectrum=proton resonance spectrum, taken at 100 MHz. The chemical shifts are given in ppm against TMS as a standard (δ=0.0), whereby s=singlet, d=doublet, t=triplet, dt=doublet-triplet, m=multiplet, ar=aromatic, py=pyridine.

Example 1

N-[4-(4-Phenyl-piperidin-1-yl)-butyl]-3-pyridin-3-yl-acrylamide (Substance 52)

7.2 g (48.5 mmol) 3-(3-pyridyl)-acrylic acid are suspended in 80 ml absolute dichloromethane and after addition of two drops pyridine, are cooled to ca. 0° C. in an ice bath under moisture exclusion. 12 ml (132 mmol) of oxalyl chloride are slowly added and the mixture is first stirred for 30 min under ice cooling and then stirred overnight at RT. Subsequently, the solvent and excess oxalyl chloride are distilled off on a rotary evaporator. In order to completely remove the oxalyl chloride, the colorless residue as dried further for two hours under high-vacuum. The acid chloride obtained in this manner is suspended without further purification in 50 ml absolute dichloromethane and cooled to ca. 0° C. in an ice bath under moisture exclusion. 10.25 g (44.1 mmol) are dissolved in 50 ml absolute dichloromethane and are added dropwise to this suspension. After complete addition, the ice bath is removed and the reaction is stirred for a further two hours at RT. The mixture is subsequently concentrated, taken up in 10% sodium hydroxide solution and extracted three times each with dichloromethane. The combined organic phases are washed with 20 ml water, dried, over sodium sulfate and the solvent is removed under vacuum. The residue is chromatographically purified over silica gel with $CHCl_3/CH_3OH$ (97/3 to 90/10) and crystallized first from 40 ml acetonitrile and subsequently from 25 ml from acetic ethyl acid ester after evaporation of the solvent: Colorless crystals with a MP. of 118–119° C.; yield 1.9 g (12%).

$C_{23}H_{29}N_3O$ (363.5).

| IR-Spectrum (KBr): | $v(NH)$ 3280 $cm^{-1}$ |
| --- | --- |
| | $v(C=O)$ 1650, 1550 $cm^{-1}$ |
| | $v(C=C)$ 1620 $cm^{-1}$ |
| $^1$H-NMR-Spectrum (CDCl$_3$): | 1.45–2.75 (13H, m, C—CH$_2$—CH$_2$—C, piperidine, N—CH$_2$) |
| | 2.95–3.20 (2H, m, piperidine) |
| | 3.25–3.60 (2H, m, CONHC$\underline{H}_2$) |
| | 6.50 (1H, d, CH=C$\underline{H}$CO, J = 15.7 Hz) |
| | 6.85–7.15 (1H, m, NH) |
| | 7.05–7.40 (6H, m, Ar, Py) |
| | 7.63 (1H, d, C$\underline{H}$=CHCO, J = 15.7 Hz) |
| | 7.70–7.80 (1H, m, Py) |
| | 8.45–8.60 (1H, m, Py) |
| | 8.65–8.80 (1H, m, Py) |

Example 2

N-{4-[4-(1H-indol-3-yl)-piperidin-1-yl]-butyl}-3-pyridin-3-yl-acrylamide (Substance 54)

Production analogous to Example 1.

Batch size: 6.3 g (42.5 mmol) 3-(3-pyridyl)-acrylic acid, 11 ml (127 mmol) oxalyl chloride and 10.5 g (38.7 mmol) 4-[4-(1H-indol-3-yl)-piperidin-1-yl]-butylamine.

In the purification, chromatography first occurs with $CHCl_3/CH_3OH/NH_4OH$ (95/5/0 to 90/10/1); subsequently, crystallization occurs twice each from 40 ml methanol: Colorless crystals with an MP. 169–171° C.; yield 1.35 g $C_{25}H_{30}N_4O$ (402.5).

| IR-Spectrum (KBr): | $v(NH)$ 3250 $cm^{-1}$ |
| --- | --- |
| | $v(C=O)$ 1660, 1540 $cm^{-1}$ |
| | $v(C=C)$ 1630 $cm^{-1}$ |
| $^1$H-NMR-Spectrum (CDCl$_3$): | 1.40–2.60 (12H, m, C—CH$_2$—CH$_2$—C, piperidine, N—CH$_2$) |
| | 2.70–3.25 (3H, m, piperidine) |
| | 3.25–3.60 (2H, m, CONHC$\underline{H}_2$) |
| | 6.48 (1H, d, CH=C$\underline{H}$CO, J = 15.6 Hz) |
| | 6.80–7.45 (6H, m, Ar, Py, NH) |
| | 7.45–7.80 (3H, m, C$\underline{H}$=CHCO, Ar, Py) |
| | 7.95–8.20 (1H, m, NH) |
| | 8.40–8.60 (1H, m, Py) |
| | 8.60–8.80 (1H, m, Py) |

Example 3

N-{4-[4-(2-oxo-2,3-Dihydro-benzoimidazol-1-yl)-piperidin-1-yl]-butyl}-3-pyridin-3-yl-acrylamide (Substance 55)

Production analogous to Example 1.

Batch size: 1.47 g (9.9 mmol) 3-(3-pyridyl)-acrylic acid, 1.15 ml (13.5 mmol) oxalyl chloride and 2.6 g (9.0 mmol) 4-[4-(2-oxo-2.3-dihydro-benzoimidazol-1-yl)-piperidin-1-yl]-butylamine.

In the purification, chroratography first occurs from 25 ml acetonitrile; subsequently, chromatography occurs with $CHCl_3/CH_3OH$ (90/10): Yield 0.2 g (5%) in the form of a colorless foam.

$C_{24}H_{29}N_5O_2$ (419.5).

| IR-Spectrum (KBr): | $v(NH)$ 3250 $cm^{-1}$ |
| --- | --- |
| | $v(C=O)$ 1650, 1540 $cm^{-1}$ |
| | $v(C=C)$ 1615 $cm^{-1}$ |
| $^1$H-NMR-Spectrum (CDCl$_3$): | 1.50–2.80 (12H, m, C—CH$_2$—CH$_2$—C, piperidine, N—CH$_2$) |
| | 3.00–3.30 (2H, m, piperidine) |
| | 3.30–3.60 (2H, m, CONHC$\underline{H}_2$) |
| | 4.31–4.60 (1H, m, piperidine) |
| | 6.40–6.65 (1H, m, NH) |
| | 6.53 (1H, d, CH=C$\underline{H}$CO, J = 15.6 Hz) |
| | 6.90–7.45 (5H, m, Ar, Py) |
| | 7.65 (1H, d, C$\underline{H}$=CHCO, J = 15.6 Hz) |
| | 7.70–7.90 (1H, m, Py) |
| | 8.45–8.60 (1H, m, Py) |
| | 8.70–8.85 (1H, m, Py) |
| | 9.00–9.15 (1H, bs, NH) |

Example 4

N-[4-(4-Benzotriazol-1-yl-piperidin-1-yl)-butyl]-3-pyridin-3-yl-acrylamide (Substance 60)

Production analogous to Example 1.

Batch size: 3.1 g (22.5 mmol) 3-(3-pyridyl)-acrylic acid, 5.4 ml (45 mmol) oxalyl chloride and 5.6 g (20.5 mmol) 4-(4-benzotriazol-1-yl-piperidin-1-yl)-butylamine.

In the purification, chromatography first occurs with $CHCl_3/CH_3OH$ (98/2 to 90/10), subsequently, crystallization occurs twice each from 200 ml cholorobutane and 400 ml isopropanol/diisopropylether (1/3): Colorless crystals with an MP. 127–129° C.; Yield 1.0 g (12%).

$C_{23}H_{28}N_6O$ (404.5).

| IR-Spectrum (KBr): | $v(NH)$ 3260 $cm^{-1}$ |
| --- | --- |
| | $v(C=O)$ 1660, 1540 $cm^{-1}$ |
| | $v(C=C)$ 1625 $cm^{-1}$ |
| $^1$H-NMR-Spectrum (CDCl$_3$): | 1.40–2.00 (4H, m, C—CH$_2$—CH$_2$—C) |
| | 2.00–2.80 (8H, m, piperidine, N-CH$_2$) |
| | 3.00–3.35 (2H, m, piperidine) |
| | 3.35–3.65 (2H, m, CONHC$\underline{H}_2$) |
| | 4.55–4.95 (1H, m, piperidine) |
| | 6.25–6.60 (1H, m, NH) |
| | 6.52 (1H, d, CH=C$\underline{H}$CO, J = 15.7 Hz) |
| | 7.20–8.20 (7H, m, C$\underline{H}$=CHCO, Ar, Py) |
| | 8.50–8.70 (1H, m, Py) |
| | 8.70–8.90 (1H, m, Py) |

Example 5

N-{4-[4-(Hydroxy-diphenylmethyl)-piperidin-1-yl]-butyl}-2-(pyridin-3-yloxy)-acetamide (Substance 36)

1.8 g (11.6 mmol) (pyridin-3-yloxy)-acetic acid and 1.7 ml (12.2 mmol) TEA are suspended in 80 ml absolute dichlormethane and cooled to ca. 0° C. under moisture exclusion. 2.1 g (13.7 mmol) 88% HOBT and 2.7 g (14.1 mmol) EDC are added and the mixture is stirred for 30 min under ice-cooling. 4,. g (13.0 mmol) 4-[4-(hydroxy-diphenylmehyl)-piperidin-1-yl]-butylamine are added and the mixture is stirred overnight without cooling. Subsequently, the batch is washed with 50 ml 1M sodium hydroxide solution and twice each with 30 ml water. The organic phase is dried over sodium sulfate and the solvent is removed under vacuum. The residue is chromatographically purified over silica gel with $CHCl_3/CH_3OH/NH_4OH$ (90/10/0 to 90/10/1): Yield 2.0 g (34%) of a colorless resin.

$C_{29}H_{35}N_3O_3$ (473.6)

| | |
|---|---|
| IR-Spectrum (KBr): | ν(NH) 3300 cm$^{-1}$ |
| | ν(C=O) 1660, 1540 cm$^{-1}$ |
| $^1$H-NMR-Spectrum (CDCl$_3$): | 1.20–3.60 (18H, m, C—CH$_2$—CH$_2$—C, N—CH$_2$, OH, CONHC$\underline{H}_2$, piperidine) |
| | 4.49 (2H, s, CO—CH$_2$) |
| | 6.70–7.05 (1H, m, NH) |
| | 7.00–7.80 (12H, m, Ar, Py) |
| | 8.20–8.50 (2H, m, Py) |

Example 6

N-[4-(4,4-Diphenyl-piperidin-1-yl)-butyl]-3-pyridin-3-yl-acrylamide (Substance 82)

2.4 g (16.0 mmol) 3-(3-pyridyl)-acrylic acid and 2.9 g (17.6 mmol) CDI are heated under reflux in 150 ml absolute THF under moisture exclusion. After an hour, this is cooled to RT and 6.0 g (19.2 mmol) 4-(4,4-diphenyl-piperidin-1-yl)-butylamine, dissolved in 25 ml absolute THF, are added dropwise. After addition, this is stirred for a further three hours at RT and left to stand overnight. The mixture is poured into 200 ml water and extracted three times each with 100 ml acetic acid ethyl ester by shaking. The combined organic phases are washed with saturated NaCl-solution, dried over sodium sulfate and the solvent is removed under vacuum. The residue is chromatographically pre-purified over silica gel with $CHCl_3/CH_3OH$ (95/5). After removal of the solvent, crystallization occurs from 130 ml isopropanol: Colorless crystals with MP. 207–208° C.: Yield 2.0 g (28%).

$C_{29}H_{33}N_3O$ (439.6).

| | |
|---|---|
| IR-Spectrum (KBr): | ν(NH) 3260 cm$^{-1}$ |
| | ν(C=O) 1650, 1550 cm$^{-1}$ |
| | ν(C=C) 1610 cm$^{-1}$ |
| $^1$H-NMR-Spectrum (CDCl$_3$): | 1.50–1.75 (4H, m, C—CH$_2$—CH$_2$—C) |
| | 2.20–2.70 (10H, m, piperidine, N-CH$_2$) |
| | 3.25–3.55 (2H, m, CONHC$\underline{H}_2$) |
| | 6.46 (1H, d, CH=C$\underline{H}$CO, J = 15.7 Hz) |
| | 7.00–7.35 (12H, m, Ar, Py) |
| | 7.60 (1H, d, C$\underline{H}$=CHCO, J = 15.7 Hz) |
| | 7.60–7.75 (1H, m, Py) |
| | 8.45–8.60 (1H, m, Py) |
| | 8.60–8.75 (1H, m, Py) |

Example 7

N-{4-[4-(6,11-Dihydro-dibenzo[b,e]thiepin-11-yliden)-piperidin-1-yl]-butyl}-3-pyridin-3-yl-propionamid.-dihydrochlorid.semi-isopropanol (Substance 110 as a dihydrochloride)

Production analogous to Example 6.

Batch size: 1.4 g (9.3 mmol) 3-(3-pyridyl)-propionic acid, 1.6 (9.9 mmol) CDI and 3.0 g (8.2 mmol) 4-[4-(6,11-dihydro-dibenzo-[b,e]thiepin-11-yliden)-piperidin-1-yl]-butylamine.

In the purification, this is chromatographically purified over silica gel with $CHCl_3/CH_3OH/NH_4OH$ (95/5/0.5).

After removal of the solvent, the residue is dissolved in 35 ml isopropanol and mixed with 3 ml 6.5M isopropanolic HCl-solution and rotated in: amorphous solid with MP. 123–135° C.: Yield 2.6 g (53%).

$C_{31}H_{35}N_3OS.2HCl.\frac{1}{2}C_3H_6O$ (600.7).

| | |
|---|---|
| IR-Spectrum (KBr): | ν(NH) 3400 cm$^{-1}$ |
| | ν(C=O) 1640, 1545 cm$^{-1}$ |
| $^1$H-NMR-Spectrum (CD$_3$OD): | 1.35–2.00 (4H, m, C—CH$_2$—CH$_2$—C) |
| | 2.30–3.75 (18H, m, piperidine, N—CH$_2$, CONHC$\underline{H}_2$, S—CH$_2$, CO—CH$_2$, Py-CH$_2$) |
| | 6.95–7.45 (8H, m, Ar) |
| | 7.90–8.10 (1H, m, Py) |
| | 8.45–8.65 (1H, m, Py) |
| | 8.65–8.85 (2H, m, Py) |

Example 8

N-{4-[4-(6,11-Dihydro-dibenzo[b,e]thiepin-11-yliden)-piperidin-1-yl]-butyl]-5-pyridin-3-yl-pentanamide (Substance 112)

Production analogous to Example 6.

Batch size: 1.6 g (9.0 mmol) 5-(3-pyridyl)-pentanic acid, 1.6 g (9.9 mmol) CDI and 3.0 g (8.2 mmol) 4-[4-(6,11-dihydro-dibenzo-[b,e]thiepin-11-yliden)-piperidin-1-yl]-butylamine.

In the purification, this is chromatographically purified over silica gel with $CHCl_3/CH_3OH/NH_4OH$ (97/3/0,3): Yield 2.4 g (55%) of a light brown resin.

$C_{33}H_{35}N_3OS$ (525.8).

| | |
|---|---|
| IR-Spectrum (KBr): | ν(NH) 3270 cm$^{-1}$ |
| | ν(C=O) 1640, 1545 cm$^{-1}$ |
| $^1$H-NMR-Spectrum (CDCl$_3$): | 1.40–1.80 (8H, m, C—CH$_2$—CH$_2$—C) |
| | 2.00–2.80 (14H, m, piperidine, N—CH$_2$, CO—CH$_2$, Py-CH$_2$) |
| | 3.10–3.40 (2H, m, CONHC$\underline{H}_2$) |
| | 3.39 (1H, d, S—CH$_2$, J = 13.3 Hz) |
| | 4.92 (1H, d, S—CH$_2$, J = 13.3 Hz) |
| | 6.05–6.30 (1H, m, NH) |
| | 6.90–7.35 (9H, m, Ar, Py) |
| | 7.40–7.60 (1H, m, Py) |
| | 8.30–8.55 (2H, m, Py) |

Example 9

N-{4-[4-(4,9-Dihydro-thieno[2,3-b]benzo[e]thiepin-4-yliden)-piperidin-1-yl]-butyl}-3-pyridin-3-yl-propionamide (Substance 117)

Production analogous to Example 6.

Batch size: 1.4 g (9.0 mmol) 3-(3-pyridyl)-propionic acid, 1.6 g (9.9 mmol) CDI and 4.0 g (10.8 mmol) 4-[4-(4,9-dihydro-thieno[2,3-b]-benzo[e]-thiepin-4-yliden)-piperidin-1-yl]butylamine.

In the purification, chromatography occurs over silica gel with $CHCl_3/CH_3OH$ (95/5 to 90/10); subsequently, this is crystallized from 25 ml acetonitrile: Colorless crystals with MP. 80–81° C.: Yield 2.9 g (64%).

$C_{29}H_{33}N_3OS_2$ (503.7).

| | |
|---|---|
| IR-Spectrum (KBr): | ν(NH) 3300 cm$^{-1}$ |
| | ν(C=O) 1670, 1535 cm$^{-1}$ |
| $^1$H-NMR-Spectrum (CDCl$_3$): | 1.25–1.70 (4H, m, C—CH$_2$—CH$_2$—C) |
| | 1.90–2.85 (12H, m, piperidine, N—CH$_2$, CO—CH$_2$) |
| | 2.85–3.10 (2H, m, Py-CH$_2$) |
| | 3.10–3.40 (2H, m, CONHC$\underline{H}_2$) |
| | 3.52 (1H, d, S—CH$_2$, J = 13.3 Hz) |
| | 4.91 (1H, d, S—CH$_2$, J = 13.3 Hz) |
| | 6.10–6.40 (1H, m, NH) |
| | 6.72 (1H, d, Ar, J = 5.2 Hz) |
| | 7.02 (1H, d, Ar, J = 5.2 Hz) |
| | 6.95–7.45 (5H, m, Ar, Py) |
| | 7.45–7.70 (1H, m, Py) |
| | 8.40–8.60 (2H, m, Py) |

Example 10

N-{4-[4-(4,9-Dihydro-thieno[2,3-b]-benzo[e]thiepin-4-yliden)-piperidin-1-yl])-butyl)}-3-pyridin-3-yl-acrylamide (Substance 118)

Production analogous to Example 6.

Batch size: 1.3 g (9.0 mmol) 3-(3-pyridyl)-acrylic acid, 1.6 g (9.9 mmol) CDI and 4.0 g (10.8 mmol) 4-[4-(4,9-dihydrothieno[2,3-b]-benzo [e]thiepin-4-yliden)-piperidin-1-yl]-butylamine.

In the purification, flash-chromatography is carried out twice with CHCl$_3$/CH$_3$OH (100/0 to 95/5 and 100/0 to 98/2); subsequently, this is crystallized from 20 ml acetic acid ethyl ester: Colorless crystals pith an MP. 131–135° C.; Yield 0.9 g (20%).

$C_{29}H_{31}N_3OS_2$ (501.7).

| | |
|---|---|
| IR-Spectrum (KBr): | ν(NH) 3300 cm$^{-1}$ |
| | ν(C=O) 1655, 1545 cm$^{-1}$ |
| | ν(C=C) 1620 cm$^{-1}$ |
| $^1$H-NMR-Spectrum (CDCl$_3$): | 1.40–1.80 (4H, m, C—CH$_2$—CH$_2$—C) |
| | 1.90–3.00 (10H, m, piperidine, N—CH$_2$) |
| | 3.25–3.55 (2H, m, CONHC$\underline{H}_2$) |
| | 3.52 (1H, d, S—CH$_2$, J = 13.4 Hz) |
| | 4.90 (1H, d, S—CH$_2$, J = 13.4 Hz) |
| | 6.49 (1H, d, CH=C$\underline{H}$CO, J = 15.7 Hz) |
| | 6.60–6.85 (1H, m, NH) |
| | 6.72 (1H, d, Ar, J = 5.2 Hz) |
| | 6.95–7.15 (1H, m, Py) |
| | 7.02 (1H, d, Ar, J = 5.2 Hz) |
| | 7.15–7.45 (4H, m, Ar) |
| | 7.62 (1H, d, C$\underline{H}$=CHCO, J = 15.7 Hz) |
| | 7.70–7.90 (1H, m, Py) |
| | 8.45–8.60 (1H, m, Py) |
| | 8.65–8.80 (1H, m, Py) |

Example 11

N-[4-(4-Diphenylphosphinoyloxy-piperidin-1-yl)-butyl]-3-pyridin-3-yl-acrylamide (Substance 188)

Production analogous to Example 1.

Batch size: 2.15 g (14.4 mmol) 3-(3-pyridyl)-acrylic acid, 4 ml (39 mmol) oxalyl chloride and 4.9 g (13.1 mmol) 4-(4-diphenyl-phosphinoyloxy-piperidin-1-yl)-butylamine.

In the purification, chromatography first occurs with CHCl$_3$/CH$_3$OH/NH$_4$OH (90/10/1); subsequently, crystallization occurs from diisopropylether: Colorless crystals with an MP. 151–153° C.: Yield 3.9 g (63%).

$C_{29}H_{34}N_3O_3P$ (503.6).

| | |
|---|---|
| IR-Spectrum (KBr): | ν(NH) 3270 cm$^{-1}$ |
| | ν(C=O) 1665, 1540 cm$^{-1}$ |
| | ν(C=C) 1625 cm$^{-1}$ |
| $^1$H-NMR-Spectrum (CDCl$_3$): | 1.40–1.80 (4H, m, C—CH$_2$—CH$_2$—C) |
| | 1.80–2.90 (10H, m, piperidine, N—CH$_2$) |
| | 3.20–3.55 (2H, m, CONHC$\underline{H}_2$) |
| | 4.30–4.65 (1H, m, piperidine) |
| | 6.50 (1H, d, CH=C$\underline{H}$CO, J = 15.7 Hz) |
| | 6.70–7.00 (1H, m, NH) |
| | 7.15–8.00 (13H, m, Ar, Py, C$\underline{H}$=CHCO) |
| | 8.45–8.65 (1H, m, Py) |
| | 8.65–8.80 (1H, m, Py) |

Example 12

N-[4-(1,4-Dioxa-8-azaspiro[4.5]dec-8-yl)-butyl]-3-pyridin-3-yl-acrylamide (Substance 92)

Production analogous to Example 6.

Batch size: 4.0 g (26.8 mmol) 3-(3-pyridyl)-acrylic acid, 5.7 g (35.2 mmol) CDI and 6.4 g (29.9 mmol) 4-(1,4-Dioxa-8-azaspiro[4.5]dec-8-yl)-butylamine.

In the purification, chromatography occurs twice over silica gel with CHCl$_3$/CH$_3$OH/NH$_4$OH (95/5/0 to 91/9/0 and 90/9/0,5): Yield 0.3 g (3%) as colorless resin.

$C_{19}H_{27}N_3O_3$ (345.4).

| | |
|---|---|
| IR-Spectrum (CH$_2$Cl$_2$): | ν(NH) 3320 cm$^{-1}$ |
| | ν(C=O) 1680, 1560 cm$^{-1}$ |
| | ν(C=C) 1640 cm$^{-1}$ |
| $^1$H-NMR-Spectrum (CDCl$_3$): | 1.40–1.95 (8H, m, C—CH$_2$—CH$_2$—C, piperidine) |
| | 2.20–2.90 (6H, m, piperidine, N—CH$_2$) |
| | 3.20–3.55 (2H, m, CONHC$\underline{H}_2$) |
| | 3.96 (4H, s, O—CH$_2$—CH$_2$—O) |
| | 6.49 (1H, d, CH=C$\underline{H}$CO, J = 15.7 Hz) |
| | 6.90–7.15 (1H, m, NH) |
| | 7.20–7.40 (1H, m, Py) |
| | 7.61 (1H, d, C$\underline{H}$=CHCO, J = 15.7 Hz) |
| | 7.70–7.90 (1H, m, Py) |
| | 8.50–8.65 (1H, m, Py) |
| | 8.65–8.80 (1H, m, Py) |

PRODUCTION OF THE STARTING SUBSTANCES

Example A 4-(4-Phenyl-piperidin-1-yl)-butylamine
a) 2-[4-(4-Phenyl-piperidin-1-yl)-butyl]-isoindolin-1,3-dione:
b)
10.0 g (62.4 mmol) 4-phenylpiperidine, 18.0 g (62.4 mmol) N-(4-bromobutyl)-phthalimide and 17.3 g (125 mmol) potassium carbonate are suspended in 100 ml DMF and stirred for three hours at 60° C. After cooling, the mixture is concentrated under vacuum and the residue is distributed between chloroform and water. The organic phase is dried over sodium sulfate and steam evaporated under vacuum until dry. The residue is chormatographically purified over silica gel with CHCl$_3$/CH$_3$OH (95/5): Yield 20.7 g.
b) 4-(4-Phenyl-piperidin-1-yl)-butylamine:
   c)
   20 g (61.2 mmol) 2-[4-(4-phenyl-piperidin-1-yl)-butyl]-isoin-dolin-1,3-dione and 6.1 g (122.5 mmol) hydrazine hydrate are heated under reflux in 250 ml ethanol for 3 hours. The cooled solution is concentrated under vacuum and the residue is taken up in chloroform. The suspension is filtered and the residue is distributed between chloroform and 10% sodium hydroxide solution. The combined organic phases are dried over sodium sulfate and steam evaporated under vacuum until dry. The resin is further processed without further purification: Yield 11.7 g (82%).

Example B

4-[4-(1H-Indol-3-yl)-piperidin-1-yl]-butylamine
a) 2-{4-[4-(1H-indol-3-yl)-piperidin-1-yl]-butyl}-isoindolin-1,3-dione:
   The reaction of the piperidine with the phthalimide occurs analogously to Example A)a).
   Batch size: 20 g (99.9 mmol) 4-(3-indoylpiperidine), 29.6 (104.9 mmol) N-(4-bromobutyl)-phthalimide and 20.3 g (149.8 mmol) potassium carbonate in 250 ml DMF.
   Purification occurs by chromatography over silica gel with CHCl$_3$/CH$_3$OH (98/2 to 95/5): Yield 33.8 g (84%).
b) 4-[4-(1H-Indol-3-yl)-piperidin-1-yl]-butylamine:
   Reaction of the phthalimide to the amine occurs analogously to Example A)b).
   Batch size: 23.5 g (58.5 mmol) 2-{4-[4-(1H-indol-3-yl)-piperi-din-1-yl]-butyl}-isoindolin-1,3-dione and 6.0 ml (117 mmol) hydrazine.hydrate in 150 ml ethanol.
   In the work-up, acetic acid ethyl ester is used instead of chloroform. The accumulated crude product is further processed without further purification: Yield 10.5 g (66%).

Example C

4-[4-(2-oxo-2,3-Dihydro-benzoimidazol-1-yl)-piperidin-1-yl]-butylamine
a) 2-{4-[4-(2-oxo-2,3-Dihydro-benzoimidazol-1-yl)-piperidin-1-yl]-butyl}-isoindolin-1,3-dione:
   Reaction of the piperidine with the phthalimide occurs analogously to Example A)a).
   Batch size: 15.0 g (69 mmol) 4-(2-oxo-2,3-dihydrobenzoimid-azol-1-yl)-piperidine, 19.4 (69 mmol) N-(4-bromobutyl)-phthalimide and 19.0 g (138 mmol) potassium carbonate in 220 ml DMF.
   The mixture is stirred at RT for 24 hours. The purification occurs by chromatography over silica gel with CHCl$_3$/CH$_3$OH (95/5): Yield 11.8 g (40%).
b) 4-[4-(2-oxo-2,3-Dihydro-benzoimidazo-1-yl)-piper4din-1-yl]-butylamine:
   Reaction of the phthalimide to the amine occurs analogously to Example A)b).
   Batch size: 11.5 g (27.4 mmol) 2-{4-[4-(2-oxo-2,3-dihydro-benzoimidazol-1-yl)-piperidin-1-yl]-butyl}-isoindolin-1,3-dione and 2.7 ml (55 mmol) hydrazine.hydrate in 60 ml ethanol. The accumulated crude product is further processed without further purification: Yield 5.1 g (64%).

Example D 4-(4-Benzotriazol-1-yl-piperidin-1-yl)-butylamine
a) 2-[4-(4-Benzotriazol-1-yl-piperidin-1-yl)-butyl]-isoindolin-1,3-dione:
   Reaction of the phthalimide to the amine occurs analogously to Example A)a).
   Batch 10.0 g (49.4 mmol 4-(4-benzotriazol-1-yl)-piperidine, 13.9 (490.4 mmol) N-(4-bromobutyl)-phthalimide and 19.0 g (144.7 mmol) potassium carbonate in 120 ml DMF.
   The purification occurs by chromatography over silica gel with CHCl$_3$/CH$_3$OH (98/2): Yield 16.3 g (88%).
b) 4-(4-Benzotriazol-1-yl-piperidin-1-yl)-butylamine:
   Reaction of the phthalimide to the amine occurs analogously to Example A)b).
   Batch size: 16.3 g (42.7 mmol) 2-[4-(4-benzotriazol-1-yl-pi-peridin-1-yl)-butyl]-isoindolin-1,3-dione and 4.8 ml (98 mmol) hydrazine.hydrate in 130 ml ethanol.
   In the work-up, acetic acid ethyl ester is used instead of chloroform. Purification occurs by chromatography over silica gel with CHCl$_3$/CH$_3$OH/NH$_4$OH (90/10/0 to 80/20/2): Yield 5.6 g (47%).

Example E

4-[4-(Hydroxy-diphenylmethyl)-piperidin-1-yl]-butylamine
a) 2-(-[4-(Hydroxy-diphenylmethyl)-piperidin-1-yl]-butyl)-isoindolin-1,3-dione:
   Reaction of the piperidine with the phthalimide occurs analogously to Example A)a).
   Batch size: 50.0 g (187 mmol) 4-(diphenyl-hydroxymethyl)-pi-peridine, 58.0 (206 mmol) N-(4-bromobutyl)-phthalimide and 31.0 g (224 mmol) potassium carbonate in 250 ml DMF.
   Purification occurs by a crystallization from 200 ml acetic acid ethyl ester. Colorless crystals with MP. 148–150° C. Yield 65.0 g (74%).
b) 4-[4-(Hydroxy-diphenylmethyl)-piperidin-1-yl]-butylamine:
   Reaction of the phthalimide to the amine occurs analogously to Example A)b).
   Batch size: 60.0 g (128 mmol) 2-{4-[4-(hydroxy-diphenyl-methyl)-piperidin-1-yl]-butyl}-isoindolin-1,3-dione and 12.8 g (256 mmol) hydrazine.hydrate in 300 ml ethanol.
   In the work-up, toluene at 50° C. is used instead of chloroform. The organic phase is cooled and the resulting precipitate is filtered off. Colorless crystals with an MP. 90° C.: Yield 36.0 g (83%).

Example F 4-(4,4-Diphenyl-piperidin-1-yl)-butylamine
a) 2-[4-(4,4-Diphenyl-piperidin-1-yl)-butyl]-isoindolin-1,3-dione:
   30.0 a (124 mmol) 4,4-Diphenylpiperidine, 35.2 g (124 mmol) N-(4-bromobutyl)-phthalimide, 25.9 g (186 mmol) potassium carbonate and 25.8 g (170 mmol) sodium iodide are suspended in 500 mmol ethyl methyl ketone and heated to boiling for five hours. Alter cooling, the solvent is distilled off and the residue is distributed between chloroform and water. The organic phase is dried over sodium sulfate and steam evaporated under vacuum until dry. The residue is crystallized from 100 ml acetonitrile. Colorless crystals with a MP. 123–125° C.: Yield 42.0 g (75%).
b) 4-(4,4-Diphenyl-piperidin-1-yl)-butylamine:
   Reaction of the phthalimide to the amine occurs analogously to Example A)b).
   Batch size: 40.0 g (90.3 mmol) 2-[4-(4,4-diphenyl-piperidin-1-yl)-butyl]-isoindolin-1,3-dione and 8.8 ml (180.6 mmol) hydrazine.hydrate in 400 ml ethanol.

In the work-up, dichloromethane is used instead of chloroform. The accumulated crude product is further processed without further purification: Yield 17.3 g (62%).

Example G

4-[4-(6,11-Dihydro-dibenzo[b,e]thiepin-11-yliden)-piperidin-1-yl]-butylamine a) 2-{4-[4-(6,11-Dihydro-dibenzo[b,e]thiepin-11-yliden)-piperi-din-1-yl]-butyl}-isoindolin-1,3-dione.hydrochloride:

The reaction of the piperidine with the phthalimide occurs analogously to Example A)a).

Batch size: 20.0 g (60.6 mmol) 4-(6,11-dihydro-dibenzo[b,e]-thiepin-1-yliden)-piperidine.hydrochloride, 19.0 (66 mmol) N-(4-bromobutyl)-phthalimide and 25.0 g (180 mmol) potassium carbonate in 150 ml DMF.

The reaction occurs overnight without heating.

In the purification, the residue is dissolved in 300 ml methanol and mixed with 20 ml 6.5M isopropanolic hydrochloric acid. The salt precipitating in the cold is drawn off and dried: Yield 39.6 g (78%).

b) 4-[4-(6,11-Dihydro-dibenzo[b,e]thiepin-11-yliden)-piperidin-1-yl]-butylamine:

The reaction of the phthalimide to the amine occurs analogously to Example A)b).

Batch size: 3.0 g (56.4 mmol) 2-{4-[4-(6,11-dihydro-dibenzo-[b,e]thiepin-11-yliden)-piperidin-1-yl]-butyl}-isoindolin-1,3-dione hydrochloride and 5.7 ml (120 mmol) hydrazine.hydrate in 300 ml ethanol.

In the work-up, toluene is used chloroform. The accumulated crude product is further processed without further purification: Yield 20.2 g (81%).

Example H

4-[4-(4,9-Dihydro-thieno[2,3-b]-benzo[b,e]thiepin-4-yliden)-piperidin-1-yl]-butylamine a) 2-{4-[4-(4,9-Dihydro-thieno[2,3-b]-benzo[e]thiepin-4-yliden)-piperidin-1-yl]-butyl}-isoindolin-1,3-dione:

The reaction of the piperidine with the phthalimide occurs analogously to Example A)a).

Batch size: 40.0 g (119.1 mmol) 4-(4,9-dihydro-thieno[2,3-b]-benzo[e]thiepin-4-yliden)-piperidine.hydrochloride, 35.6 (123.8 mmol) N-(4-bromobutyl)-phthalimide and 49.2 g (357.2 mmol) potassium carbonate in 400 ml DMF.

The reaction occurs overnight at RT.

In the work-up acetic acid ethyl ester is used instead of chloroform. In the purification, the residue is crystallized from 400 mmol dioxane/water (10/1): Yield 39.0 g (65%).

b) 4-[4-(4,9-Dihydro-thieno[2,3-b]-benzo[e]thiepin-4-yliden-piper-din-1-yl]-butylamine:

Reaction of the phthalimide to the amine occurs analogously to Example A)b).

Batch size: 47.0 g (93.9 9mmol) 2-[4-[4-(4,9-dihydro-thieno[2,3-b]-benzo [e]thiepin-4-yliden)-piperidin-1-yl]-butyl]-isoindolin-1,3-dione and 9.0 ml (187.7 mmol) hydrazine.hydrate in 470 ml ethanol.

In the work-up, toluene is used instead of chloroform. The accumulated crude product is further processed without further purification: Yield 38.0 g.

Example I 4-(4-Diphenylphosphinoyloxypiperidin-1-yl)-butylamine a) 2-[4-(4-Hydroxypiperidin-1-yl)-butyl]-isoindolin-1,3-dione:

The reaction of the piperidine with the phthalimide occurs analogously to Example A)a) under addition of sodium iodide.

Batch size: 15.0 g (146.3 mmol) 4-hydroxypiperidine, 41.8 (148.3 mmol) N-(4-bromobutyl)-phthalimide, 41.0 g (296.6 mmol) potassium carbonate and 4.5 g (30 mmol) sodium iodide in 300 ml DMF.

The accumulated crude product is further without further purification: Yield 33.2 g (74%).

b) 2-[4-(4-Diphenylphosphinoyloxy-piperidin-1-yl)-butyl]-isoindolin-1,3-dione:

20.0 g (66.1 mmol) 2-[4-(4-hydroxypiperidin-1-yl)-butyl]-isoindolin-1,3-dione and 9.2 ml (66.1 mmol) TEA are dissolved in 100 ml absolute dichloromethane and cooled to ca. 0° C. under moisture exclusion. 13.0 ml diphenylphosphinic chloride are added dropwise and the mixture is heated at RT for two hours. Subsequently, the batch is washed twice with water. The organic phase is dried over sodium sulfate and the solvent is removed under vacuum. The accumulated crude product is further processed without purification: Yield 32.0 g (96%).

c) 4-(4-Diphenylphosphinoyloxypiperidin-1-yl)-butylamine:

Reaction of the phthalimide to the amine occurs analogously to Example A)b).

Batch size: 25.0 g (49.7 mmol) 2-[4-(4-diphenylphosphinoyloxy-piperidin-1-yl]-butyl-isoindolin-1,3-dione and 5.0 g (99.5 mmol) hydrazine.hydrate in 200 ml ethanol.

In the work-up, acetic acid ethyl ester is used instead of chloroform. The accumulated crude product is further processed without purification: Yield 13.0 g (70%).

Example J 4-(1,4-Dioxa-8-azaspiro[4.5]dec-8-yl)-butylamine

2-[4-(1,4-dioxa-8-azaspiro[4.5]dec-8-yl)-butyl]-isoindolin-1,3-dione:

The reaction of the piperidine with the phthalimide occurs analogously to Example A)a).

Batch size: 9.4 g (65.6 mmol) piperidon-4-ethylenketal-18,5 g (65.6 mmol) N-(4-bromobutyl)-phthalimide and 20.0 g (144 mmol) potassium carbonate in 200 ml ethyl methyl ketone.

The reaction mixture is heated under reflux for 6 hours. The purification occurs by chromatography over silica gel with. $CHCl_3/CH_3OH$ (97/3): Yield 22.0 g (97%).

b) 4-(1,4-Dioxa-8-azaspiro[4.5]dec-6-yl)-butylamine:

Reaction of the phthalimide to the amine occurs analogously to example A)b).

Batch size: 21.9 g (63.6 mmol) 2-[4-(1,4-dioxa-8-azaspiro [4.5]dec-8-yl)-butyl]-isoindolin-1,3-dione and 6.2 ml (127 mmol) hydrazine.hydrate in 200 ml ethanol.

In the work-up, the acetic acid ethyl ester is used instead of chloroform. The accumulated crude product is further processed without further purification: Yield 6.4 g (47%).

The active ingredients according to the invention can be processed to the desired medicaments in the form of their acid addition salts, hydrates or solvates individually or in combination with each other, optionally under addition of other active ingredients. In the case of the combination of active ingredients according to the invention with other medicinals, these can also optionally be separately present next to each other in the medicine packaging, for example as tablets next to vials, depending on the requirements.

Further subject-matter of the invention is a method for the treatment of the human or animal body in which a compound or compound mixture according to formula (I), wherein the substituents have the above described meanings, is administered for treatment of tumors and/or as a cytostatic agent, cancerostatic agent or as an immunosuppressing agent, optionally in combination with further cytostatic or immunosuppressive active ingredients or other active ingredients suitable for the named indications.

Furthermore, the invention relates to a compound or compound mixture according to formula (I) for use in a diagnostic therapeutic method in which the therapeutic use is carried out in connection with one or more medical indications with tumors or for immunosuppression, optimally in combination with further pharmaceuticals suitable for the named indications.

The use of one or more compounds according to formula (I) for the production of diagnostic agents or medicaments for the treatment t he human or animal body, especially in connection with one or more medical indications in the treatment of tumors or for immunosuppression, optimally in combination with further pharmaceuticals suitable in these indications or the use of compounds according to formula (I) in a corresponding diagnosis method also represent an embodiment according to the invention, whereby the compounds for the designated medical indications are included that are excluded from the product claims in view of the definition of group G. The medical indications according to the invention of the compounds excluded from the protective scope of the compound claims are new.

The respective suitable tumor indications are illustrated in the last section of the description in the discussion of the pharmacological test results.

A method for the production of medicaments with an amount of one or more compounds according to formula (I) which are suitable for the processing of these active ingredients together with respective suitable pharmaceutically acceptable carriers and adjuvants for finished medicinal forms equally belongs to the scope of protection according to the invention.

Depending on the medical indication being considered, the respective suitable medicinal form is selected for the suitable therapeutic application. Thereby 0.001 or 0.01 to 2 mg and/or 0.1, 1, 2, 5, 10, 20, 25, 30, 50, 100, 200, 300, 500, 600, 800, 1000, 2000, 3000, 4000 or 5000 mg are considered as a single dosage unit.

The invention also relates to the use of the compounds according to formula (I) for treatment in the above indications, as well as a diagnostic agent.

The production methods of the respective suitable medicaments as well as a series of examples of medicinal forms and pharmacological activities are described in the following for better understanding of the invention. The following given examples as well as the above synthesis examples serve for illustration of the claims without limiting the protective scope. Skilled persons can correspondingly modify the invention within the framework of their normal capabilities without deviating from the protective scope.

Therapeutic Administration Forms

The production of medicaments with an amount Of one or more compounds according to the invention and/or their use in the application according to the invention occurs in the customary manner by means of common pharmaceutical technology methods. For this, the active ingredients as such or in the form of their salts are processed together with suitable, pharmaceutically acceptable adjuvants and carriers to medicinal forms suitable for the various indications and types of application. Thereby, the medicaments can be produced in such a manner that the respective desired release rate is obtained, for example a quick flooding and/or a sustained or depot effect.

Preparations for parenteral use, to which injections and infusions belong, are among the most important systemically employed medicaments for tumor treatment as well as for other indications.

Preferably, injections are administered for the treatment of tumors. These are prepared either in the form of vials or also as so-called ready-to-use injection preparations, for example as ready-to-use syringes or single use syringes in addition to perforation bottles for multiple withdrawals. Administration of the injection preparations can occur in the form of subcutaneous (s.c.), intramuscular (i.m.), intravenous (i.v.) or intracutaneous (i.c.) application. The respective suitable injection forms can especially be produced as solutions, crystal suspensions, nanoparticular or colloid-disperse systems, such as for example, hydrosols.

The injectable formulations can also be produced as concentrates which can be adjusted with aqueous isotonic dilution agents to the desired active ingredient dosage. Furthermore, they can also be produced as powders, such as for example lyophilisates, which are then preferably dissolved or dispersed immediately before application with suitable diluents. The infusions can also be formulated in the form of isotonic solutions, fat emulsions, liposome formulations, microemulsions and liquids based on mixed micells, for example, based on phospholipids. As with injection preparations, infusion formulations can also be prepared in the form of concentrates to dilute. The injectable formulations can also be applied in the form of continuous infusions as in stationary as well as in out-patient therapy, for example in the form of mini-pumps.

Albumin, plasma expanders, surface active compounds, organic solvents, pH influencing compounds, complex forming compounds or polymeric compounds can be added to the parenteral medicinal forms, especially as substances for influencing the d adsorption of the active ingredients to protein or polymers or also with the aim of decreasing the adsorption of the active ingredient to materials such as injection instruments or packaging materials, for example plastic or glass.

The active ingredients can be bound to nanoparticles in the preparations for parenteral use, for example on finely dispersed particles based on poly(meth)acrylates, polyacetates, polyglycolates, polyamino acids or polyether urethanes. The parenteral formulations can also be constructively modified as depot preparations, for example on the multiple unit principle, where the active ingredients are incorporated in a most finely distributed and/or dispersed, suspended form or as crystal suspensions, or on the single unit principle, where the active ingredient is enclosed in a medicinal form, for example, a tablet or a seed which is subsequently implanted. Often, these implantations or depot medicaments in single unit and multiple unit medicinal forms consist of so-called biodegradable polymers, such as for example, polyether urethanes of lactic and glycolic acid, polyether urethanes, polyamino acids, poly(meth)acrylates or polysaccharides.

Sterilized water, pH value influencing substances, such as for example organic and inorganic acids or bases as well as their salts, buffer substances for setting the pH value, agents for isotonicity, such as for example sodium chloride, monosodium carbonate, glucose and fructose, tensides and/or surface active substances and emulsifiers, such as for example, partial fatty acid esters of polyoxyethylene sorbitan (Tween®) or for example fatty acid esters of polyoxyethylene (Cremophor®), fatty oils such as for example peanut oil, soybean oil and castor oil, synthetic fatty acid esters, such as for example ethyl oleate, isopropyl myristate and neutral oil (Miglyol®) as well as polymer adjuvants such as for example gelatine, dextran, polyvinylpyrrolidone, organic solvent additives which increase solubility, such as for example propylene glycol, ethanol, N,N-dimethylacetamide, propyene glycol or complex forming compounds such as for example citrates and urea, preservatives, such as for example hydroxypropyl benzoate and hydroxymethyl benzoate, benzyl alcohol, anti-oxidants, such as for example sodium sulfate and stabilizers, such as for example EDTA, are suitable as adjuvants and carriers in the production of preparations for parenteral use.

In suspensions, addition of thickening agents to prevent the settling of the active ingredients from tensides and peptizers, to secure the ability of the sediment to be shaken, or complex formers, such as EDTA, ensues. This can also be achieved with the various polymeric agent complexes, for example with polyethylene glycols, polystyrol, carboxymethylcellulose, Pluronics® or polyethylene glycol sorbitan fatty acid esters. The active ingredient can also be incorporated in liquid formulations in the form of inclusion compounds, for example with cyclodextrins. As further adjuvants, dispersion agents are also suitable. For production of lyophilisates, builders are also used, such as for example mannite, dextran, saccharose, human albumin, lactose, PVP or gelatine varieties.

As long as the active ingredients are not incorporated in the liquid medicinal formulations in the form of a base, they are used in the form of their acid addition salts, hydrates or solvates in the preparations for parenteral use.

A further systemic application form of importance is peroral administration as tablets, hard or soft gelatine capsules, coated tablets, powders, pellets, microcapsules, oblong compressives, granules, chewable tablets, lozenges, gums or sachets. These solid peroral administration forms can also be prepared as sustained action and/or depot systems. Among these are medicaments with an amount of one or more micronized active ingredients, diffusions and erosion forms based on matrices, for example by using fats, wax-like and/or polymeric compounds, or so-called reservoir systems. As a retarding agent and/or agent for controlled release, film or matrix forming substances, such as for example ethylcellulose, hydroxypropylmethylcellulose, poly(meth)acrylate derivatives (for example Eudragit®), hydroxypropylmethylcellulose phthalate are suitable in organic solutions as well as in the form of aqueous dispersions. In this connection, so-called bio-adhesive preparations are also to be named in which the increased retention time in the body is achieved by intensive contact with the mucus membranes of the body. An example of a bio-adhesive polymer is the group of Carbomers®.

For sublingual application, compressives, such as for example non-disintegrating tablets in oblong form of a suitable size with a slow release of active ingredient, are especially suitable. For purposes of a targeted release of active ingredients in the various sections of the gastrointestinal tract, mixtures of pellets which release at the various places are employable, for example mixtures of gastric fluid soluble and small intestine soluble and/or gastric fluid resistant and large intestine soluble pellets. The same goal of releasing at various sections of the gastrointestinal tract can also be conceived by suitably produced laminated tablets with a core, whereby the coating of the agent is quickly released in gastric fluid and the core of the agent is slowly released in the small intestine milieu. The goal of controlled release at various sections of the gastrointestinal tract can also be attained by multilayer tablets. The pellet mixtures with differentially released agent can be filled into hard gelatine capsules.

Anti-stick and lubricant and separating agents, dispersion agents such as flame dispersed silicone dioxide, disintegrates such as various starch types, PVC, cellulose esters as granulating or retarding agents, such as for example wax-like and/or polymeric compounds on the basis of Eudragit®, cellulose or Cremophor® are used as a further adjuvants for the production of compressives, such as for example tablets or hard and soft gelatine capsules as well as coated tablets and granulates.

Anti-oxidants, sweetening agents, such as for example saccharose, xylite or mannite, masking flavors, aromatics, preservatives, colorants, buffer substances, direct tableting agents, such as for example microcrystalline cellulose, starch and starch hydrolysates (for example Celutab®), lactose, polyethylene glycols, polyvinylpyrrolidone and dicalcium phosphate, lubricants, fillers, such as lactose or starch, binding agents in the form of lactose, starch varieties, such as for example wheat or corn and/or rice starch, cellulose derivatives, for example methylcellulose, hydroxypropylcellulose or silica, talcum powder, stearates, such as for example magnesium stearate, aluminium stearate, calcium stearate, talc, siliconized talc, stearic acid, acetyl alcohol or hydrated fats, etc. are also used.

In this connection, oral therapeutic systems constructed especially on osmotic principles, such as for example GIT (gastrointestinal therapeutic system) or OROS (oral osmotic system), are also to be mentioned.

Effervescent tablets or tabsolute both of which represent immediately drinkable instant medicinal forms which are quickly dissolved or suspended in water are among the perorally administrable compressives.

Among the perorally administrable forms are also solutions, for example drops, juices and suspensions, which can be produced according to the above given method, and can still contain preservatives for increasing stability and optionally aromatics for reasons of easier intake, and colorants for better differentiation as well as antioxidants and/or vitamins and sweeteners such as sugar or artificial sweetening agents. This is also true for inspissated juices which are formulated with water before ingestion. Ion exchange resins in combination with one or more active ingredients are also to be mentioned for the production of liquid injestable forms.

A special release form consists in the preparation of so-called floating medicinal forms, for example based on tablets or pellets which develop gas after contact with body fluids and therefore float on the surface of the gastric fluid. Furthermore, so-called electronically controlled release systems can also be formulated by which active ingredient release can be selectively adjusted to individual needs.

A further group of systemic administration and also optionally topically effective medicinal forms are represented by rectally applicable medicaments. Among these are suppositories and enema formulations. The enema formulations can be prepared based on tablets with aqueous solvents for producing this administration form. Rectal capsules can also be made available based on gelatine or other carriers.

Hardened fat, such as for example Witepsol®, Massa Estarinum®, Novata®, coconut fat, glycerol-gelatine masses, glycerol-soap-gels and polyethylene glycols are suitable as suppository bases.

For long-term application with a systematic active ingredient release up to several weeks, pressed implants are suitable which are preferably formulated on the basis of so-called biodegradable polymers.

As a further important group of systemically active medicaments, transdermal systems are also to be emphasized which distinguish themselves, as with the above-mentioned rectal forms, by circumventing the liver circulation system and/or liver metabolism. These plasters can be especially prepared as transdermal systems which are capable of releasing the active ingredient in a controlled manner over longer or shorter time periods based on different layers and/or mixtures of suitable adjuvants and carriers. Aside from suitable adjuvants and carriers such as solvents and polymeric components, for example based on Eudragit®, membrane infiltration increasing substances and/or permeation promoters, such as for example oleic acid, Azone®, adipinic acid derivatives, ethanol, urea, propylglycol are suitable in the production of transdermal systems of this type for the purpose of improved and/or accelerated penetration.

As topically, locally or regionally administration medicaments, the following are suitable as special formulations: vaginally or genitally applicable emulsions, creams, foam tablets, depot implants, ovular or transurethral administration instillation solutions. For opthalmological application, highly sterile eye ointments, solutions and/or drops or creams and emulsions are suitable.

In the same manner, corresponding otological drops, ointments or creams can be designated for application to the ear. For both of the above-mentioned applications, the administration of semi-solid formulations, such as for example gels based on Carbopols® or other polymer compounds such as for example polyvinylpyrolidone and cellulose derivatives is also possible.

For customary application to the skin or also to the mucus membrane, normal emulsions, gels, ointments, creams or mixed phase and/or amphiphilic emulsion systems (oil/water-water/oil mixed phase) as well as liposomes and transfersomes can be named. Sodium algenate as a gel builder for production of a suitable foundation or cellulose derivatives, such as for example guar or xanthene gum, inorganic gel builders, such as for example aluminium hydroxides or bentonites (so-called thixotropic gel builder), polyacrylic acid derivatives, such as for example Carbopol®, polyvinylpyrolidone, microcrystalline cellulose or carboxymethylcellulose are suitable as adjuvants and/or carriers. Furthermore, amphiphilic low and high molecular weight compounds as well as phospholipids are suitable. The gels can be present either as hydrogels based on water or as hydrophobic organogels, for example based on mixtures of low and high molecular paraffin hydrocarbons and Vaseline.

Anionic, cationic or neutral tensides can be employed as emulsifiers, for example alkalized soaps, methyl soaps, amine soaps, sulfonated compounds, cationic soaps, high fatty alcohols, partial fatty acid esters of sorbitan and polyoxyethylene sorbitan, for example lanette types, wool wax, lanolin, or other synthetic products for the production of oil/water and/or water/oil emulsions.

Hydrophilic organogels can be formulated, for example, on the basis of high molecular polyethylene glycols. These gel-like forms are washable. Vaseline, natural or synthetic waxes, fatty acids, fatty alcohols, fatty acid esters, for example as mono-, di-, or triglycerides, paraffin oil or vegetable oils, hardened castor oil or coconut oil, pig fat, synthetic fats, for example based on acrylic, caprinic, lauric and stearic acid, such as for example Softisan® or triglyceride mixtures such as Miglyol® are employed as lipids in the form of fat and/or oil and/or wax-like components for the production of ointments, creams or emulsions.

Osmotically effective acids and bases, such as for example hydrochloric acid, citric acid, sodium hydroxide solution, potassium hydroxide solution, monosodium carbonate, further buffer systems, such as for example citrate, phosphate, tries-buffer or triethanolamine are used for adjusting the pH value.

Preservatives, for example such as methyl- or propyl benzoate (parabenes) or sorbic acid can be added for increasing stability.

Pastes, powders or solutions are to be mentioned as further topically applicable forms. Pastes often contain lipophilic and hydrophilic auxiliary agents with very high amounts of fatty matter as a consistency-giving base.

Powders or topically applicable powders can contain for example starch varieties such as wheat or rice starch, flame dispersed silicon dioxide or silica, which also serve as diluents, for increasing flowability as well as lubricity as well as for preventing agglomerates.

Nose drops or nose sprays serve as nasal application forms. In this connection, nebulizers or nose creams or ointments can come to use.

Furthermore, nose spray or dry powder formulations as well as controlled dosage aerosols are also suitable for systemic administration of the active ingredients.

These pressure and/or controlled dosage aerosols and dry powder formulations can be inhaled and/or insufflated. Administration forms of this type also certainly have importance for direct, regional application in the lung or bronchi and larynx. Thereby, the dry powder compositions can be formulated for example as active ingredient-soft pellets, as an active ingredient-pellet mixture with suitable carriers, such as for example lactose and/or glucose. For inhalation or insufflation, common applicators are suitable which are suitable for the treatment of the nose, mouth and/or pharynx. The active ingredients can also be applied by means of an ultrasonic nebulizing device. As a propellant gas for aerosol spray formulations and/or controlled dosage aerosols, tetrafluoroethane or HFC 134a and/or heptafluoropropane or HFC 227 are suitable, wherein non-fluorinated hydrocarbons or other propellants which are gaseous at normal pressure and room temperature, such as for example propane, butane or dimethyl ether can be preferred.

Instead of controlled dosage aerosols, propellant-free, manual pump systems can also be used.

The propellant gas aerosols can also suitably contain surface active adjuvants, such as for example isopropyl myristate, polyoxyethylene sorbitan fatty acid ester, sorbitan trioleate, lecithins or soya lecithin.

For regional application in situ, solutions for instillation, for example for transurethral administration in bladder tumors or genital tumors, or for profusion in liver tumors or other organ carcinomas are suitable.

The respective suitable medicinal forms can be produced in accordance with the prescription and procedures based on pharmaceutical-physical fundamentals as they are described for example in the following handbooks and are included in the present inventive subject-matter with respect to the production of the respective suitable medicaments:

Physical Pharmacy (A. N. Martin, J. Swarbrick, A. Cammarata), 2nd Ed., Philadelphia Pa., (1970), German version: Physikalische Pharmazie, (1987), 3rd edition, Stuttgart;

R. Voigt, M. Bornschein, Lehrbuch der pharmazeutischen Technologie, Verlag Chemie, Weinheim, (1984)., 5th edition;

P. H. List, Arzneimformenlehre, Wissenschaftliche verlagsgesellschaft mbH, Stuttgart, (1985), 4th edition;

H. Sucker, P. Fuchs, P. Speiser, Pharmazeutische Technologie, Georg Thieme Verlag, Stuttgart—New York, (1991), 2nd edition;

A. T. Florence, D. Attwood, Physicochemical Principles of Pharmacy, The Maximillan Press Ltd., Hong Kong, (1981);

L. A. Trissel, Handbook on Injectable Drugs, American Society of Hospital Pharmacists, (1994), 8th edition;

Y. W. Chien, Transdermal Controlled Systemic Medications, Marcel Dekker Inc., New York—Basel, (1987);

K. E. Avis, L. Lachmann, H. A. Liebermann, Pharmaceutical Dosage Forms: Parenteral Medications, volume 9, Marcel Dekker Inc., New York—Basel, (1986);

B. W. Müller, Controlled Drug Delivery, Paperback APV, volume 17, Wissenschaftliche Verlagsgesellschaft mbH, Stuttgart, (1987);

H. Asch, D. acetic, P. C. Schmidt, Technologie von Salben, Suspensionen and Emulsionen, Wissenschaftliche Verlagsgesellschaft mbH, Stuttgart, (1984);

H. A. Liebermann; L. Lachman, J. B. Schwartz, Pharmaceutical Desage forms: Tablets, Volume 1, Marcel Dekker Inc., New York, 2nd Edition (1989);

D. Chulin, M. Deleuil, Y. Pourcelot, Powder Technology and Pharmaceutical Processes, in J. C. Williams, T. Allen, Handbook of Powder Technology, Elsevier Amsterdam—London—New York—Tokyo, (1994);

J. T. Carstensen, Pharmaceutical Principles of Solid Dosage Forms, Technomic Publishing Co., Inc., Lancaster—Basel, (1993).

PRODUCTION EXAMPLES

1. Injection Therapeutics a) Parenteral Solution

| | |
|---|---:|
| active ingredient used according to the invention | 5.000 g |
| acid sodium phosphate | 5.000 g |
| sodium tartrate | 12.000 g |
| benzyl alcohol | 7.500 g |
| water for injection purposes | to 1000.000 ml |

The solution is produced according to the customary method, sterilized and filled into 10 ml vials. One vial contains 50 mg of the compound according to the invention.

b) Parenteral Solution

| | |
|---|---:|
| active ingredient used according to the invention | 1.000 g |
| hydrochloric acid, dilute | 5.000 g |
| sodium chloride | 6.000 g |
| water for injection purposes | to 1000.000 ml |

The solution is produced according to a customary method by stirring; the medicinal form is adjusted to a suitable pH value by acid addition and subsequently filled into 100 ml vials and sterilized. A vial contains 100 mg of the compound according to the invention.

c) Parenteral Dispersion

| | |
|---|---:|
| active ingredient used according to the invention | 10.000 g |
| soya lecithin | 20.000 g |
| saturated triglycerides | 100.000 g |
| sodium hydroxide | 7.650 g |
| water for injection purposes | to 1000.000 ml |

The active ingredient(s) used according to the invention is dispersed in the saturated triglycerides. Then the soya lecithin is added under stirring, and subsequent to this, the aqueous solution of sodium hydroxide is added with subsequent homogenization. The dispersion is sterilized and filled into 10 ml vials. A vial contains 50 mg of the compound according to the invention.

d) Biodegradable Parenteral Depot Medicinal Form

| | |
|---|---:|
| active ingredient used according to the invention | 10.000 g |
| polylactic acid/polygylcolic acid polymer | 70.000 g |
| polyvinylpyrrolidone | 0.200 g |
| gelatine | 2.000 g |
| soya lecithin | 2.000 g |
| isotonic sodium chloride solution | to 1000.000 ml |

First, the active ingredient is incorporated into the biodegradable polymer comprising polylactic acid and polyglycolic acid by a suitable method (spray drying, solvent-evaporation or phase separation) and subsequently subjected to a sterilization process. The particles are introduced into a 2-chamber ready-made syringe in which the adjuvant solution, which is also produced in a sterile manner, is filled. The biodegradable microparticles are mixed with the dispersion agent shortly before application and dispersed. A ready-made syringe contains 200 mg of the active compound according to the invention.

e) Parenteral Dispersion for Subcutaneous Instillation

| | |
|---|---:|
| active ingredient used according to the invention | 25,000 g |
| soya lecithin | 25,000 g |
| arachis oil | 400,000 g |
| benzyl alcohol | 50,000 g |
| Miglyole ® | to 1000,000 g |

The active ingredient is dispersed together with soya lecithin and arachis oil. The benzyl alcohol is dissolved in Miglyole® and added to the dispersion. The entire dispersion is sterilized and subsequently filled into vials with 2 ml content. A vial contains 50 mg active ingredient.

f) Parenteral Perfusions Solution

The solution named under example b) can also be used for perfusion of liver for example.

According to need, instead of ampules with injection solution, so-called perforation bottles (vials), which can also be optionally preserved, and infusion solutions with an amount of one or more active ingredients according to the invention can also be made available in the customary manner under addition of buffer substances for adjustment of physiological pH value and/or the isotonicity and/or a best possible suitable pH value for the medicinal form (euhydria) and optional further required nutrients, vitamins, amino acids, stablizers and other necessary adjuvants, possibly in combination with further medicinal agents suitable for the mentioned indications.

2. Solid, Peroral Administrable Medicaments a) Tablets

| | |
|---|---|
| active ingredient used according to the invention | 10.000 g |
| lactose | 5.200 g |
| starch, soluble | 1.800 g |
| hydroxypropylmethylcellulose | 900 g |
| magnesium stearate | 100 g |

The above components are mixed with each other and compacted in a conventional manner, wherein a tablet weight of 180 mg is set. Each tablet contains 100 mg active ingredient. If desired, the tablets obtained in this manner are coated, provided with a film coat and/or enterically coated.

b) Coated Tablet Core

| | |
|---|---|
| active ingredient used according to the invention | 10.000 g |
| flame dispersed silicon dioxide | 500 g |
| corn starch | 2.250 g |
| stearic acid | 350 g |
| ethanol | 3.0 l |
| gelatine | 900 g |
| purified water | 10.0 l |
| talcum | 300 g |
| magnesium stearate | 180 g |

From these components, a granulate is produced which is pressed to the desired coated tablet cores. Each core contains 50 mg of active ingredient. The core can be further processed in a customary manner to coated tablets. If desired, a gastric fluid resistant or retarding film coat can be applied in a known manner.

c) Vials for Drinking

| | |
|---|---|
| active ingredient used according to the invention | 0.050 g |
| glycerine | 0.500 g |
| sorbite, 70% solution | 0.500 g |
| sodium saccharinate | 0.010 g |
| methyl-p-hydroxybenzoate | 0.040 g |
| aromatic agent | q.s. |
| sterile water | q.s. to 5 ml |

The above-mentioned components are mixed in a customary manner to a suspension and filled in a suitable drink vial having 5 ml content.

d) Poorly Soluble Sublingual Tablets

| | |
|---|---|
| active ingredient used according to the invention | 0.030 g |
| lactose | 0.100 g |
| stearic acid | 0.004 g |
| talcum purum | 0.015 g |
| sweetener | q.s. |
| aromatic agent | q.s. |
| rice starch | q.s. to 0.500 g |

The active ingredient is compacted together with the adjuvants under high pressure to sublingual tablets, favourably in oblong form.

e) Soft Gel Capsule active ingredient used according to the invention 0.050 g
fatty, acid glyceride mixture (Miglyole®) q.s. to 0.500 g The active ingredient is impasted together with the fluid carrier mixture and mixed together with further adjuvants suitable for the encapsulation and filled into elastic soft gelatine capsules which are sealed.

f) Hard Gelatine Capsules

| | |
|---|---|
| active ingredient used according to the invention | 0.150 g |
| microcrystalline cellulose | 0.100 g |
| hydroxypropylmethylcellulose | 0.030 g |
| mannite | 0.100 g |
| ethylcellulose | 0.050 g |
| triethyl citrate | 0.010 g |

The active ingredient is, mixed together with the adjuvants, microcrystalline cellulose, hydroxypropylmethylcellulose and mannite, wet with granulation liquid and formed into pellets. These are subsequently coated with a solution of ethylcellulose and triethyl citrate in organic solvents in a fluidized-bed apparatus. A hard gelatine capsule contains 150 mg of active ingredient.

3. Topically Administrable Medicinal Forms a) Hydrophilic Ointment

| | |
|---|---|
| active ingredient used according to the invention | 0.500 g |
| Eucerinum ® anhydricum | 60.000 g |
| microcrystalline wax | 15.000 g |
| Vaseline oil | q.s. to 100.000 g |

The above-mentioned adjuvants are melted and further processed together with the active ingredient to an ointment in a customary manner.

b) Lipophilic Ointment

| | |
|---|---|
| active ingredient used according to the invention | 10.000 g |
| propylene glycol | 50.000 g |
| paraffin, liquid | 100.000 g |
| paraffin wax | 100.000 g |
| Vaseline | to 1000.000 ml |

The active ingredient(s) used according to the invention is dissolved in propylene glycol at ca. 60° C. At the same time, the lipophilic components are melted at 60–70° C. and subsequently combined with the active ingredient solution. The ointment is emulsified at first at 60–70° C. and subsequently cooled to 35–40° C. under constant emulsification and then filled in 10 g tubes. A tube contains 100 mg of the compound according to the invention.

4. Inhalation Therapeutic Agent

Further subject-matter is a pharmaceutical formulation which is characterized in that it contains an active ingredient (s) used according to the invention as a base or a physiologically acceptable salt thereof together with carriers and/or diluents customary for this and suitable for administration by means of inhalation.

In connection with the production of the medicaments, particularly suitable physiologically acceptable salts of the active ingredients are, as already illustrated in the synthesis section, acid addition salts derived from inorganic or organic acids such as for example especially hydrochloride, hydrobromide, sulfate, phosphate, maleate, tartrate, citrate, benzoate, 4-methoxybenzoate, 2- or 4-hydroxybenzoate, 4-chlorobenzoate, p-tosylate, methane sulfonate, ascorbate, salicylate, acetate, formate, succinate, lactate, glutarate, gluconate or tricarballylate.

The administration of the active ingredient(s) used of the invention by means of inhalation occurs according to the invention in conventional ways customary for administrations of this form, for example in the form of a commercial controlled dosage aerosol or in combination with a spacer. In controlled dosage aerosols, a metering valve is delivered with whose help, a dosed amount of the composition is administered. For spraying, the present compositions can be formulated for example as aqueous solutions or suspensions and be administered by means of an atomizer. Aerosol spray formulations in which the active ingredient is either suspended with one or two stabilizers in a propellant as a carrier and/or diluent, for example tetrafluoroethane or HFC 134a and/or heptafluoropropane or HFC 227 can equally be used, whereby however, non-fluorinated hydrocarbons or other propellants which are gaseous at normal pressure and room temperature, such as propane, butane or dimethyl ether, can be preferred. Thereby, propellant-free manual pump systems or dry powder systems as described below can also be used.

Suitably, the propellant aerosols can also contain surface active adjuvants, such as for example isopropyl myristate, polyoxyethylene sorbitan fatty acid ester, sorbitan trioleate, lecithins, oleic acid.

For administration by means of inhalation and/or insufflation, the medicaments with an amount of compounds according to the invention can also be formulated in the form of dry powder compositions, for example as active ingredient-soft pellets or as an active ingredient-powder mixture with a suitable carrier, such as for example lactose and/or glucose. The powder compositions can be formulated and administered as single doses or as multiple doses.

The compounds according to the invention are preferably administered by means of a controlled dosage aerosol or in the form of a dry powder dosage formulation, wherein the latter preferably contains glucose and/or lactose as a carrier substance.

As applicators for inhalation of the pharmaceutical formulations containing one or more of the active ingredient(s) used according to the invention, all applicators are generally suitable which are suitable for controlled dosage aerosols and/or a dry powder dosage formulation, such as for example usual applicators for the nose, mouth and or pharynx, or also devices standing under propellant gas for the delivery of a spray (at controlled dosage aerosol or dry powder dosage formulation) as they are also used for inhalations in the nose, mouth and/or pharynx.

A further embodiment can also consist of an aqueous solution of the active ingredient(s) used according to the invention, which also optionally contains further active ingredients and/or additives, which are applied by means of an ultrasound atomizer.

a) Controlled Dosage Aerosol

|  | Intended dose per stroke | per aerosol % by weight |
|---|---|---|
| active ingredient used according to the invention | 0.500 mg | 0.66 |
| stabilizer | 0.075 mg | 0.10 |
| HFC 134a | 75.500 mg | 99.24 | b) Controlled Dosage Aerosol

|  | Intended dose per stroke | per aerosol % by weight |
|---|---|---|
| active ingredient used according to the invention | 0.250 mg | 0.32 |
| Stabilizer | 0.038 mg | 0.05 |
| HFC 227 | 79.180 mg | 99.63 |

In the examples a) and b) the micronized active ingredient is, after previous dispersion in a small amount of the stabilizer, placed in a suspension vessel in which the bulk amount of propellant gas solution is found. The corresponding suspension is dispersed by means of a suitable stirring system (for example high performance mixer or ultrasound mixer) until an ultra-fine dispersion results. The suspension is then continuously held in flux in a filling apparatus suitable for cold propellants or pressure fillings.

Alternatively, the suspension can also be produced in a suitable cooled stabilizer solution in HFC 134a/227.

The examples c) to d) describe the composition and production of dosage dry powder formulations.

c) Dosage-Dry Powder Formulation

|  | mg/dose |
|---|---|
| active ingredient used according to the invention | 0.500 mg | d) Dosage-Dry Powder Formulation

|  | mg/dose |
|---|---|
| active ingredient used according to the invention | 0.500 mg |
| lactose Ph.Eur. | to 2.5 mg or to 5.0 mg | e) Dosage-Dry Powder Formulation

|  | mg/dose |
|---|---|
| active ingredient used according to the invention | 0.250 mg |
| lactose Ph.Eur. | to 2.5 mg or to 5.0 mg |

In example c) the active ingredient is formulated after micronization under addition of steam as pellets with an MMAD between 0,1 and 0,3 mm diameter and brought to use in a multi-dose powder applicator.

In the examples d) and e) the active ingredient is micronized, thereafter, bulk material is mixed with the lactose in the given amounts, and subsequently, filled in a multi-dose powder inhalator.

In all of the examples set forth above, the active ingredient or the medicinal agent in the form of the respective suitable pharmaceutical acceptable salt and/or acid addition salts can be present, insofar as the base is not preferred in each case.

PHARMACEUTICAL EXPERIMENTAL SECTION

1. Growth Inhibition of Human Tumor Cells

The tumor growth inhibiting activity of the substances was determined on human tumor cells in standardized in vitro test systems. In the screening tests, the substances gave $IC_{50}$-values in a concentration range of 0.1 nM to 10 µM.

Example 1

HepG2 cells derived from a human liver carcinoma plated at a density of 20,000 cells/ml in 12-well plastic dishes. Cultivation occurred in Richters IMEM-ZO nutrient medium with 5% foetal calf serum (FOS) in a tissue culture incubator with a gas mixture of 5% $CO_2$ and 95i air at a temperature of 37° C. One day after plating, the culture medium was aspirated from the cells and replaced by fresh medium which contained the respective concentrations of the test substances. For the individual concentrations and the controls without test substances, three-fold batches were done for each. Three days after the beginning of treatment, the medium was again renewed with the test compounds. After six days of substance incubation, the test was ended and the protein amount in the individual wells was determined with the sulforhodamin-B-method (according to P. Skehan et al.: New Colorimetric Cytotoxicity Assay for Anticancer-Drug Screening. J. Natl. Cancer Inst. 82: 1107–1112, 1990). The $IC_{50}$-values (defined as that concentration in which the cell growth was inhibited by 50%) was taken from the dose-response curves and given as a comparative measurement for the activity of the test compounds.

The following results were obtained:

| Test substance No. | $IC_{50}$-value [µM] |
|---|---|
| 36 | 0.6 |
| 52 | 5 |
| 55 | 0.2 |
| 110 | 0.1 |

Example 2

A549 cells derived from a human lung carcinoma plated at a density of 20,000 cells/ml in 12-well plastic dishes. Cultivation occurred in Richters IMEM-ZO nutrient medium with 5% foetal calf serum (FCS) in a tissue culture incubator with a gas mixture of 5% $CO_2$ and 95% air at a temperature of 37° C. One day after plating, the culture medium was aspirated from the cells and replaced by fresh medium which contained the respective concentrations of the test substances. For the individual concentrations and the controls without test substances, three-fold batches were done for each. Three days after the beginning of treatment, the medium was again renewed with the test compounds. After four days of substance incubation, the test was ended and the protein amount in the individual wells was determined with the sulforhodamin-B-method (according to P. Skehan et al.: New Colorimetric Cytotoxicity Assay for Anticancer-Drug Screening. J. Natl. Cancer Inst. 82: 1107–1112, 1990). The $IC_{50}$-values (defined as that concentration in which the cell growth was inhibited by 50%) was taken from the dose-response curves and given as a comparative measurement for the activity of the test compounds.

The following results were obtained:

| Test substance No. | $IC_{50}$-value [µM] |
|---|---|
| 54 | 3 |
| 60 | 0.8 |
| 112 | 5 |
| 118 | 0.2 |
| 188 | 0.2 |

Example 3

HT-29 cells derived from a human colon carcinoma plated at a density of 20,000 cells/ml in 12-well plastic dishes. Cultivation occurred in Richters IMEM-ZO nutrient medium with 5% foetal calf serum (FCS) in a tissue culture incubator with a gas mixture of 5% $CO_2$ and 95% air at a temperature of 37° C. One day after plating, the culture medium was aspirated from the cells and replace by fresh medium which contained the respective concentrations of the test substances. For the individual concentrations and the controls without test substances, three-fold batches were done for each. Three days after the beginning of treatment, the medium was again renewed with the test compounds. After four days of substance incubation, the test was ended and the protein amount in the individual wells was determined with the sulforhodamin-B-method (according to P. Skehan et al.: New Calorimetric Cytotoxicity Assay for anticancer-Drug Screening. J. Natl. Cancer Inst. 82: 1107–1112, 1990). The $IC_{50}$-values (defined as that concentration in which the cell growth was inhibited by 50%) was taken from the dose-response curves and given as a comparative measurement for the activity of the test compounds.

The following results were obtained:

| Test substance No. | $IC_{50}$-value [µM] |
|---|---|
| 54 | 2 |
| 82 | 3 |
| 188 | 0.2 |

Example 4

THP-1 cells derived from a human monocytic leukemia plated at a density of 200,000 cells/ml in 96-well plastic dishes. Cultivation occurred in RPMI 1640 nutrient medium with 10% foetal calf serum (FCS) in a tissue culture incubator with a gas mixture of 5% $CO_2$ and 95% air at a temperature of 37° C. For the individual concentrations and the controls without test substances as well as for the background with nutrient medium but without cells, threefold batches were done for each. After four days of substance incubation 20 μl WST-1 reagent (Boehringer Mannheim) was respectfully pipetted in each individual well. After 30 to 60 minute incubation in the tissue culture incubator at 37° C. and 5% $CO_2$, the light extinction was measured in an ELISA reader at 450 nm wave length. The backgrounds were each subtracted from the typical measured valves. (The $IC_{50}$-values (defined as that concentration in which the cell growth was inhibited by 50%) was taken from the dose-response curves and given as a comparative measurement for the activity of the test compounds.

The following results were obtained:

| Test substance No. | $IC_{50}$-value [μM] |
|---|---|
| 60 | 0.1 |
| 82 | 0.3 |
| 117 | 0.03 |

2. Indications

The compounds of formula (I) and their salts permit a therapeutic use in malignant illnesses of humans and animals through their excellent inhibition of the growth of tumor cells. The anti-neoplastic activity of the described substances can be used for prophylactic, adjunct, palliative, and curative treatment of solid tumors, leukemic illnesses and lymphomas as well as for decreasing or preventing metastasis formation in humans and animals. The therapeutic use is possible in the following illnesses for example: gynaecological tumors, ovarian carcinomas, testicle tumors, prostate carcinomas, skin cancer, kidney cancer, bladder tumors, oesophagus carcinomas, stomach cancer, rectal carcinomas, pancreas carcinomas, thyroid cancer, adrenal tumors, leukemia and lymphomas, Hodgkin's disease, tumor illnesses of the CNS, soft-tissue sarcomas, bone sarcomas, benign and malignant mesotheliomas, but especially intestine cancer, liver cancer, breast cancer, bronchial and lung carcinomas, melanomas, acute and chronic leukemias. Benign papillomatosis tumors can also be limited in their growth with the named substances. The broad effectiveness of the new compounds were tested for example in very different human tumor cells in vitro according to the methods described in point 1. Thereby, the following $IC_{50}$ valves were obtained for the compound Nr. 82 for example:

| Cell line | Source | $IC_{50}$-values [mM] |
|---|---|---|
| HT-29 | colon carcinoma | 3 |
| A549 | lung carcinoma | 2 |
| HepG2 | hepatocelluar carcinoma | 0.5 |
| THP-1 | monocytic leukemia | 0.3 |

From the novelty of the compounds an independent activity profile can be derived in the determined effectiveness against the various tumor types. Thus, tumors which are resistant to customary cytostatic agents, for example, can respond entirely to these substances. In addition, based on the independent characteristics, combinations of the new compounds with known pharmaceuticals used in chemotherapy are promising as long as their properties are complimented in a suitable manner. The integration of the new structures in a therapy scheme could be successful with one or more substances from the following classes for example: anti-metabolites (for example cytarabine, 5-fluorouracil, 6-mercaptopurine, methotrexate), alkylating agents (for example busulfane, carmustine, cisplatin, carboplatin, cyclophosphamide, dacarbazine, melphalane, thiotepa), DNA-intercalating substances and topoisomerase inhibitors (for example actinomycin D, daunorubicin, doxorubicin, mitomycin C, mitoxantrone, etoposide, teniposide, topotecane, irinotecane), spindle poisons (for example vincristine, navelbine, taxol, taxoter), hormonally active agents (for example tamoxifene, flutamide, formestane, gosereline) or other cytostatic agents with complex modes of action (for example L-asparaginase, bleomycin, hydroxyurea). Resistant tumor cells can be made sensitive again for example by interaction of the new compounds with a mechanism of resistance for common cytostatic agents (for example P-glycoprotein, MRP, glutathione-S-transferase, metallothionein).

3. Immunosuppressing Activity

Many anti-tumor agents have not only a cytotoxic effect on tumor cells, but also on the blood cell system. This leads to a weakening of the immune defence, which can, in turn, be specifically employed to suppress the rejection reaction after an organ transplantation for example. Also use of the main compounds, optionally in combination with other immunological diseases (for example, psoriasis or autoimmune diseases) seems likely. In order to test the possibility for a therapeutic use in illnesses of this type, the substance activity was tested on freshly isolated lymphocytes as follows:

The spleen of a Swiss mouse served as a lymphocyte source. The lymphocyte population was isolated from the spleen cell suspension over a ficoll gradient and taken up in IMEM-ZO culture medium with 0,1% dexitran 70,000 and 2% foetal calf serum. The cells were plated At a density of ca. 500,000 cells/well/ml in a 12-well plate, 1 ml doubly concentrated test substance solution was pipetted per well and this was subsequently incubated in a tissue culture incubator at 37° and 5% $CO_2$. After 2 days, a 1 ml-aliquot with 5 μl of the fluorescent dye solutions propidium iodide (8 mg/ml) and 3,3'-dihexyloxacarbocyanin iodide (40 μg/ml) each was added per well, and incubated for 3 minutes at room temperature. Subsequently, 10,000 cells per each sample were measured on a flow-through cytometer and the percentage amount of vital cells in the population was determined. By example of the dose-response curve of the substance Nr. 60, an $IC_{50}$-value of 0.5 μM was calculated.

The independent structural class of the compounds can also be expected to be successful for an efficient combination with known immunosuppressive agents such as for example cyclosporin A, tacrolimus, rapamycin, azathioprine and glucocorticoids.

What is claimed is:

1. Pyridylalkane, pyridylalkene and pyridylalkine acid amide compounds of general formula

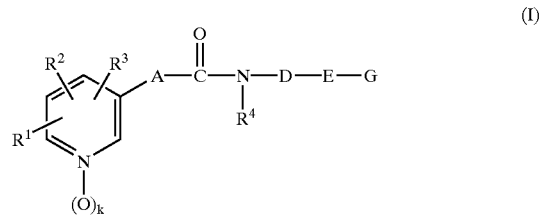

(I)

wherein

R$^1$ is selected from the group consisting of hydrogen, halogen, cyano, C$_1$–C$_6$-alkyl, C$_3$–C$_6$-alkenyl, C$_3$–C$_6$-alkinyl, trifluoromethyl, C$_3$–C$_8$-cycloalkyl, C$_1$–C$_6$-hydroxyalkyl, hydroxy, C$_1$–C$_6$-alkoxy, C$_3$–C$_6$-alkenyloxy, C$_3$–C$_6$-alkinyloxy, benzyloxy, C$_1$–C$_7$-alkanoyloxy, C$_2$–C$_7$-alkoxycarbonyloxy, C$_1$–C$_6$-alkylthio, C$_3$–C$_6$-alkenylthio, C$_3$–C$_6$-alkinylthio, C$_3$–C$_8$-cycloalkyloxy, C$_3$–C$_8$-cycloalkylthio, C$_2$–C$_7$-alkoxycarbonyl, aminocarbonyl, C$_2$–C$_7$-alkoxycarbonyl, C$_3$–C$_{13}$-dialkylaminocarbonyl, carboxy, phenyl, phenoxy, phenylthio, pyridyloxy, pyridylthio, and NR$^5$R$^6$, wherein R$^5$ and R$^6$ selected independently of each other from the group consisting of hydrogen, C$_1$–C$_6$-alkyl, C$_3$–C$_6$-alkenyl, C$_3$–C$_6$-alkinyl, benzyl and phenyl;

R$^2$ is selected from the group consisting of hydrogen, halogen, cyano, C$_1$–C$_6$-alkyl, triflurormethyl, hydroxy, C$_1$–C$_6$-alkoxy, benzyloxy and C$_1$–C$_7$-alkanoyloxy; R$^1$ and R$^2$, if adjacent, may form a bridge selected from —(CH$_2$)$_4$—, —(CH=CH)$_2$— and —CH$_2$O—CR$^7$R$^8$—O—, wherein R$^7$ and R$^8$ are selected independently from each other from hydrogen and C$_1$–C$_6$-alkyl;

R$^3$ is selected from the group consisting of hydrogen, halogen, C$_1$–C$_6$-alkyl, trifluoromethyl and C$_1$–C$_6$-hydroxyalkyl;

R$^4$ selected from the group consisting of hydrogen, C$_1$–C$_6$-alkyl, C$_3$–C$_6$-alkenyl, C$_3$–C$_6$-alkinyl, C$_3$–C$_6$-cycloalkyl, hydroxy, C$_1$–C$_6$-alkoxy and benzyloxy;

k is 0 or 1,

A is selected from the group consisting of
C$_1$–C$_6$-alkylene
a substituted C$_1$–C$_6$-alkylene, which is substituted one to three-fold by C$_1$–C$_6$-alkyl, hydroxy, C$_1$–C$_3$-alkoxy, fluorine, or phenyl,
C$_2$–C$_6$-alkylene, wherein a methylene unit is isosterically replaced by O, S, NR$^9$, CO, SO, or SO$_2$, wherein, with the exception of CO, the isosteric substitution is not adjacent to the amide group and R$^9$ is selected from the group consisting of hydrogen, C$_1$–C$_6$-alkyl, C$_3$–C$_6$-alkenyl, C$_3$–C$_6$-alkinyl, C$_1$–C$_6$-acyl and C$_1$–C$_6$-alkanesulfonyl,
1,2-cyclopropylene,
C$_2$–C$_6$-alkenylene,
a substituted C$_2$–C$_6$-alkenylene, which is substituted one to three-fold by C$_1$–C$_6$-alkyl, hydroxy, C$_1$–C$_6$-alkoxy, fluorine, cyano or phenyl,
C$_4$–C$_6$-alkadienylene,
a substituted C$_4$–C$_6$-alkadienylene, which is substituted once to twice by C$_1$–C$_3$-alkyl, fluorine, cyano or phenyl,
1,3,5-hexatrienylene,
a substituted 1,3,5-hexatrienylene, which is substituted by C$_1$–C$_3$-alkyl, fluorine, cyano or phenyl, and
ethinylene
is selected from the group consisting of C$_2$–C$_{10}$-alkylene,
a substituted C$_2$–C$_{10}$-alkylene, which is substituted once or twice by C$_1$–C$_6$-alkyl, hydroxy, or C$_1$–C$_6$-alkoxy,
C$_4$–C$_{10}$-alkenylene,
a substituted C$_4$–C$_{10}$-alkenylene, which is substituted once or twice by C$_1$–C$_6$-alkyl, hydroxy, or C$_1$–C$_6$-alkoxy,
C$_4$–C$_{10}$-alkinylene,
a substituted C$_4$–C$_{10}$-alkinylene, which is substituted once or twice by C$_1$–C$_6$-alkyl, hydroxy, or C$_1$–C$_6$-alkoxy, and
C$_2$–C$_{10}$-alkylene,
C$_2$–C$_{10}$-alkylene, C$_4$–C$_{10}$-alkenylene, or C$_4$–C$_{10}$-alkinylene, wherein one to three methylene units are isosterically replaced by O, S, NR$^{10}$, CO, SO, or SO$_2$, wherein R$^{10}$ has the same meaning as R$^9$, but is selected independently thereof;

E is selected from the group consisting of

(E1)

and

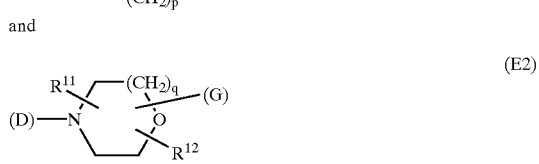

(E2)

wherein the heterocyclic ring may have a double bond and n and p are, independent of each other, 0, 1, 2 or 3 where n+p≦4, wherein q is 1, 2 or 3;

R$^{11}$ is selected from the group consisting of hydrogen, C$_1$–C$_6$-alkyl, hydroxy, hydroxymethyl, carboxy, and C$_2$–C$_7$-alkoxycarbonyl and R$^{12}$ is selected from the group consisting of hydrogen, C$_1$–C$_6$-alkyl and an oxo group adjacent to a nitrogen atom, or R$^{11}$ and R$^2$, may together, form a C$_1$–C$_3$-alkylene bridge under formation of a bicyclic ring system;

G is selected from the group consisting of G$^1$, G$^2$, G$^3$, G$^4$ and G$^5$, wherein G$^1$ is —(CH$_2$)$_r$—(CR$^{14}$R$^{15}$)$_s$—R$^{13}$ r is 0, 1, 2 or 3 and s is 0 or 1

R$^{13}$ is selected from the group consisting of
hydrogen, C$_1$–C$_6$-alkyl, C$_3$–C$_6$-alkenyl, C$_3$–C$_6$-alkinyl, C$_3$–C$_8$-cycloalkyl,
saturated or unsaturated, four to seven-membered heterocycles, which contain one or two hetero-atoms selected from N, S and O,
benzyl, phenyl,
monocyclic aromatic five and six-membered heterocycles, which contain one to three hetero-atoms selected from N, S and O and are either bound directly or over a methylene group,
anellated bi- and tricyclic aromatic and partially hydrogenated carbocyclic ring system with 8 to 16 ring atoms and at least one aromatic ring, wherein the linkage occurs either over an aromatic or a hydrogenated ring and either directly or over a methylene group, and
anellated bi- and tricyclic aromatic or partially hydrogenated heterocyclic ring systems with 8 to 16 ring atoms and at least one aromatic ring, wherein one to three ring atoms ate selected from N, S and O and the linkage occurs either over an aromatic ring or a hydrogenated ring and either directly or over a methylene group, $R^{14}$ has the same meaning as $R^{13}$, but is selected independently thereof;

$R^{15}$ is selected from the group consisting of hydrogen, hydroxy, methyl, benzyl, phenyl, monocyclic aromatic five and six-membered heterocycles, which contain one to three heteroatoms selected from N, S and O and are either bound directly or over a methylene group, anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group, anellated bi- and tricyclic aromatic and partially hydrogenated heterocyclic ring systems with 8 to 16 ring atoms and at least one aromatic ring, wherein one to three ring atoms are selected from N, S and O and the linkage can occur either over an aromatic ring or a hydrogenated ring and either directly or over a methylene group;

$G^2$ is $=(C)_u R^{13} R^{15}$ wherein, $R^{13}$ and $R^{15}$ have the above meaning and u is 0 or 1, or u=1, and $R^{13}$ and $R^{15}$ together with a carbon atom to which they are attached form a ring system selected from the group consisting of $C_2$–$C_8$-cycloalkyl, saturated, four to seven-membered heterocycles which contain one or two hetero-atoms selected from N, S and O;

anellated bi- and tricyclic partially hydrogenated carboxocyclic ring system with 8 to 16 ring atoms and at least one aromatic ring; and anellated bi- and tricyclic partially hydrogenated heterocyclic ring systems with 8 to 16 ring atoms and at least one aromatic ring, wherein one to three ring atoms are selected from N, S and O;

or, u=0, an $R^{13}$ and $R^{15}$ together with the carbon atom $C_E$ of ring E to which they are attached form a ring system $C_E R^{13} R^{15}$ selected from the group consisting of cycloalkyl, saturated, four to seven-membered heterocycles which contain one or two hetero-atoms selected from N, S and O;

anellated bi- and tricyclic partially hydrogenated carbocyclic ring systems with 8 to 16 ring atoms and at least one aromatic ring; and anellated bi- and tricyclic partially hydrogenated heterocyclic ring systems with 8 to 16 ring atoms and at least one aromatic ring, wherein 1 to 3 ring atoms can be selected from N, S and O;

$G^3$ is selected from

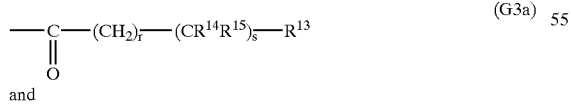 (G3a)

and

 (G3b)

wherein r, s, and the substituents $R^{13}$, $R^{14}$, and $R^{15}$ have the above meanings, or the group

—$NR^{13}R^{15}$ is a nitrogen containing heterocycle bound over the nitrogen atom which nitrogen-containing heterocycle is selected from the group consisting of saturated and unsaturated monocyclic, four to eight-membered heterocycles which, aside from the essential nitrogen atom, may contain one or two further hetero-atoms selected from N, S and O, and saturated and unsaturated bi- or tricyclic, anellated or bridges heterocycles with 8 to 16 ring atoms, which, aside from the essential nitrogen atom, may contain one or two further hetero-atoms selected from N, S and O, $G^4$ is selected from the group consisting of

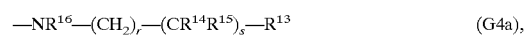 (G4a),

 (G4b)

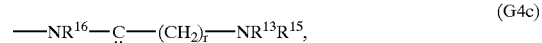 (G4c)

—$NR^{16}$—$SO_2$—$(CH_2)_r$—$R^{13}$ (G4d)

 (G4e)

and

—$NR^{16}$–$COR^{17}$ (G4f), wherein r, s and $R^{13}$, $R^{14}$, and $R^{15}$ have the above meanings and $R^{16}$ has the same meanings as $R^5$, but is selected independently thereof, $R^{17}$ is selected from the group consisting of trifluoromethyl, $C_1$–$C_6$-alkoxy, $C_3$–$C_6$-alkenyloxy and benzyloxy; and $Ar^1$ and $Ar^2$, are selected independently from each other from the group consisting of phenyl, pyridyl and naphthyl;

$G^5$ is selected from the group consisting of

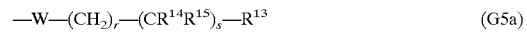 (G5a)

and

 (G5b)

wherein r, s, and $R^{13}$, $R^{14}$, $R^{15}$, $Ar^1$ and $Ar^2$ have the above meanings and W is O or S, wherein the ring systems $=CR^{13}R^{15}$, —$NR^{13}R^{15}$, —$C_E R^{13}R^{15}$ and aromatic ring systems in the substituents $R^1$, $R^2$, $R^4$, $R^5$, $R^6$, $R^{13}$, $R^{14}$, $R^{15}$, $R^{16}$, $R^{17}$, $Ar^1$ and $Ar^2$ may be substituted independently from each other by one to three of the same or different groups selected from the group consisting of halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, benzyloxy, phenoxy, mercapto, $C_1$–$c_6$-alkylthio, carboxy, $C_2$–$C_7$-carboxyalkyl, $C_2$–$C_7$-carboxyalkenyl, $C_2$–$C_7$-alkoxycarbonyl, benzyloxyalkyl, nitro, amino, mono-$C_1$–$C_6$-alkylamino, di-($C_1$–$C_6$-alkyl)amino and, for two adjacent residues on the aromatic ring, methylenedioxy, and $C_1$–$C_6$-alkoxy which is entirely or partially substituted by fluorine, wherein alkyl-, alkenyl- and cycloalkyl residues in the group $G^1$ to $G^5$ may be substituted by one or two of the same or different groups selected from hydroxy, carboxy, $C_2$–$C_7$-alkoxycarbonyl, benzyloxycarbonyl, amino, mono-$C_1$–$C_6$-alkylamino, and di-($C_1$–$C_6$-alkyl)amino, wherein G is not —$CHR^{14}$—$R^{13}$, —$C(OH)R^{14}$—$R^{13}$, =$CR^{13}R^{15}$ or —O—$CHR^{14}$—$R^{13}$,
    in the case when simultaneously
        $R^{13}$ is hydrogen, alkyl or phenyl substituted by halogen, alkyl, hydroxy or trifluoromethyl,
        $R^{14}$ and $R^{15}$ may be pyridyl or phenyl substituted with halogen, alkyl, hydroxy or trifluoromethyl,
        A is alkylene, which may be substituted with ethenylene or butadienylene,
        D is alkylene and
        E is piperidine substituted in the 4-position;

their cis- and trans-isomers, E- and Z-isomers, and their racemic or non-racemic mixtures, their pure endo- and exo-isomers and mixtures thereof;
their respective tautomers,
the corresponding acid addition salts, hydrates and solvates.

2. Compounds of general Formula (I),

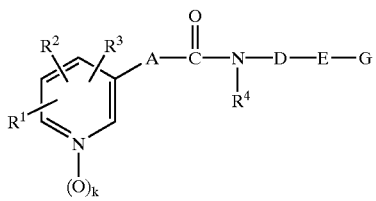

(I)

wherein
  $R^1$ is selected from the group consisting of hydrogen, halogen, cyano, $C_1$–$C_6$-alkyl, trifluoromethyl, $C_3$–$C_8$-cycloalkyl, $C_1$–$C_6$-hydroxyalkyl, hydroxy, $C_1$–$C_4$-alkoxy, benzyloxy, $C_1$–$C_4$-alkylthio, $C_1$–$C_5$-alkanoyloxy, $C_1$–$C_4$-alkylthio, $C_2$–$C_5$-alkoxycarbonyl, aminocarbonyl, $C_2$–$C_5$-alkylaminocarbonyl, $C_3$–$C_9$-dialkylaminocarbonyl, carboxy, phenyl, phenoxy, phenylthio, pyridyloxy, and $NR^5R^6$, wherein
  $R^5$ and $R^6$ are selected independently of each other from hydrogen and $C_1$–$C_6$-alkyl,
  $R^2$ is selected from the group consisting of hydrogen, halogen, cyano, $C_1$–$C_6$-alkyl, triflurormethyl, hydroxy, and $C_1$–$C_6$-alkoxy,
  $R^3$ is selected from the group consisting of hydrogen, halogen, and $C_1$–$C_6$-alkyl,
  $R^4$ selected from the group consisting of hydrogen, $C_1$–$C_6$-alkyl, $C_3$–$C_6$-alkenyl, $C_3$–$C_6$-cycloalkyl, hydroxy, $C_1$–$C_6$-alkoxy and benzyloxy,
  k is 0 or 1, A is selected from the group consisting of
  $C_2$–$C_6$-alkylene,
    a substituted $C_2$–$C_6$-alkylene, which is substituted one to three-fold by $C_1$–$C_3$-alkyl, hydroxy, fluorine, or phenyl,
    $C_2$–$C_6$-alkylene, wherein a methylene unit is isosterically replaced by O, S, $NR^9$, CO, or $SO_2$, wherein, with the exception of CO, the isosteric substitution is not adjacent to the amide group and $R^9$ is selected from the group consisting of hydrogen, $C_1$–$C_6$-alkyl, $C_1$–$C_6$-acyl and methanesulfonyl;
  1,2-cyclopropylene,
  $C_2$–$C_6$-alkenylene,
  a substituted $C_2$–$C_6$-alkenylene, which is substituted one to three-fold by $C_1$–$C_3$-alkyl, hydroxy, fluorine, cyano or phenyl,
  $C_4$–$C_6$-alkadienylene,
  a substituted $C_4$–$C_6$-alkadienylene, which is substituted once to twice by $C_1$–$C_3$-alkyl, fluorine, cyano or phenyl,
  1,3,5-hexatrienylene,
  a substituted 1,3,5-hexatrienylene, which is substituted by $C_1$–$C_3$-alkyl, fluorine, or cyano, and
  ethinylene D is selected from-the group consisting of $C_2$–$C_{10}$-alkylene,
  $C_2$–$C_{10}$-alkylene, which is substituted once or twice by $C_1$–$C_6$-alkyl or hydroxy,
  $C_4$–$C_{10}$-alkenylene,
  $C_4$–$C_{10}$-alkenylene, which is substituted once or twice by $C_1$–$C_3$-alkyl or hydroxy,
  $C_4$–$C_{10}$-alkinylene,
  $C_4$–$C_{10}$-alkinylene, which is substituted once or twice by $C_1$–$C_3$-alkyl or hydroxy, and
  $C_2$–$C_{10}$-alkylene, $C_4$–$C_{10}$-alkenylene, or $C_4$–$C_{10}$-alkinylene, wherein one to three methyleneunits are isosterically replaced by O, S, $NR^{10}$, CO, SO, or $SO_2$, wherein
  $R^{10}$ has the same meaning as $R^9$, but is selected independently thereof;

E is selected from the group consisting of

(E1)

and

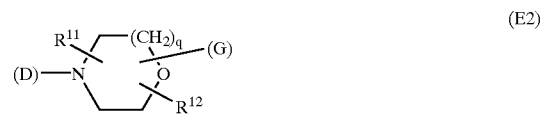

(E2)

wherein the heterocyclic ring may have a double bond and
n and p are, independent of each other, 0, 1, 2 or 3 where n+p≦4, and
q is 1 or 2;
$R^{11}$ is selected from the group consisting of hydrogen, $C_1$–$C_3$-alkyl, hydroxy, hydroxymethyl, carboxy, and $C_2$–$C_7$-alkoxycarbonyl and
$R^{12}$ is selected from the group consisting of hydrogen and an oxo group adjacent to a nitrogen atom or
$R^{11}$ and $R^{12}$, together, form a $C_1$–$C_3$-alkylene bridge under formation of a bicyclic ring system;

G is selected from the group consisting of $G^1$, $G^2$, $G^3$, $G^4$ and $G^5$, wherein $G^1$ is —$(CH_2)_r$—$(CR^{14}R^{15})_s$—$R^{13}$ wherein r is 0, 1, or 2, s is 0 or 1 and $R^{13}$ is selected from the group consisting of
hydrogen, $C_1$–$C_6$-alkyl, $C_3$–$C_6$-alkenyl, $C_3$–$C_6$-alkinyl, $C_3$–$C_8$-cycloalkyl, benzyl, phenyl,
monocyclic aromatic five and six-membered heterocycles, which contain one to three heteroatoms selected from N, S and O and are either bound directly or over a methylene group,
anellated bi- and tricyclic aromatic and partially hydrogenated carbocyclic ring system with 8 to 16 ring atoms and at least one aromatic ring, wherein the linkage can occur either over an aromatic or a hydrogenated ring and either directly or over a methylene group, and
anellated bi- and tricyclic aromatic or partially hydrogenated heterocyclic ring systems with 8 to 16 ring atoms and at least one aromatic ring, wherein one to three ring atoms can be selected from N, S and O and the linkage can occur either over an aromatic ring or a hydrogenated ring and either directly or over a methylene group, $R^{14}$ has the same meaning as $R^{13}$, but is selected independently thereof;

$R^{15}$ is selected from the group consisting of
hydrogen, hydroxy, methyl, benzyl, phenyl, monocyclic aromatic five and six-membered heterocycles, which contain one to three hetero-atoms selected from N, S and O and are either bound directly or over a methylene group,
anellated bi- and tricyclic aromatic and partially hydrated carbocyclic ring systems with 8 to 16 ring atoms and at least one aromatic ring, wherein the linkage can occur either over an aromatic or a hydrogenated ring and either directly or over a methylene group, and
anellated bi- and tricyclic aromatic and partially hydrogenated hetertocyclic ring systems with 8 to 16 ring atoms and at least one aromatic ring, wherein one to three ring atoms are selected from N, S and O and the linkage can occur either over an aromatic ring or a hydrogenated ring and either directly or over a methylene group;

$G^2$ is $=(C)_u R^{13} R^{15}$ wherein $R^{13}$ and $R^{15}$ have the above meaning and u is 0 or 1,
or u=1, and $R^{13}$ and $R^{15}$ together with a carbon atom to which they are attached form a ring selected from the group consisting of
anellated bi- and tricyclic partially hydrated carboxocyclic ring system with 8 to 16 ring atoms and at least one aromatic ring and
anellated bi- and tricyclic partially hydrated heterocyclic ring systems with 8 to 16 ring atoms and at least one aromatic ring, wherein 1 to 3 ring atoms are selected from N, S and O; or
u=0, and $R^{13}$ and $R^{15}$ together with the carbon atom $C_E$ of ring E to which they are attached form a ring system $C_E R^{13} R^{15}$ selected from the group consisting of
saturated, four to seven-membered heterocycles which contain one or two hetero-atoms selected from N, S and O,
anellated bi- and tricyclic partially hydrogenated carbocyclic ring systems with 8 to 16 ring atoms and at least one aromatic ring; and
anellated bi- and tricyclic partially hydrogenated heterocyclic ring systems with 8 to 16 ring atoms and at least one aromatic ring, wherein 1 to 3 ring atoms are selected from N, S and O;

$G^3$ is selected from the group consisting of

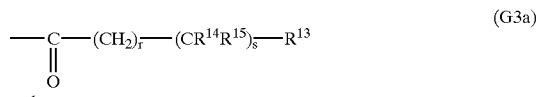 (G3a)

and

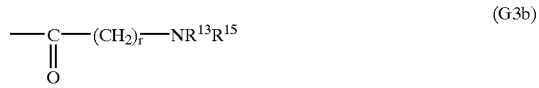 (G3b)

wherein r, s and $R^{13}$, $R^{14}$, and $R^{15}$ have the above meanings, or the group

 —$NR^{13}R^{15}$ is a nitrogen containing heterocycle bound over the nitrogen atom which nitrogen-containing heterocycle is selected from the group consisting of saturated and unsaturated monocyclic, four to eight-membered heterocycles which, aside from the essential nitrogen atom, may contain one or two further hetero-atoms selected from N, S and O, and
saturated or unsaturated bi- or tricyclic, anellated and bridged heterocycles with 8 to 16 ring atoms, which, aside from the essential nitrogen atom, may contain one or two further hetero-atoms selected from N, S and O;

$G^4$ is selected from the group consisting of

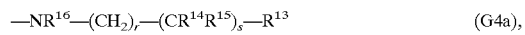 (G4a),

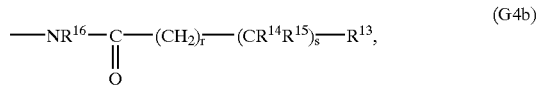 (G4b)

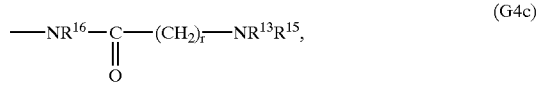 (G4c)

 (G4d),

 (G4e)

and —$NR^{16}$—$COR^{17}$ (G4f)

wherein r, s, $R^{13}$, $R^{14}$, and $R^{15}$ and the group —$NR^{13}R^{15}$ have the above meanings and $R^{16}$ is selected form the group consisting of hydrogen, $C_1$–$C_6$-alkyl, $C_3$–$C_6$-alkenyl, $C_3$–$C_6$-alkinyl, benzyl and phenyl, $R^{17}$ is selected from the group consisting of trifluoromethyl, $C_1$–$C_6$-alkoxy, $C_3$–$C_6$-alkenyloxy and benzyloxy, and Ar¹ and Ar², are selected independently from each other from the group consisting of phenyl, pyridyl and naphthyl, G⁵ is

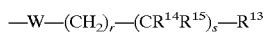 (G5a)

or

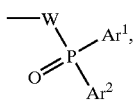 (G5b)

wherein r, s and $R^{13}$, $R^{14}$, and $R^{15}$, $Ar^1$ and $Ar^2$ have the above meanings and W is O or S, wherein the ring systems =CR$^{13}$R$^{15}$s, —NR$^{13}$R$^{15}$ and C$_E$R$^{13}$R$^{15}$ and aromatic ring systems in the substituents R$^1$, R$^4$, R$^5$, R$^{13}$, R$^{14}$, R$^{15}$, R$^{16}$, R$^{17}$, Ar$^1$ and Ar$^2$ may be substituted independently from each other by one to three of the same or different groups selected from the group consisting of halogen, cyano, C$_1$–C$_6$-alkyl, trifluoromethyl, C$_3$–C$_8$-cycloalkyl, phenyl, benzyl, hydroxy, C$_1$–C$_6$-hydroxyalkyl, C$_1$–C$_6$-alkoxy, benzyloxy, phenoxy, mercapto, C$_1$–C$_1$-alkylthio, carboxy, C$_2$–C$_7$-carboxyalkyl, C$_2$–C$_7$-carboxyalkenyl, C$_2$–C$_7$-alkoxycarbonyl, benzyloxyalkyl, nitro, amino, mono-C$_1$–C$_6$-alkylamino, di-(C$_1$–C$_6$-alkyl)amino and, for two adjacent residues on the aromatic ring, methylenedioxy, C$_1$–C$_6$-alkoxy which is entirely or partially substituted by fluorine, and alkyl-, alkenyl- and cycloalkyl residues in the group G$^1$ to G$^5$ may be substituted by one or two of the same or different groups selected from the group consisting of hydroxy, carboxy, C$_2$–C$_7$-alkoxycarbonyl, benzyloxycarbonyl, amino, mono-C$_1$–C$_6$-alkylamino, and di-(C$_1$–C$_6$-alkyl)amino; their salts, isomers and tautomers.

3. Compounds of general Formula (I) according to claim 3, wherein:

R$^1$ is selected from the group consisting of hydrogen, halogen, cyano, methyl, ethyl, trifluoromethyl, hydroxy, C$_1$–C$_4$-alkoxy, benzyloxy, C$_1$–C$_5$-alkanoyloxy, methylthio, ethylthio, methoxycarbonyl, tert-butoxycarbonyl aminocarbonyl, carboxy, phenoxy, and phenylthio, R$^2$ is selected from the group consisting of hydrogen, halogen, trifluromethyl and hydroxy, R$^3$ is selected from the group consisting of hydrogen and halogen, R$^4$ selected from the group consisting of hydrogen, C$_1$–C$_3$-alkyl, allyl, hydroxy and C$_1$–C$_3$-alkoxy, k is 0 or 1, A is selected from the group consisting of
C$_2$–C$_6$-alkylene,
a substituted C$_2$–C$_6$-alkylene, which is substituted once or twice by C$_1$–C$_3$-alkyl, hydroxy and fluorine,
C$_2$–C$_6$-alkylene, wherein a methylene unit is isosterically replaced by O, S, CO, or SO$_2$, wherein, with the exception of CO, the isosteric substitution cannot be adjacent to the amide group,
C$_2$–C$_6$-alkenylene,
a substituted C$_2$–C$_6$-alkenylene, which is substituted once or twice by C$_1$–C$_3$-alkyl, hydroxy or fluorine,
C$_4$–C$_6$-alkadienylene,
a substituted C$_4$–C$_6$-alkadienylene, which is substituted by C$_1$–C$_3$-alkyl, or one or two fluorine atoms,
1,3,5-hexatrienylene, and
a substituted 1,3,5-hexatrienylene, which is substituted by fluorine;

D is selected from the group consisting of
C$_2$–C$_8$-alkylene,
a substituted C$_2$–C$_8$-alkylene, which is substituted once or twice by methyl or hydroxy,
C$_4$–C$_8$-alkenylene,
a substituted C$_4$–C$_8$-alkenylene, which is substituted once or twice by methyl or hydroxy,
C$_4$–C$_8$-alkinylene,
a substituted C$_4$–C$_8$-alkinylene, which is substituted once or twice by methyl or hydroxy; and
C$_2$–C$_8$-alkylene, C$_4$–C$_8$-alkenylene, or C$_4$–C$_8$-alkinylene, wherein one to three methylene units are isosterically replaced by O, S, NH, N(CH$_3$)N (COCH$_3$), N(SO$_2$CH$_3$), CO, SO, or S$_2$;

E is selected from the group consisting of

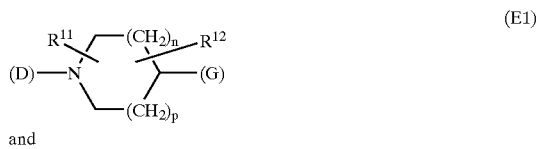 (E1)

and

 (E2)

wherein the heterocyclic ring may have a double bond and n and p are independent of each other the number 0, 1, 2 or 3 where n+p≦3, and q is 1 or 2;

R$^{11}$ is selected from the group consisting of hydrogen, C$_1$–C$_3$-alkyl, hydroxymethyl, and carboxy, and R$^{12}$ is selected from the group consisting of hydrogen and an oxo group adjacent to a nitrogen atom G is selected from the group consisting of G$^1$, G$^2$, G$^3$, G$^4$ and G$^5$, wherein G$^1$ is —(CH$_2$)$_r$—(CR$^{14}$R$^{15}$)$_s$—R$^{13}$ r is 0, 1 or 2 s is 0 or 1,

R$^{13}$ is selected from the group consisting of
hydrogen, C$_1$–C$_6$-alkyl, C$_3$–C$_8$-cycloalkyl, benzyl, phenyl,
benzocyclobutyl, indanyl, indenyl, oxoindanyl, napthyl, dihydronaphthyl, tetrahydronaphthyl, biphenylenyl, fluroenyl, oxofluorenyl, anthryl, dihydroanthryl oxodihydroanthryl, dioxodihydroanthryl, phenanthryl, dibenzocycloheptenyl, dihydrodibenzocycloheptenyl, oxodihydrodibenzocycloheptenyl, dihydrodibenzocyclooctenyl, tetrahydrodibenzocyclooctenyl,
furyl, thienyl, pyrrolyl, oxazolyl, isoxazolyl, thiazolyl, isothiazolyl, pyrazolyl, imidazolyl, oxadiazolyl, thiadiazolyl, triazolyl, pyridyl, pyrazinyl, pyridazinyl, pyrimidinyl, triazinyl, benzofuryl, dihydrobenzofuryl, benzothienyl, dihydrobenzothienyl, indolyl, indolinyl, isoindolinyl, oxoindolinyl, dioxoindolinyl, benzooxazolyl, oxobenzooxazolinyl, benzoisoxazolyl, oxobenzoisoxazolinyl, benzbthiazolyl, oxobenzothiazolinyl, benzoisothiazolyl, oxobenzoisothiazolinyl, benzoimidazolyl, oxobenzoimidazolinyl, indazolyl, oxoindazolinyl, benzofurazanyl, benzothiadiazolyl, benzotriazolyl, oxazolopyridyl, oxodihydrooxazolopyridyl, thiazolopyridyl, oxodihydrothiazolopyridyl, isothiazolopyridyl, imidazopyridyl, oxodihydroimidazopyridyl, thienopyrimidinyl, chromanyl, chromanonyl, benzopyranyl, chromonyl, quinolyl, isochinolyl, dihydroquinolinyl, oxodihydroquinolinyl, tetrahydroquinolinyl, oxotetrahydroquinolinyl, benzodioxanyl, quinoxalinyl, quinazolinyl, naphthyridinyl, carbazolyl, tetrahydrocarbazolyl, pyridoiondolyl, acridinyl, oxodihydroacridinyl, phenanthridinyl, oxodihydrophenanthridinyl, dihydrobenzoisoquinolinyl, oxodihydrobenzoisoquinolinyl, phenothiazinyl, dihydrodibenzooxepinyl, oxodihydrodibenzooxepinyl, benzocycloptathienyl, oxobenzocycloheptathienyl, dihydrothienobenzothiepinyl, oxodihydrothienobenzothiepinyl, dihydrodibenzothiepinyl, oxodihyrodibenzothiepinyl, octahydrodibenzothiepinyl, dibenzoazepinyl, dihydrodibenzoazepinyl, oxodihydrodibenzoazepinyl, octahydrodibenzoazepinyl, benzocycloheptapyridy, oxobenzocycloheptapyridyl, oxobenzocycloheptapyridyl, pyridobenzoazepinyl, dihydropyridobenzoazepinyl, oxodihyrdopyridobenzoazyepinyl, dihydropyridobenzodiazepinyl, oxodihydropyridobenzodiazepinyl, dihydrodibenzooxazepinyl, dihydropyridobenzooxazyepinyl, dihydropyridobenzooxazepinyl, oxodihydropyridobenzooxazepinyl, dihydrodibenzothiazepinyl, oxodihydrodibenzothiazepinyl, dihydropyridobenzothiazepinyl and oxodihydropyridobenzothiazepinyl bound directly or over a methylene group;

$R^{14}$ has the same meaning as $R^{13}$ but is selected independently thereof;

$R^{15}$ is selected from the group consisting of hydrogen, hydroxy, methyl, benzyl, phenyl, indanyl, indenyl, naphthyl, tetrahydronaphthyl, furyl, thienyl, pyrrolyl, oxazolyl, isoxazolyl, thiazolyl, isothiazolyl, pyrazolyl, imidazolyl, oxadiazolyl, thiadiazolyl, triazolyl, pyridyl, pyrazinyl, pyridazinyl, pyrimidinyl, triazinyl, benzofuryl, benzothienyl, indolyl, indolinyl, benzoxazolyl, benzothiazolyl, benzimidazolyl, chromanyl, quinolinyl, and tetrahydroquinolinyl bound directly or over a methylene group;

$G^2$ is $=(C)_u R^{13} R^{15}$ wherein $R^{13}$ and $R^{15}$ have the above meaning and u is 0 or 1, or u=1, and $R^{13}$ and $R^{15}$ together with a carbon atom to which they are attached form a ring system selected from the group consisting of indanyl, tetrahydronaphthyl, fluoroenyl, dihydroanthryl, tetrahydrobenzocycloheptenyl, dibenzocycloheptenyl, dihydrocycloheptenyl, dihydrodibenzocycloheptenyl, tetrahydroquinolinyl, dihydroacridinyl, dihydrodibenzooxepinyl, dihydrothienobenzothiepinyl, dihyrdodibenzothiepinyl, dibenzoazepinyl, dihydridibenzoazepinyl, benzocycloheptapyridinyl, dihydrobenzocycloheptapyridinyl, pyridobenzoazepinyl, and dihydropyridobenzoazepinyl;

or u=0, and $R^{13}$ and $R^{15}$ together with ring E to which they are attached form a spirocycle $ER^{13}R^{s15}$ selected from the group consisting of dioxaazaspirononane, dithioazaspirononane, oxadiazaspirononane, oxadiazaspirononandione, triazaspirononane, triazaspirononandione, diazaspriodecanone, diazaspirodecandione, dioxaazaspirodecane, dithiaazaspirodecane, oxadiazaspirodecane, triazaspriodecane, triazaspirodecanone, triazaspirodecandione, dioxaazaspiroundecane, dithiaazasprioundecane, oxadiazaspiroundecanone, triazaspiroundecanone, spiro[benzodioxol-pyrrolidine], spiro[benzodioxolpiperidine], spiro[benzodioxin-piperidine] or spiro[dihydrobenzoxazin-piperdine];

$G^3$ is selected from

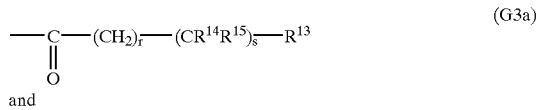 (G3a)

and

 (G3b)

wherein r, s and $R^{13}$, $R^{14}$ and $R^{15}$ can have the above meanings or the group

represents a nitrogen-containing ring bound over the nitrogen atom which nitrogen-containing ring is selected from the group consisting of pyrrolidine, piperidine, hexahydroazepine, octahydroazocine, piperazine, hexahydrodiazepine, morpholine, hexahydroxazepine, thiomorpholine, thiomorpholin-1, 1-dioxide, 2-azabicyclo[2.2.1]heptane, 7-azabicyclo[2.2.1]heptane, 2,5-diazabicyclo[2.2.1]heptane, 2-azabicyclo[2.2.2]octane, 8-azabicyclo[3.2.1]octane, 2,5-diazabicyclo[2.2.2]octane, indoline, isoindoline, (1H)-dihydroquinoline, (1H)-tetrahydroquinoline, (2H)-tetrahydroisoquinoline, (4H)-dihydrobenzooxazine, (4H)-dihydrobenzothiazine, (1H)-tetrahydrobenzo[b]azepine, (1H)-tetrahydrobenzo[c]azepine, (1H)-retrahydrobenzo[d]azepine, (5H)-tetrahydrobenzo[b]oxazepine, (5H)-tetrahydrobenzo[b]thiazepine, 1,2,3,4-tetrahydro-9H-pyrido[3,4-b]indole, carbazole, (10H)-dihydroacridine, (10H)-dihydrophenanthridine, 1,2,3,4-tetrahydroacridanone, (10H)-phenoxazine, (10H)-phenothiazine, (5H)-dibenzoazepine, (5H)-dihydrodibenzoazepine, (5-octahydrodibenzoazepine, dihydrobenzo[d,e]isoquinoline, (5H)-dihydrodibenzodiazepine, (5H)-benzo[b]pyrido[f]azepine, (5H)-dihydrbbenzo[b]pyrido[f]azepine, (11H)-dihydrodibenzo[b,e]oxazepine, (11H)-dihydrodibenzo[b,e]thiazepine, (10H)-dihydrodibenzo[b,f]oxazepine, (10)-dihydrodibenzo-[b,f]thiazepine, (5H)-tetrahydrodibenzoazocine, (11H)-dihydrobenzo[e]pyrido[b]-1, 4-diazepin-6-one and (11H)-dihydrobenzo[b]pyrido[e]-1, 4-diazepin-5-one;

$G^4$ is selected from the group consisting of

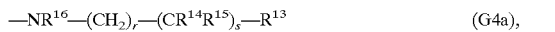  (G4a)

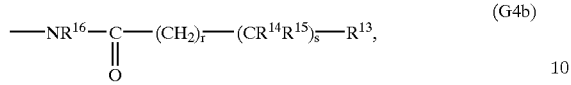  (G4b)

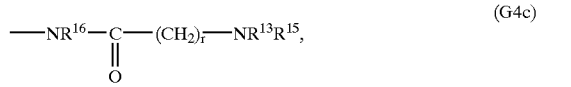  (G4c)

  (G4d),

  (G4e)

and —NR$^{16}$—COR$^{17}$  (G4f), wherein r, s and R$^{13}$, R$^{14}$, and R$^{15}$ have the above meanings;

R$^{16}$ is selected form the group consisting of hydrogen, C$_1$–C$_6$-alkyl, benzyl and phenyl;

R$^{17}$ is selected from the group consisting of trifluoromethyl, C$_1$–C$_6$-alkoxy, and benzyoxy; and Ar$^1$ and Ar$^2$, are selected independently from each other from the group consisting of phenyl, pyridyl and naphthyl;

$G^5$ is selected from the group consisting of

  (G5a)

and

  (G5b)

wherein r, s, and R$^{13}$, R$^{14}$ and R$^{15}$, Ar$^1$ and Ar$^2$ have the above meanings, and W is O, and the ring systems =CR$^{13}$R$^{15}$, —NR$^{13}$R$^{15}$ and ER$^{13}$R$^{15}$ as well as aromatic ring systems in the substituents R$^1$, R$^{13}$, R$^{14}$, R$^{15}$, R$^{16}$, R$^{17}$, Ar$^1$ and Ar$^2$ may be substituted-independently from each other by one to three of the same or different groups selected from the group consisting of halogen, cyano, C$_1$–C$_6$-alkyl, trifluoromethyl, C$_3$–C$_8$-cycloalkyl, phenyl, benzyl, hydroxy, C$_1$–C$_6$-hydroxyalkyl, C$_1$–C$_6$-alkoxy, benzyloxy, phenoxy, mercapto, C$_1$–C$_6$-alkylthio, carboxy, C$_2$–C$_7$-carboxyalkyl, C$_2$–C$_7$-carboxyalkenyl, C$_2$–C$_7$-alkoxycarbonyl, benzyloxycarbonyl, nitro, amino, mono-C$_1$–C$_6$-alkylamino, di-(C$_1$–C$_6$-alkyl) amino and, for two adjacent residues on the aromatic ring, methylenedioxy, C$_1$–C$_6$-alkoxy entirely or partially substituted by fluorine, alkyl-, alkenyl- and cycloalkyl residues in the group G$^1$ to G$^5$ may be substituted by one or two of the same or different groups selected from the group consisting of hydroxy, carboxy, C$_2$–C$_7$-alkoxycarbonyl, benzyloxycarbonyl, amino, mono-C$_1$–C$_6$-alkylamino, and di-(C$_1$–C$_6$-alkyl)-amino;

their salts, isomers and tautomers.

4. Compounds of general formula according to claim 3, wherein

R$^1$ is selected from the group consisting of hydrogen, fluorine, chlorine, bromine, methyl, ethyl, trifluoromethyl, hydroxy, C$_1$–C$_4$-alkoxy, methylthio, ethlythio, carboxy and phenoxy;

R$^2$ is selected from the group consisting of hydrogen, chlorine and methyl;

R$^3$ is hydrogen;

R$^4$ is selected from the group consisting of hydrogen, C$_1$–C$_3$-alkyl and hydroxy;

k is 0

A is selected from the group consisting of
C$_2$–C$_6$-alkylene,
a substituted C$_2$–C$_6$-alkylene, which is substituted once or twice by hydroxy or fluorine;
C$_2$–C$_6$-alkylene, wherein a methylene unit is isosterically replaced by O, S or CO, wherein, with the exception of CO, the isosteric substitution cannot be adjacent to the amide group;
C$_2$–C$_6$-alkenylene,
a substituted C$_2$–C$_6$-alkenylene which is substituted by C$_0$–C$_3$-alkyl or fluorine; and
C$_4$–C$_6$-al kadienylene;

D is selected from the group consisting of
C$_4$–C$_8$-alkylene,
a substituted C$_4$–C$_8$-alkylene, which is substituted by methyl or hydroxy,
C$_4$–C$_8$-alkenylene,
a substituted C$_4$–C$_8$-alkenylene, which is substituted by hydroxy,
C$_4$–C$_8$-alkinylene,
a substituted C$_4$–C$_8$-alkinylene, which is substituted by hydroxy, and
C$_4$–C$_8$-alkylene, C$_4$–C$_8$-alkenylene, C$_4$–C$_8$-alkinylene, wherein
a methylene unit is respectively isosterically replaced by O, NH, N(CH$_3$), CO, or SO$_2$;
an ethylene group is isosterically replaced by a group NH—CO or CO—NH or a propylene group is isosterically replaced bu a group NH—CO—O or O—CO—NH;

E is selected from the group consisting of pyrrolidine, piperidine, hexahydroazepine or morpholine, wherein the ring may be substituted by a methyl group or by an oxo group adjacent to a nitrogen atom;

G is methoxycarbonylamino, ethoxycarbonylamino, tertbutoxycarbonylamino, benzyloxycarbonylamino, trifluoroacetylamino, diphenylphosphinoylamino, diphenylphosphinoyloxy, diphenylmethyloxy, or a group selected from the group consisting of
—(CH$_2$)$_r$—(CR$^{14}$R$^{15}$)$_s$—R$^{13}$,
=(C)$_u$R$^{13}$R$^{15}$,

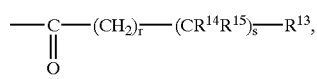

-continued

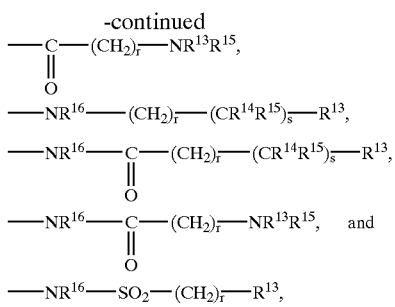

wherein
r is 0 or 1,
s is 0 or 1,
u is 0 or 1,
$R^{13}$ is selected from the group consisting of
hydrogen, methyl, benzyl, phenyl,
indanyl, indenyl, oxoindanyl, napthyl, tetrahydronaphthyl, fluroenyl, anthryl, phenanthryl, dibenzocycloheptenyl, dihydrodibenzocycloheptenyl or oxodihydrodibenzocycloheptenyl, thienyl, thiazolyl, imidazolyl, oxadiazolyl, thiadiazolyl, triazolyl, pyridyl, pyrazinyl, pyridazinyl, pyrimidinyl, benzofuryl, benzothienyl, indolyl, indolinyl, isoindolinyl, oxoindolinyl, dioxoindolinyl, benzooxazolyl, oxobenzooxazolinyl,
benzoisoxazolyl, oxobenzoisoxazolinyl, benzothiazolyl, oxobenzothiazolinyl, benzoisothiazolyl, oxobenzoisothiazolinyl, benzoimidazolyl, oxobenzoimidazolinyl, benzotriazolyl, oxazolopyridyl, oxodihydrooxazolopyridyl, thiazolopyridyl, oxodihydrothiazolopyridyl, imidazopyridy, oxodihydroimidazopyridyl, quinolyl, isochinolyl, dihydroquinolinyl, oxodihydroquinolinyl, tetrahydroquinolinyl, oxotetrahydroquinolinyl, carbazolyl, tertahydrocarbazolyl, pyridoindolyl, acridinyl, oxodihydroacridinyl, phenanthridinyl, dihydrophenanthridinyl, oxodihydrophenanthridinyl, dihydrobenzoisoquinolinyl, oxodihydrobenzoisoquinolinyl, phenothiazinyl, dihydrodibenzooxepinyl, benzocycloptathienyl, dihydrothienobenzothiepinyl, dihydrodibenzothiepinyl, dibenzoazepinyl, dihydrodibenzoazepinyl, oxodihydrodibenzoazepinyl, benzocycloheptapyridy, ocodihydrobenzocycloheptapyridyl, pyridobenzoazepinyl, dihydropyridobenzoazepinyl, oxodihyrdopyridobenzoazyepinyl, dihydropyridobenzodiazepinyl, oxodihydropyridobenzodiazepinyl, dihydrodibenzooxazepinyl, dihydropyridobenzooxazyepinyl, dihydrodibenzothiazepinyl and dihydropyridobenzothiazepinyl;
$R^{14}$ is selected from the group consisting of hydrogen, methyl, benzyl, and phenyl;
$R^{15}$ is selected from the group consisting of hydrogen, hydroxy, methyl, benzyl, phenyl, indanyl, indenyl, naphthyl, tetrahydronaphthyl, furyl, thienyl, pyridyl, pyrazinyl, pyridazinyl, pyrimidinyl, benzofuryl, benzothienyl, indolyl, indolinyl, benzoxazolyl, benzothiazolyl, benzimidazolyl, quinolinyl, and tetrahydroquinolinyl;

$R^{16}$ is selected from the group consisting of hydrogen, $C_1$–$C_4$-alkyl, benzyl, and phenyl;
$Ar^1$ and $Ar^2$ are selected independent from each other from the group consisting of phenyl, pyridyl and naphthyl;
or for u=1, $R^{13}$ and $R^{15}$ together with a carbon atom $(C)_u$ may form a ring which is selected from the group consisting of
indanyl, tetrahydronaphthyl, fluroenyl, tetrahydrobenzocycloheptenyl, dibenzocycloheptenyl, dihydrodibenzocycloheptenyl, tetrahydroquinolinyl, dihydrodibenzooxepinyl, dihydrothienobenzothiepinyl, dihydrodibenzothiepinyl, dibenzoazepi-nyl, dihydrodibenzoazepinyl, benzocycloheptapyridinyl, dihydrobenzocycloheptapyridinyl, pyridobenzoazepiyl, dihydropyridobenzoazepinyl,
or for u=0, $R^{13}$ and $R^{15}$ together with ring E to which they are attached may form a spirocycle $ER^{13}R^{15}$ selected from the group consisting of
dioxaazaspirodecane, dithiaaazaspirodecane, diazaspirodecanone, diazaspirodecandione, triazaspriodecanone, triazaspirodecandione, dioxaazaspiroundecane, dithiaazaspiroundecane, oxadiazaspriroundecanone, triazaspriroundecanone, spiro[benzodioxol-pyrrolidin], spiro[benzodioxol-piperidine], spiro-[benzodioxin-piperidine], and spiro[dihydrobenzooxazin-piperidine];
the group $NR^{13}R^{15}$ represents a heterocyclic ring bound over the nitrogen atom which heterocycle ring is selected from the group consisting of: piperidine, hexahydroazepine, piperazine, hexahydroazepine, morpholine, thiomorpholine, indoline, isoindine, (1H)-dihydroquinoline, (1H)-tetrahydroquinoline, (2H)-tetrahydroisoquinoline, (4H)-dihydrobenzooxazine, (4H)-dihydrobenzothiazine, (1H)-tetrahydrobenzo[b]azepine, (1H)-tetrahydrobenzo[c]azepine, (1H)-tetrahydrobenzo[d]azepine, (5H)-tetrahydrobenzo[b]oxazepine, (5H)-tetrahydrobenzo[b]thiazepine, carbazole, (10H)-dihydroacridine, (10H)-dihydrophenanthridine, (5H)-dibenzoazepine, (5H)-dihydrodibenzoazepine, (5H)-dihydrodibenzodiazepine, (5H)-benzo[b]pyrido[f]azepine, (5H)-dihydrobenzo[b]pyrido[f]azepine, (5H)-dihydrodibenzo[b,e]oxazepine, (11H)-dihydrodibenzo[b,e]thiazepine, (10H)-dihydrodibenzo[b,f]oxazepine, (10H)-dihydrodibenzo[b,f]thiazepine, (11H)-dihydrobenzo[e]pyrido[b]-1,4-diazepin-6-one and (11H)-dihydrobenzo[b]pyrido[e]-1,4-diazepin-5-one,
wherein the ring systems $(C)_uR^{13}R^{15}$, $-NR^{13}R^{15}$ and $ER^{13}R^{15}$ and aromatic ring systems in the substituents $R^1$, $R^{13}$, $R^{14}$, $R^{15}$, $Ar^1$ and $Ar^2$ may be substituted independently of each other by one to three of the same or different groups selected from the group consisting of halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, $C_1$–$C_6$-alkoxy entirely or partially substituted by benzyloxy, pehnoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, mono-$C_1$–$C_6$-alkylamino, di-($C_1$–$C_6$-alkyl)-amino and, for two adjacent residues on the aromatic ring, methoylenedioxy, and
wherein alkyl-, alkenyl- and cycloalkyl residues in the groups G may be substituted by one or two of the same or different groups selected from the group consisting of hydroxy, carboxy, $C_2$–$C_7$-alkoxycarbonyl, benzyloxycarbonyl, amino, mono-$C_1$–$C_6$-alkylamino and di-($C_1$–$C_6$-alkyl)-amino.

5. Compounds of general formula (I) according to claim 4, wherein $R^1$ is selected from the group consisting of hydrogen, fluorine, methyl, trifluoromethyl, and ethylthio;

$R^2$, $R^3$ and $R^4$ are each hydrogen;

k is 0;

A is selected from the group consisting of
ethylene, propylene or butylene which may be substitued by hydroxy or one or two fluorine atoms or $OCH_2$ or $SCH_2$;
ethylene, and 1,3-butadienylene;

D is selected from the group consisting of $C_4$–$C_6$-alkylene which may be substituted by hydroxy;
$C_4$–$C_6$ alkenylene;
$C_4$–$C_6$ alkinylene;
$C_1$–$C_6$ alkylene, $C_4$–$C_6$ alkenylene or $C_4$–$C_6$ alkinylene, wherein one or two methylene units is isosterically replaced by O, NH, CO or $SO_2$, E is piperidine G is selected from the group consisting of diphenylmethyl, diphenylhydroxymethyl, diphenylmethylene, naphthyl, tetrahydronaphthyl, tetrahydronaphthylidene, fluoroenyl, fluorenylidene, tetrahydrobenzocycloheptenyl or tetrahydrobenzocycloheptenylidene, dihydrodibenzocycloheptenyl, dihydrodibenzocycloheptenylidene, gem-diphenyl, phenyl-thienylmethyl, phenyl-thienylmethylene, phenyl-pyridylmethyl, tetrahydroquinolinyl, tetrahydroisoquinolinyl, benzocycloheptapyridinyl, benzocycloheptapyridinylidene, dihydrobenzocycloheptapyridinyl, dihydrobenzocycloheptapyridinylidene, dihydrodibenzooxepinyl, dihydrodibenzooxepinylidene, dihydrodibenzothiepinyl, dihydrodibenzothiepinylidene, dihydrobenzothienothiepinyl or dihydrobenzothienothiepinylidene; indolyl, oxobenzoimidazolyl, oxobenzothiazolyl, benzoisothiazolyl, benzotriazolyl, dibenzylaminaocarbonyl, diphenylaminocarbonyl, indolinyl-N-carbonyl, isoindolinyl-N-carbonyl, tetrahydroquinolinyl-N-carbonyl, tetrahydrobenzoazepinyl-N-carbonyl; diphenylmethylamino, kiphenylmethyl-methylamino, dibenzylamino, benzylphenylamno, triphenylmenthylamno; acetylamino, pivaloylamino, phenylacetylamino, diphenylacetylamino, diphenylpropionylamino, naphtyhylacetylamino, benzoylamino, benzoylmethylamino, naphthoylamino, oxofluorenylcarbonylamino, furoylamino, pyridylacetylamino or pyridylcarbonylamino, benzylaminoscarbonylamino, naphthylmethylaminocarbonylamino, indanylaminocarbonylamino, tetrahydronaphthylaminocarbonyl, dibenzylaminocarbonylamino, phenylylaminocarbonylamino, naphthlaminocarbonylamino, benzylphenylaminocarbonylamino, diphenylaminocarbonylamino, indolinyl-N-carbonylamino, isoindolinyl-N-carbonylamino, tetrahydroquinolinyl-N-carbonylamino, tetrahydrobenzoazepinyl-N-carbonylamino, carbazolyl-N-carbonylamino, dihydrophenanthridinyl-N-carbonylamino, dihydrodibenzoazepin-N-carbonylamino, dihydrobenzopyridoazepinyl-N-carbonylamino, oxodihydrobenzopyridodiazepinyl-N-carbonylamino, methanesulfonylamino, tolylsulfonylamino, naphthylsulfonylamino, diphenylphosphinoylamino, diphenylmethyloxy, and diphenylphosphinoyloxy, wherein aromatic ring systems may be substituted independently of each other by one to three of the same or different groups selected from the group consisting of halogen, cyano, $C_1$–$C_6$-Alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, mono-$C_1$–$C_6$-alkylamino, di-($C_1$–$C_6$-alkyl)-amino and, for two adjacent residues on the aromatic ring, methylenedioxy, alkyl-, alkenyl- and cycloalkyl residues in the group G can be substitutedby one or two of the same of different groups selected from the group consisting of hydroxy, carboxy, $C_2$–$C_7$-alkoxycarbonyl, benzyloxycarbonyl, amino, mono-$C_1$–$C_6$-alkylamino, di-($C_1$–$C_6$,-alkyl) amino; and their salts, isomers and tautomers.

6. Compounds according to general formula (I) according to claim 5, selected from the group consisting of N-[4-(4-phenyl-piperidin-1-yl)-butyl]-3-pyridin-3-yl-acrylamide;

N-{4-[4-(1H-indol-3-yl)-piperidin-1-yl]-butyl}-3-pyridin-3-yl-acrylamide;

N-{4-[4-(2-oxo-2,3-dihydro-benzoimidazol-1-yl)-piperidin-1-yl]-butyl}-3-pyridin-3-yl-acrylamide, N-[4-(4-benzotruazol-1-yl-piperidin-1-yl]-butyl]-3-pyridin-3-yl-acrylamide;

N-{4-[4-(hydroxy-diphenylmethyl)-piperidin-1-yl]-butyl}-2-(pyridin-3-yloxy)-acetamide;

N-[4-(4,4-diphenyl-piperidin-1-yl)-butyl]-3-pyridin-3-yl-acrylamide;

N-{4-[4-(6,11-dihydro-dibenzo[b,e]thiepin-11-yliden)-piperidin-1-yl]-butyl}-3-pyridin-3-yl-propionamide dihydrochloride/semi-isopropanol;

N-{4-[4-(6,11-dihydro-dibenzo[b,e]thiepin-11-yliden)-piperidin-1-yl]-butyl}-5-pyridin-3-yl-pentanamide;

N-{4-[4-(4,9-dihydro-thieno[2,3-b]-benzo[e]thiepin-4-yliden)-piperidin-1-yl]-butyl}-3-pyridin-3-yl-propionamide;

N-{4-[4-(4,9-dihydro-thieno[2,3-b]-benzo[e]thiepin-4-yliden)-piperidin-1-yl]-butyl}-3-pyridin-3-yl-acrylamide;

N-[4-(4-diphenylphosphinoyloxy-piperidin-1-yl)-butyl]-3-pyridin-3-yl-acrylamide; and N-[4-(1,4-dioxa-8-azaspiro[4.5]dec-8-yl)-butyl]-3-pyridin-3-yl-acrylamide.

7. A pharmaceutical composition comprising a compound of formula (I)

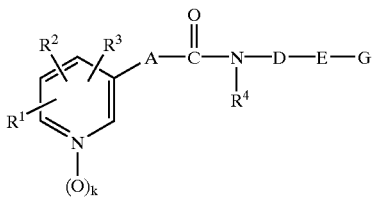

wherein

R$^1$ is selected from the group consisting of hydrogen, halogen, cyano, C$_1$–C$_6$-alkyl, C$_3$–C$_6$-alkenyl, C$_3$–C$_6$-alkinyl, trifluoromethyl, C$_3$–C$_8$-cycloalkyl, C$_1$–C$_6$-hydroxyalkyl, hydroxy, C$_1$–C$_6$-alkoxy, C$_3$–C$_6$-alkenyloxy, C$_3$–C$_6$-alkinyloxy, benzyloxy, C$_1$–C$_7$-alkanoyloxy, C$_2$–C$_7$-alkoxycarbonyloxy, C$_1$–C$_6$-alkylthio, C$_3$–C$_6$-alkenylthio, C$_3$–C$_6$-alkinylthio, C$_3$–C$_8$-cycloalkyloxy, C$_3$–C$_8$-cycloalkylthio, C$_2$–C$_7$-alkoxycarbonyl, aminocarbonyl, C$_2$–C$_7$-alkoxycarbonyl, C$_3$–C$_{13}$-dialkylaminocarbonyl, carboxy, phenyl, phenoxy, phenylthio, pyridyloxy, pyridylthio, and NR$^5$R$^6$, wherein R$^5$ and R$^6$ selected independently of each other from the group consisting of hydrogen, C$_1$–C$_6$-alkyl, C$_3$–C$_6$-alkenyl, C$_3$–C$_6$-alkinyl, benzyl and phenyl;

R$^2$ is selected from the group consisting of hydrogen, halogen, cyano, C$_1$–C$_6$-alkyl, triflurormethyl, hydroxy, C$_1$–C$_1$-alkoxy, benzyloxy and C$_1$–C$_7$-alkanoyloxy; R$^1$ and R$^2$, if adjacent, may form a bridge selected from —(CH$_2$)$_4$—, —(CH=CH)$_2$— and —CH$_2$O—CR$^7$R$^8$—O—, wherein R$^7$ and R$^8$ are selected independently from each other from hydrogen and C$_1$–C$_6$-alkyl;

R$^3$ is selected from the group consisting of hydrogen, halogen, C$_1$–C$_6$-alkyl, trifluoromethyl and C$_1$–C$_6$-hydroxyalkyl;

R$^4$ selected from the group consisting of hydrogen, C$_1$–C$_6$-alkyl, C$_3$–C$_6$-alkenyl, C$_3$–C$_6$-alkinyl, C$_3$–C$_6$-cycloalkyl, hydroxy, C$_1$–C$_6$-alkoxy and benzyloxy;

k is 0 or 1,

A is selected from the group consisting of
C$_1$–C$_6$-alkylene
a substituted C$_1$–C$_6$-alkylene, which is substituted one to three-fold by C$_1$–C$_6$-alkyl, hydroxy, C$_1$–C$_3$-alkoxy, fluorine, or phenyl,
C$_2$–C$_6$-alkylene, wherein a methylene unit is isosterically replaced by O, S, NR$^9$, CO, SO, or SO$_2$, wherein, with the exception of CO, the isosteric substitution is not adjacent to the amide group and R$^9$ is selected from the
group consisting of hydrogen, C$_1$–C$_6$-alkyl, C$_3$–C$_6$-alkenyl, C$_1$–C$_6$-alkinyl, C$_1$–C$_6$-acyl and C$_1$–C$_6$-alkanesulfonyl,
1,2-cyclopropylene,
C$_2$–C$_6$-alkenylene,
a substituted C$_2$–C$_6$-alkenylene, which is substituted one to three-fold by C$_1$–C$_6$-alkyl, hydroxy, C$_1$–C$_6$-alkoxy, fluorine, cyano or phenyl,
C$_4$–C$_6$-alkadienylene,
a substituted C$_4$–C$_6$-alkadienylene, which is substituted once to twice by C$_1$–C$_3$-alkyl, fluorine, cyano or phenyl,
1,3,5-hexatrienylene,
a substituted 1,3,5-hexatrienylene, which is substituted by C$_1$–C$_3$-alkyl, fluorine, cyano or phenyl, and ethinylene D is selected from the group consisting of C$_2$–C$_{10}$-alkylene,
a substituted C$_2$–C$_{10}$-alkylene, which is substituted once or twice by C$_1$–C$_6$-alkyl, hydroxy, or C$_1$–C$_6$-alkoxy,
C$_4$–C$_{10}$-alkenylene,
a substituted C$_4$–C$_{10}$-alkenylene, which is substituted once or twice by C$_1$–C$_6$-alkyl, hydroxy, or C$_1$–C$_6$-alkoxy,
C$_4$–C$_{10}$-alkinylene,
a substituted C$_4$–C$_{10}$-alkinylene, which is substituted once or twice by C$_1$–C$_6$-alkyl, hydroxy, or C$_1$–C$_6$-alkoxy, and
C$_2$–C$_{10}$-alkylene,
C$_2$–C$_{10}$-alkylene, C$_4$–C$_{10}$-alkenylene, or C$_4$–C$_{10}$-alkinylene, wherein one to three methylene units are isosterically replaced by O, S, NR$^{10}$, CO, SO, or SO$_2$, wherein R$^{10}$ has the same meaning as R$^9$, but is selected independently thereof;

E is selected from the group consisting of

(E1)

and

(E2)

wherein the heterocyclic ring may have a double bond and n and p are, independent of each other, 0, 1, 2 or 3 where n+p≧4, wherein q is 1, 2 or 3;

R$^{11}$ is selected from the group consisting of hydrogen, C$_1$–C$_6$-alkyl, hydroxy, hydroxymethyl, carboxy, and C$_2$–C$_7$-alkoxycarbonyl and R$^{12}$ is selected from the group consisting of hydrogen, C$_1$–C$_6$-alkyl and an oxo group adjacent to a nitrogen atom, or R$^{11}$ and R$^{12}$, may together, form a C$_1$–C$_3$-alkylene bridge under formation of a bicyclic ring system;

G is selected from the group consisting of G$^1$, G$^2$, G$^3$, G$^4$ and G$^5$, wherein G$^1$ is —(CH$_2$)$_r$—(CR$^{14}$R$^{15}$)$_s$—R$^{13}$ r is 0, 1, 2 or 3 and s is 0 or 1

R$^{13}$ is selected from the group consisting of
hydrogen, C$_1$–C$_6$-alkyl, C$_3$–C$_6$-alkenyl, C$_3$–C$_6$-alkinyl, C$_3$–C$_8$-cycloalkyl,
saturated or unsaturated, four to seven-membered heterocycles, which contain one or two hetero-atoms selected from N, S and O, benzyl, phenyl,
monocyclic aromatic five and six-membered heterocycles, which contain one to three hetero-atoms selected from N, S and O and are either bound directly or over a methylene group,
anellated bi- and tricyclic aromatic and partially hydrogenated carbocyclic ringsystem with 8 to 16 ring atoms and at least one aromatic ring, wherein the linkage occurs either over an aromatic or a hydrogenated ring and either directly or over a methylene group, and anellated bi- and tricyclic aromatic or partially hydrogenated heterocyclic ring systems with 8 to 16 ring atoms and at least one aromatic ring, wherein one to three ring atoms are selected from N, S and O and the linkage occurs either over an aromatic ring or a hydrogenated ring and either directly or over a methylene group, $R^{14}$ has the same meaning as $R^{13}$, but is selected independently thereof;

$R^{15}$ is selected from the group consisting of hydrogen, hydroxy, methyl, benzyl, phenyl, monocyclic aromatic five and six-membered heterocycles, which contain one to three heteroatoms selected from N, S and O and are either bound directly or over a methylene group, anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group, anellated bi- and tricyclic aromatic and partially hydrogenated heterocyclic ring systems with 8 to 16 ring atoms and at least one aromatic ring, wherein one to three ring atoms are selected from N, S and O and the linkage can occur either over an aromatic ring or a hydrogenated ring and either directly or over a methylene group;

$G^2$ is $=(C)_G R^{13} R^{15}$ wherein, $R^{13}$ and $R^{15}$ have the above meaning and u is 0 or 1, or u=1, and $R^{13}$ and $R^{15}$ together with a carbon atom to which they are attached form a ring system selected from the group consisting of $C_2$–$C_8$-cycloalkyl, saturated, four to seven-membered heterocycles which contain one or two hetero-atoms selected-from N, S and O;

anellated bi- and tricyclic partially hydrogenated carboxocyclic ring system with 8 to 16 ring atoms and at least one aromatic ring; and anellated bi- and tricyclic partially hydrogenated heterocyclic ring systems with 8 to 16 ring atoms and at least one aromatic ring, wherein one to three ring atoms are selected from N, S and O;

or, u=0, and $R^{13}$ and $R^{15}$ together with the carbon atom $C_E$ of ring E to which they are attached form a ring system $C_E R^{13} R^{15}$ selected from the group consisting of cycloalkyl, saturated, four to seven-membered heterocycles which contain one or two hetero-atoms selected from N, S and O;

anellated bi- and tricyclic partially hydrogenated carbocyclic ring systems with 8 to 16 ring atoms and at least one aromatic ring; and anellated bi- and tricyclic partially hydrogenated heterocyclic ring systems with 8 to 16 ring atoms and at least one aromatic ring, wherein 1 to 3 ring atoms can be selected from N, S and O;

$G^3$ is selected from

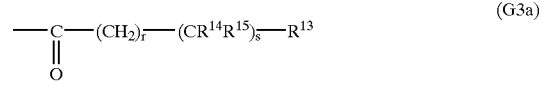

(G3a)

and

(G3b)

wherein r, s, and the substituents $R^{13}$, $R^{14}$, and $R^{15}$ have the above meanings, or the group

is a nitrogen containing heterocycle bound over the nitrogen atom which nitrogen-containing heterocycle is selected from the group consisting of saturated and unsaturated monocyclic, four to eight-membered heterocycles which, aside from the essential nitrogen atom, may contain one or two further hetero-atoms selected from N, S and O, and saturated and unsaturated bi- or tricyclic, anellated or bridges heterocycles with 8 to 16 ring atoms, which, aside from the essential nitrogen atom, may contain one or two further hetero-atoms selected from N, S and O, $G^4$ is selected from the group consisting of

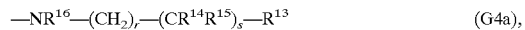

(G4a),

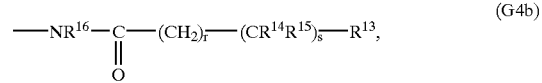

(G4b)

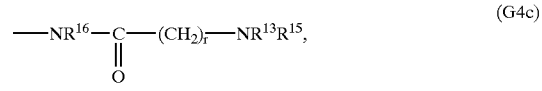

(G4c)

(G4d),

(G4e)

and —NR$^{16}$—COR$^{17}$ (G4f), wherein r, s and $R^{13}$, $R^{14}$, and $R^{15}$ have the above meanings and $R^{16}$ has the same meanings as $R^5$, but is selected independently thereof, $R^{17}$ is selected from the group consisting of trifluoromethyl, $C_1$–$C_6$-alkoxy, $C_3$–$C_6$-alkenyloxy and benzyloxy; and $Ar^1$ and $Ar^2$, are selected independently from each other from the group consisting of phenyl, pyridyl and naphthyl;

$G^5$ is selected from the group consisting of

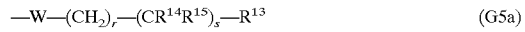

(G5a)

and

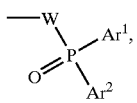

(G5b)

wherein r, s, and $R^{13}$, $R^{14}$, $R^{15}$, $Ar^1$ and $Ar^2$ have the above meanings and W is O or S, wherein the ring systems $=CR^{13}R^{15}$, $-NR^{13}R^{15}$, $-C_ER^{13}R^{15}$ and aromatic ring systems in the substituents $R^1, R^2, R^4, R^5, R^6, R^{13}, R^{14}, R^{15}, R^{16}, R^{17}, Ar^1$ and $Ar^2$ may be substituted independenitly from each other by one to three of the same or different groups selected from the group consisting of halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxyalkyl, nitro, amino, mono-$C_1$–$C_6$-alkylamino, di-($C_1$–$C_6$-alkyl)amino and, for two adjacent residues on the aromatic ring, methyl enedioxy, and $C_1$–$C_6$-alkoxy which is entirely or partially substituted by fluorine, wherein alkyl-, alkenyl- and cycloalkyl residues in the group $G^1$ to $G^5$ may be substituted by one or two of the same or different groups selected from hydroxy, carboxy, $C_2$–$C_7$-alkoxycarbonyl, benzyloxycarbonyl, amino, mono-$C_1$–$C_6$-alkylamino, and di-($C_1$–$C_6$-alkyl)amino, wherein G is not $-CHR^{14}-R^{13}$, $-C(OH)R^{14}-R^{13}$, $=CR^{13}R^{15}$ or $-O-CHR^{14}-R^{13}$, in the case when simultaneously $R^{13}$ is hydrogen, alkyl or phenyl substituted by halogen, alkyl, hydroxy or trifluoromethyl, $R^{14}$ and $R^{15}$ may be pyridyl or phenyl substituted with halogen, alkyl, hydroxy or trifluoromethyl, A is alkylene, which may be substituted with ethenylene or butadienylene, D is alkylene and E is piperidine substituted in the 4-position;

their cis- and trans-isomers, E- and Z-isomers, and their racemic or non-racemic mixtures, their pure endo- and exoisomers and mixtures thereof;

their respective tautomers, the corresponding acid addition salts, hydrates and solvates.

8. The pharmaceutical composition of claim 7 further comprising ingredients selected from the group consisting of a pharmaceutically acceptable carrier, toxicologically safe adjuvants, other active ingredients, and mixtures thereof.

9. The pharmaceutical composition of claim 7 which is present in a form selected from the group consisting of solid, peroral administrable form as a tablet, capsule, coated tablet, sustained action or gastric juice-resistant preparation, peroral administrable solution, suspension, effervescent tablet, tabs, sachets, and sustained action form.

10. The pharmaceutical composition of claim 7 which is present in a form selected from the group consisting of a suitable injection or infusion preparation together with suitable pharmaceutically acceptable carriers and adjuvants, a sustained action form, as a parenteral depot medicinal form, implant, a concentrate, powder, and lyophilisate.

11. The pharmaceutical composition of claim 7 which is present in the form selected from the group consisting of an inhalation therapeutic agent and a spray together with suitable pharmaceutically acceptable propellants, carriers and adjuvants.

12. The pharmaceutical composition of claim 7 which is present in the form of a transdermal therapeutic system for systemic treatment.

13. The pharmaceutical composition of claim 7 which is present in the form of a gastrointestinal therapeutic system (GITS) for systemic treatment.

14. The pharmaceutical composition of claim 7 which is present in a form selected from the group consisting of a salve, suspension, emulsion, a balm, plaster, and an externally applicable solution.

15. The pharmaceutical composition of claim 7 which is present in a form selected from the group consisting of a rectal, genital, transurethal administrable emulsion, a solution, a liposomal solution, an implant, suppository, and a capsule.

16. The pharmaceutical composition of claim 7 which is present in the form selected from the group consisting of a composition capable of being applied nasally, otologically, and opthalmologically.

17. The pharmaceutical composition of claim 7 which is present in the form of a buccally applicable form.

18. The pharmaceutical composition of claim 7 wherein a dosage unit for single administration contains about 0.001 to about 5000 mg active ingredient.

19. The pharmaceutical composition of claim 18 wherein a dosage unit for a single administration contains about 0.01 to about 100 mg active ingredient.

20. The pharmaceutical composition of claim 18 wherein a dosage unit for a single administration contains about 1 to about 10 mg active ingredient.

21. A method of inhibiting tumor cell growth in a human or animal body comprising administering to the human or animal body in need thereof an amount of a pharmaceutical composition effective for inhibiting tumor cell growth, wherein the pharmaceutical composition includes a compound of general formula (I)

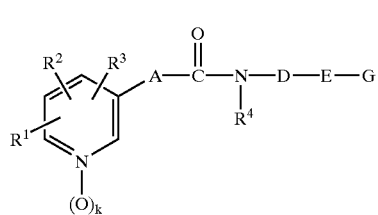

(I)

wherein $R^1$ is selected from the group consisting of hydrogen, halogen, cyano, $C_1$–$C_6$-alkyl, $C_3$–$C_6$-alkenyl, $C_3$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkoxycarbonyl, $C_3$–$C_{13}$-dialkylaminocarbonyl, carboxy, phenyl, phenoxy, phenylthio, pyridyloxy, pyridylthio, and $NR^5R^6$, wherein $R^5$ and $R^6$ selected independently of each other from the group consisting of hydrogen, $C_1$–$C_6$-alkyl, $C_3$–$C_6$-alkenyl, $C_3$–$C_6$-alkinyl, benzyl and phenyl;

$R^2$ is selected from the group consisting of hydrogen, halogen, cyano, $C_1$–$C_6$-alkyl, triflurormethyl, hydroxy, $C_1$–$C_6$-alkoxy, benzyloxy and $C_1$–$C_7$-alkanoyloxy; $R^1$ and $R^2$, if adjacent, may form a bridge selected from —$(CH_2)_4$—, —$(CH=CH)_2$— and —$CH_2O$—$CR^7R^8$—O—, wherein $R^7$ and $R^8$ are selected independently from each other from hydrogen and $C_1$–$C_6$-alkyl;

$R^3$ is selected from the group consisting of hydrogen, halogen, $C_1$–$C_6$-alkyl, trifluoromethyl and $C_1$–$C_6$-hydroxyalkyl;

$R^4$ selected from the group consisting of hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy and benzyloxy;

k is 0 or 1,

A is selected from the group consisting of
  $C_1$–$C_6$-alkylene
  a substituted $C_1$–$C_6$-alkylene, which is substituted one to three-fold by $C_1$–$C_6$-alkyl, hydroxy, $C_1$–$C_3$-alkoxy, fluorine, or phenyl,
  $C_2$–$C_6$-alkylene, wherein a methylene unit is isosterically replaced by O, S, $NR^9$, CO, SO, or $SO_2$, wherein, with the exception of CO, the isosteric substitution is not adjacent to the amide group and $R^9$ is selected from the group consisting of hydrogen, $C_1$–$C_6$-alkyl, $C_3$–$C_6$-alkenyl, $C_3$–$C_6$-alkinyl, $C_1$–$C_6$-acyl and $C_1$–$C_6$-alkanesulfonyl,
  1,2-cyclopropylene,
  $C_2$–$C_6$-alkenylene,
  a substituted $C_2$–$C_6$-alkenylene, which is substituted one to three-fold by $C_1$–$C_6$-alkyl, hydroxy, $C_1$–$C_6$-alkoxy, fluorine, cyano or phenyl,
  $C_4$–$C_6$-alkadienylene,
  a substituted $C_4$–$C_6$-alkadienylene, which is substituted once to twice by $C_1$–$C_3$-alkyl, fluorine, cyano or phenyl,
  1,3,5-hexatrienylene,
  a substituted 1,3,5-hexatrienylene, which is substituted by $C_1$–$C_3$-alkyl, fluorine, cyano or phenyl, and
  ethinylene D is selected from the group consisting of $C_2$–$C_{10}$-alkylene,
  a substituted $C_2$–$C_{10}$-alkylene, which is substituted once or twice by $C_1$–$C_6$-alkyl, hydroxy, or $C_1$–$C_6$-alkoxy,
  $C_4$–$C_{10}$-alkenylene,
  a substituted $C_4$–$C_{10}$-alkenylene, which is substituted once or twice by $C_1$–$C_6$-alkyl, hydroxy, or $C_1$–$C_6$-alkoxy,
  $C_4$–$C_{10}$-alkinylene,
  a substituted $C_4$–$C_{10}$-alkinylene, which is substituted once or twice by $C_1$–$C_6$-alkyl, hydroxy, or $C_1$–$C_6$-alkoxy, and
  $C_2$–$C_{10}$-alkylene,
  $C_2$–$C_{10}$-alkylene, $C_4$–$C_{10}$-alkenylene, or $C_4$–$C_{10}$-alkinylene, wherein one to three methylene units are isosterically replaced by O, S, $NR^{10}$, CO, SO, or $SO^2$, wherein $R^{10}$ has the same meaning as $R^9$, but is selected independently thereof;

E is selected from the group consisting of

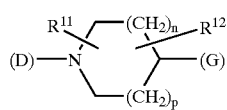

(E1)

and

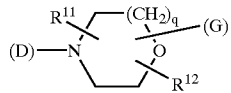

(E2)

wherein the heterocyclic ring may have a double bond and n and p are, independent of each other, 0, 1, 2 or 3 where n+p≧4, wherein q is 1, 2 or 3;

$R^{11}$ is selected from the group consisting of hydrogen, $C_1$–$C_6$-alkyl, hydroxy, hydroxymethyl, carboxy, and $C_2$–$C_7$-alkoxycarbonyl and $R^{12}$ is selected from the group consisting of hydrogen, $C_1$–$C_6$-alkyl and an oxo group adjacent to a nitrogen atom, or $R^{11}$ and $R^{12}$, may together, form a $C_1$–$C_3$-alkylene bridge under formation of a bicyclic ring system;

G is selected from the group consisting of $G^1$, $G^2$, $G^3$, $G^4$ and $G^5$, wherein $G^1$ is —$(CH_2)_r$—$(CR^{14}R^{15})_s$—$R^{13}$ r is 0, 1, 2 or 3 and s is 0 or 1

$R^{13}$ is selected from the group consisting of
  hydrogen, $C_1$–$C_6$-alkyl, $C_3$–$C_6$-alkenyl, $C_3$–$C_6$-alkinyl, $C_3$–$C_8$-cycloalkyl,
  saturated or unsaturated, four to seven-membered heterocycles, which contain one or two hetero-atoms selected from N, S and O,
  benzyl, phenyl,
  monocyclic aromatic five and six-membered heterocycles, which contain one to three hetero-atoms selected from N, S and O and are either bound directly or over a methylene group,
  anellated bi- and tricyclic aromatic and partially hydrogenated carbocyclic ring system with 8 to 16 ring atoms and at least; one aromatic ring, wherein the linkage occurs either over an aromatic or a hydrogenated ring and either directly or over a methylene group, and
  anellated bi- and tricyclic aromatic or partially hydrogenated heterocyclic ring systems with 8 to 16 ring atoms and at least one aromatic ring, wherein one to three ring atoms are selected from N, S and O and the linkage occurs either over an aromatic ring or a hydrogenated ring and either directly or over a methylene group, $R^{14}$ has the same meaning as $R^{13}$, but is selected independently thereof;

$R^{15}$ is selected from the group consisting of hydrogen, hydroxy, methyl, benzyl, phenyl, monocyclic aromatic five and six-membered heterocycles, which contain one to three hetero-atoms selected from N, S and O and are either bound directly or over a methylene group,
  anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group,
  anellated bi- and tricyclic aromatic and partially hydrogenated heterocyclic ring systems with 8 to 16 ring atoms and at least one aromatic ring, wherein one to three ring atoms are selected from N, S and O and the linkage can occur either over an aromatic ring or a hydrogenated ring and either directly or over a methylene group;

$G^2$ is $=(C)_u R^{13}R^{15}$ wherein, $R^{13}$ and $R^{15}$ have the above meaning and u is 0 or 1, or u=1, and $R^{13}$ and $R^{15}$ together with a carbon atom to which they are attached form a ring system selected from the group consisting of $C_2$–$C_8$-cycloalkyl saturated, four to seven-membered heterocycles which contain one or two hetero-atoms selected from N, S and O;

anellated bi- and tricyclic partially hydrogenated carboxocyclic ring system with 8 to 16 ring atoms and at least one aromatic ring; and anellated bi- and tricyclic partially hydrogenated heterocyclic ring systems with 8 to 16 ring atoms and at least one aromatic ring, wherein one to three ring atoms are selected from N, S and O;

or, u=0, and $R^{13}$ and $R^{15}$ together with the carbon atom $C_E$ of ring E to which they are attached form a ring system $C_E R^{13}R^{15}$ selected from the group consisting of cycloalkyl, saturated, four to seven-membered heterocycles which contain one or two hetero-atoms selected from N, S and O;

anellated bi- and tricyclic partially hydrogenated carbocyclic ring systems with 8 to 16 ring atoms and at least one aromatic ring; and anellated bi- and tricyclic partially hydrogenated heterocyclic ring systems with 8 to 16 ring atoms and at least one aromatic ring, wherein 1 to 3 ring atoms can be selected from N, S and O;

$G^3$ is selected from

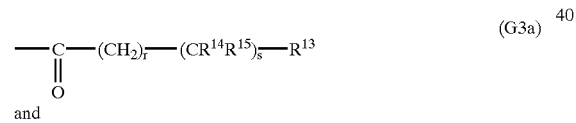

(G3a)

and

(G3b)

wherein r, s, and the substituents $R^{13}$, $R^{14}$, and $R^{15}$ have the above meanings, or the group

is a nitrogen containing heterocycle bound over the nitrogen atom which nitrogen-containing heterocycle is selected from the group consisting of saturated and unsaturated monocyclic, four to eight-membered heterocycles which, aside from the essential nitrogen atom, may contain one or two further hetero-atoms selected from N, S and O, and saturated and unsaturated bi- or tricyclic, anellated or bridges heterocycles with 8 to 16 ring atoms, which, aside from the essential nitrogen atom, may contain one or two further hetero-atoms selected from N, S and O, $G^4$ is selected from the group consisting of

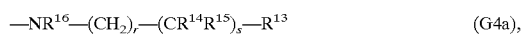 (G4a),

 (G4b)

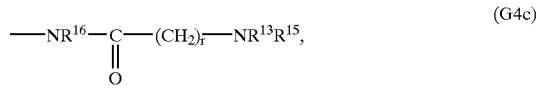 (G4c)

 (G4d),

 (G4e)

and —NR$^{16}$—COR$^{17}$ (G4f), wherein r, s and $R^{13}$, $R^{14}$, and $R^{15}$ have the above meanings and $R^{16}$ has the same meanings as $R^5$, but is selected independently thereof, $R^{17}$ is selected from the group consisting of trifluoromethyl, $C_1$–$C_6$-alkoxy, $C_3$–$C_6$-alkenyloxy and benzyloxy; and Ar$^1$ and Ar$^2$, are selected independently from each other from the group consisting of phenyl, pyridyl and naphthyl;

$G^5$ is selected from the group consisting of

 (G5a)

and

 (G5b)

wherein r, s, and $R^{13}$, $R^{14}$, $R^{15}$, Ar$^1$ and Ar$^2$ have the above meanings and W is O or S, wherein the ring systems $=CR^{13}R^{15}$, —NR$^{13}R^{15}$, —$C_E R^{13}R^{15}$ and aromatic ring systems in the substituents $R^1$, $R^2$, $R^4$, $R^5R^6$, $R^{13}$, $R^{14}$, $R^{15}$, $R^{16}$, $R^{17}$, Ar$^1$ and Ar$^2$ may be substituted independently from each other by one to three of the same or different groups selected from the group consisting of halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, benzyloxy, phenoxy, mercapto, $C_1$–$C_1$-alkylthio, carboxy, $C_2$–$C_7$-carboxyalkyl, $C_2$–$C_7$-carboxyalkenyl, $C_2$–$C_7$-alkoxycarbonyl, benzyloxyalkyl, nitro, amino, mono-$C_1$–$C_6$-alkylamino, di-($C_1$–$C_6$-alkyl)amino and, for two adjacent residues on the aromatic ring, methylenedioxy, and $C_1$–$C_6$-alkoxy which is entirely or partially substituted by fluorine, wherein alkyl-, alkenyl- and cycloalkyl residues in the group $G^1$ to $G^5$ may be substituted by one or two of the same or different groups selected from hydroxy, carboxy, $C_2$–$C_7$-alkoxycarbonyl, benzyloxycarbonyl, amino, mono-$C_1$–$C_6$-alkylamino, and di-($C_1$–$C_6$-alkyl)amino.

22. A method of suppressing autoimmune diseases in a human or animal body comprising administering to the human or animal body in need thereof an amount of a pharmaceutical composition effective for suppressing autoimmune reactions, wherein the pharmaceutical composition includes a compound of general formula (I)

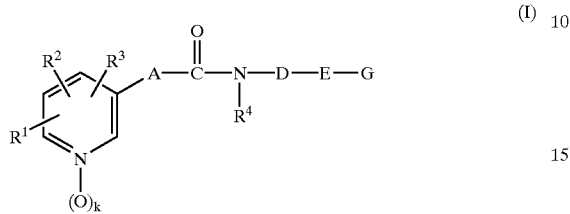

(I)

wherein $R^1$ is selected from the group consisting of hydrogen, halogen, cyano, $C_1$–$C_6$-alkyl, $C_3$–$C_6$-alkenyl, $C_3$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkoxycarbonyl, $C_3$–$C_{13}$-dialkylaminocarbonyl, carboxy, phenyl, phenoxy, phenylthio, pyridyloxy, pyridylthio, and $NR^5R^6$, wherein $R^5$ and $R^6$ selected independently of each other from the group consisting of hydrogen, $C_1$–$C_6$-alkyl, $C_3$–$C_6$-alkenyl, $C_3$–$C_6$-alkinyl, benzyl and phenyl;

$R^2$ is selected from the group consisting of hydrogen, halogen, cyano, $C_1$–$C_6$-alkyl, triflurormethyl, hydroxy, $C_1$–$C_6$-alkoxy, benzyloxy and $C_1$–$C_7$-alkanoyloxy; $R^1$ and $R^2$, if adjacent, may form a bridge selected from —$(CH_2)_4$—, —$(CH=CH)_2$— and —$CH_2O$—$CR^7R^8$—$O$—, wherein $R^7$ and $R^8$ are selected independently from each other from hydrogen and $C_1$–$C_6$-alkyl;

$R^3$ is selected from the group consisting of hydrogen, halogen, $C_1$–$C_6$-alkyl, trifluoromethyl and $C_1$–$C_6$-hydroxyalkyl;

$R^4$ selected from the group consisting of hydrogen, $C_1$–$C_6$-alkyl, $C_3$–$C_7$-alkenyl, $C_3$–$C_6$-alkinyl, $C_3$–$C_6$-cycloalkyl, hydroxy, $C_1$–$C_6$-alkoxy and benzyloxy;

k is 0 or 1,

A is selected from the group consisting of $C_1$–$C_6$-alkylene a substituted $C_1$–$C_6$-alkylene, which is substituted one to three-fold by $C_1$–$C_6$-alkyl, hydroxy, $C_1$–$C_3$-alkoxy, fluorine, or phenyl, $C_2$–$C_6$-alkylene, wherein a methylene unit is isosterically replaced by O, S, $NR^9$, CO, SO, or $SO^2$, wherein, with the exception of CO, the isosteric substitution is not adjacent to the amide group and $R^9$ is selected from the group consisting of hydrogen, $C_1$–$C_6$-alkyl, $C_3$–$C_6$-alkenyl, $C_3$–$C_6$-alkinyl, $C_1$–$C_6$-acyl and $C_1$–$C_6$-alkanesulfonyl, 1,2-cyclopropylene, $C_2$–$C_6$-alkenylene, a substituted $C_2$–$C_6$-alkenylene, which is substituted one to three-fold by $C_1$–$C_6$-alkyl, hydroxy, $C_1$–$C_6$-alkoxy, fluorine, cyano or phenyl, $C_4$–$C_6$-alkadienylene, a substituted $C_4$–$C_6$-alkadienylene, which is substituted once to twice by $C_1$–$C_3$-alkyl, fluorine, cyano or phenyl, 1,3,5-hexatrienylene, a substituted 1,3,5-hexatrienylene, which is substituted by $C_1$–$C_3$-alkyl, fluorine, cyano or phenyl, and ethinylene D is selected from the group consisting of $C_2$–$C_{10}$-alkylene, a substituted $C_2$–$C_{10}$-alkylene, which is substituted once or twice by $C_1$–$C_6$-alkyl, hydroxy, or $C_1$–$C_6$-alkoxy, $C_4$–$C_{10}$-alkenylene, a substituted $C_4$–$C_{10}$-alkenylene, which is substituted once or twice by $C_1$–$C_6$-alkyl, hydroxy, or $C_1$–$C_6$-alkoxy, $C_4$–$C_{10}$-alkinylene, a substituted $C_4$–$C_{10}$-alkinylene, which is substituted once or twice by $C_1$–$C_6$-alkyl, hydroxy, or $C_1$–$C_6$-alkoxy, and $C_2$–$C_{10}$-alkylene, $C_2$–$C_{10}$-alkylene, $C_4$–$C_{10}$-alkenylene, or $C_4$–$C_{10}$-alkinylene, wherein one to three methylene units are isosterically replaced by O, S, $NR^{10}$, CO, SO, or $SO_2$, wherein $R^{10}$ has the same meaning as $R^9$, but is selected independently thereof;

E is selected from the group consisting of

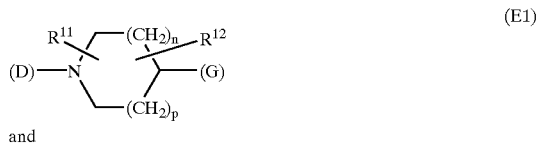

(E1)

and

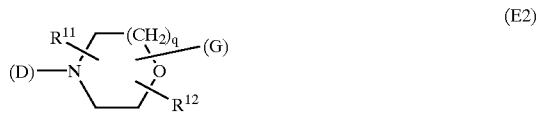

(E2)

wherein the heterocyclic ring may have a double bond and n and p are, independent of each other, 0, 1, 2 or 3 where n+p≧4, wherein q is 1, 2 or 3;

$R^{11}$ is selected from the group consisting of hydrogen, $C_1$–$C_6$-alkyl, hydroxy, hydroxymethyl, carboxy, and $C_2$–$C_7$-alkoxycarbonyl and $R^{12}$ is selected from the group consisting of hydrogen, $C_1$–$C_6$-alkyl and an oxo group adjacent to a nitrogen atom, or $R^{11}$ and $R^{12}$, may together, form a $C_1$–$C_3$-alkylene bridge under formation of a bicyclic ring system;

G is selected from the group consisting of $G^1$, $G^2$, $G^3$, $G^4$, and $G^5$, wherein $G^1$ is —$(CH_2)_r$—$(CR^{14}R^{15})_s$—$R^{13}$ r is 0, 1, 2 or 3 and s is 0 or 1

$R^{13}$ is selected from the group consisting of hydrogen, $C_1$–$C_6$-alkyl, $C_3$–$C_6$-alkenyl, $C_3$–$C_6$-alkinyl, $C_3$–$C_8$-cycloalkyl, saturated or unsaturated, four to seven-membered heterocycles, which contain one or two hetero-atoms selected from N, S and O, benzyl, phenyl, monocyclic aromatic five and six-membered heterocycles, which contain one to three heteroatoms selected from N, S and O and are either bound directly or over a methylene group, anellated bi- and tricyclic aromatic and partially, hydrogenated carbocyclic ring system with 8 to 16 ring atoms and at least one aromatic ring, wherein the linkage occurs either over an aromatic or a hydrogenated ring and either directly or over a methylene group, and anellated bi- and tricyclic aromatic or partially hydrogenated heterocyclic ring systems with 8 to 16 ring atoms and at least one aromatic ring, wherein one to three ring atoms are selected from N, S and O and the linkage occurs either over an aromatic ring or a hydrogenated ring and either directly or over a methylene group, $R^{14}$ has the same meaning as $R^{13}$, but is selected independently thereof;

$R^{15}$ is selected from the group consisting of hydrogen, hydroxy, methyl, benzyl, phenyl, monocyclic aromatic five and six-membered heterocycles, which contain one to three hetero-atoms selected from N, S and O and are either bound directly or over a methylene group, anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group, anellated bi- and tricyclic aromatic and partially hydrogenated heterocyclic ring systems with 8 to 16 ring atoms and at least one aromatic ring, wherein one to three ring atoms are selected from N, S and O and the linkage can occur either over an aromatic ring or a hydrogenated ring and either directly or over a methylene group;

$G^2$ is $=(C)_u R^{13} R^{15}$ wherein, $R^{13}$ and $R^{15}$ have the above meaning and u is 0 or 1, or u=1, and $R^{13}$ and $R^{15}$ together with a carbon atom to which they are attached form a ring system selected from the group consisting of $C_2$–$C_8$-cycloalkyl, saturated, four to seven-membered heterocycles which contain one or two hetero-atoms selected from N, S and O;

anellated bi- and tricyclic partially hydrogenated carboxocyclic ring system with 8 to 16 ring atoms and at least one aromatic ring; and anellated bi-and tricyclic partially hydrogenated heterocyclic ring systems with 8 to 16 ring atoms and at least one aromatic ring, wherein one to three ring atoms are selected from N, S and O;

or, u=0, and $R^{13}$ and $R^{15}$ together with the carbon atom $C_E$ of ring E to which they are attached form a ring system $C_E R^{13} R^{15}$ selected from the group consisting of cycloalkyl, saturated, four to seven-membered heterocycles which contain one or two hetero-atoms selected from N, S and O;

anellated bi- and tricyclic partially hydrogenated carbocyclic ring systems with 8 to 16 ring atoms and at least one aromatic ring; and anellated bi- and tricyclic partially hydrogenated heterocyclic ring systems with 8 to 16 ring atoms and at least one aromatic ring, wherein 1 to 3 ring atoms can be selected from N, S and O;

$G^3$ is selected from

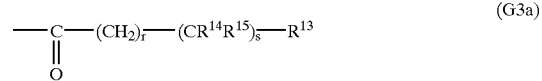 (G3a)

and

 (G3b)

wherein r, s, and the substituents $R^{13}$, $R^{14}$, and $R^{15}$ have the above meanings, or the group

—$NR^{13}R^{15}$ is a nitrogen containing heterocycle bound over the nitrogen atom which nitrogen-containing heterocycle is selected from the group consisting of saturated and unsaturated monocyclic, four to eight-membered heterocycles which, aside from the essential nitrogen atom, may contain one or two further hetero-atoms selected from N, S and O, and saturated and unsaturated bi- or tricyclic, anellated or bridges heterocycles with 8 to 16 ring atoms, which, aside from the essential nitrogen atom, may contain one or two further hetero-atoms selected from N, S and O, $G^4$ is selected from the group consisting of

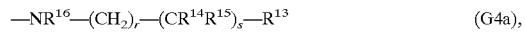 (G4a),

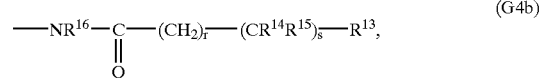 (G4b)

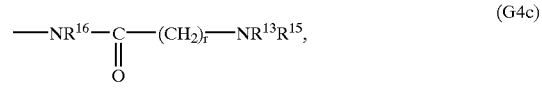 (G4c)

 (G4d),

 (G4e)

and —$NR^{16}COR^{17}$ (G4f), wherein r, s and $R^{13}$, $R^{14}$, and $R^{15}$ have the above meanings and $R^{16}$ has the same meanings as $R^5$, but is selected independently thereof, $R^{17}$ is selected from the group consisting of trifluoromethyl, $C_1$–$C_6$-alkoxy, $C_3$–$C_6$-alkenyloxy and benzyloxy; and $Ar^1$ and $Ar^2$, are selected independently from each other from the group consisting of phenyl, pyridyl and naphthyl;

$G^5$ is selected from the group consisting of

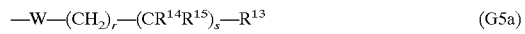 (G5a)

and

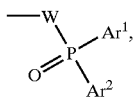
(G5b)

wherein r, s, and $R^{13}$, $R^{14}$, $R^{15}$, $Ar^1$ and $Ar^2$ have the above meanings and W is O or S, wherein the ring systems $=CR^{13}R^{15}$, $-NR^{13}R^{15}$, $-C_ER^{13}R^{15}$ and aromatic ring systems in the substituents $R^1$, $R^2$, $R^4$, $R^5$, $R^6$, $R^{13}$, $R^{14}$, $R^{15}$, $R^{16}$, $R^{17}$, $Ar^1$ and $Ar^2$ may be substituted independently from each other by one to three of the same or different groups selected from the group consisting of halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxyalkyl, nitro, amino, mono-$C_1$–$C_6$-alkylamino, di-($C_1$–$C_6$-alkyl)amino and, for two adjacent residues on the aromatic ring, methylenedioxy, and $C_1$–$C_6$-alkoxy which is entirely or partially substituted by fluorine, wherein alkyl-, alkenyl- and cycloalkyl residues in the group $G^1$ to $G^5$ may be substituted by one or two of the same or different groups selected from hydroxy, carboxy, $C_2$–$C_7$-alkoxycarbonyl, benzyloxycarbonyl, amino, mono-$C_1$–$C_6$-alkylamino, and di-($C_1$–$C_6$-alkyl)amino.

23. A method for production of compounds according to formula (I)

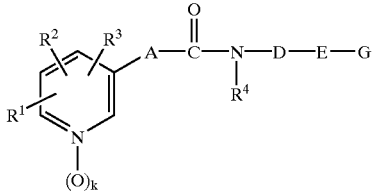
(I)

wherein compounds of a formula

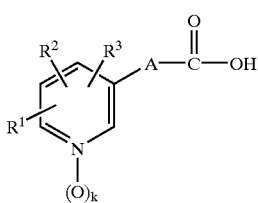
(II)

are reacted with free base or acid addition salts of formula (III)

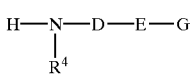
(III)

wherein $R^1$ is selected from the group consisting of hydrogen, halogen, cyano, $C_1$–$C_6$-alkyl, $C_3$–$C_6$-alkenyl, $C_3$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkoxycarbonyl, $C_3$–$C_{13}$-dialkylaminocarbonyl, carboxy, phenyl, phenoxy, phenylthio, pyridyloxy, pyridylthio, and $NR^5R^6$, wherein $R^5$ and $R^6$ selected independently of each other from the group consisting of hydrogen, $C_1$–$C_6$-alkyl, $C_3$–$C_6$-alkenyl, $C_3$–$C_6$-alkinyl, benzyl and phenyl;

$R^2$ is selected from the group consisting of hydrogen, halogen, cyano, $C_1$–$C_6$-alkyl, triflurormethyl, hydroxy, $C_1$–$C_6$-alkoxy, benzyloxy and $C_1$–$C_7$-alkanoyloxy; $R^1$ and $R^2$, if adjacent, may form a bridge selected from $-(CH_2)_4-$, $-(CH=CH)_2-$ and $-CH_2O-CR^7R^8-O-$, wherein $R^7$ and $R^8$ are selected independently from each other from hydrogen and $C_1$–$C_6$-alkyl;

$R^3$ is selected from the group consisting of hydrogen, halogen, $C_1$–$C_6$-alkyl, trifluoromethyl and $C_1$–$C_6$-hydroxyalkyl;

$R^4$ selected from the group consisting of hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy and benzyloxy;

k is 0 or 1,

A is selected from the group consisting of
$C_1$–$C_6$-alkylene
a substituted $C_1$–$C_6$-alkylene, which is substituted one to three-fold by $C_1$–$C_6$-alkyl, hydroxy, $C_1$–$C_3$-alkoxy, fluorine, or phenyl,
$C_2$–$C_6$-alkylene, wherein a methylene unit is isosterically replaced by O, S, $NR^9$, CO, SO, or $SO_2$, wherein, with the exception of CO, the isosteric substitution is not adjacent to the amide group and $R^9$ is selected from the group consisting of hydrogen, $C_1$–$C_6$-alkyl, $C_3$–$C_6$-alkenyl, $C_3$–$C_6$-alkinyl, $C_1$–$C_6$-acyl and $C_1$–$C_6$-alkanesulfonyl,
1,2-cyclopropylene,
$C_2$–$C_6$-alkenylene,
a substituted $C_2$–$C_6$-alkenylene, which is substituted one to three-fold by $C_1$–$C_6$-alkyl, hydroxy, $C_1$–$C_6$-alkoxy, fluorine, cyano or phenyl,
$C_4$–$C_6$-alkadienylene,
a substituted $C_4$–$C_6$-alkadienylene, which is substituted once to twice by $C_1$–$C_3$-alkyl, fluorine, cyano or phenyl,
1,3,5-hexatrienylene,
a substituted 1,3,5-hexatrienylene, which is substituted by $C_1$–$C_3$-alkyl, fluorine, cyano or phenyl, and ethinylene D is selected from the group consisting of $C_2$–$C_{10}$-alkylene,
a substituted $C_2$–$C_{10}$-alkylene, which is substituted once or twice by $C_1$–$C_6$-alkyl, hydroxy, or $C_1$–$C_6$-alkoxy,
$C_4$–$C_{10}$-alkenylene,
a substituted $C_4$–$C_{10}$-alkenylene, which is substituted once or twice by $C_1$–$C_6$-alkyl, hydroxy, or $C_1$–$C_6$-alkoxy,
$C_4$–$C_{10}$-alkinylene,
a substituted $C_4$–$C_{10}$-alkinylene, which is substituted once or twice by $C_1$–$C_6$-alkyl, hydroxy, or $C_1$–$C_6$-alkoxy, and $C_2$–$C_{10}$-alkylene, $C_2$–$C_{10}$-alkylene, $C_4$–$C_{10}$-alkenylene, or $C_4$–$C_{10}$-alkinylene, wherein one to three methylene units are isosterically replaced by O, S, $NR^{10}$, CO, SO, or $SO_2$, wherein $R^{10}$ has the same meaning as $R^9$, but is selected independently thereof;

E is selected from the group consisting of

(E1)

and

(E2)

wherein the heterocyclic ring may have a double bond and n and p are, independent of each other, 0, 1, 2 or 3 where n+p≧4, wherein q is 1, 2 or 3;

$R^{11}$ is selected from the group consisting of hydrogen, $C_1$–$C_6$-alkyl, hydroxy, hydroxymethyl, carboxy, and $C_2$–$C_7$-alkoxycarbonyl and $R^{12}$ is selected from the group consisting of hydrogen, $C_1$–$C_6$-alkyl and an oxo group adjacent to a nitrogen atom, or $R^{11}$ and $R^{12}$, may together, form a $C_1$–$C_3$-alkylene bridge under formation of a bicyclic ring system;

G is selected from the group consisting of $G^1$, $G^2$, $G^3$, $G^4$ and $G^5$, wherein $G^1$ is —$(CH_2)_r$—$(CR^{14}R^{15})_s$—$R^{13}$ r is 0, 1, 2 or 3 and s is 0 or 1

$R^{13}$ is selected from the group consisting of
  hydrogen, $C_1$–$C_6$-alkyl, $C_3$–$C_6$-alkenyl, $C_3$–$C_6$-alkinyl, $C_3$–$C_8$-cycloalkyl,
  saturated or unsaturated, four to seven-membered heterocycles, which contain one or two hetero-atoms selected from N, S and O,
  benzyl, phenyl,
  monocyclic aromatic five and six-membered heterocycles, which contain one to three heteroatoms selected from N, S and O and are either bound directly or over a methylene group,
  anellated bi- and tricyclic aromatic and partially hydrogenated carbocyclic ring system with 8 to 16 ring atoms and at least one aromatic ring, wherein the linkage occurs either over an aromatic or a hydrogenated ring and either directly or over a methylene group, and
  anellated bi- and tricyclic aromatic or partially hydrogenated heterocyclic ring systems with 8 to 16 ring atoms and at least one aromatic ring, wherein one to three ring atoms are selected from N, S and O and the linkage occurs either over an aromatic ring or a hydrogenated ring andeither directly or over a methylene group, $R^{14}$ has the same meaning as $R^{13}$, but is selected independently thereof;

$R^{15}$ is selected from the group consisting of hydrogen, hydroxy, methyl, benzyl, phenyl,
  monocyclic aromatic five and six-membered heterocycles, which contain one to three heteroatoms selected from N, S and O and are either bound directly or over a methylene group,
  anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group,
  anellated bi- and tricyclic aromatic and partially hydrogenated heterocyclic ring systems with 8 to 16 ring atoms and at least one aromatic ring, wherein one to three ring atoms are selected from N, S and O and the linkage can occur either over an aromatic ring or a hydrogenated ring and either directly or over a methylene group;

$G^2$ is =$(C)_u R^{13} R^{15}$ wherein, $R^{13}$ and $R^{15}$ have the above meaning and u is 0 or 1, or
  u=1, and $R^{13}$ and $R^{15}$ together with a carbon atom to which they are attached form a ring system selected from the group consisting of $C_2$–$C_8$-cycloalkyl,
  saturated, four to seven-membered heterocycles which contain one or two hetero-atoms selected from N, S and O;
  anellated bi- and tricyclic partially hydrogenated carboxocyclic ring system with 8 to 16 ring atoms and at least one aromatic ring; and anellated bi-and tricyclic partially hydrogenated heterocyclic ring systems with 8 to 16 ring atoms and at least one aromatic ring, wherein one to three ring atoms are selected from N, S and O;
  or, u=0, and $R^{13}$ and $R^{15}$ together with the carbon atom $C_E$ of ring E to which they are attached form a ring system $C_E R^{13} R^{15}$ selected from the group consisting of
  cycloalkyl, saturated, four to seven-membered heterocycles which contain one or two hetero-atoms selected from N, S and O;
  anellated bi- and tricyclic partially hydrogenated carbocyclic ring systems with 8 to 16 ring atoms and at least one aromatic ring; and
  anellated bi- and tricyclic partially hydrogenated heterocyclic ring systems with 8 to 16 ring atoms and at least one aromatic ring, wherein 1 to 3 ring atoms can be selected from N, S and O;

$G^3$ s selected from

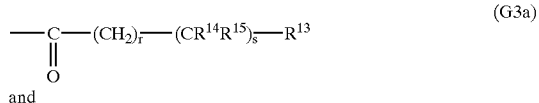
(G3a)

and

(G3b)

wherein r, s, and the substituents $R^{13}$, $R^{14}$, and $R^{15}$ have the above meanings, or the group

—$NR^{13}R^{15}$ is a nitrogen containing heterocycle bound over the nitrogen atom which nitrogen-containing heterocycle is selected from the group consisting of saturated and unsaturated monocyclic, four to eight-membered heterocycles which, aside from the essential nitrogen atom, may contain one or two further hetero-atoms selected from N, S and O, and saturated and unsaturated bi- or tricyclic, anellated or bridges heterocycles with 8 to 16 ring atoms, which, aside from the essential nitrogen atom, may contain one or two further hetero-atoms selected from N, S and O, $G^4$ is selected from the group consisting of

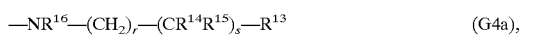 (G4a),

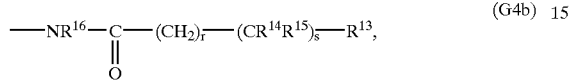 (G4b),

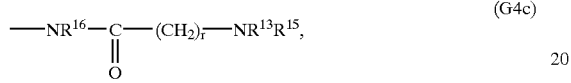 (G4c),

 (G4d),

 (G4e), and —NR$^{16}$—COR$^{17}$ (G4f), wherein r, s and R$^{13}$, R$^{14}$, and R$^{15}$ have the above meanings and R$^{16}$ has the same meanings as R$^5$, but is selected independently thereof, R$^{17}$ is selected from the group consisting of trifluoromethyl, C$_1$–C$_6$-alkoxy, C$_3$–C$_6$-alkenyloxy and benzyloxy; and Ar$^1$ and Ar$^2$, are selected independently from each other from the group consisting of phenyl, pyridyl and naphthyl;

G$^5$ is selected from the group consisting of

 (G5a)

and

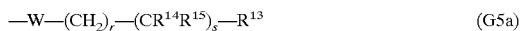 (G5b)

wherein r, s, and R$^{13}$, R$^{14}$, R$^{15}$, Ar$^1$ and Ar$^2$ have the above meanings and W is O or S, wherein the ring systems =CR$^{13}$R$^{15}$, —NR$^{13}$R$^{15}$, $^C_E$R$^{13}$R$^{15}$ and aromatic ring systems in the substituents R$^1$, R$^2$, R$^4$, R$^5$, R$^6$, R$^{13}$, R$^{14}$, R$^{15}$, R$^{16}$, R$^7$, Ar$^1$ and Ar$^2$ may be substituted independently from each other by one to three of the same or different groups selected from the group consisting of halogen, cyano, C$_1$–C$_6$-alkyl, trifluoromethyl, C$_3$–C$_8$-cycloalkyl, phenyl, benzyl, hydroxy; C$_{1-6}$-hydroxyalkyl, C$_1$–C$_6$-alkoxy, benzyloxy, phenoxy, mercapto, C$_1$–C$_6$-alkylthio, carboxy, C$_2$–C$_7$-carboxyalkyl, C$_2$–C$_7$-carboxyalkenyl, C$_2$–C$_7$-alkoxycarbonyl, benzyloxyalkyl, nitro, amino, mono-C$_1$–C$_6$-alkylamino, di-(C$_1$–C$_6$-alkyl)amino and, for two adjacent residues on the aromatic ring, methylenedioxy, and C$_1$–C$_6$-alkoxy which is entirely or partially substituted by fluorine, wherein alkyl-, alkenyl- and cycloalkyl residues in the group G$^1$ to G$^5$ may be substituted by one or two of the same or different groups selected from hydroxy, carboxy, C$_2$–C$_7$-alkoxycarbonyl, benzyloxycarbonyl, amino, mono-C$_1$–C$_6$-alkylamino, and di-(C$_1$–C$_6$-alkyl)amino, wherein G is not —CHR$^{14}$—R$^{13}$, —C(OH)R$^{14}$—R$^{13}$, =CR$^{13}$R$^{15}$ or —O—CHR$^{14}$—R$^{13}$, in the case when simultaneously R$^{13}$ is hydrogen, alkyl or phenyl substituted by halogen, alkyl, hydroxy or trifluoromethyl, R$^{14}$ and R$^{15}$ may be pyridyl or phenyl substituted with halogen, alkyl, hydroxy or trifluoromethyl, A is alkylene, which may be substituted with ethenylene or butadienylene, D is alkylene and E is piperidine substituted in the 4-position;

their cis- and trans-isomers, E- and Z-isomers, and their racemic or non-racemic mixtures, their pure endo- and exo-isomers and mixtures thereof;

their respective tautomers, the corresponding acid addition salts, hydrates and solvates.

24. A method for production of compounds according to

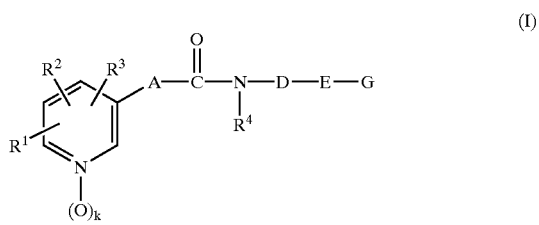 (I)

wherein compounds of a formula

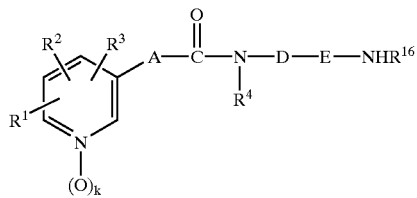

are reacted with compounds of formulas (IVa) to (IVe), wherein (IVa) to (IVe) are

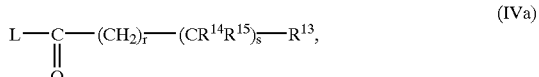 (IVa)

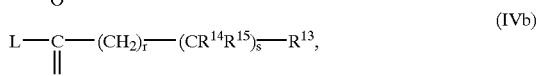 (IVb)

-continued

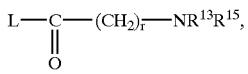  (IVc)

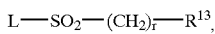  (IVd)

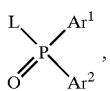  (IVe)

wherein L is a leaving group and wherein $R^1$ is selected from the group consisting of hydrogen, halogen, cyano, $C_1$–$C_6$-alkyl, $C_3$–$C_6$-alkenyl, $C_3$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkoxycarbonyl, $C_3$–$C_3$-dialkylaminocarbonyl, carboxy, phenyl, phenoxy, phenylthio, pyridyloxy, pyridylthio, and $NR^5R^6$, wherein $R^5$ and $R^6$ selected independently of each other from the group consisting of hydrogen, $C_1$–$C_6$-alkyl, $C_3$–$C_6$-alkenyl, $C_3$–$C_6$-alkinyl, benzyl and phenyl;

$R^2$ is selected from the group consisting of hydrogen, halogen, cyano, $C_1$–$C_6$-alkyl, triflurormethyl, hydroxy, $C_1$–$C_6$-alkoxy, benzyloxy and $C_1$–$C_7$-alkanoyloxy; $R^1$ and $R^2$, if adjacent, may form a bridge selected from —$(CH_2)_4$—, —$(CH=CH)_2$— and —$CH_2O$—$CR^7R^8$—O—, wherein $R^7$ and $R^8$ are selected independently from each other from hydrogen and $C_1$–$C_6$-alkyl;

$R^3$ is selected from the group consisting of hydrogen, halogen, $C_1$–$C_6$-alkyl, trifluoromethyl and $C_1$–$C_6$-hydroxyalkyl;

$R^4$ selected from the group consisting of hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy and benzyloxy;

k is 0 or 1,

A is selected from the group consisting of
$C_1$–$C_6$-alkylene
a substituted $C_1$–$C_6$-alkylene, which is substituted one to three-fold by $C_1$–$C_6$-alkyl, hydroxy, $C_1$–$C_3$-alkoxy, fluorine, or phenyl,
$C_2$–$C_6$-alkylene, wherein a methylene unit is isosterically replaced by O, S, $NR^9$, CO, SO, or $SO_2$, wherein, with the exception of CO, the isosteric substitution is not adjacent to the amide group and $R^9$ is selected from the group consisting of hydrogen, $C_1$–$C_6$-alkyl, $C_3$–$C_6$-alkenyl, $C_3$–$C_6$-alkinyl, $C_1$–$C_6$-acyl and $C_1$–$C_6$-alkanesulfonyl,
1,2-cyclopropylene,
$C_2$–$C_6$-alkenylene,
a substituted $C_2$–$C_6$-alkenylene, which is substituted one to three-fold by $C_1$–$C_6$-alkyl, hydroxy, $C_1$–$C_6$-alkoxy, fluorine, cyano or phenyl,
$C_4$–$C_6$-alkadienylene,
a substituted $C_4$–$C_6$-alkadienylene, which is substituted once to twice by $C_1$–$C_3$-alkyl, fluorine, cyano or phenyl,
1,3,5-hexatrienylene,
a substituted 1,3,5-hexatrienylene, which is substituted by $C_1$–$C_3$-alkyl, fluorine, cyano or phenyl, and
ethinylene D is selected from the group consisting of $C_2$–$C_{10}$-alkylene,
a substituted $C_2$–$C_{10}$-alkylene, which is substituted once or twice by $C_1$–$C_6$-alkyl, hydroxy, or $C_1$–$C_6$-alkoxy,
$C_4$–$C_{10}$-alkenylene,
a substituted $C_4$–$C_{10}$-alkenylene, which is substituted once or twice by $C_1$–$C_6$-alkyl, hydroxy, or $C_1$–$C_6$-alkoxy,
$C_4$–$C_{10}$-alkinylene,
a substituted $C_4$–$C_{10}$-alkinylene, which is substituted once or twice by $C_1$–$C_6$-alkyl, hydroxy, or $C_1$–$C_6$-alkoxy, and
$C_2$–$C_{10}$-alkylene,
$C_2$–$C_{10}$-alkylene, $C_4$–$C_{10}$-alkenylene, or $C_4$–$C_{10}$-alkinylene, wherein one to three methylene units are isosterically replaced by O, S, $NR^{10}$, CO, SO, or $SO_2$, wherein $R^{10}$ has the same meaning as $R^9$, but is selected independently thereof;

E is selected from the group consisting of

  (E1)

and

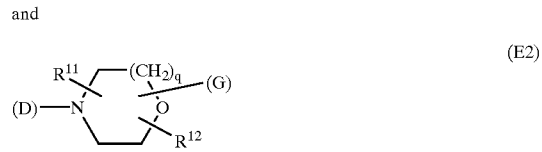  (E2)

wherein the heterocyclic ring may have a double bond and n and p are, independent of each other, 0, 1, 2 or 3 where $n+p \leq 4$, wherein q is 1, 2 or 3;

$R^{11}$ is selected from the group consisting of hydrogen, $C_1$–$C_6$-alkyl, hydroxy, hydroxymethyl, carboxy, and $C_2$–$C_7$-alkoxycarbonyl and $R^{12}$ is selected from the group consisting of hydrogen, $C_1$–$C_6$-alkyl and an oxo group adjacent to a nitrogen atom, or $R^{11}$ and $R^{12}$, may together, form a $C_1$–$C_3$-alkylene bridge under formation of a bicyclic ring system;

G is selected from the group-consisting of

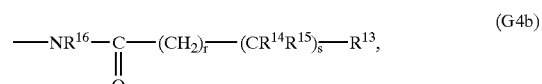  (G4b)

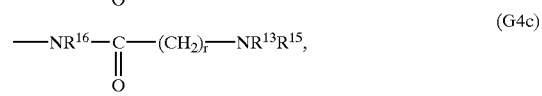  (G4c)

  (G4d)

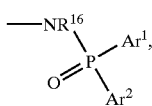
(G4e)

r is 0, 1, 2 or 3 and
s is 0 or 1
$R^{13}$ is selected from the group consisting of
hydrogen, $C_1$–$C_6$-alkyl, $C_3$–$C_6$-alkenyl, $C_3$–$C_6$-alkinyl, $C_3$–$C_8$-cycloalkyl,
saturated or unsaturated, four to seven-membered heterocycles, which contain one or two hetero-atoms selected from N, S and O,
benzyl, phenyl,
monocyclic aromatic five and six-membered heterocycles, which contain one to three hetero-atoms selected from N, S and O and are either bound directly or over a methylene group,
anellated bi- and tricyclic aromatic and partially hydrogenated carbocyclic ring system with 8 to 16 ring atoms and at least one aromatic ring, wherein the linkage occurs either over an aromatic or a hydrogenated ring and either directly or over a methylene group, and
anellated bi- and tricyclic aromatic or partially hydrogenated heterocyclic ring systems with 8 to 16 ring atoms and at least one aromatic ring, wherein one to three ring atoms are selected from N, S and O and the linkage occurs either over an aromatic ring or a hydrogenated ring and either directly or over a methylene group,
$R^{14}$ has the same meaning as $R^{13}$, but is selected independently thereof;
$R^{15}$ is selected from the group consisting of hydrogen, hydroxy, methyl, benzyl, phenyl,
monocyclic aromatic five and six-membered heterocycles, which contain one to three hetero-atoms selected from N, S and O and are either bound directly or over a methylene group,
anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group,
anellated bi- and tricyclic aromatic and partially hydrogenated heterocyclic ring systems with 8 to 16 ring atoms and at least one aromatic ring, wherein one to three ring atoms are selected from N, S and O and the linkage can occur either over an aromatic ring or a hydrogenated ring and either directly or over a methylene group;
$R^{16}$ has the same meanings as $R^5$, but is selected independently thereof,
$R^{17}$ is selected from the group consisting of trifluoromethyl, $C_1$–$C_6$-alkoxy, $C_3$–$C_6$-alkenyloxy and benzyloxy; and
$Ar^1$ and $Ar^2$, are selected independently from each other from the group consisting of phenyl, pyridyl and naphthyl;
wherein aromatic ring systems in the substituents $R^1$, $R^2$, $R^3$, $R^4$, $R^5$, $R^6$, $R^{13}$, $R^{14}$, $R^{15}$, $R^{16}$, $R^{17}$, $Ar^1$ and $Ar^2$ may be substituted independently from each other by one to three of the same or different groups selected from the group consisting of halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxyalkyl, nitro, amino, mono-$C_1$–$C_6$-alkylamino, di-($C_1$–$C_6$-alkyl)amino and, for two adjacent residues on the aromatic ring, methylenedioxy, and $C_1$–$C_6$-alkoxy which is entirely or partially substituted by fluorine.

25. A method for production of compounds according to formula (I)

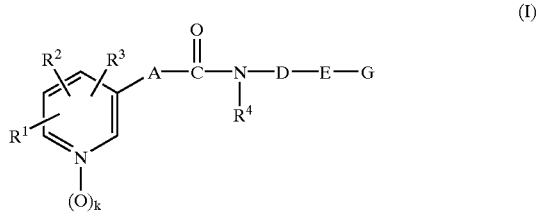
(I)

where G is —$NR^{16}$—$(CH_2)_r(CR^{14}R^{15})_s$—$R^{13}$ but not —$NHR^{16}$,
wherein compounds of a formula

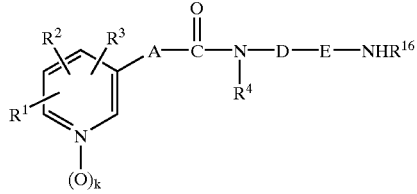

are reacted with compounds of formula

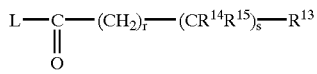

wherein L is a leaving group,
wherein
$R^1$ is selected from the group consisting of hydrogen, halogen, cyano, $C_1$–$C_6$-alkyl, $C_3$–$C_6$-alkenyl, $C_3$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkoxycarbonyl, $C_3$–$C_{13}$-dialkylaminocarbonyl, carboxy, phenyl, phenoxy, phenylthio, pyridyloxy, pyridylthio, and $NR^5R^6$, wherein
$R^5$ and $R^6$ selected independently of each other from the group consisting of hydrogen, $C_1$–$C_6$-alkyl, $C_3$–$C_6$-alkenyl, $C_3$–$C_6$-alkinyl, benzyl and phenyl;
$R^2$ is selected from the group consisting of hydrogen, halogen, cyano, $C_1$–$C_6$-alkyl, triflurormethyl, hydroxy, $C_1$–$C_6$-alkoxy, benzyloxy and $C_1$–$C_7$-alkanoyloxy; $R^1$ and $R^2$, if adjacent, may form a bridge selected from —$(CH_2)_4$—, —$(CH=CH)_2$— and —$CH_2O$—$CR^7R^8$—O—, wherein
$R^7$ and $R^8$ are selected independently from each other from hydrogen and $C_1$–$C_6$-alkyl;

$R^3$ is selected from the group consisting of hydrogen, halogen, $C_1$–$C_6$-alkyl, trifluoromethyl and $C_1$–$C_6$-hydroxyalkyl;

$R^4$ selected from the group consisting of hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy and benzyloxy;

k is 0 or 1,

A is selected from the group consisting of
   $C_1$–$C_6$-alkylene
   a substituted $C_1$–$C_6$-alkylene, which is substituted one to three-fold by $C_1$–$C_6$-alkyl, hydroxy, $C_1$–$C_3$-alkoxy, fluorine, or phenyl,
   $C_2$–$C_6$-alkylene, wherein a methylene unit is isosterically replaced by O, S, $NR^9$, CO, SO, or $SO_2$, wherein, with the exception of CO, the isosteric substitution is not adjacent to the amide group and $R^9$ is selected from the group consisting of hydrogen, $C_1$–$C_6$-alkyl, $C_3$–$C_6$-alkenyl, $C_3$–$C_6$-alkinyl, $C_1$–$C_6$-acyl and $C_1$–$C_6$-alkanesulfonyl,
   1,2-cyclopropylene,
   $C_2$–$C_6$-alkenylene,
   a substituted $C_2$–$C_6$-alkenylene, which is substituted one to three-fold by $C_1$–$C_6$-alkyl, hydroxy, $C_1$–$C_6$-alkoxy, fluorine, cyano or phenyl,
   $C_4$–$C_6$-alkadienylene,
   a substituted $C_4$–$C_6$-alkadienylene, which is substituted once to twice by $C_1$–$C_3$-alkyl, fluorine, cyano or phenyl,
   1,3,5-hexatrienylene,
   a substituted 1,3,5-hexatrienylene, which is substituted by $C_1$–$C_3$-alkyl, fluorine, cyano or phenyl, and
   ethinylene D is selected from the group consisting of $C_2$–$C_{10}$-alkylene,
   a substituted $C_2$–$C_{10}$-alkylene, which is substituted once or twice by $C_1$–$C_6$-alkyl, hydroxy, or $C_1$–$C_6$-alkoxy,
   $C_4$–$C_{10}$-alkenylene,
   a substituted $C_4$–$C_{10}$-alkenylene, which is substituted once or twice by $C_1$–$C_6$-alkyl, hydroxy, or $C_1$–$C_6$-alkoxy,
   $C_4$–$C_{10}$-alkinylene,
   a substituted $C_4$–$C_{10}$-alkinylene, which is substituted once or twice by $C_1$–$C_6$-alkyl, hydroxy, or $C_1$–$C_6$-alkoxy, and
   $C_2$–$C_{10}$-alkylene,
   $C_2$–$C_{10}$-alkylene, $C_4$–$C_{10}$-alkenylene, or $C_4$–$C_{10}$-alkinylene, wherein one to three methylene units are isosterically replaced by O, S, $NR^{10}$, CO, SO, or $SO_2$, wherein $R^{10}$ has the same meaning as $R^9$, but is selected independently thereof;

E is selected from the group consisting of

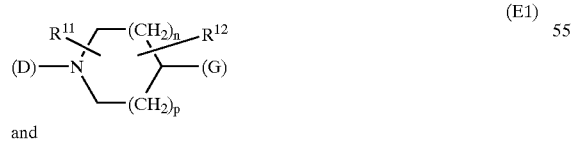
(E1)

and

(E2)

wherein the heterocyclic ring may have a double bond and n and p are, independent of each other, 0, 1, 2 or 3 where n+p≦4, wherein q is 1, 2 or 3;

$R^{11}$ is selected from the group consisting of, hydrogen, $C_1$–$C_6$-alkyl, hydroxy, hydroxymethyl, carboxy, and $C_2$–$C_7$-alkoxycarbonyl and $R^{12}$ is selected from the group consisting of hydrogen, $C_1$–$C_6$-alkyl and an oxo group adjacent to a nitrogen atom, or $R^{11}$ and $R^{12}$ may together, form a $C_1$–$C_3$-alkylene bridge under formation of a bicyclic ring system;

$R^{13}$ is selected from the group consisting of
   hydrogen, $C_1$–$C_6$-alkyl, $C_3$–$C_6$-alkenyl, $C_3$–$C_6$-alkinyl, $C_3$–$C_8$-cycloalkyl,
   saturated or unsaturated, four to seven-membered heterocycles, which contain one or two hetero-atoms selected from N, S and O,
   benzyl, phenyl,
   monocyclic aromatic five and six-membered heterocycles, which contain one to three hetero-atoms selected from N, S and O and are either bound directly or over a methylene group,
   anellated bi- and tricyclic aromatic and partially hydrogenated carbocyclic ring system with 8 to 16 ring atoms and at least one aromatic ring, wherein the linkage occurs either over an aromatic or a hydrogenated ring and either directly or over a methylene group, and
   anellated bi- and tricyclic aromatic or partially hydrogenated heterocyclic ring systems with 8 to 16 ring atoms and at least one aromatic ring, wherein one to three ring atoms are selected from N, S and O and the linkage occurs either over an aromatic ring or a hydrogenated ring and either directly or over a methylene group, $R^{14}$ has the same meaning as $R^{13}$, but is selected independently thereof;

$R^{15}$ is selected from the group consisting of hydrogen, hydroxy, methyl, benzyl, phenyl, monocyclic aromatic five and six-membered heterocycles, which contain one to three hetero-atoms selected from N, S and O and are either bound directly or over a methylene group,
   anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group,
   anellated bi- and tricyclic aromatic and partially hydrogenated heterocyclic ring systems with 8 to 16 ring atoms and at least one aromatic ring, wherein one to three ring atoms are selected from N, S and O and the linkage can occur either over an aromatic ring or a hydrogenated ring and either directly or over a methylene group;

$R^{16}$ has the same meanings as $R^5$, but is selected independently thereof, $R^{17}$ is selected from the group consisting of trifluoromethyl, $C_1$–$C_6$-alkoxy, $C_3$–$C_6$-alkenyloxy and benzyloxy; and $Ar^1$ and $Ar^2$, are selected independently from each other from the group consisting of phenyl, pyridyl and naphthyl;

wherein aromatic ring systems in the substituents $R^1$, $R^2$, $R^4$, $R^5$, $R^6$, $R^{13}$, $R^{14}$, $R^{15}$, $R^{16}$, $R^{17}$, $Ar^1$ and $Ar^2$ may be substituted independently from each other by one to three of the same or different groups selected from the group consisting of halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxyalkyl, nitro, amino, mono-$C_1$–$C_6$-alkylamino, di-($C_1$–$C_6$-alkyl)amino and, for two adjacent residues on the aromatic ring, methylenedioxy, and $C_1$–$C_6$-alkoxy which is entirely or partially substituted by fluorine.

26. A method for production of compounds according to formula (I)

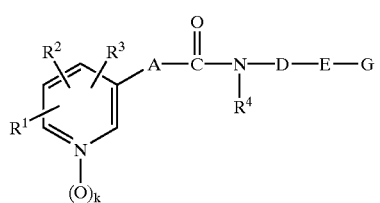

(I)

wherein compounds of a formula

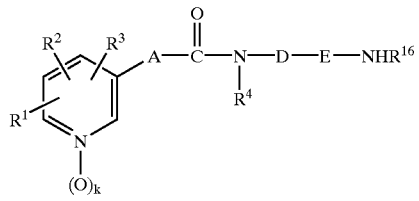

are reacted with a carboxylic acid, carbamic acid, sulfonic acid or phosphinic acid of formulas (Vb) to (Ve), wherein (Vb) to (Ve) are —HOOC—(CH$_2$)$_r$—(CR$^{14}$R$^{15}$)$_s$—R$^{13}$ (Vb), —HOOC—(CH$_2$)$_r$—NR$^{13}$R$^{15}$ (Vc)

—HOOC—SO$_2$—(CH$_2$)$_r$—R$^{13}$ (Vd), (Ve)

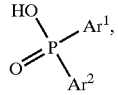

wherein

R$^1$ is selected from the group consisting of hydrogen, halogen, cyano, $C_1$–$C_6$-alkyl, $C_3$–$C_6$-alkenyl, $C_1$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkoxycarbonyl, $C_3$–$C_{13}$-dialkylaminocarbonyl, carboxy, phenyl, phenoxy, phenylthio, pyridyloxy, pyridylthio, and NR$^5$R$^6$, wherein R$^5$ and R$^6$ selected independently of each other from the group consisting of hydrogen, $C_1$–$C_6$-alkyl, $C_3$–$C_6$-alkenyl, $C_3$–$C_6$-alkinyl, benzyl and phenyl;

R$^2$ is selected from the group consisting of hydrogen, halogen, cyano, $C_1$–$C_6$-alkyl, triflurormethyl, hydroxy, $C_1$–$C_6$-alkoxy, benzyloxy and $C_1$–$C_7$-alkanoyloxy; R$^1$ and R$^2$, if adjacent, may form a bridge selected from —(CH$_2$)$_4$—, —(CH=CH)$_2$— and —CH$_2$O—CR$^7$R$^8$—O—, wherein R$^7$ and R$^8$ are selected independently from each other from hydrogen and $C_1$–$C_6$-alkyl;

R$^3$ is selected from the group consisting of hydrogen, halogen, $C_1$–$C_6$-alkyl, trifluoromethyl and $C_1$–$C_6$-hydroxyalkyl;

R$^4$ selected from the group consisting of hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy and benzyloxy;

k is 0 or 1,

A is selected from the group consisting of
$C_1$–$C_6$-alkylene
a substituted $C_1$–$C_6$-alkylene, which is substituted one to three-fold by $C_1$–$C_6$-alkyl, hydroxy, $C_1$–$C_3$-alkoxy, fluorine, or phenyl,
$C_2$–$C_6$-alkylene, wherein a methylene unit is isosterically replaced by O, S, NR$^9$, CO, SO, or SO$_2$, wherein, with the exception of CO, the isosteric substitution is not adjacent to the amide group and R$^9$ is selected from the group consisting of hydrogen, $C_1$–$C_6$-alkyl, $C_3$–$C_6$-alkenyl, $C_3$–$C_6$-alkinyl, $C_1$–$C_6$-acyl and $C_1$–$C_6$-alkanesulfonyl,
1,2-cyclopropylene,
$C_2$–$C_6$-alkenylene,
a substituted $C_2$–$C_6$-alkenylene, which is substituted one to three-fold by $C_1$–$C_6$-alkyl, hydroxy, $C_1$–$C_6$-alkoxy, fluorine, cyano or phenyl,
$C_1$–$C_6$-alkadienylene,
a substituted $C_4$–$C_6$-alkadienylene, which is substituted once to twice by $C_1$–$C_3$-alkyl, fluorine, cyano or phenyl,
1,3,5-hexatrienylene,
a substituted 1,3,5-hexatrienylene, which is substituted by $C_1$–$C_3$-alkyl, fluorine, cyano or phenyl, and
ethinylene D is selected from the group consisting of
$C_2$–$C_{10}$-alkylene,
a substituted $C_2$–$C_{10}$-alkylene, which is substituted once or twice by $C_1$–$C_6$-alkyl, hydroxy, or $C_1$–$C_6$-alkoxy,
$C_4$–$C_{10}$-alkenylene,
a substituted $C_4$–$C_{10}$-alkenylene, which is substituted once or twice by $C_1$–$C_6$-alkyl, hydroxy, or $C_1$–$C_6$-alkoxy,
$C_4$–$C_{10}$-alkinylene,
a substituted $C_4$–$C_{10}$-alkinylene, which is substituted once or twice by $C_1$–$C_6$-alkyl, hydroxy, or $C_1$–$C_6$-alkoxy, and
$C_2$–$C_{10}$-alkylene,
$C_2$–$C_{10}$-alkylene, $C_4$–$C_{10}$-alkenylene, or $C_4$–$C_{10}$-alkinylene, wherein one to three methylene units are isosterically replaced by O, S, NR$^{10}$, CO, SO, or SO$_2$, wherein R$^{10}$ has the same meaning as R$^9$, but is selected independently thereof;

E is selected from the group consisting of

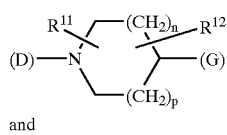 (E1)

and

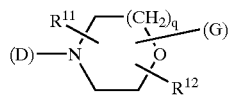 (E2)

wherein the heterocyclic ring may have a double bond and n and p are, independent of each other, 0, 1, 2 or 3 where n+p≤4, wherein q is 1, 2 or 3;

$R^{11}$ is selected from the group consisting of hydrogen, $C_1$–$C_6$-alkyl, hydroxy, hydroxymethyl, carboxy, and $C_2$–$C_7$-alkoxycarbonyl and $R^{12}$ is selected from the group consisting of hydrogen, $C_1$–$C_6$-alkyl and an oxo group adjacent to a nitrogen atom, or $R^{11}$ and $R^{12}$, may together, form a $C_1$–$C_3$-alkylene bridge under formation of a bicyclic ring system;

G is selected from the group consisting of

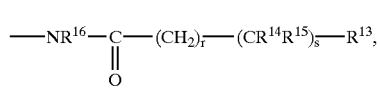 (G4b)

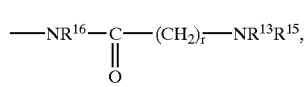 (G4c)

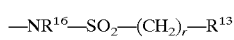 (G4d), and 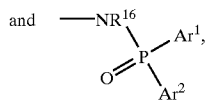 (G4e)

wherein
r is 0, 1, 2 or 3 and
s is 0 or 1

$R^{13}$ is selected from the group consisting of
hydrogen, $C_1$–$C_6$-alkyl, $C_3$–$C_6$-alkenyl, $C_3$–$C_6$-alkinyl, $C_3$–$C_8$-cycloalkyl,
saturated or unsaturated, four to seven-membered heterocycles, which contain one or two hetero-atoms selected from N, S and O,
benzyl, phenyl,
monocyclic aromatic five and six-membered heterocycles, which contain one to three heteroatoms selected from N, S and O and are either bound directly or over a methylene group,
anellated bi- and tricyclic aromatic and partially hydrogenated carbocyclic ring system with 8 to 16 ring atoms and at least one aromatic ring, wherein the linkage occurs either over an aromatic or a hydrogenated ring and either directly or over a methylene group, and anellated bi- and tricyclic aromatic or partially hydrogenated heterocyclic ring systems with 8 to 16 ring atoms and at least one aromatic ring, wherein one to three ring atoms are selected from N, S and O and the linkage occurs either over an aromatic ring or a hydrogenated ring and either directly or over a methylene group, $R^{14}$ has the same meaning as $R^{13}$, but is selected independently thereof;

$R^{15}$ is selected from the group consisting of hydrogen, hydroxy, methyl, benzyl, phenyl, monocyclic aromatic five and six-membered heterocycles, which contain one to three hetero-atoms selected from N, S and O and are either bound directly or over a methylene group,
anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group,
anellated bi- and tricyclic aromatic and partially hydrogenated heterocyclic ring systems with 8 to 16 ring atoms and at least one aromatic ring, wherein one to three ring atoms are selected from N, S and O and the linkage can occur either over an aromatic ring or a hydrogenated ring and either directly or over a methylene group;

$R^{16}$ has the same meanings as $R^5$, but is selected independently thereof, $R^{17}$ is selected from the group consisting of trifluoromethyl, $C_1$–$C_6$-alkoxy, $C_3$–$C_6$-alkenyloxy and benzyloxy; and $Ar^1$ and $Ar^2$, are selected independently from each other from the group consisting of phenyl, pyridyl and naphthyl;

wherein aromatic ring systems in the substituents $R^1$, $R^2$, $R^4$, $R^5$, $R^6$, $R^{13}$, $R^{14}$, $R^{15}$, $R^{16}$, $R^{17}$, $Ar^1$ and $Ar^2$ may be substituted independently from each other by one to three of the same or different groups selected from the group consisting of halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxyalkyl, nitro, amino, mono-$C_1$–$C_6$-alkylamino, di-($C_1$–$C_6$-alkyl)amino and, for two adjacent residues on the aromatic ring, methylenedioxy, and $C_1$–$C_6$-alkoxy which is entirely or partially substituted by fluorine.

27. A method for production of compounds according to formula (I)

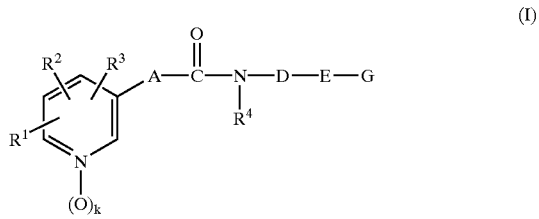 (I)

where G is

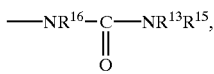

wherein compounds of a formula

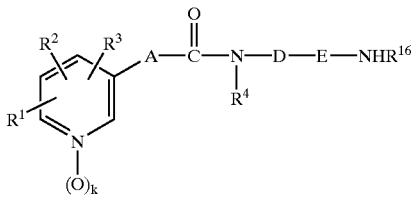

are reacted with

H—NR$^{13}$R$^{15}$ (VI)

wherein

R$^1$ is selected from the group consisting of hydrogen, halogen, cyano, C$_1$–C$_6$-alkyl, C$_3$–C$_6$-alkenyl, C$_3$–C$_6$-alkinyl, trifluoromethyl, C$_3$–C$_8$-cycloalkyl, C$_1$–C$_6$-hydroxyalkyl, hydroxy, C$_1$–C$_6$-alkoxy, C$_3$–C$_6$-alkenyloxy, C$_3$–C$_6$-alkinyloxy, benzyloxy, C$_1$–C$_7$-alkanoyloxy, C$_2$–C$_7$-alkoxycarbonyloxy, C$_1$–C$_6$-alkylthio, C$_3$–C$_6$-alkenylthio, C$_3$–C$_6$-alkinylthio, C$_3$–C$_8$-cycloalkyloxy, C$_3$–C$_8$-cycloalkylthio, C$_2$–C$_7$-alkoxycarbonyl, aminocarbonyl, C$_2$–C$_7$-alkoxycarbonyl, C$_3$–C$_{13}$-dialkylaminocarbonyl, carboxy, phenyl, phenoxy, phenylthio, pyridyloxy, pyridylthio, and NR$^5$R$^6$, wherein R$^5$ and R$^6$ selected independently of each other from the group consisting of hydrogen, C$_1$–C$_6$-alkyl, C$_3$–C$_6$-alkenyl, C$_3$–C$_6$-alkinyl, benzyl and phenyl;

R$^2$ is selected from the group consisting of hydrogen, halogen, cyano, C$_1$–C$_6$-alkyl, triflurormethyl, hydroxy, C$_1$–C$_6$-alkoxy, benzyloxy and C$_1$–C$_7$-alkanoyloxy; R$^1$ and R$^2$, if adjacent, may form a bridge selected from —(CH$_2$)$_4$—, —(CH=CH)$_2$— and —CH$_2$O—CR$^7$R$^8$—O—, wherein R$^7$ and R$^8$ are selected independently from each other from hydrogen and C$_1$–C$_6$-alkyl;

R$^3$ is selected from the group consisting of hydrogen, halogen, C$_1$–C$_6$-alkyl, trifluoromethyl and C$_1$–C$_6$-hydroxyalkyl;

R$^4$ selected from the group consisting of hydrogen, C$_1$–C$_6$-alkyl, C$_3$–C$_6$-alkenyl, C$_3$–C$_6$-alkinyl, C$_3$–C$_6$-cycloalkyl, hydroxy, C$_1$–C$_6$-alkoxy and benzyloxy;

k is 0 or 1,

A is selected from the group consisting of
C$_1$–C$_6$-alkylene
a substituted C$_1$–C$_6$-aalkylene, which is substituted one to three-fold by C$_1$–C$_6$-alkyl, hydroxy, C$_1$–C$_3$-alkoxy, fluorine, or phenyl,
C$_2$–C$_6$-alkenylene, wherein a methylene unit is isosterically replaced by O, S, NR$^9$, CO, SO, or SO$_2$, wherein, with the exception of CO, the isosteric substitution is not adjacent to the amide group and R$^9$ is selected from the group consisting of hydrogen, C$_1$–C$_6$-alkyl, C$_3$–C$_6$-alkenyl, C$_3$–C$_6$-alkinyl, C$_1$–C$_6$-acyl and C$_1$–C$_6$-alkanesulfonyl,
1,2-cyclopropylene,
C$_2$–C$_6$-alkenylene,
a substituted C$_2$–C$_6$-alkenylene, which is substituted one to three-fold by C$_1$–C$_6$-alkyl, hydroxy, C$_1$–C$_6$-alkoxy, fluorine, cyano or phenyl,
C$_4$–C$_6$-alkadienylene,
a substituted C$_4$–C$_6$-alkadienylene, which is substituted once to twice by C$_1$–C$_3$-alkyl, fluorine, cyano or phenyl,
1,3,5-hexatrienylene,
a substituted 1,3,5-hexatrienylene, which is substituted by C$_1$–C$_3$-alkyl, fluorine, cyano or phenyl, and
ethinylene D is selected from the group consisting of
C$_2$–C$_{10}$-alkylene,
a substituted C$_2$–C$_{10}$-alkylene, which is substituted once or twice by C$_1$–C$_6$-alkyl, hydroxy, or C$_1$–C$_6$-alkoxy,
C$_4$–C$_{10}$-alkenylene,
a substituted C$_4$–C$_{10}$-alkenylene, which is substituted once or twice by C$_1$–C$_6$-alkyl, hydroxy, or C$_1$–C$_6$-alkoxy,
C$_4$–C$_{10}$-alkinylene,
a substituted C$_4$–C$_{10}$-alkinylene, which is substituted once or twice by C$_1$–C$_6$-alkyl, hydroxy, or C$_1$–C$_6$-alkoxy, and
C$_2$–C$_{10}$-alkylene, C$_2$–C$_{10}$-alkylene, C$_4$–C$_{10}$-alkenylene, or C$_4$–C$_{10}$-alkinylene, wherein one to three methylene units are isosterically replaced by O, S, NR$^{10}$, CO, SO, or SO$_2$, wherein R$^{10}$ has the same meaning as R$^9$, but is selected independently thereof;

E is selected from the group consisting of

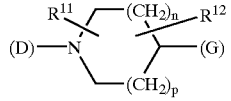

(E1)

and

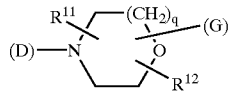

(E2)

wherein the heterocyclic ring may have a double bond and n and p are, independent of each other, 0, 1, 2 or 3 where n+p≦4, wherein q is 1, 2 or 3;

R$^{11}$ is selected from the group consisting of hydrogen, C$_1$–C$_6$-alkyl, hydroxy, hydroxymethyl, carboxy, and C$_2$–C$_7$-alkoxycarbonyl and R$^{12}$ is selected from the group consisting of hydrogen, C$_1$–C$_6$-alkyl and an oxo group adjacent to a nitrogen atom, or R$^{11}$ and R$^{12}$ may together, form a C$_1$–C$_3$-alkylene bridge under formation of a bicyclic ring system;

R$^{13}$ is selected from the group consisting of
hydrogen, C$_1$–C$_6$-alkyl, C$_3$–C$_6$-alkenyl, C$_3$–C$_6$-alkinyl, C$_3$–C$_8$-cycloalkyl,
saturated or unsaturated, four to seven-membered heterocycles, which contain one or two hetero-atoms selected from N, S and O,
benzyl, phenyl,
monocyclic aromatic five and six-membered heterocycles, which contain one to three heteroatoms selected from N, S and O and are either bound directly or over a methylene group, anellated bi- and tricyclic aromatic and partially hydrogenated carbocyclic ring system with 8 to 16 ring atoms and at least one aromatic ring, wherein the linkage occurs either over an aromatic or a hydrogenated ring and either directly or over a methylene group, and anellated bi- and tricyclic aromatic or partially hydrogenated heterocyclic ring systems with 8 to 16 ring atoms and at least one aromatic ring, wherein one to three ring atoms are selected from N, S and Q and the linkage occurs either over an aromatic ring or a hydrogenated ring and either directly or over a methylene group, $R^{14}$ has the same meaning as $R^{13}$, but is selected independently thereof;

$R^{15}$ is selected from the group consisting of hydrogen, hydroxy, methyl, benzyl, phenyl, monocyclic aromatic five and six-membered heterocycles, which contain one to three hetero-atoms selected from N, S and O and are either bound directly or over a methylene group, anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group, anellated bi- and tricyclic aromatic and partially hydrogenated heterocyclic ring systems with 8 to 16 ring atoms and atleast one aromatic ring, wherein one to three ring atoms are selected from N, S and O and the linkage can occur either over an aromatic ring or a hydrogenated ring and either directly or over a methylene group;

$R^{16}$ has the same meanings as $R^5$, but is selected independently thereof, $R^{17}$ is selected from the group consisting of trifluoromethyl, $C_1$–$C_6$-alkoxy, $C_3$–$C_6$-alkenyloxy and benzyloxy; and $Ar^1$ and $Ar^2$, are selected independently from each other from the group consisting of phenyl, pyridyl and naphthyl;

wherein aromatic ring systems in the substituents $R^1$, $R^2$, $R^4$, $R^5$, $R^6$, $R^{13}$, $R^{14}$, $R^{15}$, $R^{16}$, $R^{17}$, $Ar^1$ and $Ar^2$ may be substituted independently from each other by one to three of the same or different groups selected from the group consisting of halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxyalkyl, nitro, amino, mono-$C_1$–$C_6$-alkylamino, di-($C_1$–$C_6$-alkyl)amino and, for two adjacent residues on the aromatic ring, methylenedioxy, and $C_1$–$C_6$-alkoxy which is entirely or partially substituted by fluorine.

28. A method for production of compounds according to formula (I)

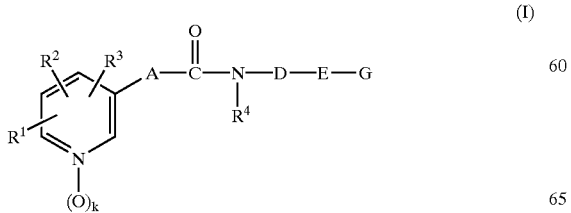
(I)

where G is

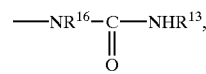

wherein compounds of formula

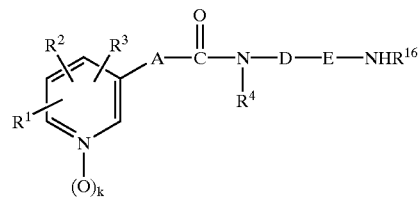

are reacted with an isocyanate having the formula

 (VII)

wherein $R^1$ is selected from the group consisting of hydrogen, halogen, cyano, $C_1$–$C_6$-alkyl, $C_3$–$C_6$-alkenyl, $C_3$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkoxycarbonyl, $C_3$–$C_3$-dialkylaminocarbonyl, carboxy, phenyl, phenoxy, phenylthio, pyridyloxy, pyridylthio, and $NR^5R^6$, wherein $R^5$ and $R^6$ selected independently of each other from the group consisting of hydrogen, $C_1$–$C_6$-alkyl, $C_3$–$C_6$-alkenyl, $C_3$–$C_6$-alkinyl, benzyl and phenyl;

$R^2$ is selected from the group consisting of hydrogen, halogen, cyano, $C_1$–$C_6$-alkyl, triflurormethyl, hydroxy, $C_1$–$C_6$-alkoxy, benzyloxy and $C_1$–$C_7$-alkanoyloxy; $R^1$ and $R^2$, if adjacent, may form a bridge selected from —$(CH_2)_4$—, —$(CH=CH)_2$— and —$CH_2O$—$CR^7R^8$—$O$—, wherein $R^7$ and $R^8$ are selected independently from each other from hydrogen and $C_1$–$C_6$-alkyl;

$R^3$ is selected from the group consisting of hydrogen, halogen, $C_1$–$C_6$-alkyl, trifluoromethyl and $C_1$–$C_6$-hydroxyalkyl;

$R^4$ selected from the group consisting of hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy and benzyloxy;

k is 0 or 1,

A is selected from the group consisting of $C_1$–$C_6$-alkylene a substituted $C_1$–$C_6$-alkylene, which is substituted one to three-fold by $C_1$–$C_6$-alkyl, hydroxy, $C_1$–$C_3$-alkoxy, fluorine, or phenyl, $C_2$–$C_6$-alkylene, wherein a methylene unit is isosterically replaced by O, S, $NR^9$, CO, SO, or $SO_2$, wherein, with the exception of CO, the isosteric substitution is not adjacent to the amide group and $R^9$ is selected from the group consisting of hydrogen, $C_1$–$C_6$-alkyl, $C_3$–$C_6$-alkenyl, $C_3$–$C_6$-alkinyl, $C_1$–$C_6$-acyl and $C_1$–$C_6$-alkanesulfonyl, 1,2-cyclopropylene, $C_2$–$C_6$-alkenylene, a substituted $C_2$–$C_6$-alkenylene, which is substituted one to three-fold by $C_1$–$C_6$-alkyl, hydroxy, $C_1$–$C_6$-alkoxy, fluorine, cyano or phenyl, $C_4$–$C_6$-alkadienylene,
a substituted $C_4$–$C_6$-alkadienylene, which is substituted once to twice by $C_1$–$C_3$-alkyl, fluorine, cyano or phenyl,
1,3,5-hexatrienylene,
a substituted 1,3,5-hexatrienylene, which is substituted by $C_1$–$C_3$-alkyl, fluorine, cyano or phenyl, and
ethinylene D is selected from the group consisting of
$C_2$–$C_{10}$-alkylene,
a substituted $C_2$–$C_{10}$-alkylene, which is substituted once or twice by $C_1$–$C_6$-alkyl, hydroxy, or $C_1$–$C_6$-alkoxy,
$C_4$–$C_{10}$-alkenylene,
a substituted $C_4$–$C_{10}$-alkenylene, which is substituted once or twice by $C_1$–$C_6$-alkyl, hydroxy, or $C_1$–$C_6$-alkoxy, $C_4$–$C_{10}$-alkinylene,
a substituted $C_4$–$C_{10}$-alkinylene, which is substituted once or twice by $C_1$–$C_6$-alkyl, hydroxy, or $C_1$–$C_6$-alkoxy, and
$C_2$–$C_{10}$-alkylene,
$C_2$–$C_{10}$-alkylene, $C_4$–$C_{10}$-alkenylene, or $C_4$–$C_{10}$-alkinylene, wherein one to three methylene units are isosterically replaced by O, S, $NR^{10}$, CO, SO, or $SO_2$, wherein $R^{10}$ has the same meaning as $R^9$, but is selected independently thereof;

E is selected from the group consisting of

and

wherein the heterocyclic ring may have a double bond and
n and p are, independent of each other, 0, 1, 2 or 3 where n+p≦4, wherein
q is 1, 2 or 3;
$R^{11}$ is selected from the group consisting of hydrogen, $C_1$–$C_6$-alkyl, hydroxy, hydroxymethyl, carboxy, and $C_2$–$C_7$-alkoxycarbonyl and
$R^{12}$ is selected from the group consisting of hydrogen, $C_1$–$C_6$-alkyl and an oxo group adjacent to a nitrogen atom, or
$R^{11}$ and $R^{12}$, may together, form a $C_1$–$C_3$-alkylene bridge under formation of a bicyclic ring system;
$R^{13}$ is selected from the group consisting of hydrogen, $C_1$–$C_6$-alkyl, $C_3$–$C_6$-alkenyl, $C_3$–$C_6$-alkinyl, $C_3$–$C_8$-cycloalkyl,
saturated or unsaturated, four to seven-membered heterocycles, which contain one or two hetero-atoms selected from N, S and O,
benzyl, phenyl,
monocyclic aromatic five and six-membered heterocycles, which contain one to three hetero-atoms selected from N, S and O and are either bound directly or over a methylene group,
anellated bi- and tricyclic aromatic and partially hydrogenated carbocyclic ring system with 8 to 16 ring atoms and at least one aromatic ring, wherein the linkage occurs either over an aromatic or a hydrogenated ring and either directly or over a methylene group, and
anellated bi- and tricyclic aromatic or partially hydrogenated heterocyclic ring systems with 8 to 16 ring atoms and at least one aromatic ring, wherein one to three ring atoms are selected from N, S and O and the linkage occurs either over an aromatic ring or a hydrogenated ring and either directly or over a methylene group,
$R^{14}$ has the same meaning as $R^{13}$, but is selected independently thereof;
$R^{15}$ is selected from the group consisting of hydrogen, hydroxy, methyl, benzyl, phenyl,
monocyclic aromatic five and six-membered heterocycles, which contain one to three heteroatoms selected from N, S and O and are either bound directly or over a methylene group,
anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group,
anellated bi- and tricyclic aromatic and partially hydrogenated heterocyclic ring systems with 8 to 16 ring atoms and at least one aromatic ring, wherein one to three ring atoms are selected from N, S and O and the linkage can occur either over an aromatic ring or a hydrogenated ring and either directly or over a methylene group;
$R^{16}$ has the same meanings as $R^5$, but is selected independently thereof,
$R^{17}$ is selected from the group consisting of trifluoromethyl, $C_1$–$C_6$-alkoxy, $C_3$–$C_6$-alkenyloxy and benzyloxy; and
$Ar^1$ and $Ar^2$, are selected independently from each other from the group consisting of phenyl, pyridyl and naphthyl;
wherein aromatic ring systems in the substituents $R^1$, $R^2$, $R^4$, $R^5$, $R^6$, $R^{13}$, $R^{14}$, $R^{15}$, $R^{16}$, $R^{17}$, $Ar^1$ and $Ar^2$ may be substituted independently from each other by one to three of the same or different groups selected from the group consisting of halogen, cyano, $C_1$–$C_6$-alkyl, trifluoromethyl, $C_3$–$C_8$-cycloalkyl, phenyl, benzyl hydroxy, $C_1$–$C_6$-hydroxyalkyl, $C_1$–$C_6$-alkoxy, benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxyalkyl, nitro, amino, mono-$C_1$–$C_6$-alkylamino, di-($C_1$–$C_6$-alkyl)amino and, for two adjacent residues on the aromatic ring, methylenedioxy, and $C_1$–$C_6$-alkoxy which is entirely or partially substituted by fluorine.

29. A method of inhibiting tumor cell growth in a human or animal body, wherein the tumor cells are selected from the group consisting of liver tumors, lung carcinomas, rhabdomyosaromcomas, kidney clear cell carcinoma, colon carcinoma, prostrate carcinoma, ER positive mamma carcinoma, small cell lung carcinoma, osteosarcoma, malignant melanoma, ER, PgR positive mamma carcinoma, glioblastoma, astrocytoma, retinoblastoma, Burkiff's lymphoma, myeloma, and combinations thereof, the method comprising administering to the human or animal body in need thereof an amount of a pharmaceutical composition effective for inhibiting tumor cell growth, wherein the pharmaceutical composition includes a compound of general formula (I)

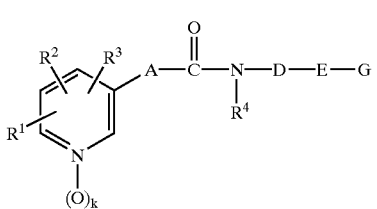

wherein $R^1$ is selected from the group consisting of hydrogen, halogen, cyano, $C_1$–$C_6$-alkyl, $C_3$–$C_6$-alkenyl, $C_3$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkoxycarbonyl, $C_3$–$C_{13}$-dialkylaminocarbonyl, carboxy, phenyl, phenoxy, phenylthio, pyridyloxy, pyridylthio, and $NR^5R^6$, wherein $R^5$ and $R^6$ selected independently of each other from the group consisting of hydrogen, $C_1$–$C_6$-alkyl, $C_3$–$C_6$-alkenyl, $C_3$–$C_6$-alkinyl, benzyl and phenyl;

$R^2$ is selected from the group consisting of hydrogen, halogen, cyano, $C_1$–$C_6$-alkyl, triflurormethyl, hydroxy, $C_1$–$C_6$-alkoxy, benzyloxy and $C_1$–$C_7$-alkanoyloxy; $R^1$ and $R^2$, if adjacent, may form a bridge selected from —$(CH_2)_4$—, —$(CH=CH)_2$— and —$CH_2O$—$CR^7R^8$—O—, wherein $R^7$ and $R^8$ are selected independently from each other from hydrogen and $C_1$–$C_6$-alkyl;

$R^3$ is selected from the group consisting of hydrogen, halogen, $C_1$–$C_6$-alkyl, trifluoromethyl and $C_1$–$C_6$-hydroxyalkyl;

$R^4$ selected from thegroup consisting of hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy and benzyloxy;

k is 0 or 1,

A is selected from the group consisting of
$C_1$–$C_6$-alkylene
a substituted $C_1$–$C_6$-alkylene, which is substituted one to three-fold by $C_1$–$C_6$-alkyl, hydroxy, $C_1$–$C_3$-alkoxy, fluorine, or phenyl,
$C_2$–$C_6$-alkylene, wherein a methylene unit is isosterically replaced by O, S, $NR^9$, CO, SO, or $SO_2$, wherein, with the exception of CO, the isosteric substitution is not adjacent to the amide group and $R^9$ is selected from the group consisting of hydrogen, $C_1$–$C_6$-alkyl, $C_3$–$C_6$-alkenyl, $C_3$–$C_6$-alkinyl, $C_1$–$C_6$-acyl and $C_1$–$C_6$-alkanesulfonyl,
1,2-cyclopropylene,
$C_2$–$C_6$-alkenylene,
a substituted $C_2$–$C_6$-alkenylene, which is substituted one to three-fold by $C_1$–$C_6$-alkyl, hydroxy, $C_1$–$C_6$-alkoxy, fluorine, cyano or phenyl,
$C_4$–$C_6$-alkadienylene,
a substituted $C_4$–$C_6$-alkadienylene, which is substituted once to twice by $C_1$–$C_3$-alkyl, fluorine, cyano or phenyl,
1,3,5-hexatrienylene,
a substituted 1,3,5-hexatrienylene, which is substituted by $C_1$–$C_3$-alkyl, fluorine, cyano or phenyl, and
ethinylene D is selected from the group consisting of
$C_2$–$C_{10}$-alkylene,
a substituted $C_2$–$C_{10}$-alkylene, which is substituted once or twice by $C_1$–$C_6$-alkyl, hydroxy, or $C_1$–$C_6$-alkoxy,
$C_4$–$C_{10}$-alkenylene,
a substituted $C_4$–$C_{10}$-alkenylene, which is substituted once or twice by $C_1$–$C_6$-alkyl, hydroxy, or $C_1$–$C_6$-alkoxy,
$C_4$–$C_{10}$-alkinylene,
a substituted $C_4$–$C_{10}$-alkinylene, which is substituted once or twice by $C_1$–$C_6$-alkyl, hydroxy, or $C_1$–$C_6$-alkoxy, and
$C_2$–$C_{10}$-alkylene,
$C_2$–$C_{10}$-alkylene, $C_4$–$C_{10}$-alkenylene, or $C_4$–$C_{10}$-alkinylene, wherein one to three methylene units are is6sterically replaced by O, S, $NR^{10}$, CO, SO, or $SO_2$, wherein $R^{10}$ has the same meaning as $R^9$, but is selected independently thereof;

E is selected from the group consisting of

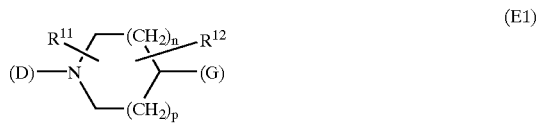

and

wherein the heterocyclic ring may have a double bond and n and p are, independent of each other, 0, 1, 2 or 3 where n+p≦4, wherein q is 1, 2 or 3;

$R^{11}$ is selected from the group consisting of hydrogen, $C_1$–$C_6$-alkyl, hydroxy, hydroxymethyl, carboxy, and $C_2$–$C_7$-alkoxycarbonyl and $R^{12}$ is selected from the group consisting of hydrogen, $C_1$–$C_6$-alkyl and an oxo group adjacent to a nitrogen atom, or $R^{11}$ and $R^{12}$, may together, form a $C_1$–$C_3$-alkylene bridge under formation of a bicyclic ring system;

G is selected from the group consisting of $G^1$, $G^2$, $G^3$, $G^4$ and $G^5$, wherein $G^1$ is —$(CH_2)_r$—$(CR^{14}R^{15})_s$—$R^{13}$ r is 0, 1, 2 or 3 and s is 0 or 1

$R^{13}$ is selected from the group consisting of hydrogen, $C_1$–$C_6$-alkyl, $C_3$–$C_6$-alkenyl, $C_3$–$C_6$-alkinyl, $C_3$–$C_8$-cycloalkyl,
saturated or unsaturated, four to seven-membered heterocycles, which contain one or two hetero-atoms selected from N, S and O,
benzyl, phenyl,
monocyclic aromatic five and six-membered heterocycles, which contain one to three heteroatoms selected from N, S and O and are either bound directly or over a methylene group, anellated bi- and tricyclic aromatic and partially hydrogenated carbocyclic ring system with 8 to 16 ring atoms and at least one aromatic ring, wherein the linkage occurs either over an aromatic or a hydrogenated ring and either directly or over a methylene group, and anellated bi- and tricyclic aromatic or partially hydrogenated heterocyclic ring systems with 8 to 16 ring atoms and at least one aromatic ring, wherein one to three ring atoms are selected from N, S and O and the linkage occurs either over an aromatic ring or a hydrogenated ring and either directly or over a methylene group, $R^{14}$ has the same meaning as $R^{13}$, but is selected independently thereof;

$R^{15}$ is selected from the group consisting of hydrogen, hydroxy, methyl, benzyl, phenyl,
monocyclic aromatic five and six-membered heterocycles, which contain one to three hetero-atoms selected from N, S and O and are either bound directly or over a methylene group, anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group, anellated bi- and tricyclic aromatic and partially hydrogenated heterocyclic ring systems with 8 to 16 ring atoms and at least one aromatic ring, wherein one to three ring atoms are selected from N, S and O and the linkage can occur either over an aromatic ring or a hydrogenated ring and either directly or over a methylene group;

$G^2$ is $=(C)_u R^{13} R^{15}$ wherein, $R^{13}$ and $R^{15}$ have the above meaning and u is 0 or 1, or
u=1, and $R^{13}$ and $R^{15}$ together with a carbon atom to which they are attached form a ring system selected from the group consisting of $C_2$–$C_8$-cycloalkyl,
saturated, four to seven-membered heterocycles which contain one or two hetero-atoms selected from N, S and O;
anellated bi- and tricyclic partially hydrogenated carboxocyclic ring system with 8 to 16 ring atoms and at least one aromatic ring; and anellated bi-and tricyclic partially hydrogenated heterocyclic ring systems with 8 to 16 ring atoms and at least one aromatic ring, wherein one to three ring atoms are selected from N, S and O;
or, u=0, and $R^{13}$ and $R^{15}$ together with the carbon atom $C_E$ of ring E to which they are attached form a ring system $C_E R^{13} R^{15}$ selected from the group consisting of
cycloalkyl, saturated, four to seven-membered heterocycles which contain one or two hetero-atoms selected from N, S and O;
anellated bi- and tricyclic partially hydrogenated carbocyclic ring systems with 8 to 16 ring atoms and at least one aromatic ring; and
anellated bi- and tricyclic partially hydrogenated heterocyclic ring systems with 8 to 16 ring atoms and at least one aromatic ring, wherein 1 to 3 ring atoms can be selected from N, S and O;

$G^3$ is selected from

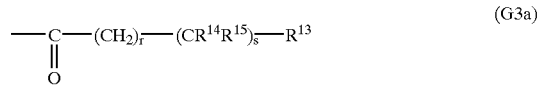

(G3a)

and

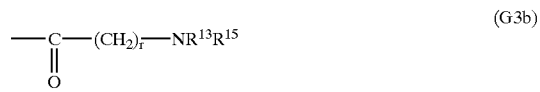

(G3b)

wherein r, s, and the substituents $R^{13}$, $R^{14}$, and $R^{15}$ have the above meanings, or the group

—$NR^{13}R^{15}$ is a nitrogen containing heterocycle bound over the nitrogen atom which nitrogen-containing heterocycle is selected from the group consisting of
saturated and unsaturated monocyclic, four to eight-membered heterocycles which, aside from the essential nitrogen atom, may contain one or two further hetero-atoms selected from N, S and O, and
saturated and unsaturated bi- or tricyclic, anellated or bridges heterocycles with 8 to 16 ring atoms, which, aside from the essential nitrogen atom, may contain one or two further hetero-atoms selected from N, S and O, $G^4$ is selected from the group consisting of

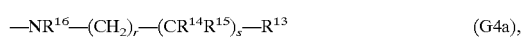

(G4a),

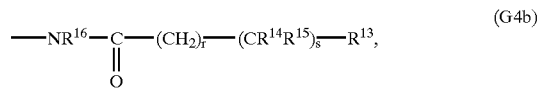

(G4b)

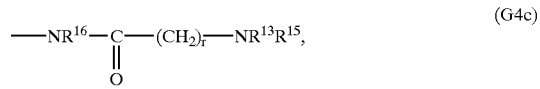

(G4c)

(G4d),

(G4e)

and

(G4f), wherein r, s and $R^{13}$, $R^{14}$, and $R^{15}$ have the above meanings and $R^{16}$ has the same meanings as $R^5$, but is selected independently thereof, $R^{17}$ is selected from the group consisting of trifluoromethyl, $C_1$–$C_6$-alkoxy, $C_3$–$C_6$-alkenyloxy and benzyloxy; and $Ar^1$ and $Ar^2$, are selected independently from each other from the group consisting of phenyl, pyridyl and naphthyl;

$G^5$ is selected from the group consisting of $$—W—(CH_2)_r—(CR^{14}R^{15})_s—R^{13} \quad \text{(G5a)}$$

and

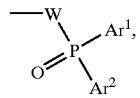 (G5b)

wherein r, s, and $R^{13}$, $R^{14}$, $R^{15}$, $Ar^1$ and $Ar^2$ have the above meanings and W is O or S, wherein the ring systems $=CR^{13}R^{15}$, $—NR^{13}R^{15}$, $—C_ER^{13}R^{15}$ and aromatic ring systems in the substituents $R^1$, $R^2$, $R^4$, $R^5$, $R^6$, $R^{13}$, $R^{14}$, $R^{15}$, $R^{16}$, $R^{17}$, $Ar^1$ and $Ar^2$ may be substituted independently from each other by one to three of the same or different groups selected from the group consisting of halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxyalkyl, nitro, amino, mono-$C_1$–$C_6$-alkylamino, di-($C_1$–$C_6$-alkyl)amino and, for two adjacent residues on the aromatic ring, methylenedioxy, and $C_1$–$C_6$-alkoxy which is entirely or partially substituted by fluorine, wherein alkenyl- and cycloalkyl residues in the group $G^1$ to $G^5$ may be substituted by one or two of the same or different groups selected from hydroxy, carboxy, $C_2$–$C_7$-alkoxycarbonyl, benzyloxycarbonyl, amino, mono-$C_1$–$C_6$-alkylamino, and di-($C_1$–$C_6$-alkyl)amino.

\* \* \* \* \*